(12) United States Patent
Grawunder

(10) Patent No.: US 10,174,309 B2
(45) Date of Patent: Jan. 8, 2019

(54) TRANSPOSITION-MEDIATED IDENTIFICATION OF SPECIFIC BINDING OR FUNCTIONAL PROTEINS

(71) Applicant: NBE-Therapeutics LLC, Basel (CH)

(72) Inventor: Ulf Grawunder, Basel (CH)

(73) Assignee: NBE-THERAPEUTICS LLC, Basel (CH)

( * ) Notice: Subject to any disclaimer, the term of this patent is extended or adjusted under 35 U.S.C. 154(b) by 0 days.

(21) Appl. No.: 14/414,981

(22) PCT Filed: Jul. 18, 2013

(86) PCT No.: PCT/EP2013/065214
§ 371 (c)(1),
(2) Date: Jan. 15, 2015

(87) PCT Pub. No.: WO2014/013026
PCT Pub. Date: Jan. 23, 2014

(65) Prior Publication Data
US 2015/0152406 A1    Jun. 4, 2015

Related U.S. Application Data

(60) Provisional application No. 61/673,144, filed on Jul. 18, 2012.

(30) Foreign Application Priority Data

Jul. 30, 2012   (EP) .................................... 12178529

(51) Int. Cl.
*C12N 1/06*     (2006.01)
*C12N 15/10*    (2006.01)
(Continued)

(52) U.S. Cl.
CPC .......... *C12N 15/1055* (2013.01); *C07K 16/28* (2013.01); *C12N 5/10* (2013.01);
(Continued)

(58) Field of Classification Search
None
See application file for complete search history.

(56) References Cited

U.S. PATENT DOCUMENTS 6,096,551 A * 8/2000 Barbas .................... C40B 40/02
436/6
7,863,425 B2 * 1/2011 Crystal ................ A61K 39/025
435/340
(Continued)

FOREIGN PATENT DOCUMENTS

JP    2005-532071 A    10/2005
JP    2010-538659 A    12/2010
(Continued)

OTHER PUBLICATIONS

Manz et al. (1995) Proc. Natl. Acad. Sci. USA vol. 92, pp. 1921-1925.*
(Continued)

*Primary Examiner* — Aaron A Priest
(74) *Attorney, Agent, or Firm* — Lathrop Gage LLP; James H. Velema, Esq.; Alan W. Steele

(57) ABSTRACT

The method disclosed herein describes a novel technology offering unparalleled efficiency, flexibility, utility and speed for the discovery and optimization of polypeptides having desired binding specificity and/or functionality, including antigen-binding molecules such as antibodies and fragments thereof, for desired functional and/or binding phenotypes. The novel method is based on transposable constructs and diverse DNA libraries cloned into transposable vectors and their transfection into host cells by concomitant transient
(Continued)

Figure 4:
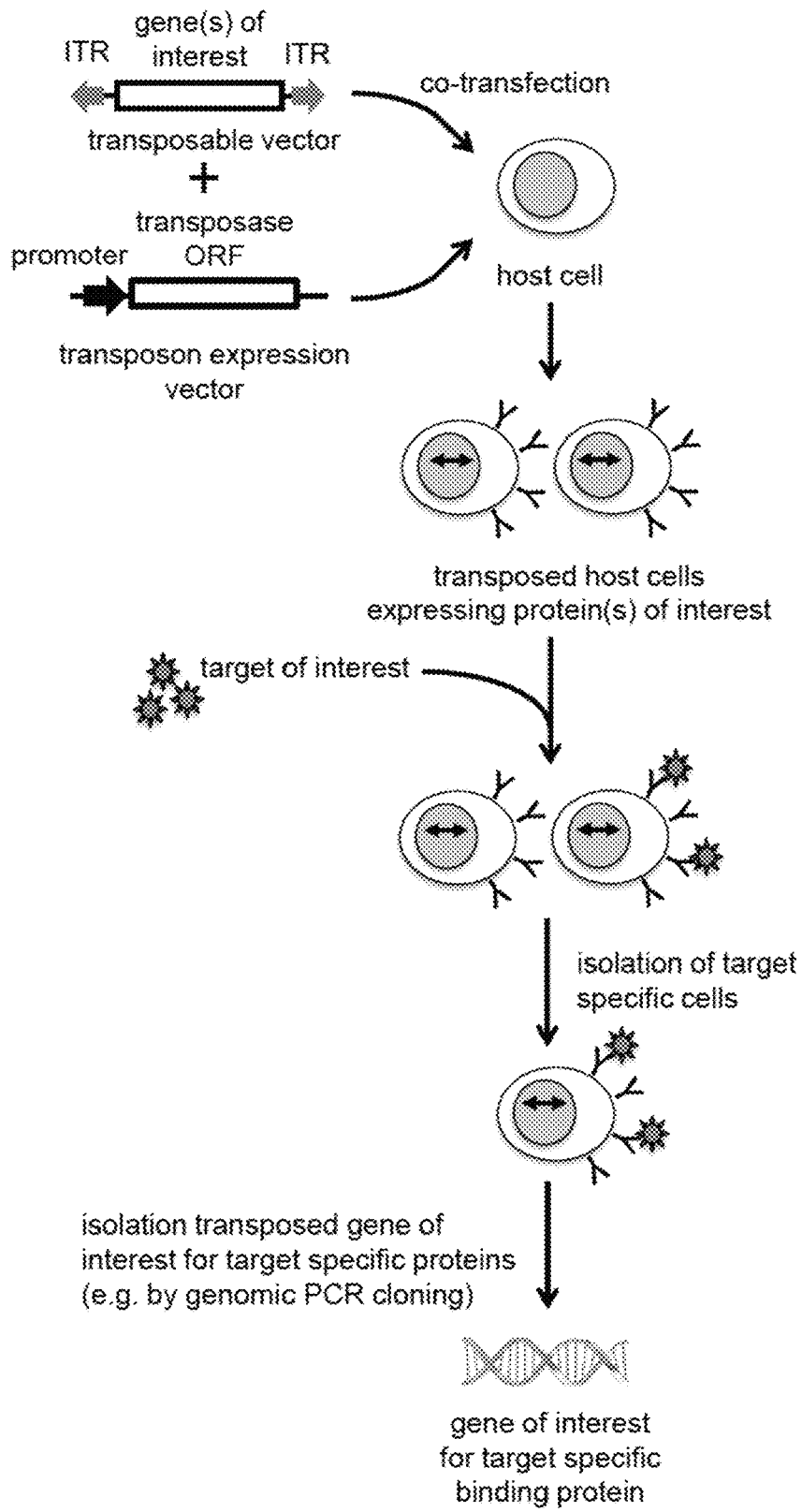

expression of a functional transposase enzyme. This ensures an efficient, stable introduction of the transposon-based expression vectors into vertebrate host cells in one step, which can then be screened for a desired functional or binding phenotype of the expressed proteins, after which the relevant coding sequences for the expressed proteins, including antibodies and fragments thereof, can be identified by standard cloning and DNA sequencing techniques.

7 Claims, 19 Drawing Sheets

Specification includes a Sequence Listing.

(51) Int. Cl.
*C12N 5/10* (2006.01)
*G01N 33/68* (2006.01)
*C07K 16/28* (2006.01)
*C12N 9/12* (2006.01)

(52) U.S. Cl.
CPC ....... *C12N 9/1241* (2013.01); *C12N 15/1082* (2013.01); *G01N 33/6854* (2013.01); *C07K 2317/14* (2013.01); *C07K 2317/55* (2013.01); *C07K 2317/56* (2013.01); *C07K 2317/622* (2013.01)

(56) References Cited

U.S. PATENT DOCUMENTS

| | | | | |
|---|---|---|---|---|
| 2003/0232395 | A1* | 12/2003 | Hufton .................. | C07K 16/00 506/1 |
| 2009/0042297 | A1* | 2/2009 | George, Jr. .......... | C12N 15/907 435/455 |
| 2009/0226922 | A1* | 9/2009 | Grawunder ...... | C07K 14/43595 435/6.16 |
| 2012/0196327 | A1 | 8/2012 | Kurokawa et al. | |

FOREIGN PATENT DOCUMENTS

| | | |
|---|---|---|
| JP | 2011-525103 A | 9/2011 |
| JP | 2012-511920 A | 5/2012 |
| WO | 2004/005322 A2 | 1/2004 |
| WO | 2009/039166 A1 | 3/2009 |
| WO | 2009/087230 A1 | 7/2009 |
| WO | 2009/109368 A1 | 9/2009 |
| WO | 2010/069913 A1 | 6/2010 |
| WO | 2012/081628 A1 | 6/2012 |

OTHER PUBLICATIONS

Mátés et al. (Molecular evolution of a novel hyperactive Sleeping Beauty transposase enables robust stable gene transfer in vertebrates, Nature Genetics 41, 753-761 (2009), Published online: May 3, 2009).*
Chew et al. (Genetic screens using the piggyBac transposon, Methods. Apr. 2011;53(4):366-71. doi: 10.1016/j.ymeth.2010.12. 022. Epub Dec. 23, 2010).*
Hoogenboom (Selecting and screening recombinant antibody libraries, Nat Biotechnol. Sep. 2005;23(9):1105-16).*
McKown et al. (Identification of a transposon Tn7-dependent DNA-binding activity that recognizes the ends of Tn7, Proc Natl Acad Sci U S A. Nov. 1987;84(22):7807-11).*
Arciszewska et al. (Transposon Tn7. cis-Acting sequences in transposition and transposition immunity, J Mol Biol. May 5, 1989;207(1):35-52).*
Zhou et al. (Development of a novel mammalian cell surface antibody display platform, MAbs. Sep.-Oct. 2010; 2(5): 508-518).*
Hackett et al. (A Transposon and Transposase System for Human Application, Mol Ther. Apr. 2010; 18(4): 674-683).*
Chew et al. (Genetic screens using the piggyBac transposon, Methods. Apr. 2011;53(4):366-71. Epub Dec. 23, 2010).*
Yusa et al. (A hyperactive piggyBac transposase for mammalian applications, Jan. 25, 2011, vol. 108 No. 4).*
Li et al. (Identification of HBsAg-specific antibodies from a mammalian cell displayed full-length human antibody library of healthy immunized donor, Cell Mol Immunol. Mar. 2012; 9(2): 184-190, Published online Dec. 19, 2011).*
Ho et al. (Mammalian Cell Display for Antibody Engineering, Methods Mol Biol. 2009; 525: 337-xiv).*
Beerli et al. (Isolation of human monoclonal antibodies by mammalian cell display, PNAS, Sep. 23, 2008, vol. 105 No. 38).*
Chiang, et al., Construction of a mariner-based transposon for epitope-tagging and genomic targeting. Gene. Aug. 21, 2002;296(1-2):179-85.
Hensel, et al., Simultaneous identification of bacterial virulence genes by negative selection. Science. Jul. 21, 1995;269 (5222):400-3.
International Search Report and Written Opinion for Application No. PCT/EP2013/065214, dated Oct. 14, 2013 (10 pages).
Kempeni, Joachim, Preliminary results of early clinical trials with the fully human anti-TNFalpha monoclonal antibody D2E7. Ann Rheum Dis. Nov. 1999;58 Suppl 1:I70-2.
Urban, et al., Selection of functional human antibodies from retroviral display libraries. Nucleic Acids Res. Feb. 24, 2005;33(4):e35.
International Preliminary Report on Patentability for Application No. PCT/EP2013/065214, dated Jan. 29, 2015 (6 pages).
Chinese Office Action for Application No. 201380048308.7, dated May 17, 2016 (14 pages).
Kie, F., et al., Enhancement on exogenous gene integrity and gene expression by sleeping beauty transposon system. Masters Thesis, 2009, vol. 1, 146 pages. Chinese language document with English abstract (p. 5).
Isaacs, A. T., et al., "Engineered Resistance to Plasmodium falciparum Development in Transgenic Anopheles stephensi," PLOS Pathogens, 2011, v. 7, pp. 1-13.
Japanese Notice of Allowance, dated Nov. 1, 2016, for corresponding JP Application No. 2015-522101 (5 pages).
Kahlig, K. M., et al., "Multiplexed transposon-mediated stable gene transfer in human cells," PNAS, 2010, v. 107, pp. 1343-1348.
Matasci, M., et al., "The PiggyBac transposon enhances the frequency of CHO stable cell line generation and yields recombinant lines with superior productivity and stability," Biotechnol. Bioeng., 2011, v. 108, pp. 2141-2150.
Mates, L, et al., "Molecular evolution of a novel hyperactive Sleeping Beauty transposase enables robust stable gene transfer in vertebrates," Nature Genetics, 2009, v. 41, pp. 753-761.
New Zealand Office Action for Application No. 705074, dated Mar. 24, 2016 (7 pages).
Japanese Office Action for Application No. 2015-522101, dated Jun. 21, 2016 (11 pages).
Birch, J.R., et al., Antibody production. Adv Drug Deliv Rev. Aug. 7, 2006;58(5-6):671-85. Epub May 22, 2006.
Bradbury, A.R., et al., Antibodies from phage antibody libraries. J Immunol Methods. Jul. 2004;290(1-2):29-49.
Hackett PB et al, "A Transposon and Transposase System for Human Application," Molecular Therapy, 2010, v. 18, pp. 674-683.
Harel Inbar, N., et al., Selection of antibodies from synthetic antibody libraries. Arch Biochem Biophys. Oct. 15, 2012;526(2):87-98. doi: 10.1016/j.abb.2011.12.028. Epub Jan. 8, 2012.
Meir, Y-J. J., et al., "Transposon-based vector systems for gene therapy clinical trials: Challenges and Considerations," Chang Gung Med J, 2011, vol. 34 No. 6, pp. 565-579.
New Zealand Office Action for Application No. 705074, dated Oct. 31, 2016 (4 pages).
Japanese Office Action for Application No. 2015-522101, dated Jan. 26, 2016 (7 pages).

* cited by examiner

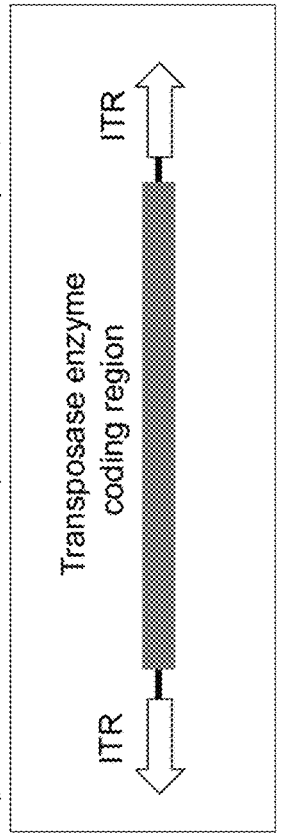
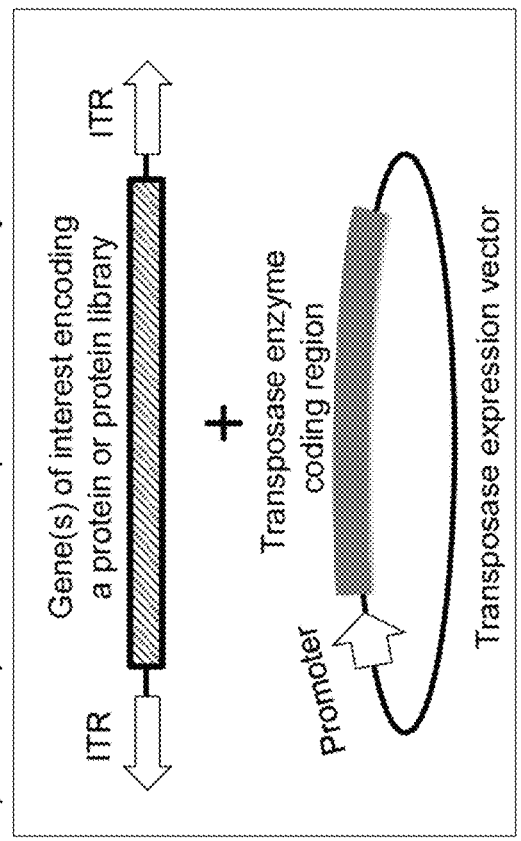
Fig. 1:

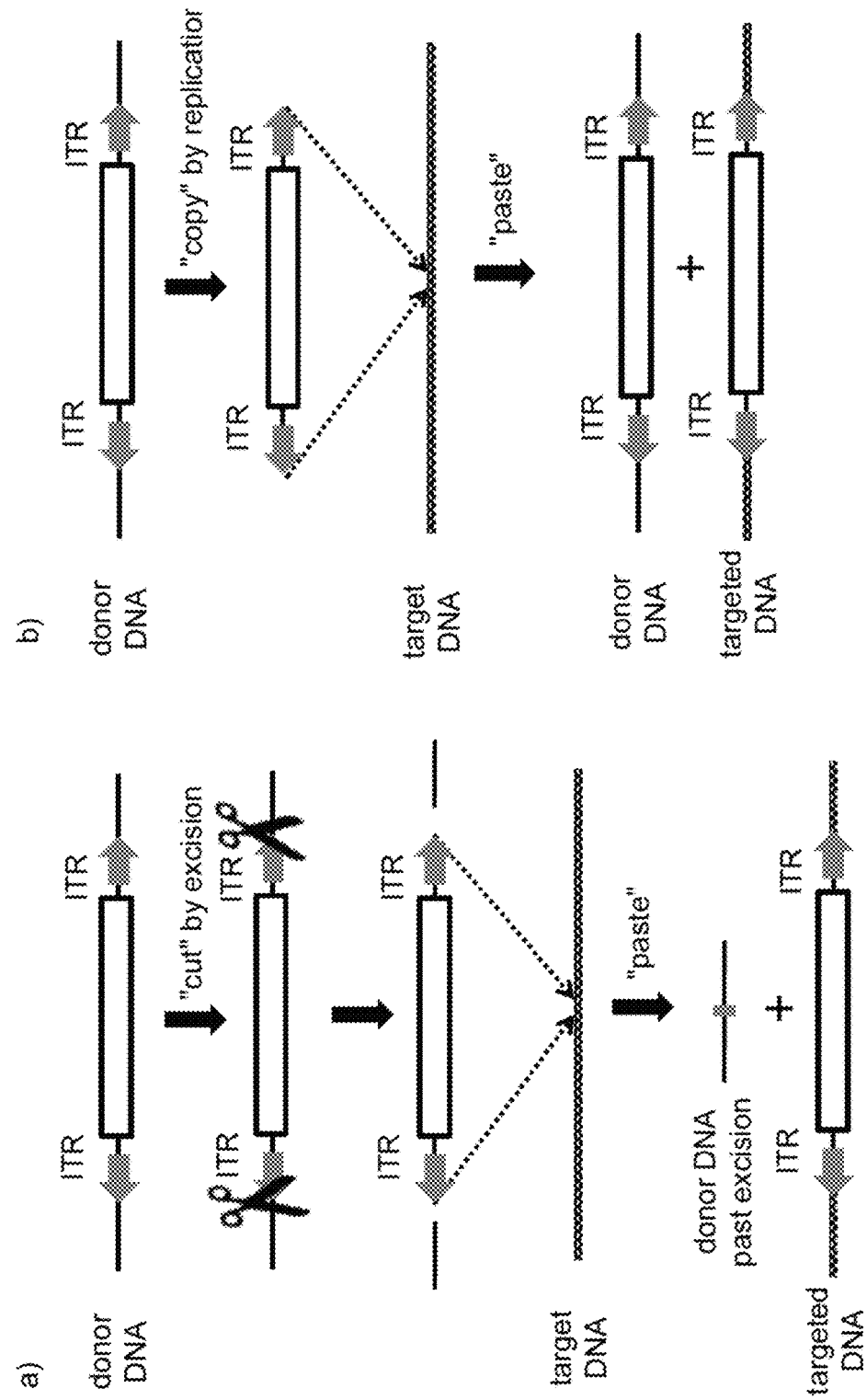

Fig. 3:

| Transposon Family (Transposon) | Species origin | Host cell range |
|---|---|---|
| PiggyBac | Trichoplusia ni | Mouse, Human, Pig |
| Tc1-mariner (Sleeping Beauty) | salmonid | Zebrafish, Xenopus, Mouse, Human |
| (Frog Prince) | R. pipiens | Human, Hamster, Xenopus, Zebrafish |
| (Himar1) | H. irritans | Human |
| (Passport) | P. platessa | Human, Monkey, Hamster, Turkey, Chicken, Pig |
| (Minos) | D. hydei | Human, Mouse |
| hAT (Tol1, Tol2) | O. latipe | Zebrafish, Xenopus, Mouse, Human, Chicken |
| Ac/Ds | Z. mays | Zebrafish, Human |
| PIF, Harbinger, Harbinger3-DR | D. rerio | Zebrafish, Human |
| (Hsmar1) | H. sapiens | Human, Zebrafish |

Fig. 10:
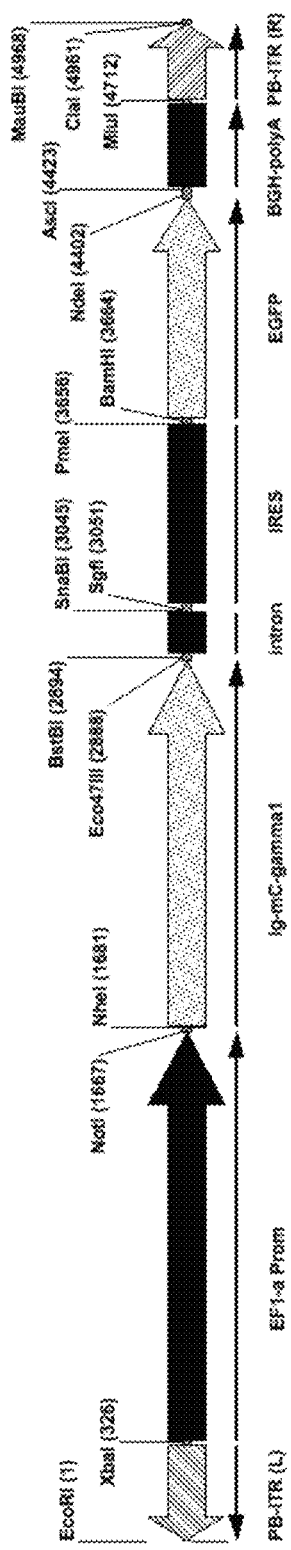
Functional elements and restriction enzyme sites in 4975 bp long DNA fragment Seq-ID20
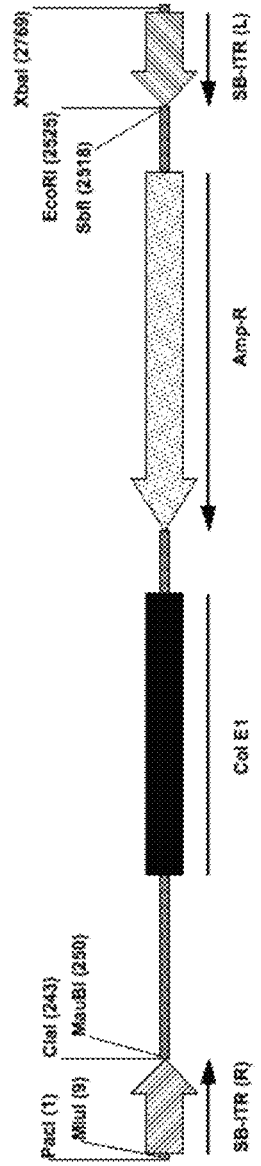
Functional elements and restriction enzyme sites in 2774 bp long DNA fragment Seq-ID21

Fig. 15

```
NotI
GCGGCCGCATGGACATGAGGGTCCCCGCTCAGCTCCTGGGGCTCCTGCTGCTCTGGCTCCCAGGTGCCAAATGTGACA
         ▶ M  D  M  R  V  P  A  Q  L  L  G  L  L  L  W  L  P  G  A  K  C  D
TCCAGATGACCCAGTCTCCTTCCACCCTGTCTGCATCTGTAGGAGACAGAGTCACCATCACTTGCCGGGCCAGTCAGA
▶ I  Q  M  T  Q  S  P  S  T  L  S  A  S  V  G  D  R  V  T  I  T  C  R  A  S  Q
GTATTAGTAGCTGGTTGGCCTGGTATCAGCAGAAACCAGGGAAAGCCCCTAAGCTCCTGATCTATGATGCCTCCAGTT
▶ S  I  S  S  W  L  A  W  Y  Q  Q  K  P  G  K  A  P  K  L  L  I  Y  D  A  S  S
TGGAAAGTGGGGTCCCATCAAGGTTCAGCGGCAGTGGATCTGGGACAGAATTCACTCTCACCATCAGCAGCCTGCAGC
▶ L  E  S  G  V  P  S  R  F  S  G  S  G  S  G  T  E  F  T  L  T  I  S  S  L  Q
CTGATGATTTTGCAACTTATTACTGCCAACAGNNKNNKNNKNNKNNKACTTTTGGCCAGGGGACCAAGCTGGAGA
▶ P  D  D  F  A  T  Y  Y  C  Q  Q  -  -  -  -  -  -  T  F  G  Q  G  T  K  L  E
         BsiWI
TCAAACGTACGGTGGCTGCACCATCTGTCTTCATCTTCCCGCCATCTGATGAGCAGTTGAAATCTGGAACTGCCTCTG
▶ I  K  R  T  V  A  A  P  S  V  F  I  F  P  P  S  D  E  Q  L  K  S  G  T  A  S
TTGTGTGCCTGCTGAATAACTTCTATCCCAGAGAGGCCAAAGTACAGTGGAAGGTGGATAACGCCCTCCAATCGGGTA
▶ V  V  C  L  L  N  N  F  Y  P  R  E  A  K  V  Q  W  K  V  D  N  A  L  Q  S  G
ACTCCCAGGAGAGTGTCACAGAGCAGGACAGCAAGGACAGCACCTACAGCCTCAGCAGCACCCTGACGCTGAGCAAAG
▶ N  S  Q  E  S  V  T  E  Q  D  S  K  D  S  T  Y  S  L  S  S  T  L  T  L  S  K
CAGACTACGAGAAACACAAAGTCTACGCCTGCGAAGTCACCCATCAGGGCCTGAGCTCGCCCGTCACAAAGAGCTTCA
▶ A  D  Y  E  K  H  K  V  Y  A  C  E  V  T  H  Q  G  L  S  S  P  V  T  K  S  F
                   AsuII
ACAGGGGAGAGTGTTAGCCCTTTCGAA
▶ N  R  G  E  C  •
```

Fig. 16

```
NotI
GCGGCCGCATGGAGTTTGGGCTGAGCTGGGTTTTCCTCGTTGCTCTTTTAAGAGGTGTCCAGTGTCAGGTGCAGCTGG
         ▶ M  E  F  G  L  S  W  V  F  L  V  A  L  L  R  G  V  Q  C  Q  V  Q  L
TGGAGTCTGGGGGAGGCGTGGTCCAGCCTGGGAGGTCCCTGAGACTCTCCTGTGCAGCCTCTGGATTCACCTTCAGTA
▶ V  E  S  G  G  G  V  V  Q  P  G  R  S  L  R  L  S  C  A  A  S  G  F  T  F  S
GCTATGCTATGCACTGGGTCCGCCAGGCTCCAGGCAAGGGGCTAGAGTGGGTGGCAGTTATATCATATGATGGAAGTA
▶ S  Y  A  M  H  W  V  R  Q  A  P  G  K  G  L  E  W  V  A  V  I  S  Y  D  G  S
ATAAATACTACGCAGACTCCGTGAAGGGCCGATTCACCATCTCCAGAGACAATTCCAAGAACACGCTGTATCTGCAAA
▶ N  K  Y  Y  A  D  S  V  K  G  R  F  T  I  S  R  D  N  S  K  N  T  L  Y  L  Q
TGAACAGCCTGAGAGCTGAGGACACGGCTGTGTATTACTGTGCGAGRGNNKNNKNNKNNKGACNNKTGGGGCCAAGGAA
▶ M  N  S  L  R  A  E  D  T  A  V  Y  Y  C  A  -  -  -  -  -  -  D  -  W  G  Q  G
             NheI
CCCTGGTCACCGTCTCCTCAGCTAGCACCAAGGGCCCATCGGTCTTCCCCCTGGCACCCTCCTCCAAGAGCACCTCTG
▶ T  L  V  T  V  S  S  A  S  T  K  G  P  S  V  F  P  L  A  P  S  S  K  S  T  S
GGGGCACAGCCAGCCCTGGGCTGCCTGGTCAAGGACTACTTCCCCGAACCGGTGACGGTGTCGTGGAACTCAGGCGCCC
▶ G  G  T  A  A  L  G  C  L  V  K  D  Y  F  P  E  P  V  T  V  S  W  N  S  G  A
TGACCAGCGGCGTGCACACCTTCCCGGCTGTCCTACAGTCCTCAGGACTCTACTCCCTCAGCAGCGTGGTGACCGTGC
▶ L  T  S  G  V  H  T  F  P  A  V  L  Q  S  S  G  L  Y  S  L  S  S  V  V  T  V
CCTCCAGCAGCTTGGGCACCCAGACCTACATCTGCAACGTGAATCACAAGCCCAGCAACACCAAGGTGGACAAGAAAG
▶ P  S  S  L  G  T  Q  T  Y  I  C  N  V  N  H  K  P  S  N  T  K  V  D  K  K
TTGAGCCCAAATCTTGTGACAAAACTCACACATGCCCACCGTGCCCAGCACCTGAACTCCTGGGGGGACCGTCAGTCT
▶ V  E  P  K  S  C  D  K  T  H  T  C  P  P  C  P  A  P  E  L  L  G  G  P  S  V
TCCTCTTCCCCCCAAAACCCAAGGACACCCTCATGATCTCCCGGACCCCTGAGGTCACATGCGTGGTGGTGGACGTGA
▶ F  L  F  P  P  K  P  K  D  T  L  M  I  S  R  T  P  E  V  T  C  V  V  V  D  V
GCCACGAAGACCCTGAGGTCAAGTTCAACTGGTACGTGGACGGCGTGGAGGTGCATAATGCCAAGACAAAGCCGCGGG
▶ S  H  E  D  P  E  V  K  F  N  W  Y  V  D  G  V  E  V  H  N  A  K  T  K  P  R
AGGAGCAGTACAACAGCACGTACCGTGTGGTCAGCGTCCTCACCGTCCTGCACCAGGACTGGCTGAATGGCAAGGAGT
▶ E  E  Q  Y  N  S  T  Y  R  V  V  S  V  L  T  V  L  H  Q  D  W  L  N  G  K  E
ACAAGTGCAAGGTCTCCAACAAAGCCCTCCCAGCCCCCATCGAGAAAACCATCTCCAAAGCCAAAGGGCAGCCCCGAG
▶ Y  K  C  K  V  S  N  K  A  L  P  A  P  I  E  K  T  I  S  K  A  K  G  Q  P  R
AACCACAGGTGTACACCCTGCCCCCATCCCGGGATGAGCTGACCAAGAACCAGGTCAGCCTGACCTGCCTGGTCAAAG
▶ E  P  Q  V  Y  T  L  P  P  S  R  D  E  L  T  K  N  Q  V  S  L  T  C  L  V  K
GCTTCTATCCCAGCGACATCGCCGTGGAGTGGGAGAGCAATGGGCAGCCGGAGAACAACTACAAGACCACGCCTCCCG
▶ G  F  Y  P  S  D  I  A  V  E  W  E  S  N  G  Q  P  E  N  N  Y  K  T  T  P  P
TGCTGGACTCCGACGGCTCCTTCTTCCTCTACAGCAAGCTCACCGTGGACAAGAGCAGGTGGCAGCAGGGGAACGTCT
▶ V  L  D  S  D  G  S  F  F  L  Y  S  K  L  T  V  D  K  S  R  W  Q  Q  G  N  V
TCTCATGCTCCGTGATGCATGAGGCTCTGCACAACCACTACACACAGAAGAGCCTCTCCCTGTCTCCGGGAGCTGCAAC
▶ F  S  C  S  V  M  H  E  A  L  H  N  H  Y  T  Q  K  S  L  S  L  S  P  E  L  Q
TGGAGGAGAGCTGTGCCGAGGCGCAGGACGGGGAGCTGGACGGGCTGTGGACGACCATCACCATCTTCATCACACTCT
▶ L  E  E  S  C  A  E  A  Q  D  G  E  L  D  G  L  W  T  T  I  T  I  F  I  T  L
TCCTGTTAAGCGTGTGCTACAGTGCCACCGTCACCTTCTTCAAGGTGAAGTGGATCTTCTCCTCGGTGGTGGACCTGA
▶ F  L  L  S  V  C  Y  S  A  T  V  T  F  F  K  V  K  W  I  F  S  S  V  V  D  L
                                                             Eco47III
AGCAGACCATCATCCCCGACTACAGGAACATGATCGGACAGGGGGCCTAGTAAGCTTAGCGCT
▶ K  Q  T  I  I  P  D  Y  R  N  M  I  G  Q  G  A  -  -
```

Fig. 17
A
*JK template: ScaI strategy (AGT/ACT)*
... AGT ACT TTC GGC ...
... TCA TGA AAG CCG ...
      T   F   G
ACT TTC GGC ...
TGA AAG CCG ... => *linearized template*
 T   F   G
B
*JH template: DrdI strategy (GACNNNN/NNGTC)*
.GA CAT TGG GGT CAG ...
.CT GTA ACC CCA GTC ...
        W   G   Q
G GGT CAG ...
ACC CCA GTC ... => *linearized template*
 W   G   Q

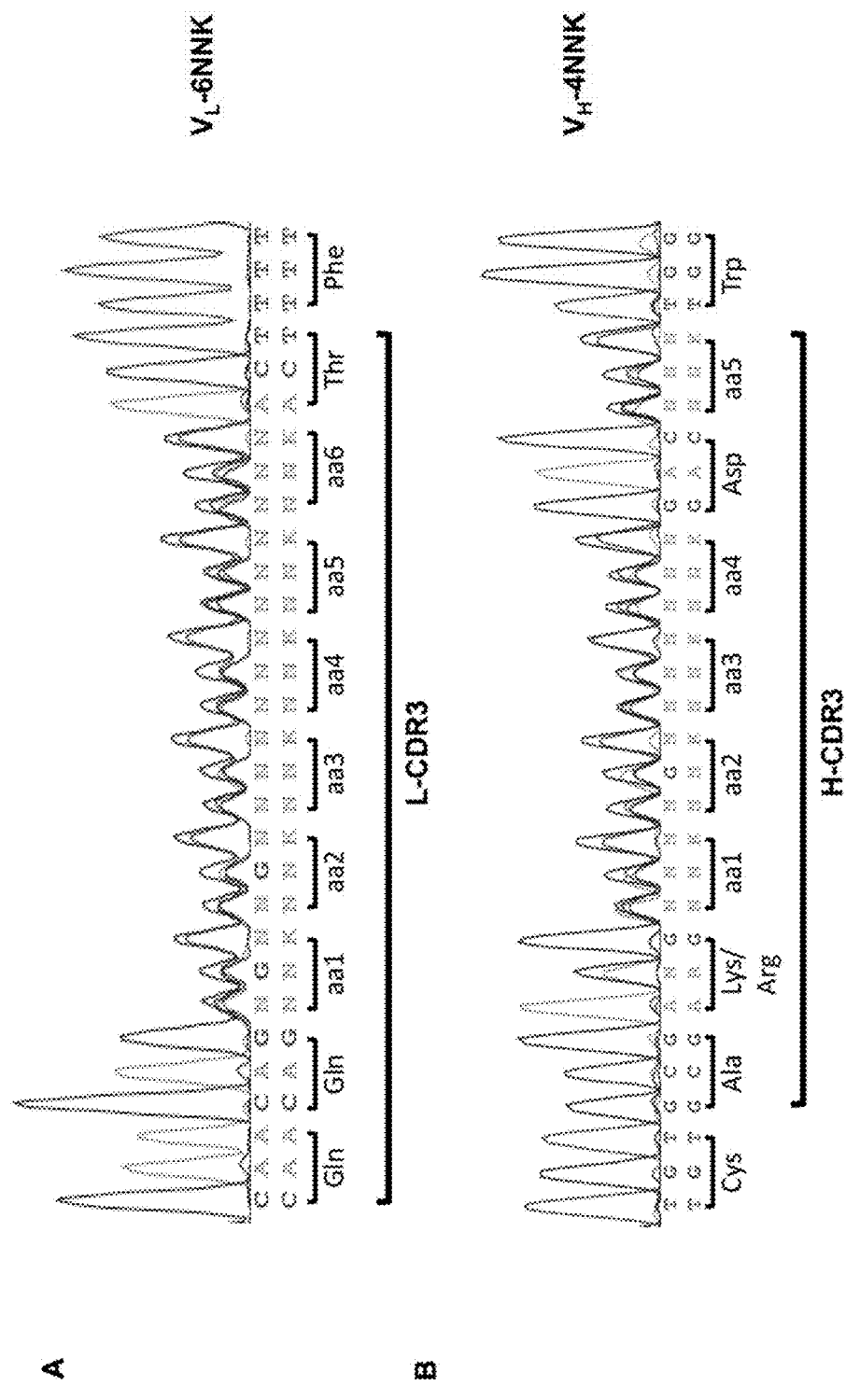

TRANSPOSITION-MEDIATED IDENTIFICATION OF SPECIFIC BINDING OR FUNCTIONAL PROTEINS

FIELD OF THE INVENTION

Technologies for the identification of specific functional and binding proteins.

BACKGROUND OF THE INVENTION

The discovery of target-specific proteins, including antibodies and fragments thereof, is of significant commercial interest, because the selection of highly selective functional proteins or binding proteins, including antibodies and fragments thereof, has a high potential for the development of new biological entities (NBEs) with novel therapeutic properties that very specifically integrate, or interfere with biological processes, and therefore are predicted to display lower side-effect profiles than conventional new chemical entities (NCEs). In that respect, particularly the development of highly target-specific, therapeutic antibodies, and antibody-based therapeutics, have paved the way to completely novel therapies with improved efficacy. As a consequence, therapeutic monoclonal antibodies represent the fastest growing segment in the development of new drugs over the last decade, and presently generate about USD 50 billion global revenues, which accounts for a significant share of the total global market of pharmaceutical drugs.

Therefore, efficient and innovative technologies, that allow the discovery of highly potent, but also well tolerated therapeutic proteins, in particular antibody-based therapeutics, are in high demand.

In order to identify a protein with a desired functionality or a specific binding property, as is the case for antibodies, it is required to generate, to functionally express and to screen large, diverse collections, or libraries of proteins, including antibodies and fragments thereof, for desired functional properties or target binding specificity. A number of technologies have been developed over the past twenty years, which allow expression of diverse protein libraries either in host cells, or on viral and phage particles and methods for their high-throughput screening and/or panning toward a desired functional property, or binding phenotype.

Standard, state-of-the-art technologies to achieve identification of target-specific binders or proteins with desired functional properties include, e.g. phage-display, retroviral display, bacterial display, yeast display and various mammalian cell display technologies, in combination with solid surface binding (panning) and/or other enrichment techniques. All of these technologies are covered by various patents and pending patent applications.

While phage and prokaryotic display systems have been established and are widely adopted in the biotech industry and in academia for the identification of target-specific binders, including antibody fragments (Hoogenboom, *Nature Biotechnology* 23, 1105-1116 (2005)), they suffer from a variety of limitations, including the inability to express full-length versions of larger proteins, including full-length antibodies, the lack of proper post-translational modification, the lack of proper folding by vertebrate chaperones, and, in the case of antibodies, an artificially enforced heavy and light chain combination. Therefore, in case of antibody discovery by these methods, "reformatting" into full-length antibodies and mammalian cell expression is required. Due to the above-mentioned limitations this frequently results in antibodies with unfavorable biophysical properties (e.g. low stability, tendency to aggregate, diminished affinity), limiting the therapeutic and diagnostic potential of such proteins. This, on one hand, leads to significant attrition rates in the development of lead molecules generated by these methods, and, on the other hand, requires significant effort to correct the biophysical and molecular liabilities in these proteins for further downstream drug development.

Therefore, protein and antibody discovery technologies have been developed using lower eukaryotic (e.g. yeast) and, more recently, also mammalian cell expression systems for the identification of proteins with desired properties, as these technologies allow (i) expression of larger, full-length proteins, including full-length antibodies, (ii) better or normal post-translational modification, and, (iii) in case of antibodies, proper heavy-light chain pairing (Beerli & Rader, *mAbs* 2, 365-378 (2010)). This, in aggregate, selects for proteins with favorable biophysical properties that have a higher potential in drug development and therapeutic use.

Although expression and screening of proteins in vertebrate cells would be most desirable, because vertebrate cells (e.g. hamster CHO, human HEK-293, or chicken DT40 cells) are preferred expression systems for the production of larger therapeutic proteins, such as antibodies, these technologies are currently also associated with a number of limitations, which has lead to a slow adoption of these technologies in academia and industry.

First, vertebrate cells are not as efficiently and stably genetically modified, as, e.g. prokaryotic or lower eukaryotic cells like yeast. Therefore, its remains a challenge to generate diverse (complex) enough vertebrate cell based proteins libraries, from which candidates with desired properties or highest binding affinities can be identified. Second, in order to efficiently isolate proteins with desired properties, usually iterative rounds of cell enrichment are required. Vertebrate expression either by transient transfection of plasmids (Higuchi et al. *J. Immunol. Methods* 202, 193-204 (1997)), or transient viral expression systems, like sindbis or vaccinia virus (Beerli et al. *PNAS* 105, 14336-14341 (2008), and WO02102885) do not allow multiple rounds of cell selection required to efficiently enrich highly specific proteins, and these methods are therefore either restricted to screening of small, pre-enriched libraries of proteins, or they do require tedious virus isolation/cell re-infection cycles.

In order to achieve stable expression of binding proteins and antibodies in vertebrate cells, that do allow multiple rounds of selections based on stable genotype-phenotype coupling, technologies have been developed, utilizing specific recombinases (flp/frt recombinase system, Zhou et al. *mAbs* 5, 508-518 (2010)), or retroviral vectors (WO2009109368). However, the flp/frt recombination is a low-efficient system for stable integration of genes into vertebrate host cell genomes and therefore, again, only applicable to small, pre-selected libraries, or the optimization of selected protein or antibody candidates.

In comparison to the flp/frt recombinase system, retroviral vectors allow more efficient stable genetic modification of vertebrate host cells and the generation of more complex cellular libraries. However, (i) they are restricted to only selected permissible cell lines, (ii) they represent a biosafety risk, when human cells are utilized, (iii) retroviral expression vectors are subject to unwanted mutagenesis of the library sequences due to low-fidelity reverse transcription, (iv) retroviral vectors do not allow integration of genomic expression cassettes with intact intron/exon structure, due to splicing of the retroviral genome prior to packaging of the vector into retroviral particles, (v) retroviruses are subject to uncontrollable and unfavorable homologous recombination of library sequences during packaging of the viral genomes, (vi) are subject to retroviral silencing, and (vii) require a tedious two-step packaging-cell transfection/host-cell infection procedure. All these limitations represent significant challenges and limitations, and introduce significant complexities for the utility of retroviral vector based approaches in generating high-quality/high complexity vertebrate cell libraries for efficient target-specific protein, or antibody discovery.

Therefore, clearly a need exists for a more efficient, more controllable and straightforward technology that allows the generation of high-quality and highly complex vertebrate cell based libraries expressing diverse libraries of proteins including antibodies and fragments thereof from which proteins with highly specific function and/or binding properties and high affinities can be isolated.

(b) Transposases/Transposition:

Transposons, or transposable elements (TEs), are genetic elements with the capability to stably integrate into host cell genomes, a process that is called transposition (Ivies et al. *Mobile DNA* 1, 25 (2010)) (incorporated herein by reference in its entirety). TEs were already postulated in the 1950s by Barbara McClintock in genetic studies with maize, but the first functional models for transposition have been described for bacterial TEs at the end of the 1970s (Shapiro, *PNAS* 76, 1933-1937 (1979)) (incorporated herein by reference in its entirety).

Meanwhile it is clear that TEs are present in the genome of every organism, and genomic sequencing has revealed that approximately 45% of the human genome is transposon derived (International Human Genome Sequencing Consortium *Nature* 409: 860-921 (2001)) (incorporated herein by reference in its entirety). However, as opposed to invertebrates, where functional (or autonomous) TEs have been identified (FIG. 1a), humans and most higher vertebrates do not contain functional TEs. It has been hypothesized that evolutionary selective pressure against the mutagenic potential of TEs lead to their functional inactivation millions of years ago during evolution.

Autonomous TEs comprise DNA that encodes a transposase enzyme located in between two inverted terminal repeat sequences (ITRs), which are recognized by the transposase enzyme encoded in between the ITRs and which can catalyze the transposition of the TE into any double stranded DNA sequence (FIG. 1a). There are two different classes of transposons: class I, or retrotransposons, that mobilize via an RNA intermediate and a "copy-and-paste" mechanism (FIG. 2b), and class II, or DNA transposons, that mobilize via excision-integration, or a "cut-and-paste" mechanism (FIG. 2a) (Ivics et al. *Nat. Methods* 6, 415-422(2009)) (incorporated herein by reference in its entirety).

Bacterial, lower eukaryotic (e.g. yeast) and invertebrate transposons appear to be largely species specific, and cannot be used for efficient transposition of DNA in vertebrate cells. Only, after a first active transposon had been artificially reconstructed by sequence shuffling of inactive TEs from fish, which was therefore called "Sleeping Beauty" (Ivics et al. *Cell* 91, 501-510 (1997)) (incorporated herein by reference in its entirety), did it become possible to successfully achieve DNA integration by transposition into vertebrate cells, including human cells. Sleeping Beauty is a class II DNA transposon belonging to the Tc1/mariner family of transposons (Ni et al. *Briefings Funct. Genomics Proteomics* 7, 444-453 (2008)) (incorporated herein by reference in its entirety). In the meantime, additional functional transposons have been identified or reconstructed from different species, including *Drosophila*, frog and even human genomes, that all have been shown to allow DNA transposition into vertebrate and also human host cell genomes (FIG. 3). Each of these transposons, have advantages and disadvantages that are related to transposition efficiency, stability of expression, genetic payload capacity, etc.

To date, transposon-mediated technologies for the expression of diverse libraries of proteins, including antibodies and fragments thereof, in vertebrate host cells for the isolation of target specific, functional binding proteins, including antibodies and fragments thereof, have not been disclosed in the prior art.

BRIEF SUMMARY OF THE INVENTION

The method disclosed herein describes a novel technology offering unparalleled efficiency, flexibility, utility and speed for the discovery and optimization of polypeptides having a desired binding specificity and/or functionality, including antigen-binding molecules such as antibodies and fragments thereof, for desired functional and/or binding phenotypes. The novel method is based on transposable constructs and diverse DNA libraries cloned into transposable vectors and their transfection into host cells by concomitant transient expression of a functional transposase enzyme. This ensures an efficient, stable introduction of the transposon-based expression vectors into vertebrate host cells in one step, which can then be screened for a desired functional or binding phenotype of the expressed proteins, after which the relevant coding sequences for the expressed proteins, including antibodies and fragments thereof, can be identified by standard cloning and DNA sequencing techniques.

In one embodiment, the invention is broadly directed to a method for identifying a polypeptide having a desired binding specificity or functionality, comprising:

(i) generating a diverse collection of polynucleotides encoding polypeptides having different binding specificities or functionalities, wherein said polynucleotides comprise a sequence coding for a polypeptide disposed between first and second inverted terminal repeat sequences that are recognized by and functional with a least one transposase enzyme;

(ii) introducing the diverse collection of polynucleotides of (i) into host cells;

(iii) expressing at least one transposase enzyme functional with said inverted terminal repeat sequences in said host cells so that said diverse collection of polynucleotides is integrated into the host cell genome to provide a host cell population that expresses said diverse collection of polynucleotides encoding polypeptides having different binding specificities or functionalities;

(iv) screening said host cells to identify a host cell expressing a polypeptide having a desired binding specificity or functionality; and (v) isolating the polynucleotide sequence encoding said polypeptide from said host cell.

In a preferred embodiment, the polynucleotides are DNA molecules. In one embodiment, the diverse collection of polynucleotides comprises a ligand-binding sequence of a receptor, or a target binding sequence of a binding molecule. In a preferred embodiment, the polynucleotides comprise a sequence encoding an antigen-binding molecule, such as an antibody $V_H$ or $V_L$ domain, or an antigen-binding fragment thereof, or antibody heavy or light chains that are full-length (i.e., which include the constant region). In certain embodiments, the polynucleotides may comprise a sequence encoding both a $V_H$ and $V_L$ region, or both antibody heavy and light chains. In another embodiment, the polynucleotides comprise a sequence encoding a single-chain Fv or a Fab domain.

In one embodiment, the diverse collection of polynucleotides is generated by subjecting V region gene sequences to PCR under mutagenizing conditions, for example, by PCR amplification of V region repertoires from vertebrate B cells. In another embodiment, the diverse collection of polynucleotides is generated by gene synthesis (e.g., by randomization of sequences encoding a polypeptide having known binding specificity and/or functionality). In one useful embodiment, the diverse collection of polynucleotides comprises plasmid vectors. In another useful embodiment, the diverse collection of polynucleotides comprises double-stranded DNA PCR amplicons. The plasmid vectors may comprise a sequence encoding a marker gene, such as a fluorescent marker, a cell surface marker, or a selectable marker. The marker gene sequence may be upstream or downstream of the sequence encoding the polypeptide having a binding specificity or functionality, but between the inverted terminal repeat sequences. Alternatively, the marker gene sequence may be downstream of said sequence encoding a polypeptide having binding specificity or functionality and separated by an internal ribosomal entry site.

In some embodiments, the diverse collection of polynucleotides encode a plurality of antigen-binding molecules of a vertebrate, such as a mammal, e.g., a human.

In one embodiment, step (ii) of the method comprises introducing into host cells polynucleotides comprising sequences encoding immunoglobulin $V_H$ or $V_L$ regions, or antigen-binding fragments thereof, and wherein said $V_H$ and $V_L$ region sequences are encoded on separate vectors. In another embodiment, step (ii) of the method of the invention comprises introducing into host cells polynucleotides comprising sequences encoding full-length immunoglobulin heavy or light chains, or antigen-binding fragments thereof, wherein said full-length heavy and light chain sequences are on separate vectors. The vectors may be introduced into the host cells simultaneously or sequentially. In another embodiment, sequences encoding $V_H$ and $V_L$ regions or full-length heavy and light chains are introduced into host cells on the same vector. In the event that the $V_H$ and $V_L$ sequences or the full-length antibody heavy and light chain sequences are introduced into the host cells on different vectors, it is useful for the inverted terminal repeat sequences on each vector to be recognized by and functional with different transposase enzymes.

The host cells are preferably vertebrate cells, and preferably mammalian cells, such as rodent or human cells. Lymphoid cells, e.g., B cells, are particularly useful. B cells may be progenitor B cells or precursor B cells such as, for example, Abelson-Murine Leukemia virus transformed progenitor B cells or precursor B cells and early, immunoglobulin-null EBV transformed human proB and preB cells. Other useful host cells include B cell lines such as Sp2/0 cells, NS0 cells, X63 cells, and Ag8653 cells, or common mammalian cell lines such as CHO cells, Per.C6 cells, BHK cells, and 293 cells.

In one embodiment of the method of the invention, the expressing step (iii) comprises introducing into said host cells an expression vector encoding a transposase enzyme that recognizes and is functional with at least one inverted terminal repeat sequence in the polynucleotides. The vector encoding the transposase enzyme may be introduced into the host cells concurrently with or prior to or subsequent to the diverse collection of polynucleotides. In one embodiment, the transposase enzyme is transiently expressed in said host cell. Alternatively, the expressing step (iii) may comprise inducing an inducible expression system that is stably integrated into the host cell genome, such as, for example, a tetracycline-inducible or tamoxifen-inducible system. In a preferred embodiment, step (iii) comprises expressing in the host cell(s) a vector comprising a functional Sleeping Beauty transposase or a functional PiggyBac transposase. In one useful embodiment, step (iii) comprises expressing in said host cell a vector comprising SEQ ID NO:11. In another useful embodiment, the vector encodes SEQ ID NO:12, or a sequence with at least 95% amino acid sequence homology and having the same or similar inverted terminal repeat sequence specificity.

In another useful embodiment, step (iii) comprises expressing in said host cell a vector comprising SEQ ID NO:17. In another useful embodiment, the vector encodes SEQ ID NO:18, or a sequence with at least 95% amino acid sequence homology and having the same or similar inverted terminal repeat sequence specificity.

In one embodiment of the method of the invention, the screening step (iv) comprises magnetic activated cell sorting (MACS), fluorescence activated cell sorting (FACS), panning against molecules immobilized on a solid surface panning, selection for binding to cell-membrane associated molecules incorporated into a cellular, natural or artificially reconstituted lipid bilayer membrane, or high-throughput screening of individual cell clones in multi-well format for a desired functional or binding phenotype. In one embodiment, the screening step (iv) comprises screening to identify polypeptides having a desired target-binding specificity or functionality. In a preferred embodiment, the screening step (iv) comprises screening to identify antigen-binding molecules having desired antigen specificity. In one useful embodiment, the screening step further comprises screening to identify antigen-binding molecules having one or more desired functional properties. The screening step (iv) may comprise multiple cell enrichment cycles with host cell expansion between individual cell enrichment cycles.

In one embodiment of the method of the invention, the step (v) of isolating the polynucleotide sequence encoding the polypeptide having a desired binding specificity or functionality comprises genomic or RT-PCR amplification or next-generation deep sequencing. In one useful embodiment, the polynucleotide sequence isolated in step (v) is subjected to affinity optimization. This can be done by subjecting the isolated polynucleotide sequence to PCR or RT-PCR under mutagenizing conditions. In another useful embodiment, the mutagenized sequence is then further subjected to steps (i)-(v) of the method of the invention. In a preferred embodiment, the polynucleotide sequence obtained in (v) comprises a sequence encoding a $V_H$ or $V_L$ region of an antibody, or an antigen-binding fragment thereof, and wherein said antibody optimization comprises introducing one or more mutations into a complementarity determining region or framework region of said $V_H$ or $V_L$.

In one useful embodiment, the inverted terminal repeat sequences are from the PiggyBac transposon system and are recognized by and functional with the PiggyBac transposase. In one embodiment, the sequence encoding the upstream PiggyBac inverted terminal repeat sequence comprises SEQ ID NO: 1. In another embodiment, the sequence encoding the downstream PiggyBac inverted terminal repeat sequence comprises SEQ ID NO:2.

In another useful embodiment, the inverted terminal repeat sequences are from the Sleeping Beauty transposon system and are recognized by and functional with the Sleeping Beauty transposase. In one embodiment, the sequence encoding the upstream Sleeping Beauty inverted terminal repeat sequence comprises SEQ ID NO:14. In another embodiment, the sequence encoding the downstream Sleeping Beauty inverted terminal repeat sequence comprises SEQ ID NO:15.

In one embodiment of the invention, the polynucleotides comprise $V_H$ or $V_L$ region sequences encoding a sequence derived from a human anti-TNF alpha antibody. In one embodiment, the human anti-TNF alpha antibody is D2E7.

In a useful embodiment, step (iii) comprises introducing into said host cell a vector comprising a sequence encoding a functional PiggyBac transposase. In one embodiment the vector comprises SEQ ID NO:11. In another embodiment, the vector encodes SEQ ID NO:12, or a sequence with at least 95% amino acid sequence homology and having the same or similar inverted terminal repeat sequence specificity.

In another useful embodiment, step (iii) comprises expressing in said host cell a vector comprising SEQ ID NO:17. In another useful embodiment, the vector encodes SEQ ID NO:18, or a sequence with at least 95% amino acid sequence homology and having the same or similar inverted terminal repeat sequence specificity.

In preferred embodiments, the inverted terminal repeat sequences are recognized by and functional with at least one transposase selected from the group consisting of: PiggyBac, Sleeping Beauty, Frog Prince, Himar1, Passport, Minos, hAT, Tol1, Tol2, Ac/Ds, PIF, Harbinger, Harbinger3-DR, and Hsmar1.

The present invention is further directed to a library of polynucleotide molecules encoding polypeptides having different binding specificities or functionalities, comprising a plurality of polynucleotide molecules, wherein said polynucleotide molecules comprise a sequence encoding a polypeptide having a binding specificity or functionality disposed between inverted terminal repeat sequences that are recognized by and functional with at least one transposase enzyme. Preferably the polynucleotides are DNA molecules and comprise a ligand-binding sequence of a receptor or a target-binding sequence of a binding molecule. In a particularly preferred embodiment, the library comprises polynucleotides, wherein each polynucleotide comprises a sequence encoding an antigen-binding sequence of an antibody. In one embodiment, the library comprises polynucleotides encoding a $V_H$ or $V_L$ region of an antibody or an antigen-binding fragment thereof. Alternatively, the polynucleotides may encode a $V_H$ region and a $V_L$ region. In a preferred embodiment, the polynucleotides of the library comprise a sequence encoding a full-length antibody heavy or light chain (i.e., including the constant region) or an antigen-binding fragment thereof. Alternatively, the polynucleotides may encode both a full-length immunoglobulin heavy and light chain. In other embodiments, the polynucleotides of the library comprise a sequence encoding a single-chain Fv or a Fab domain. In preferred embodiments, the polynucleotides of the library are in the form of plasmids or double stranded DNA PCR amplicons. In certain embodiments, the plasmids of the library comprise a marker gene. In another embodiment, the plasmids comprise a sequence encoding a transposase enzyme that recognizes and is functional with the inverted terminal repeat sequences. In one embodiment, the library of the invention comprises polynucleotides that encode the full-length immunoglobulin heavy chain including the natural intron/exon structure of an antibody heavy chain. The full-length immunoglobulin heavy chain may comprise the endogenous membrane anchor domain.

The present invention is also directed to a method for generating a library of transposable polynucleotides encoding polypeptides having different binding specificities or functionality, comprising (i) generating a diverse collection of polynucleotides comprising sequences encoding polypeptides having different binding specificities or functionalities, wherein said polynucleotides comprise a sequence encoding polypeptide having a binding specificity or functionality disposed between inverted terminal repeat sequences that are recognized by and functional with a least one transposase enzyme.

The present invention is also directed to a vector comprising a sequence encoding a $V_H$ or $V_L$ region of an antibody, or antigen-binding portion thereof, disposed between inverted terminal repeat sequences that are recognized by and functional with at least one transposase enzyme. In certain embodiments, the vector encodes a full-length heavy or light chain of an immunoglobulin. Preferably, the sequence encoding the $V_H$ or $V_L$ or the heavy or light chain is a randomized sequence generated by, for example, PCR amplification under mutagenizing conditions or gene synthesis. In one embodiment, the vector comprises inverted terminal repeat sequences that are recognized by and functional with the PiggyBac transposase. In another embodiment, the inverted terminal repeat sequences are recognized by and functional with the Sleeping Beauty transposase. In one embodiment, the vector comprises a VH or VL region sequence derived from an anti-TNF alpha antibody such as, for example, D2E7. In certain embodiments, the vector comprises at least one sequence selected from the group consisting of: SEQ ID NO:5, SEQ ID NO:8, SEQ ID NO:9, SEQ ID NO:10, SEQ ID NO:11, SEQ ID NO:13, SEQ ID NO:16, SEQ ID NO:17, and SEQ ID NO:19, SEQ ID NO: 20, SEQ ID NO:21, SEQ ID NO:22, SEQ ID NO:23, SEQ ID NO:24, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41.

The present invention is also directed to a host cell comprising a vector of the invention as described above. In a preferred embodiment, the host cell further comprises an expression vector comprising a sequence encoding a transposase that recognizes and is functional with at least one inverted terminal repeat sequence in the vector encoding said $V_H$ or $V_L$ region sequence.

The present invention is still further directed to antigen-binding molecules, e.g., antibodies, produced by a method comprising claim 1.

The present invention is also directed to a method for generating a population of host cells capable of expressing polypeptides having different binding specificities or functionalities, comprising:

(i) generating a diverse collection of polynucleotides comprising sequences encoding polypeptides having different binding specificities or functionalities, wherein said polynucleotides comprise a sequence encoding a polypeptide having a binding specificity or functionality disposed between inverted terminal repeat sequences that are recognized by and functional with a least one transposase enzyme; and (ii) introducing said diverse collection of polynucleotides into host cells.

BRIEF DESCRIPTION OF THE DRAWINGS/FIGURES

FIG. 1: a.) This drawing depicts the configuration of an autonomous transposable element (TE), which can transpose or "jump" into any target DNA sequence. The key components of a TE are an active transposase enzyme that recognizes the inverted terminal repeats (ITRs) flanking the transposase enzyme itself up- and downstream of its sequence. TEs catalyze either the copying or the excision of the TE, and the integration in unrelated target DNA sequences. b.) This drawing depicts the configuration of a transposon vector system, in which the expression of an active transposase enzyme is effected by an expression vector that is not coupled to the TE itself. Instead, the TE may contain any sequence(s), or gene(s) of interest that is/are cloned in between the up- and downstream ITRs. Integration of the TE containing any sequence(s), or gene(s) of interest (e.g. a DNA library encoding a library of proteins) may integrate into unrelated target DNA sequences, if the transposase enzyme expression is provided in trans, e.g. by a separate transposase expression construct, as depicted here.

FIG. 2: a) This drawing depicts the two different ways how TEs can "jump" or transpose into unrelated target DNA. For group II transposons, the transposase enzyme in a first step recognizes the ITRs of the transposable element and catalyzes the excision of the TE from DNA. In a second step, the excised TE is inserted into unrelated target DNA sequence, which is also catalyzed by the transposase enzyme. This results in a "cut-and-paste" mechanism of transposition. For group I transposons (shown in b.) the coding information of the TE is first replicated (e.g. transcribed and reverse transcribed, in the case of retrotransposons) and the replicated TE then integrates into unrelated target DNA sequence, which is catalyzed by the transposase enzyme. This results in a "copy-and-paste" mechanism of transposition.

FIG. 3: This figure provides an overview of active transposase enzymes that have been identified and/or reconstructed from dormant, inactive TEs, and that have been shown to be able to confer transposition in various vertebrate and also human cells, as provided in the table. The table has been adapted from Table I of publication Ni et al. *Briefings Functional Genomics Proteomics* 7, 444-453 (2008) (incorporated herein by reference in its entirety)

FIG. 4: This figure outlines the principle of the method disclosed herein, for the isolation of coding information for proteins, including antibodies and fragments thereof, with a desired function, e.g. the binding to a target of interest, as depicted here. The gene(s) of interest, e.g. a diverse transposable DNA library encoding proteins, including antibody polypeptide chains or fragments thereof, that is cloned in between inverted terminal repeats (ITRs) of a transposable construct is introduced into a vertebrate host cell together with an expression vector for an active transposase enzyme (see top of the drawing). The expression of the transposon enzyme in said host cells in trans and the presence of the gene(s) of interest cloned in between ITRs that can be recognized by the transposase enzyme allows the stable integration of the ITR-flanked gene(s) of interest into the genome of the host cells, which can then stably express the protein(s) of interest encoded by the genes of interest. The cellular library expressing the protein(s) of interest can then be screened for a desired functionality of the expressed proteins, e.g., but not limited to the binding to a target protein of interest, as depicted here. By means of cell separation techniques known in the art, e.g. MACS or FACS, the cells expressing the protein(s) of interest with the desired phenotype and which therefore contain the corresponding genotype, can be isolated and the coding information for the gene(s) of interest can be retrieve from the isolated cells by cloning techniques known in the art, e.g. but not limited to genomic PCR cloning, as depicted here.

Figure 5:
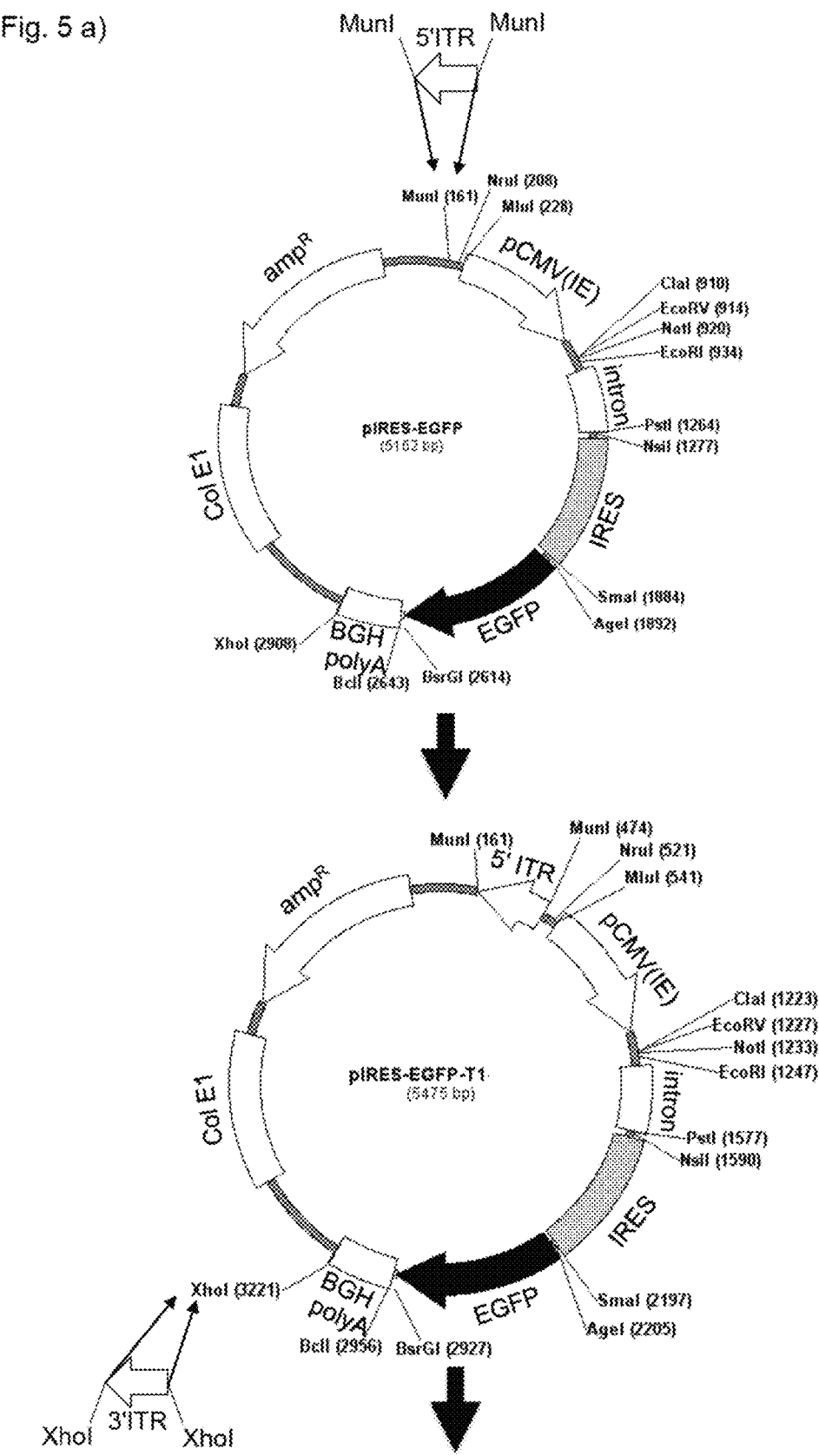
Figure 5:
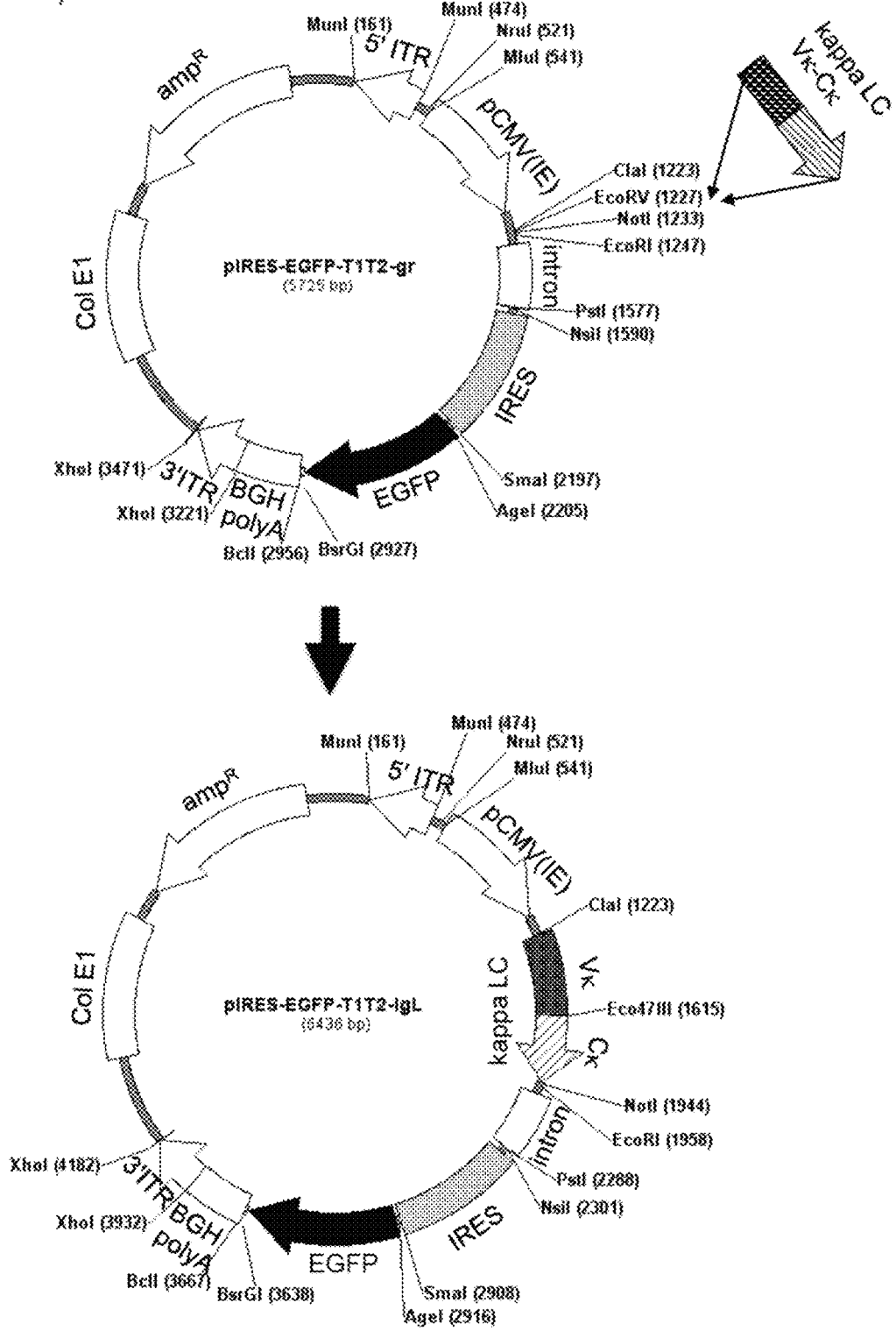

FIGS. 5a) and 5b): This drawing outlines the cloning strategy for the generation of a transposable human immunoglobulin (Ig) kappa light chain (LC) expression vector, as described in Example 1. FIG. 5 a.) depicts the cloning strategy for the insertion of 5'- and 3'-ITRs from the PiggyBac transposon into the mammalian expression vector pIRES-EGFP (Invitrogen, Carlsbad, Calif., USA), which already contains the strong mammalian cell promoter element pCMV(IE) (immediate early promoter of CMV), and intron/polyA signals for strong mammalian host cell expression. In addition, downstream of the ClaI, EcoRV, NotI, EcoRI containing multiple cloning site, into which gene(s) of interest can be cloned, pIRES-EGFP contains an internal ribosomal entry site (IRES) with a downstream ORF of enhanced green fluorescent protein (EGFP), which effects the coupling of expression of gene(s) of interest cloned upstream of the IRES. Bacterial functional elements (ampicillin resistance gene, $amp^R$) and a bacterial origin of replication (Col E1) for amplification and selection of the plasmid in *E. coli* are depicted as well. The resulting PiggyBac ITRs containing plasmid is designated pIRES-EGFP-T1T2. FIG. 5b) then depicts the insertion of a gene synthesized human Ig kappa LC into the unique EcoRV restriction enzyme site of pIRES-EGFP-T1-T2, which positions the human Ig kappa LC upstream of the IRES-EGFP cassette, and thereby couples the expression of the human Ig kappa LC to EGFP marker gene expression. The insertion of the human Ig kappa LC results in transposable human Ig kappa LC expression vector pIRES-EGFP-T1T2-IgL. The drawings show selected unique restriction enzyme sites in the plasmids, as well as selected duplicated sites resulting from cloning steps.

Figure 6:
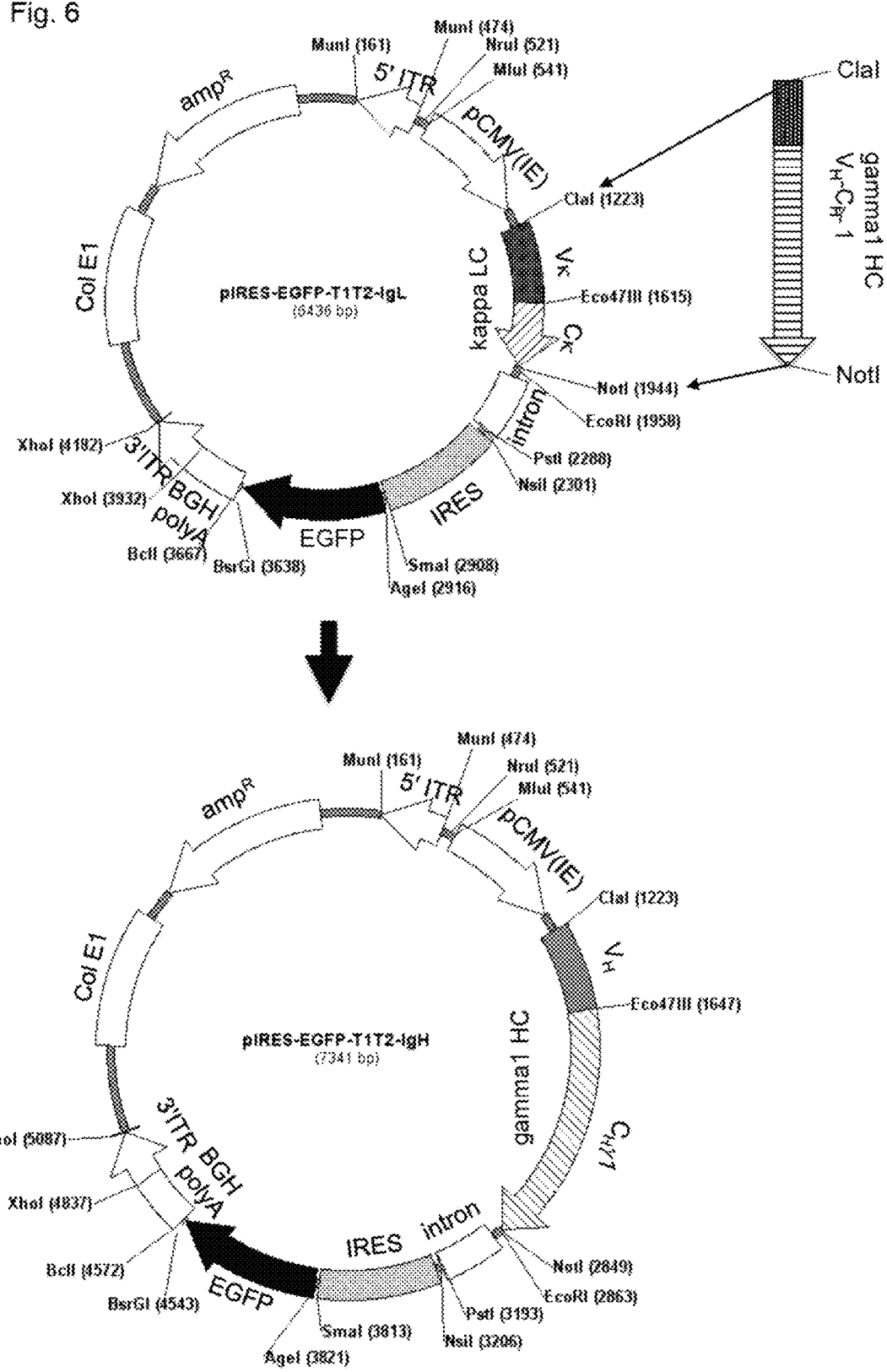

FIG. 6: This drawing outlines the cloning of a transposable human immunoglobulin (Ig) gamma 1 heavy chain (HC) expression vector, which can be generated by exchange of the human Ig kappa LC open reading frame (ORF) against the ORF for a human Ig gamma 1 HC ORF. The design of the final Ig gamma 1 HC ORF is similar, also with regard to the engineering of a unique Eco47III restriction enzyme site separating the variable (V) from the constant (C) coding regions, which allows the exchange of a single antibody V coding region against a diverse library of antibody V coding regions, as described in Example 3.

Figure 7:
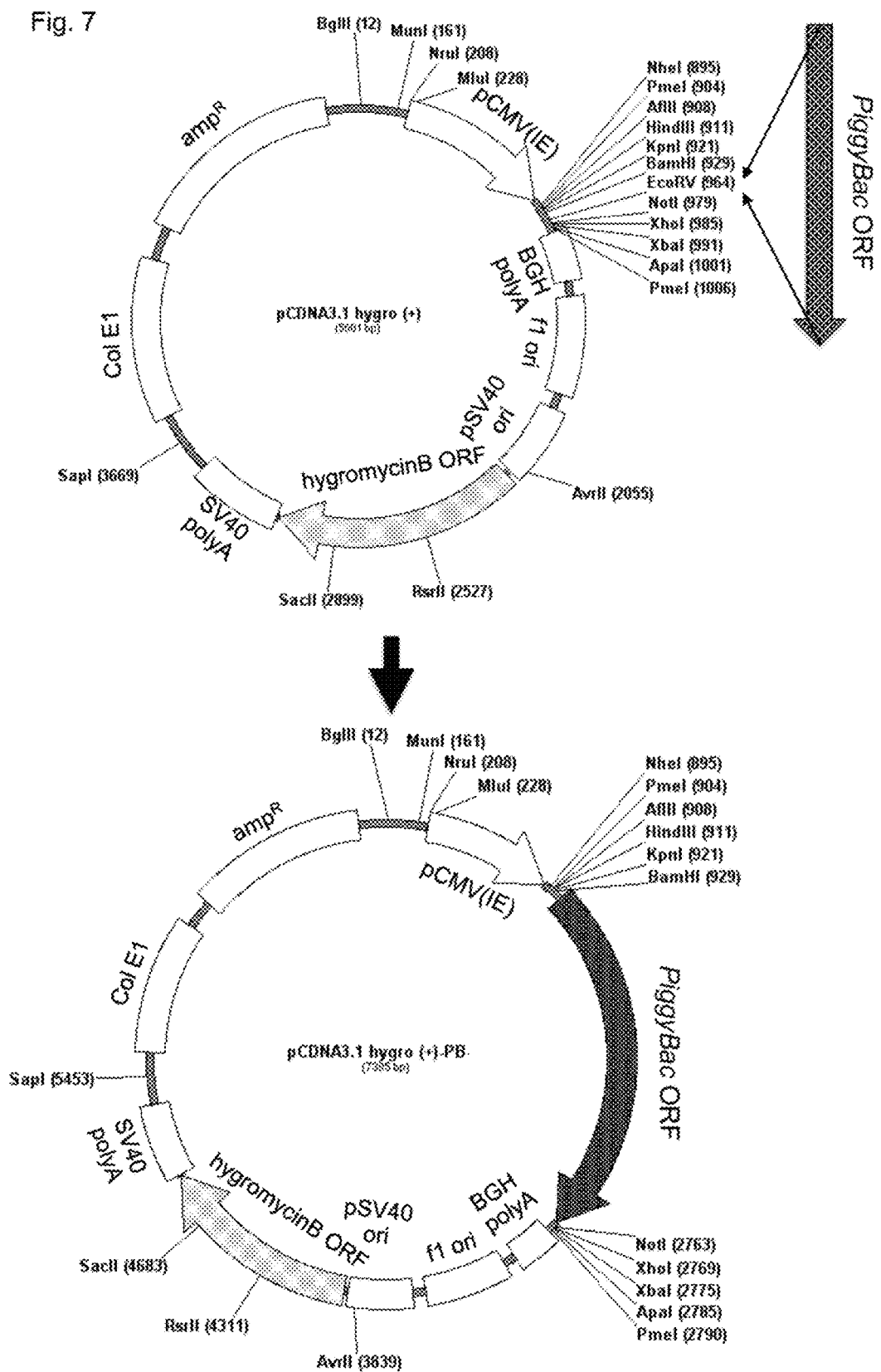

FIG. 7: This drawing depicts the cloning of a mammalian PiggyBac transposase enzyme expression vector, as described in the Example 4, using pCDNA3.1(+) hygro as the backbone of the mammalian expression vector, into which the gene synthesized ORF from PiggyBac transposase is cloned into the unique EcoRV restriction enzyme site of pCDNA3.1(+) hygro, resulting in PiggyBac transposon expression vector pCDNA3.1(+) hygro-PB expression vector pCDNA3.1(+) hygro-PB. Also in this drawing the relative position of other mammalian functional elements (CMV-IE promoter, BGH-polyA signal, SV40-polyA segment, hygromycin B ORF) and bacterial functional elements (ampicillin resistance gene, ampR, origin of replication, ColE1), as well as selected relevant restriction enzyme recognition sites are shown.

Figure 8:
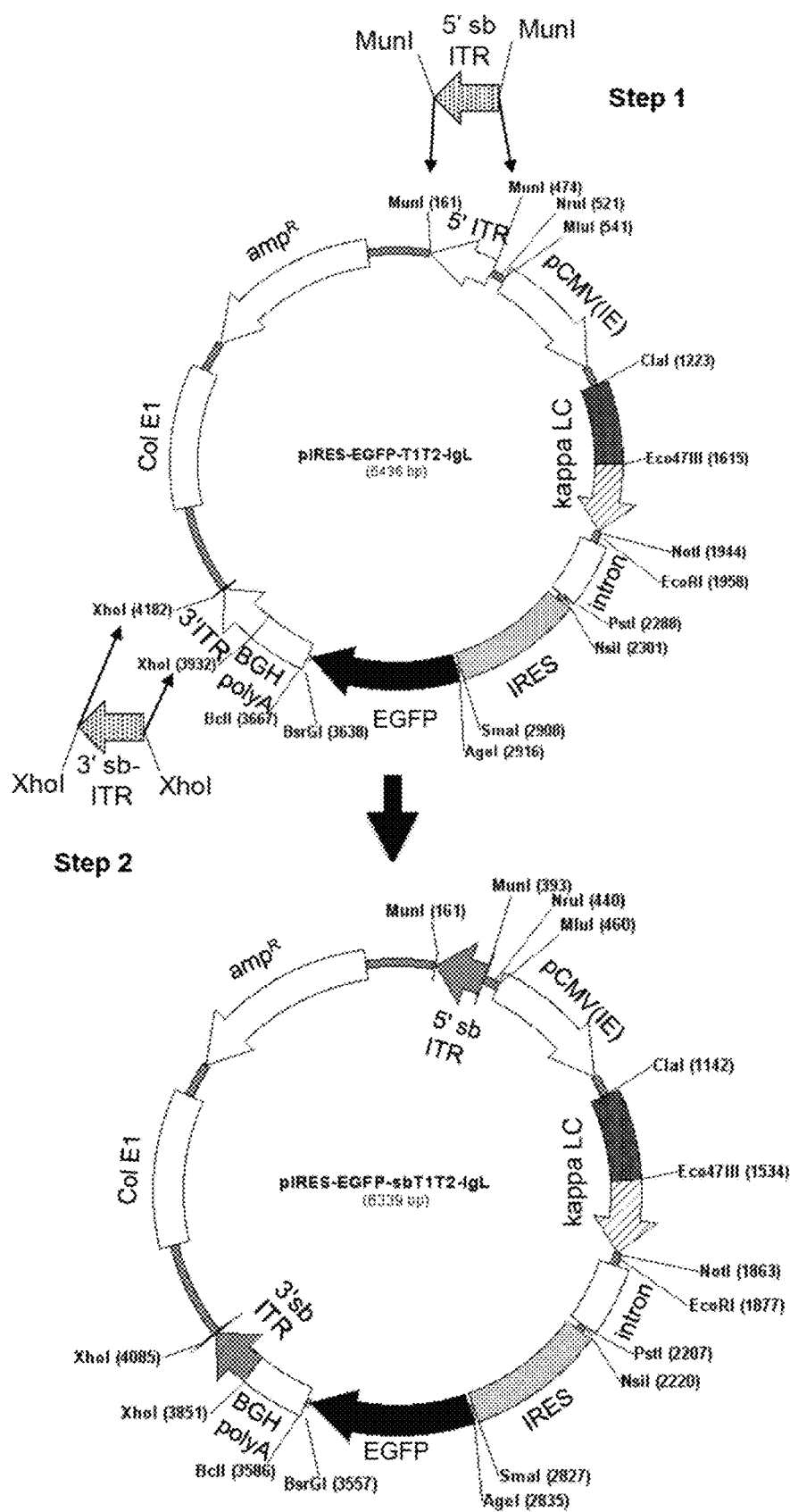

FIG. 8: This drawing depicts the cloning of a Sleeping Beauty transposable human immunoglobulin kappa light chain (Ig-kappa LC) expression vector, as described in Example 5. The cloning can be performed by sequentially replacing the PiggyBac 5' and 3' ITRs with Sleeping Beauty 5' and 3'ITRs in construct pIRES-EGFP-T1T2-IgL. Also in this drawing the relative position of other mammalian functional elements (CMV-IE promoter, BGH-polyA signal, SV40-polyA segment, hygromycin B ORF) and bacterial functional elements (ampicillin resistance gene, ampR, origin of replication, ColE1), as well as selected relevant restriction enzyme recognition sites are shown.

Figure 9:
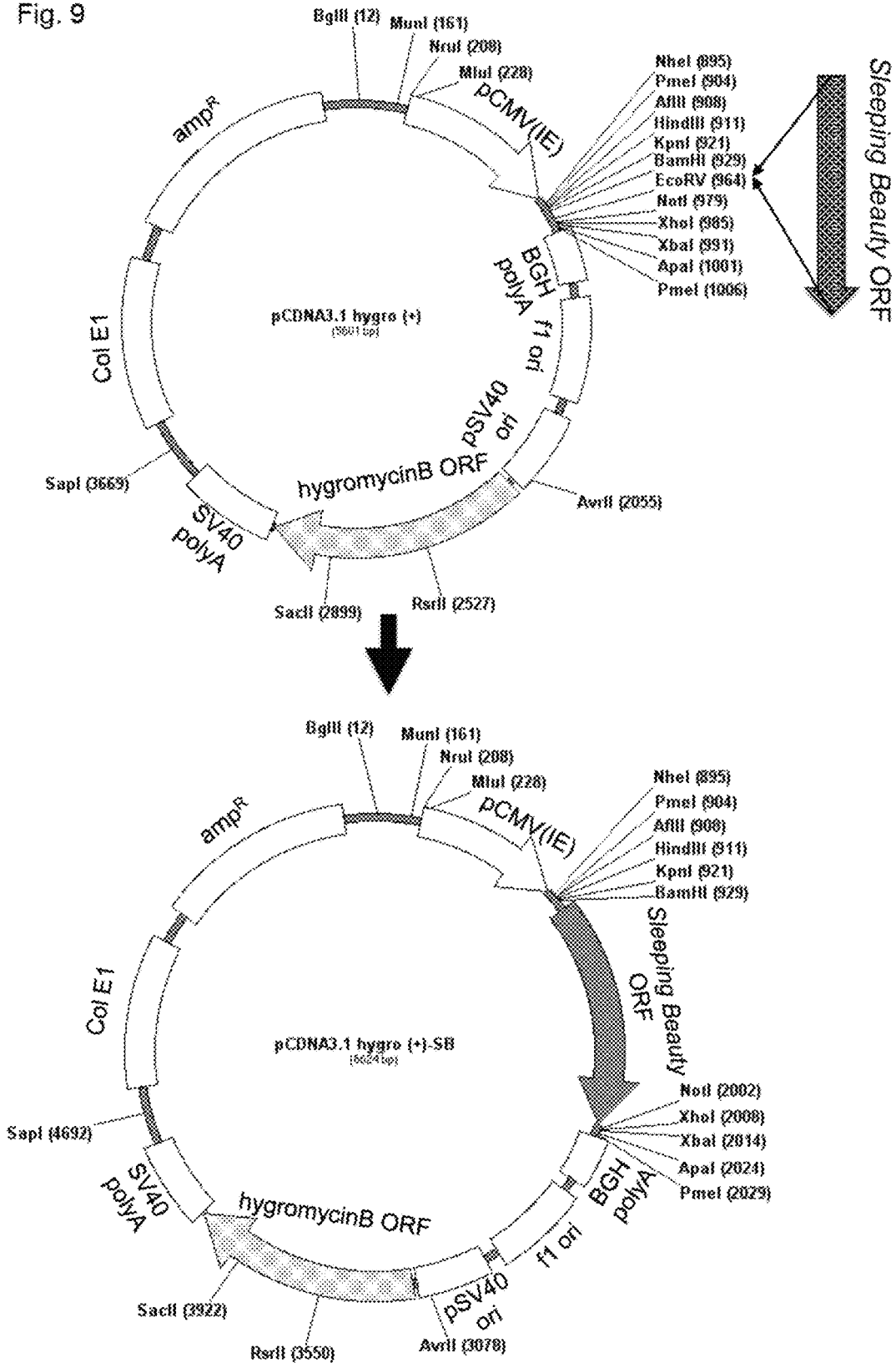

FIG. 9: This drawing depicts the cloning of a mammalian Sleeping Beauty transposase enzyme expression vector, as described in the Example 6, using pCDNA3.1(+) hygro as the backbone of the mammalian expression vector, into which the gene synthesized ORF from Sleeping Beauty transposase is cloned into the unique EcoRV restriction enzyme site of pCDNA3.1(+) hygro, resulting in Sleeping Beauty transposon expression vector pCDNA3.1(+) hygro-SB. Also in this drawing the relative position of other mammalian functional elements (CMV-IE promoter, BGH-polyA signal, SV40-polyA segment, hygromycin B ORF) and bacterial functional elements (ampicillin resistance gene, ampR, origin of replication, ColE1), as well as selected relevant restriction enzyme recognition sites are shown.

FIG. 10: This drawing shows the arrangement of functional elements and position of selected unique restriction enzyme sites within the gene-synthesized DNA fragments 1.) and 2.) that were utilized in Example 4, in order to clone both "empty" IgH chain expression vectors allowing transposition utilizing either PiggyBac or Sleeping Beauty transposase. The origin of the functional elements is disclosed in detail in the description of the Example.

Figure 11:
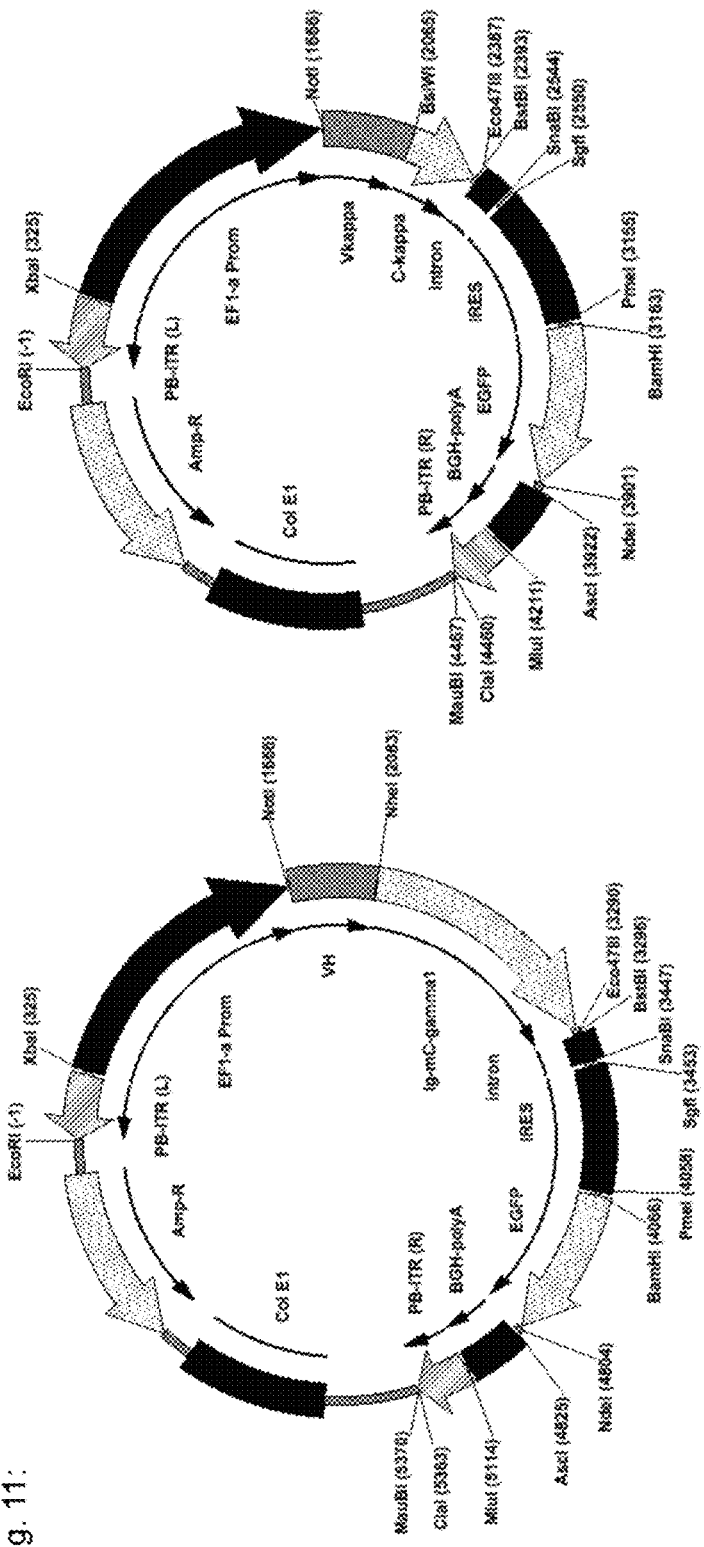

FIG. 11: This drawing shows the final design and plasmid map of the transposable expression vectors for human, membrane bound Ig-gamma1 heavy chains (left) and human Ig kappa light chains (right). For the IgH expression vector, the $V_H$-coding region may be replaced by $V_H$ coding regions of any other monoclonal antibody, or by a $V_H$-gene library, using unique restriction enzyme sites NotI and NheI, flanking the $V_H$ coding region in this vector. For the IgL expression vector, the $V_L$-coding region may be replaced by $V_L$ coding regions of any other monoclonal antibody, or by a $V_L$-gene library, using unique restriction enzyme sites NotI and BsiWI, flanking the $V_L$ coding region in this vector. The 8 vector constructions for PiggyBac and Sleeping Beauty transposable IgH and IgL vectors, disclosed in detail in Example 4 all share this general design. The two vector maps displayed here correspond to the vector maps of pPB-EGFP-HC-Ac10 (left) and pPB-EGFP-LC-Ac10 (right), and the additional vectors for hBU12 heavy chain (HC) or light chain (LC), containing either PiggyBac or Sleeping Beauty ITRs, are provided in the tables below. Sequences of all vectors in this figure are provided in Example 4.

Figure 12:
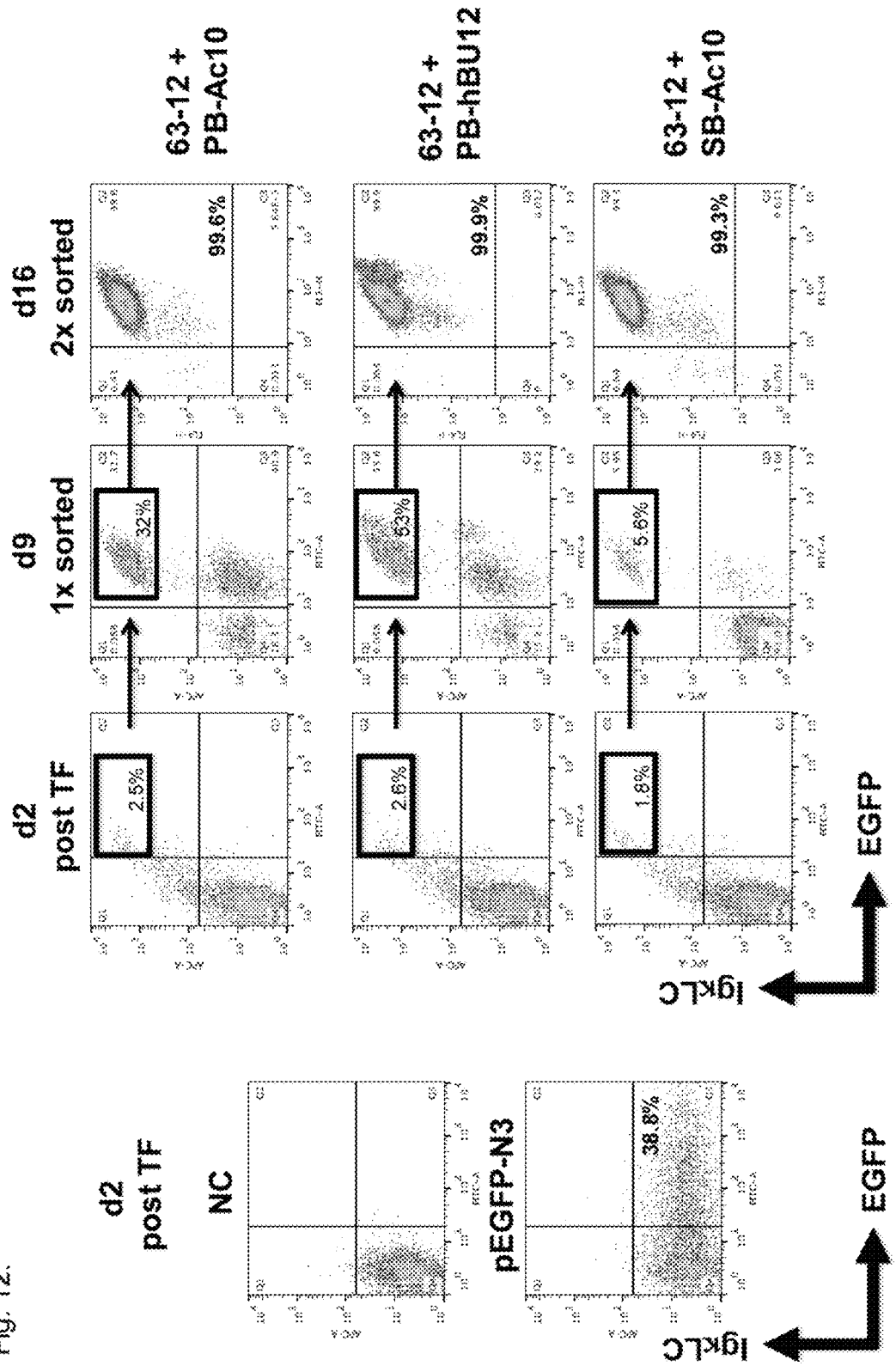

FIG. 12: This figure shows two dimensional FACS dot-plots, in which the surface expression of human IgG from transfected and transposed IgHC and IgLC expression vectors is detected on the surface of 63-12 A-MuLV transformed murine proB cells derived from RAG-2-deficient mice. d2 post TF means that the FACS analysis was performed 2 days after transfection of vector constructs into 63-12 cells. The FACS plots in the left-hand column represents negative and positive controls for the transfection. NC=mock electroporation of cells without plasmid DNA. pEGFP-N3=transfection control with pEGFP-N3 control vector, which controls for the transfection efficiency by rendering transfected cells green. The second column from the left shows FACS plots from 63-12 cells co-transfected with either PiggyBac-transposase vector, pPB-EGFP-HC-Ac10, pPB-EGFP-LC-Ac10 vectors (top row), or PiggyBac-transposase vector, pPB-EGFP-HC-hBU12, pPB-EGFP-LC-hBU12 vectors (middle row), or with Sleeping Beauty-transposase vector, pSB-EGFP-HC-Ac10, pSB-EGFP-LC-Ac10 vectors (bottom row). The second-left column labeled "d2 post TF" shows the analysis for cells expressing IgG on the cell surface (Y-axis) and EGFP expression (X-axis) two days post co-transfection of the vectors as mentioned above. Surface IgG and EGFP double positive cells were FACS sorted as indicated by the rectangular gate. The second-right column labeled "d9 1× sorted" shows the analysis of surface IgG and EGFP expression in the cell population that was sorted at day 2 after transfection, analyzed in the same way. Sorting gates for the second FACS sort are also provided as rectangular gates. The rightmost column labeled "d16 2× sorted" shows the analysis of surface IgG and EGFP expression of the cell populations that had been re-sorted at day 9 after transfection, and analyzed in the same way for surface IgG and EGFP expression as in the previous experiments.

Figure 13:
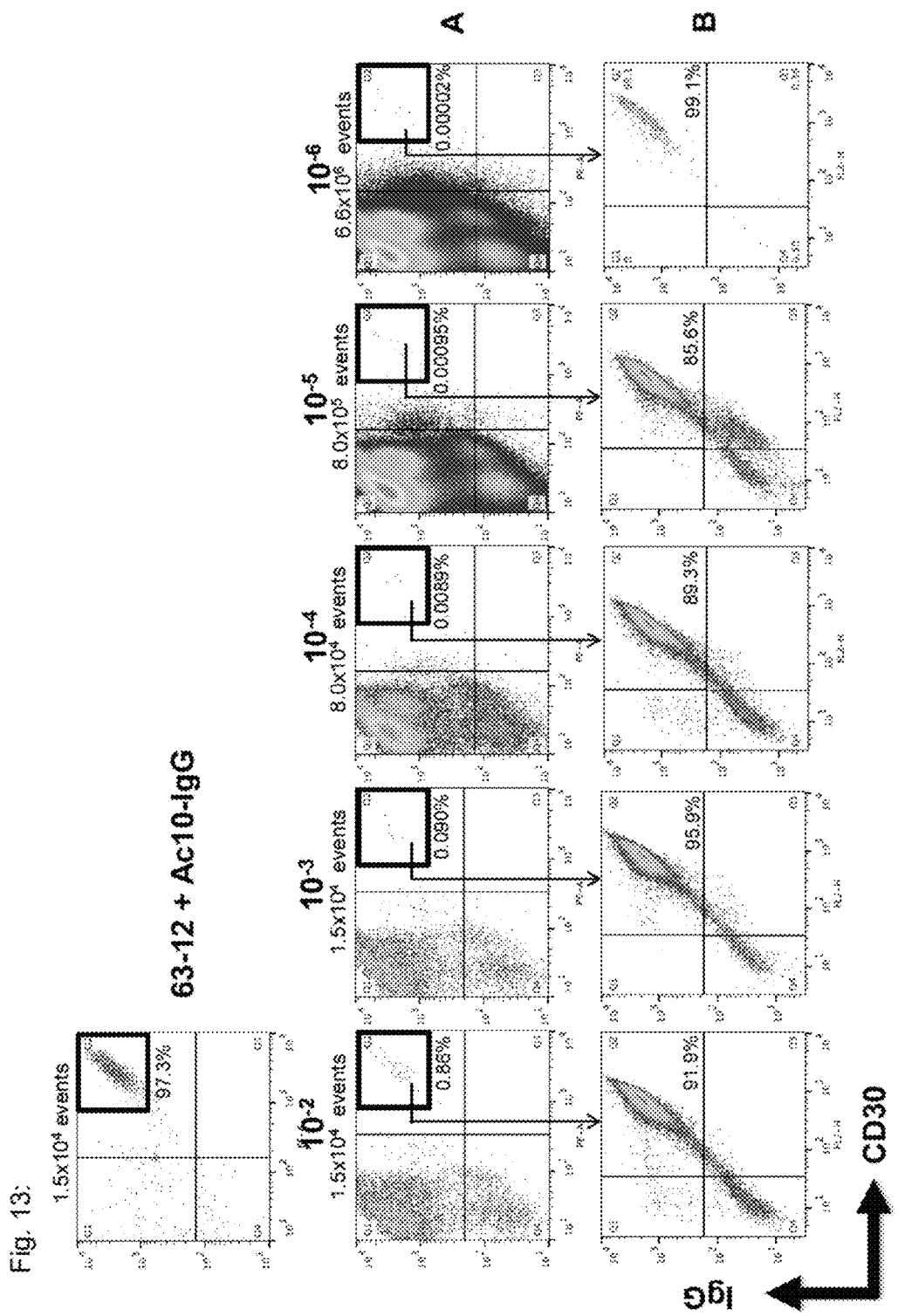

FIG. 13: This figure depicts the demonstration that proB cells expressing CD30-specific IgG on the surface of 63-12 cells can specifically be stained and detected by CD30 antigen, and that the CD30-specific cells be detected and re-isolated from a large population of cells expressing surface IgG of unrelated specificity (here CD19), in which the CD30-specific cells have been spiked in with decreasing frequency. The FACS dot-plot on top shows the detection of IgG (via anti-kappaLC staining) and CD30 binding (via CD30-antigen staining) on the surface of the positive control cells, which are 63-12 cells stably transposed and 2× sorted for expressing human anti-CD30 IgG, clone Ac10 on the cell surface. As expected, a quite pure population (97.3%) of IgG-positive/CD30-reactive was detectable in the upper right quadrant of the FACS-dot-plot. The numbers on top of each FACS-plot indicates the number of live cells based on FSC/SSC gating that were acquired in each experiment. The middle row shows the FACS analysis for IgG-positive/CD30 reactive cells detectable in a background of IgGpositive/CD19 specific cells. The number above the number of events indicates the dilution factor of anti-CD30 specific IgG positive cells that were used for the generation of the "spiked-in" population of anti-CD30 mAb IgG positive cells in a background of anti-CD19 mAb IgG positive cells. The sorting gates are indicated that were used to specifically isolate IgG-positive/CD30 antigen reactive cells from the spiked-in populations. Larger numbers of events needed to be acquired in order to allow detection and isolation of the IgG-positive/CD30 cells at higher dilutions. The lower row of FACS plots then shows the re-analysis of sorted cells after the cells had been expanded for 12 days for the same parameters (IgG-expression & CD30 antigen specificity).

Figure 14:
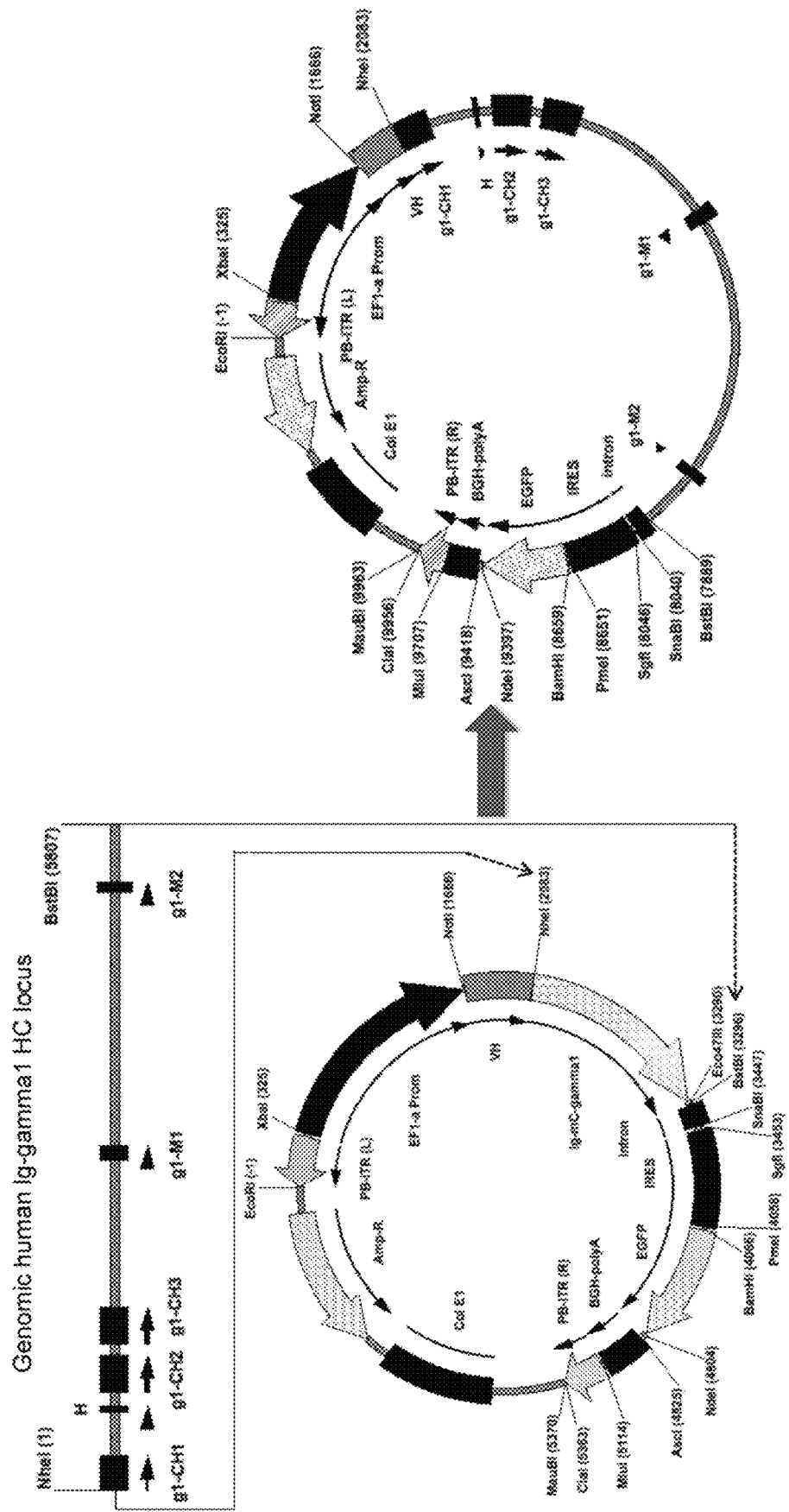

FIG. 14: This figure shows the cloning of a transposable vector for a human Ig-gamma1 heavy chain (HC) in genomic configuration. The linear fragment on top represents the human gamma1 exon and introns for membrane-bound Ig-gamma1-HC, with flanking NheI and BstBI restriction sites added to allow ligation into Ig-gamma1 HC cDNA vector pPB-EGFP-HC-Ac10. H-designates the Hinge-region exon, M1 and M2 represent the exons encoding the trans-membrane region of surface expressed Ig heavy chain. With a simple one-step ligation the cDNA C-gamma1 region of the transposable human heavy chain vector is replaced by its genomic counterpart as indicated in the figure. Using this strategy, the $V_H$ coding region will be ligated in-frame to the $C_H1$ coding exon of human C-gamma1.

FIG. 15: This figure shows the sequence and overall design of the kappa light chain library. CDR3 coding region is underlined. Useful restriction sites are indicated.

FIG. 16: This figure shows the sequence and overall design of the gamma heavy chain library, showing as an example the library fragment randomized using the NNK4 randomization strategy. The gamma heavy chain library fragments randomized using the NNK6, NNK8 and NNK10 randomization strategies differ only in the number of randomized amino acid residues in the HCDR3 region. HCDR3 coding region is underlined. The ARG codon encodes Lysine and Arginine. Useful restriction sites are indicated.

FIG. 17: This figure shows the digestion of PCR templates prior to amplification with primers. (A) Digestion of pUC57_Jkappa2-Ckappa with the restriction endonuclease Seal produces a blunt-ended DNA fragment ideal for priming with the primer LCDR3-NNK6-F. (B) Digestion of pUC57_$J_H$4 with the restriction endonuclease DrdI produces a DNA fragment ideal for priming with the primers HCDR3-NNK4-F, HCDR3-NNK6-F, HCDR3-NNK8-F, and HCDR3-NNK10-F FIG. 18: This figure shows the electropherograms spanning the randomized LCDR3 and HCDR3 region of the PCR amplicons generated to diversify the LCDR3 region by the NNK-6 approach for Vkappa (A), and the HCDR3 region by the NNK4-approach for $V_H$, as disclosed in Examples 12 and 13, respectively.

DETAILED DESCRIPTION OF THE INVENTION

Definitions

As used herein, "diverse collection" means a plurality of variants or mutants of particular functional or binding proteins exhibiting differences in the encoding nucleotide sequences or in the primary amino acid sequences, which define different functionalities or binding properties.

As used herein, "library" means a plurality of polynucleotides encoding polypeptides having different binding specificities and/or functionalities. In certain embodiments, the library may comprise polynucleotides encoding at least $10^2$, at least $10^3$, at least $10^4$, at least $10^5$, at least $10^6$, at least $10^7$, at least $10^8$, or at least $10^9$ unique polypeptides, such as, for example, full-length antibody heavy or light chains or VH or VL domains.

As used herein, "inverted terminal repeat sequence" or "ITR" means a sequence identified at the 5' or 3' termini of transposable elements that are recognized by transposases and which mediate the transposition of the ITRs including intervening coding information from one DNA construct or locus to another DNA construct or locus.

As used herein, "transposase" means an enzyme that has the capacity to recognize and to bind to ITRs and to mediate the mobilization of a transposable element from one target DNA sequence to another target DNA sequence.

As used herein, "antigen binding molecule" refers in its broadest sense to a molecule that specifically binds an antigenic determinant. A non-limiting example of an antigen binding molecule is an antibody or fragment thereof that retains antigen-specific binding. By "specifically binds" is meant that the binding is selective for the antigen and can be discriminated from unwanted or nonspecific interactions.

As used herein, the term "antibody" is intended to include whole antibody molecules, including monoclonal, polyclonal and multispecific (e.g., bispecific) antibodies, as well as antibody fragments having an Fc region and retaining binding specificity, and fusion proteins that include a region equivalent to the Fc region of an immunoglobulin and that retain binding specificity. Also encompassed are antibody fragments that retain binding specificity including, but not limited to, VH fragments, VL fragments, Fab fragments, F(ab')$_2$ fragments, scFv fragments, Fv fragments, minibodies, diabodies, triabodies, and tetrabodies (see, e.g., Hudson and Souriau, *Nature Med.* 9: 129-134 (2003)) (incorporated by reference in its entirety).

An embodiment of the invention disclosed herein is a method for the identification of specific functional or binding polypeptides, including, but not limited to antibody chains or fragments thereof (FIG. 4), which comprises:

i. cloning of diverse transposable DNA libraries encoding proteins, including antibody polypeptide chains or fragments thereof, in between inverted terminal repeats (ITRs) derived from transposable elements and recognizable by and functional with at least one transposase enzyme, ii. introduction of one or more diverse transposable DNA libraries of step (i) into vertebrate host cells by standard methods known in the art, iii. providing temporary expression of at least one functional transposase enzyme in said vertebrate host cells in trans, such that said one or more diverse transposable DNA libraries are stably integrated into the vertebrate host cell genomes, thereby providing a vertebrate host cell population that then stably expresses diverse libraries of proteins, including antibody chains or fragments thereof, iv. screening of said diverse cellular libraries, stably expressing proteins, including antibodies or fragments thereof, for a desired functional or binding phenotype by methods known in the art, v. optionally, including iterative enrichment cycles with the stably genetically modified vertebrate host cells for a desired binding or functional phenotype, and vi. isolation of the corresponding genes from the enriched host cells encoding the desired binding or functional phenotype by standard cloning methods, known in the art, for instance, but not limited to, PCR (polymerase chain reaction), using primers specific for the sequences contained in the one or more transposed DNA library constructs.

A preferred embodiment of step (i) is to generate diverse transposable DNA libraries either by gene synthesis, or by polymerase chain reaction (PCR) using appropriate primers for the amplification of diverse protein coding regions, and DNA templates comprising a diversity of binding proteins, including antibodies, or fragments thereof, by methods known in the art.

For the generation of diverse antibody libraries, a diverse collection of antibody heavy and light chain sequences may be generated by standard gene synthesis in which the V region coding sequences may be randomized at certain positions, e.g. but not limited to, any or all of the complementarity determining regions (CDRs) of the antibody heavy or light chain V-regions. The diversity can be restricted to individual CDRs of the V-regions, or to a particular or several framework positions, and/or to particular positions in one or more of the CDR regions. The V regions with designed variations, as described above, can be synthesized as a fragment encoding entire antibody heavy or light chains that are flanked by inverted terminal repeats functional for at least one desired transposase enzyme. Preferably, the DNA library containing diverse variable domains encoding V regions for antibody heavy or light chains is generated, and flanked by appropriate cloning sites, including but not limited to restriction enzyme recognition sites, that are compatible with cloning sites in antibody heavy or light chain expression vectors. Useful transposon expression systems for use in the methods of the invention include, for example, the PiggyBac transposon system as described, for example, in U.S. Pat. Nos. 6,218,185; 6,551,825; 6,962,810; 7,105,343; and 7,932,088 (the entire contents of each of which are hereby incorporated by reference) and the Sleeping Beauty transposon system as described in U.S. Pat. Nos. 6,489,458; 7,148,203; 7,160,682; US 2011 117072; US 2004 077572; and US 2006 252140 (the entire contents of each of which are hereby incorporated by reference.)

Diverse antibody heavy and light chain libraries may also be obtained from B cell populations isolated from desired vertebrate species, preferably humans, and preferably from cellular compartments containing B cells, e.g., but not limited to peripheral or cord blood, and lymphoid organs like bone marrow, spleen, tonsils and lymph-node tissues. In this case, diverse antibody V region sequences for antibody heavy and light chains can be isolated by RT-PCR or by genomic PCR using antibody heavy and light chain specific degenerate PCR primer pairs, that can amplify the majority of V-region families by providing upstream primers that bind to homologous sequences upstream of, or within leader sequences, upstream of or within V-region frameworks, and by providing downstream primers that bind in regions of homology within or downstream of the J joining gene segment of variable domain coding regions, or within or downstream of the coding regions of the constant regions of antibody heavy or light chains.

The PCR primer sets utilized for the amplification of diverse variable coding regions may be flanked by appropriate cloning sites, e.g. but not limited to restriction enzyme recognition sites, that are compatible with cloning sites in antibody heavy or light chain expression vectors.

The transposable DNA libraries of step (i) encoding diverse proteins, including antibodies and antibody fragments thereof, can be provided in the form of plasmid libraries, in which the gene-synthesized or the PCR amplified transposable DNA libraries are cloned using appropriate cloning sites, as mentioned above. Alternatively, the transposable DNA libraries encoding diverse libraries of binding proteins, such as antibodies and fragments thereof, can be provided in form of linear, double-stranded DNA constructs, directly as a result of DNA synthesis, or as a result of PCR amplification. The latter approach of providing the transposable DNA libraries as linear double-stranded DNA PCR amplicons, that have not been cloned into expression vectors or plasmids (in comparison to all other vertebrate cell expression systems) has the advantage that the maximum molecular complexity of the transposable DNA libraries is maintained and not compromised by a limited cloning or ligation efficiency into an expression vector. In contrast, cloning by ligation, or otherwise, into plasmid expression or shuttle vectors is a necessary intermediate for all other plasmid-based or viral vector based vertebrate cell expression systems.

However, the use of plasmid-based transposon expression vectors containing the diverse transposable DNA libraries encoding diverse binding proteins, including antibodies and antibody fragments thereof, has the advantage that these expression vectors can be engineered to contain additional functional elements, that allow the screening, or, alternatively, the selection for stably transposed vertebrate host cells for the stable integration of the transposon expression vector in transposed vertebrate host cells.

This is achieved by providing in operable linkage to the diverse transposable DNA libraries, i.e. cloned into the transposon expression vectors in cis, expression cassettes for marker genes including, but not limited to, fluorescent marker proteins (e.g. green, yellow, red, or blue fluorescent proteins, and enhanced versions thereof, as known in the art), or expression cassettes for cell surface markers including, but not limited to, CD markers, against which specific diagnostic antibodies or other diagnostic tools are available.

Alternatively, expression cassettes for selectable markers, that allow selection of transposed vertebrate host cells for antibiotic resistance, including, but not limited to, puromycin, hygromycinB, bleomycin, neomycin resistance, can be provided in operable linkage to the diverse transposable DNA libraries, i.e. cloned into the transposon expression vectors in cis.

The operable linkage can be achieved by cloning of said expression cassettes for marker genes or antibiotic resistance markers, either up- or downstream of the coding regions comprising said diverse transposable DNA libraries, but within the inverted terminal repeats of the transposon vector.

Alternatively, the operable linkage can be achieved by cloning of the coding regions for said marker or antibiotic resistance genes downstream of the coding regions comprising said diverse transposable DNA libraries, but separated by internal ribosomal entry site (IRES) sequences, that ensure transcriptional coupling of the expression of said diverse transposable DNA libraries with said marker or antibiotic resistance genes, and thereby allowing the screening for or selection of stably transposed vertebrate host cells.

In step (ii) of the method disclosed herein, said diverse transposable DNA libraries encoding diverse libraries of proteins, including antibodies and fragments thereof, are introduced into desired vertebrate host cells by methods known in the art to efficiently transfer DNA across vertebrate cell membranes, including, but not limited to, DNA-transfection using liposomes, Calcium phosphate, DEAE-dextran, polyethyleneimide (PEI) magnetic particles, or by protoplast fusion, mechanical transfection, including physical, or ballistic methods (gene gun), or by nucleofection. Any of the above-mentioned methods and other appropriate methods to transfer DNA into vertebrate host cells may be used individually, or in combination for step (ii) of the method disclosed herein.

In the case of dimeric proteins, including, but not limited to, antibodies and fragments thereof, it is a useful embodiment of the method disclosed herein to introduce diverse transposable DNA libraries and/or transposon vectors for antibody heavy or light chains contained in separate transposable vectors, which can independently be introduced into the vertebrate host cells. This either allows the sequential introduction of diverse transposable DNA libraries for antibody heavy or light chains into said cells, or their simultaneous introduction of diverse transposable DNA libraries for antibody heavy or light chains, which, in either case, allows the random shuffling of any antibody heavy with any antibody light chain encoded by the at least two separate diverse transposable DNA libraries.

Another useful embodiment of the previous embodiment is to utilize separate transposon vectors and/or diverse DNA transposable libraries for antibody heavy and light chains, where said constructs or libraries are contained on transposable vectors recognized by different transposase enzymes (FIG. 3). This allows the independent transposition of antibody heavy and antibody light chain constructs without interference between the two different transposase enzymes, as one transposable vector is only recognized and transposed by its specific transposase enzyme. In case of sequential transposition of transposable vectors or DNA libraries encoding antibody heavy or light chains, the advantage of utilizing different transposase enzymes with different ITR sequences is, that upon the second transposition event, the first already stably transposed construct is not again mobilized for further transposition.

This embodiment also allows the discovery of antibodies by the method of guided selection (Guo-Qiang et al. *Methods Mol. Biol.* 562, 133-142 (2009)) (incorporated herein by reference in its entirety). Guided selection can e.g. be used for the conversion of any non-human antibody specific for a desired target/epitope specificity and with a desired functionality into a fully human antibody, where the same target/epitope specificity and functionality is preserved. The principle of guided selection entails the expression of a single antibody chain (heavy or light chain) of a reference (the "guiding") antibody, in combination with a diverse library of the complementary antibody chains (i.e. light, or heavy chain, respectively), and screening of these heavy-light chain combinations for the desired functional or binding phenotype. This way, the first antibody chain, "guides" the selection of one or more complementary antibody chains from the diverse library for the desired functional or binding phenotype. Once the one or more novel complementary antibody chains are isolated, they can be cloned in expression vectors and again be used to "guide" the selection of the second, complementary antibody chain from a diverse antibody chain library. The end-result of this two-step process is that both original antibody heavy and light chains of a reference antibody are replaced by unrelated and novel antibody chain sequences from the diverse libraries, but where the novel antibody heavy-light chain combination exhibits the same, or similar functional or binding properties of the original reference antibody. Therefore, this method requires the ability to independently express antibody heavy and light chain constructs or libraries in the vertebrate host cells, which can be achieved by the preferred embodiment to provide antibody heavy and light chain expression cassettes in different transposable vector systems, recognized by different transposon enzymes.

However, diverse transposable DNA libraries can also be constructed in a way, that the coding regions for multimeric proteins, including antibodies and fragments thereof, are contained in the same transposon vector, i.e. where the expression of the at least two different subunits of a multimeric protein, for example $V_H$ and $V_L$ regions or full-length heavy and light chains, is operably linked by cloning of the respective expression cassettes or coding regions into the same transposable vector.

Useful vertebrate host cells for the introduction of transposable constructs and/or transposable DNA libraries of step (ii) are cells from vertebrate species that can be or that are immortalized and that can be cultured in appropriate cell culture media and under conditions known in the art. These include, but are not limited to, cells from e.g. frogs, fish, avians, but preferably from mammalian species, including, but not limited to, cells from rodents, ruminants, non-human primate species and humans, with cells from rodent or human origin being preferred.

Useful cell types from the above-mentioned species include, but are not limited to cells of the lymphoid lineage, which can be cultured in suspension and at high densities, with B-lineage derived cells being preferred, as they endogenously express all the required proteins, factors, chaperones, and post-translational enzymes for optimal expression of many proteins, in particular of antibodies, or antibody-based proteins. Of B-lineage derived vertebrate cells, those are preferred that represent early differentiation stages, and are known as progenitor (pro) or precursor (pre) B cells, because said pro- or preB cells in most cases do not express endogenous antibody chains that could interfere with exogenous or heterologous antibody chain expression that are part of the method disclosed herein.

Useful pro- and pre-B lineage cells from rodent origin are Abelson-Murine Leukemia virus (A-MuLV) transformed proB and preB cells (Alt et al. *Cell* 27, 381-390(1981)) (incorporated herein by reference in its entirety)) that express all necessary components for antibody expression and also for their proper surface deposition, including the B cell receptor components Ig-alpha (CD79a, or mb-1), and Ig-beta (CD79b, or B-29) (Hombach et al. *Nature* 343, 760-762 (1990)) (incorporated herein by reference in its entirety), but as mentioned above, mostly lack the expression of endogenous antibody or immunoglobulin chains. Here, A-MuLV transformed pro- and preB cells are preferred that are derived from mouse mutants, including, but not limited to, mouse mutants defective in recombination activating gene-1 (RAG-1), or recombination activating gene-2 (RAG-2), or animals carrying other mutations in genes required for V(D)J recombination, e.g. XRCC4, DNA-ligase IV, Ku70, or Ku80, Artemis, DNA-dependent protein kinase, catalytic subunit (DNA-PK$_{cs}$), and thus lack the ability to normally express of endogenous antibody polypeptides.

Additional useful types of progenitor (pro) and precursor (pre) B lineage cells are early, immunoglobulin-null (Ig-null) EBV transformed human proB and preB cells (Kubagawa et al. *PNAS* 85, 875-879(1988)) (incorporated herein by reference in its entirety) that also express all the required factors for expression, post-translational modification and surface expression of exogenous antibodies (including CD79a and CD79b).

Other host cells of the B lineage can be used, that represent plasma cell differentiation stages of the B cell lineage, preferably, but not limited to Ig-null myeloma cell lines, like Sp2/0, NSO, X63, Ag8653, and other myeloma and plasmacytoma cells, known in the art. Optionally, these cell lines may be stably transfected or stably genetically modified by other means than transfection, in order to over-express B cell receptor components Ig-alpha (CD79a, or mb-1), and Ig-beta (CD79b, or B-29), in case optimal surface deposition of exogenously expressed antibodies is desired.

Other, non-lymphoid mammalian cells lines, including but not limited to, industry-standard antibody expression host cells, including, but not limited to, CHO cells, Per.C6 cells, BHK cells and 293 cells may be used as host cells for the method disclosed herein, and each of these cells may optionally also be stably transfected or stably genetically modified to over-express B cell receptor components Ig-alpha (CD79a, or mb-1), and Ig-beta (CD79b, or B-29), in case optimal surface deposition of exogenously expressed antibodies is desired.

Essentially, any vertebrate host cell, which is transfectable, can be used for the method disclosed herein, which represents a major advantage in comparison to any viral expression systems, such as, but not limited to vaccinia virus, retroviral, adenoviral, or sindbis virus expression systems, because the method disclosed herein exhibits no host cell restriction due to virus tropism for certain species or cell types, and furthermore can be used with all vertebrate cells, including human cells, at the lowest biosafety level, adding to its general utility.

Step (iii) of the method disclosed herein results in the stable genetic modification of desired vertebrate host cells with the transfected transposable constructs of step (ii) by temporary, or transient expression of a functional transposase enzyme, such that a stable population of vertebrate host cells is generated that expresses diverse libraries of proteins encoded by said constructs.

A useful embodiment of step (iii) is to transiently introduce into the host cells, preferably by co-transfection, as described above, a vertebrate expression vector encoding a functional transposase enzyme together with said at least one diverse transposable DNA library. It is to be understood that transient co-transfection or co-integration of a transposase expression vector can either be performed simultaneously, or shortly before or after the transfer of the transposable constructs and/or diverse transposable DNA libraries into the vertebrate host cells, such that the transiently expressed transposase can optimally use the transiently introduced transposable vectors of step (ii) for the integration of the transposable DNA library into the vertebrate host cell genome.

Another useful embodiment of step (iii) is to effect the stable integration of the introduced transposable vectors and/or transposable DNA libraries of step (ii) by transiently expressing a functional transposase enzyme by means of an inducible expression system known in the art, that is already stably integrated into the vertebrate host cell genome. Such inducible and transient expression of a functional transposase may be achieved by e.g., tetracycline inducible (tet-on/tet-off) or tamoxifen-inducible promoter systems known in the art. In this case, only the one or more transposable vector or DNA library needs to be introduced into the host cell genome, and the stable transposition of the constructs and the stable expression of the proteins encoded by the one or more transposable vector or DNA library is effected by the transiently switched on expression of the functional transposase enzyme in the host cells.

Step (iv) of the method disclosed herein effects the isolation of transposed vertebrate host cells expressing proteins with a desired functionality or binding phenotype.

A preferred embodiment of step (iv) is to screen for and to isolate the transposed host cells of step (iii) expressing desired proteins, including antibodies and fragments thereof, with target-binding assays and by means of standard cell separation techniques, like magnetic activated cell sorting (MACS) or high-speed fluorescence activated cell sorting (FACS) known in the art. Especially, in a first enrichment step of a specific population of transposed vertebrate host cells, where large number of cells need to be processed, it is preferred to isolate target specific cells from a large number of non-specific cells by MACS-based techniques.

Particularly, for additional and iterative cell enrichment cycles, FACS enrichment is preferred, as potentially fewer numbers of cells need to be processed, and because multi channel flow cytometry allows the simultaneous enrichment of functionalities, including, but not limited to, binding to a specific target of more than one species, or the specific screening for particular epitopes using epitope-specific competing antibodies in the FACS screen.

If proteins, including antibodies and fragments thereof, are to be discovered that interact with soluble binding partners, these binding partners are preferably labeled with specific labels or tags, such as but not limited to biotin, myc, or HA-tags known in the art, that can be detected by secondary reagents, e.g. but not limited to, streptavidin or antibodies, that themselves are labeled magnetically (for MACS based cell enrichment) or with fluorochromes (for FACS based cell enrichment), so that the cell separation techniques can be applied.

If proteins, including antibodies and fragments thereof are to be discovered against membrane bound proteins, which cannot easily be expressed as soluble proteins, like e.g. but not limited to, tetraspannins, 7-transmembrane spanners (like G-coupled protein coupled receptors), or ion-channels, these may be expressed in viral particles, or overexpressed in specific cell lines, which are then used for labeling or panning methods known in the art, which can enrich the vertebrate host cells expressing the proteins from the transposed constructs, including antibodies and fragments thereof.

Due to the stable genotype-phenotype coupling in the stably transposed vertebrate host cell population, a useful embodiment of step (v) is to repeat cell enrichment cycles for a desired functional or binding phenotype, until a distinct population of cells is obtained that is associated with a desired functional or binding phenotype. Optionally, individual cell clones can be isolated e.g., but not limited to, by single-cell sorting using flow cytometry technology, or by limiting dilution, in order to recover the transposed DNA information from individual cell clones that are coupled to a particular, desired functional or binding phenotype.

For the identification of functional target-specific antibodies it is often favorable to not only screen and to select for a particular binding phenotype, but to additionally screen for additional functional properties of target specific antibodies, in particular antagonistic or agonistic effects in biological assay.

Therefore, it is desirable to be able to efficiently "switch" cell membrane bound antibody expression to secreted antibody expression in the vertebrate host cells with sufficient yields, in order to produce enough quantity of a particular antibody clone for functional assays.

In natural B lineage cells the switch from membrane bound to secreted antibody expression occurs via a mechanism of alternative splicing, in which in preB and B cells an alternative splice donor near the 3'end of the last heavy chain constant region exon is preferentially spliced to a splice acceptor of a membrane anchor exon downstream of the heavy chain constant regions exons. This way, an antibody heavy chain is produced in B cells with an extended C-terminal, membrane spanning domain, that anchors the heavy chain and thereby the entire heavy-light chain containing antibody in the cell membrane. The C-terminal, membrane spanning domain also interacts non-covalently with the membrane spanning components Ig-alpha (CD79a or mb-1) and Ig-beta (CD79b or B29), which likely results in better membrane anchoring and higher surface immunoglobulin expression in B lineage cells.

Once, a B cell differentiates further to the plasma cell stage, the alternative splicing does not occur anymore and the alternative splice donor near the 3' end of the last heavy chain constant region is no longer recognized or utilized, and the mRNA template is terminated downstream of the heavy chain constant region stop codon, and a heavy chain of a secreted antibody is translated.

In order to exploit this natural mechanism of alternative splicing and "switching" from membrane bound to secreted expression of expressed antibodies, it is a useful embodiment of the method disclosed herein to construct the transposable vectors and diverse DNA libraries encoding proteins, including antibodies or fragments thereof, in such a way that the natural intron/exon structure of a constant antibody heavy chain, including the exons encoding the membrane spanning domains is maintained. This embodiment represents a clear advantage against retroviral expression systems, as the retroviral vector genome is already spliced before it is packaged into a retroviral particle and stably transduced into the host cell genome.

Other viral vector systems may be restricted in the length of the DNA insert that can be incorporated into the vectors, thereby precluding the cloning of larger genomic regions into such expression vectors and thereby preventing the exploitation of the natural "switching" from membrane-bound to secreted antibody expression by alternative splicing. Certain transposons (e.g. Tol2, see FIG. 3), have been characterized to be able to efficiently transpose more than 10 kb DNA fragments into vertebrate host cells without any loss in transposition efficiency (Kawakami *Genome Biol.* 8, *Suppl I*, S7 (2007)) (incorporated herein by reference in its entirety). Therefore, it is a useful embodiment of the method disclosed herein to construct transposable expression vectors comprising genomic exon/intron structures for better and proper expression and for the natural regulation switching from membrane bound to secreted antibody expression. The methods of the invention are useful to transpose DNA fragments at least 5 kb, at least 6 kb, at least 7 kb, at least 8 kb, at least 9 kb, at least 10 kb in size into host cell genomes.

The differentiation of earlier B lineage differentiation stage that favors membrane bound antibody expression, to a later, plasma cell stage, that favors secreted antibody expression can be induced by B cell differentiation factors, such as, but not limited to, CD40/IL4 triggering, or stimulation by mitogens, such as, but not limited to, lipopolysaccharide (LPS), or other polyclonal activators, *Staph. aureus* Cowan (SAC) strain activators, and CpG nucleotides, or any combination thereof.

Preferably, this differentiation is effected in transformed cells, in which the proliferation can artificially be inhibited, such that proper B cell differentiation can again occur, as it has been described for A-MuLV transformed murine preB cells, in which the Abelson tyrosine kinase is specifically inhibited by the tyrosine inhibitor Gleevec (Muljo et al. *Nat. Immunol* 4, 31-37 (2003)) (incorporated herein by reference in its entirety). Therefore, it is a preferred embodiment to utilize Ig-null A-MuLV transformed murine preB cells for the method, which by treatment with Gleevec, can again differentiate to more mature B cell stages, including plasma cells, which then secrete sufficient amounts of secreted antibody for additional functional testing on the basis of alternative splicing of genomic heavy chain expression constructs. It is a preferred embodiment of the method disclosed herein, to further improve such B-lineage cell differentiation by stable overexpression of anti-apoptotic factors, known in the art, including, but not limited to, bcl-2 or bcl-$x_L$.

After step (iv), the enrichment of transposed vertebrate host cells as described above has been performed, optionally, additional cell enrichments according to the above-mentioned methods may be performed (step (v)), until cell populations, or individual cells are isolated expressing proteins, including antibodies and fragments thereof, with desired functional and/or binding properties.

Step (vi) of the method disclosed herein is then performed in order to isolate the relevant coding information contained in the transposed vertebrate host cells, isolated for a desired functional and/or binding property.

A useful embodiment of step (vi) for the isolation cloning and sequencing of the relevant coding information for a desired functional or binding protein, including an antibody or antibody fragment thereof, contained in the isolated cells, is to utilize genomic or RT-PCR amplification with specific primer pairs for the relevant coding information comprised in the transposed DNA constructs, and to sequence the genomic or RT-PCR amplicons either directly, or after sub-cloning into sequencing vectors, known in the art, e.g., but not limited into TA- or Gateway-cloning vectors.

Cloning and sequencing of the relevant coding information for a desired functional or binding protein, including an antibody or antibody fragment thereof, as described in the previous paragraph by genomic or RT-PCR amplification can also be performed with transposable IgH and IgL expression vector, such that the binding protein coding region cannot only be identified, but at the same time also be expressed upon stable transposition into mammalian host cells as disclosed herein. For the expression of secreted antibodies this would only require the use of transposable Ig heavy chain expression vectors lacking the IgH transmembrane spanning coding region.

Another useful embodiment of step (vi) is to subject the enriched cell populations of steps (iv) or (v), which exhibit a desired functional or binding phenotype to next-generation ("deep") sequencing (Reddy et al. *Nat. Biotech.* 28, 965-969 (2010)) (incorporated herein by reference in its entirety), in order to retrieve directly and in one step a representative set of several thousands of sequences for the coding information contained in the transposed DNA constructs. Based on a bioinformatics analysis of the relative frequency of sequences identified from the enriched cell populations, it allows a prediction about which sequences encoded a functional or binding protein, including an antibody or fragment thereof (Reddy et al. *Nat. Biotech.* 28, 965-969 (2010)) (incorporated herein by reference in its entirety). Statistically overrepresented sequences are then resynthesized and cloned into expression vector for expression as recombinant proteins, antibodies or fragments thereof, in order to characterize them functionally and for their binding properties. This method can significantly accelerate the identification of relevant sequences within a functionally and phenotypically enriched cell population, that expresses proteins with functional or target specific properties.

Yet another useful embodiment of the method disclosed herein is to utilize transposition-mediated vertebrate cell expression of proteins, including antibodies or fragments thereof, for the mutagenesis and optimization of desired proteins, including the affinity optimization of antibodies and fragments thereof.

This can be achieved by isolating the genes encoding the proteins, including antibody chains or fragments thereof, from transposed vertebrate cell populations enriched for a desired binding or functional phenotype according to the methods disclosed in step (iv), such as but not limited to, by genomic PCR or RT-PCR amplification under mutagenizing conditions, know in the art. The mutagenized sequences can then be re-cloned into transposition vectors and then again be transposed into vertebrate host cells, in order to subject them to screening according to the methods disclosed herein, for improved functional or binding properties.

In one useful embodiment of this approach, specific primers are used that allow the PCR amplification under mutagenizing conditions of complete transposed constructs, including the flanking ITRs.

By this method a mutagenized PCR amplicon containing a defined average frequency of random mutations is generated from the functionally or phenotypically selected transposed cells. Said PCR amplicon with controlled mutations (variations) of the original templates can now directly be re-transposed into new vertebrate host cells, according to preferred embodiments disclosed in the methods applicable in step (ii).

The main advantage of this method over other approaches of genetically modifying vertebrate cells is, that with this technology no time-consuming re-cloning of the mutagenized PCR amplicons and time consuming quality control of the mutagenized sequences into expression vectors is required, which is a mandatory requirement in all other plasmid-based or viral expression systems, if a mutagenized sequence shall be subjected to another round of screening.

Because transposition of DNA only requires the presence of ITRs flanking the coding region of genes of interest, PCR-amplified mutagenized PCR amplicons can directly be re-introduced and re-transposed into novel vertebrate host cells for expression and screening for improved properties and/or affinity matured mutants.

Taken together, the methods disclosed herein, of utilizing TEs for the stable genetic modification of vertebrate host cells with transposable constructs and/or diverse transposable DNA libraries encoding proteins, including antibodies and fragments thereof, offers unparalleled efficiency, flexibility, utility and speed for the discovery and optimization of said proteins for optimal desired functional or binding phenotypes.

EXAMPLES

Example 1: Instruction for Cloning of Basic PiggyBac Transposable Light Chain Expression Vector for Human Antibody Kappa Light Chains Compatible with the PiggyBac Transposase Enzyme A basic transposable expression vector for human kappa light chains can be generated by cloning of the ITRs from the PiggyBac transposon up and downstream of a human immunoglobulin kappa light chain expression cassette.

For this, as a first step, the minimal sequences for the up- and downstream ITRs of the PiggyBac transposon can be derived from pXLBacII (published in U.S. Pat. No. 7,105, 343) (incorporated herein by reference in its entirety) and can be gene synthesized with flanking restriction enzyme sites for cloning into the mammalian expression vector pIRES-EGFP (PT3157-5, order #6064-1, Invitrogen-Life Technologies, Carlsbad, Calif., USA)

The upstream PiggyBac ITR sequence with the 5' terminal repeat has to be gene synthesized with flanking MunI restriction enzyme sequence, compatible with a unique MunI restriction enzyme site in pIRES-EGFP, and additional four random nucleotides (in lowercase letters) allowing proper restriction enzyme digestion. This sequence is provided in SEQ ID NO:1.

The downstream PiggyBac ITR sequence with the 3' terminal repeat has to be gene synthesized with flanking XhoI restriction enzyme sequence compatible with a unique XhoI restriction enzyme site in pIRES-EGFP, and additional four random nucleotides allowing proper restriction enzyme digestion. This sequence is provided in SEQ ID NO:2. Upon MunI restriction enzyme digestion of the gene synthesized SEQ ID NO:1, the DNA fragment can be ligated into MunI linearized pIRES-EGFP, generating pIRES-EGFP-TR1 according to standard methods, known in the art. The proper orientation of the insert can be verified by diagnostic restriction enzyme digestion, and/or by DNA sequencing of the cloned construct (FIG. 5a).

In a next step gene synthesized and XhoI digested DNA fragment SEQ ID NO:2, can be ligated into XhoI linearized pIRES-EGFP-T1 (FIG. 5a) by standard methods known in the art, in order to generate pIRES-EGFP-T1T2, containing both PiggyBac ITRs up and downstream of the IRES-EGFP expression cassette (FIG. 5b). The proper orientation of the insert can be verified by diagnostic restriction enzyme digestion, and/or by DNA sequencing of the cloned construct (FIG. 5b).

For the cloning of a human immunoglobulin kappa light chain into the vector pIRES-EGFP-T1T2, the human Ig kappa light chain from human anti-TNF-alpha specific antibody D2E7 can be synthesized, which can be retrieved from European patent application EP 1 285 930 A2 (incorporated herein by reference in its entirety).

The coding region for human Ig kappa light chain of human anti-TNF-alpha specific antibody D2E7, in which the V region of D2E7 is fused in frame to a Vk1-27 leader sequence (Genbank entry: X63398.1, which is the closest germ-line gene V-kappa family member V-kappa of D2E7), and to the human kappa constant region (Genbank entry: J00241) has the following nucleotide sequence, which is provided in SEQ ID NO:3.

The nucleotide sequence of SEQ ID NO:3 translates in the amino acid sequence SEQ ID NO:4. The DNA fragment SEQ ID NO:3 encoding the D2E7 Ig kappa light chain can be gene synthesized and directly ligated by blunt-ended ligation into the unique EcoRV restriction enzyme site (which is also a blunt cutter), by methods know in the art, resulting in construct pIRES-EGFP-T1T2-IgL (FIG. 5b)

SEQ ID NO:3 has been engineered to contain a unique Eco47III restriction enzyme site in between the V-kappa and the C-kappa coding regions (highlighted in boldface and underlined), which allows the replacement of V-kappa regions in this construct against other V-kappa regions or V-kappa libraries, using a unique restriction enzyme upstream of V-kappa coding region in the construct, together with Eco47III. The proper orientation of the kappa light chain insert can be verified by diagnostic restriction enzyme digestion, and/or by DNA sequencing of the cloned construct (FIG. 5b).

The entire sequence for the transposable human antibody kappa light chain vector pIRES-EGFP-T1T2-IgL is provided in sequence SEQ ID NO:5.

Sequences Referred to in this Example 1:

SEQ ID NO:1 (327 bp long PiggyBac 5'-ITR sequence. The MunI restriction enzyme sites at each end are underlined and typed in boldface print, the random nucleotide additions at the termini are printed in lowercase)

Seq-ID2 (264 bp long PiggyBac 3'-ITR sequence. The XhoI restriction enzyme sites at each end are underlined and typed in boldface print, the random nucleotide additions at the termini are printed in lowercase)

SEQ ID NO:3 (711 bp long Ig-kappaLC coding region of anti-TNF-alpha-specific mAb D2E7)

SEQ ID NO:4 (236 amino acids long sequence of anti-TNF-alpha-specific mAb D2E7)

SEQ ID NO:5 (6436 bp long DNA sequence of PiggyBac transposable Ig-kappa-LC expression vector pIRES-EGFP-T1T2-IgL)

Example 2: Instruction for Cloning of a Basic PiggyBac Transposable Heavy Chain Expression Vector for Membrane Spanning Human Antibody Gamma1 Heavy Chains In order to clone a transposable Ig heavy chain expression vector, the kappa light chain ORF from pIRES-EGFP-T1T2-IgL (SEQ ID NO:5) needs to be exchanged with an ORF encoding a fully human IgG1 heavy chain coding region.

For the replacement of the human kappa light chain in vector pIRES-EGFP-T1T2-IgL by a human immunoglobulin gamma-1 heavy chain, the $V_H$ region of antibody D2E7, which is specific for human TNF-alpha (see: EP 1 285 930 A2) (incorporated herein by reference in its entirety) can be synthesized. For this, a leader sequence of a close germ-line $V_H3$-region family member is fused in frame to the $V_H$ region of antibody D2E7, which then is fused in frame to the coding region of a human gamma1 constant region (Genbank: J00228) including the membrane spanning exons (Genbank: X52847). In order to be able to replace the human Ig kappa light chain from pIRES-EGFP-T1T2-IgL, unique ClaI and NotI restriction enzyme sites need to be present at the 5' and the 3' end of the sequence (underlined), respectively. Additionally, four nucleotides flanking the restriction enzyme sites (highlighted in lowercase letters at the ends of the sequence) allow proper restriction enzyme digestion of the gene-synthesized DNA fragment and ligation into the ClaI-NotI linearized pIRES-EGFP-T1T2-IgL backbone, according to standard methods. The sequence that needs to be gene synthesized is provided in SEQ ID NO:6.

From the start codon in position 11 of SEQ ID NO:6 (highlighted in boldface print), this nucleotide sequence translates to the human IgG1 heavy chain of anti-TNF-alpha specific clone D2E7 (see: EP 1 285 930 A2) (incorporated herein by reference in its entirety), but including the human gamma1 transmembrane exons M1 and M2. The protein translation of SEQ ID NO:6 is provided in SEQ ID NO:7. The DNA fragment SEQ ID NO:6 encoding the D2E7 Ig gamma-1 heavy chain can then be double-digested by ClaI and NotI restriction enzymes and directionally ligated into ClaI and NotI linearized pIRES-EGFP-T1T2-IgL, resulting in construct pIRES-EGFP-T1T2-IgH (FIG. 6).

SEQ ID NO:6 has also been engineered to contain a unique Eco47III restriction enzyme site in between the V-heavy variable and the C-gamma1 constant coding regions (highlighted in boldface and underlined in SEQ ID NO:7), which allows the replacement of V-heavy regions in this construct against other V-heavy regions or V-heavy libraries, using a unique restriction enzyme upstream of V-heavy coding region in the construct, together with Eco47III. The correct ligation of the insert can be verified by diagnostic restriction enzyme digestion, and/or by DNA sequencing of the cloned construct (FIG. 6).

The entire sequence for the transposable human antibody gamma-1 heavy chain vector pIRES-EGFP-T1T2-IgH is provided in sequence SEQ ID NO:8

Examples 1 and 2 provide instructions for the cloning of basic PiggyBac transposable expression vectors for human antibody kappa light and human gamma-1 heavy chains (membrane bound form) and therefore for full-length, membrane bound human IgG1, that can be utilized for the reduction to practice of the invention.

Sequences Referred to in this Example 2:
SEQ ID NO:6 (1642 bp long DNA fragment containing the coding region for membrane bound Ig-gamma1-HC of anti-TNF-alpha-specific mAb D2E7)
SEQ ID NO:7 (539 amino acids long sequence of membrane bound Ig-gamma1-HC of anti-TNFalpha antibody
SEQ ID NO:8 (7341 bp long DNA sequence of PiggyBac transposable human Ig-gamma1-membrane-HC expression vector pIRES-EGFP-T1T2-IgH)

Example 3: Instructions for Cloning of Basic Transposable Light Chain Expression Vector for Human Antibody Kappa Light Chains Compatible with the Sleeping Beauty Transposase Enzyme In order to transpose human immunoglobulin heavy and light chain expression vectors contained in a transposable vector independently into host cells, a transposable immunoglobulin light chain construct with different inverted terminal repeat (ITR) sequences can be constructed that are recognized by the Sleeping Beauty transposase.

For this, the human Ig-kappa light chain expression vector pIRES-EGFP-T1T2-IgL (SEQ ID NO:5) of example 1 can be used to replace the 5' and 3' ITRs of the PiggyBac transposon system, contained in this vector, with the 5' and 3' ITRs of the Sleeping Beauty transposon system. The sequences for the Sleeping Beauty 5'ITR and 3'ITR, recognized and functional with the Sleeping Beauty transposase, can be retrieved from patent document U.S. Pat. No. 7,160, 682B1/US2003154500A1.

The upstream Sleeping beauty ITR sequence with the 5' terminal repeat has to be gene synthesized with flanking MunI restriction enzyme sequences, allowing the replacement of the MunI flanked PiggyBac 5'ITR in construct pIRES-EGFP-T1T2-IgL (SEQ ID NO:5) of example 1 by the Sleeping Beauty 5'ITR sequence. This sequence is provided as SEQ ID NO:14 below, at the end of this Example.

The downstream Sleeping beauty ITR sequence with the 3' terminal repeat (also published in US7160682B1/US2003154500A1) has to be gene synthesized with flanking XhoI restriction enzyme sequences, allowing the replacement of the XhoI flanked PiggyBac 3'ITR in construct pIRES-EGFP-T1T2-IgL (SEQ ID NO:5) of example 1 by the Sleeping beauty 3'ITR sequence. This sequence is as provided in SEQ ID NO:15 below, at the end of this Example (XhoI restriction enzyme sites are highlighted in boldface print and 4 additional flanking random nucleotides, allowing proper restriction enzyme digestion of the gene synthesized fragment, are indicated in lowercase letters):

In a first step, the MunI-flanked PiggyBac 5'ITR of construct pIRES-EGFP-T1T2-IgL (SEQ ID NO:5) has to be replaced by the Sleeping Beauty 5'ITR by digesting pIRES-EGFP-T1T2-IgL (SEQ ID NO:5) with MunI restriction enzyme and by ligating the MunI digested gene-synthesized fragment from SEQ ID NO:14 into the MunI linearized vector backbone of pIRES-EGFP-T1T2-IgL (SEQ ID NO:5). The correct orientation of Sleeping Beauty 5'ITR can be checked by diagnostic restriction enzyme digestions and/or DNA sequencing. The resulting plasmid is called pIRES-EGFP-sbT1-pbT2-IgL (FIG. 8).

In a second step, the XhoI-flanked PiggyBac 3'ITR of construct still contained in pIRES-EGFP-sbT1-pbT2-IgL has to be replaced by the Sleeping Beauty 3'ITR by digesting pIRES-EGFP-sbT1-pbT2-IgL with XhoI restriction enzyme and by ligating the XhoI digested gene-synthesized fragment from SEQ ID NO:15 into the XhoI linearized vector backbone of pIRES-EGFP-sbT1-pbT2-IgL. The correct orientation of Sleeping Beauty 3'ITR can be checked by diagnostic restriction enzyme digestions and/or DNA sequencing. The resulting plasmid is called pIRES-EGFP-sbT1T2-IgL (FIG. 8).

The entire sequence of the Ig-kappa LC expression vector pIRES-EGFP-sbT1T2-IgL transposable by the Sleeping Beauty transposase is provided in SEQ ID NO:16 below, at the end of this Example.

Sequences Referred to in this Example 3:
SEQ ID NO:14 (246 bp long DNA fragment containing the 5'ITR of the Sleeping Beauty transposon system. Flanking MunI restriction enzyme sites are printed in boldface and underlined)
SEQ ID NO:15 (248 bp long DNA fragment containing the 3'ITR of the Sleeping Beauty transposon system)

SEQ ID NO:16 (6339 bp long DNA sequence of Sleeping Beauty transposable Ig-kappa-LC expression vector pIRES-EGFP-sbT1T2-IgL)

Example 4: Cloning of PiggyBac and Sleeping Beauty Transposable Vectors for Membrane Bound Human $IgG_1$ In addition to the cloning instructions for basic PiggyBac transposable IgH and IgL expression vectors provided in Examples 1 and 2, and the construction of a basic Sleeping Beauty transposable IgL expression vector provided in Example 3, additionally cloning of improved PiggyBac and Sleeping Beauty transposable IgH and IgL expression vectors for a chimeric anti-humanCD30 mAb and for a humanized anti-humanCD19 mAb has been performed, in order to reduce the invention to practice.

For this, in a first step, the following two gene fragments have been synthesized (commissioned to Genscript, Piscataway, N.J., USA):

1.) A 4975 bp DNA fragment containing an expression cassette, in which the expression of a human membrane bound $IgG_1$ heavy chain is driven by the EF1-alpha promoter (basepairs 1-1335 of Clontech expression vector pEF1-alpha-IRES, Cat-No. #631970), and in which the expression of Ig chains is linked to EGFP expression via an internal ribosomal entry site (IRES). The DNA sequences for the IRES and EGFP regions were derived from pIRES-EGFP (basepairs 1299-1884 and 1905-2621, respectively, of Clontech expression vector pIRES-EGFP (Cat.-No. #6064-1, Life Technologies). In addition, the synthesized DNA fragment contained a chimeric intron positioned in between the Ig constant coding region and the IRES sequence, whose sequence was derived from pCI mammalian expression vector (basepairs 857-989. od Promega, Cat.-No. #E1731). At the 3' end of the expression cassette the synthesized fragment contained a bovine growth hormone polyadenylation signal (BGH-polyA), whose sequence was derived from pCDNA3.1-hygro(+) expression vector (basepairs 1021-1235 of Invitrogen-Life Technologies, Cat.-No. #V870-20). The expression cassette was flanked up- and downstream by PiggyBac transposon ITRs already disclosed in SEQ ID NO:1 and SEQ ID NO:2 further above.

A map of the elements and their arrangement in the gene-synthesized DNA fragment is provided in FIG. 10, including additionally added unique restriction enzyme sites that can be used to excise or to replace any of the functional elements of the expression cassette.

The sequence of the 4975 bp long gene-synthesized fragment is provided as SEQ ID NO:20 below, at the end of this Example.

It shall be noted here that the gene synthesized expression cassette for human IgH chains provided in SEQ ID NO:20, on purpose, did not yet contain the coding region for a $V_H$ domain, such that the construct can be used for the insertion of any desired $V_H$ coding region and/or $V_H$ coding gene library using unique restriction enzyme sites Nod and NheI. This construct therefore is designated "empty" Ig-gamma1-HC expression cassette.

2.) In order to provide a plasmid backbone for the transposable expression cassette of SEQ ID NO:20, a 2774 bp long DNA fragment had been gene synthesized (performed by Genscript, Piscataway, N.J., USA) that contained a bacterial ColE1 on and an ampicillin resistance gene. The sequence information for these plasmid backbone components were derived from the plasmid backbone of expression vector pCI (Promega, Cat.-No. #E1731). The synthetic gene fragment additionally contained 5' and 3' ITRs of the Sleeping Beauty transposon, already disclosed in SEQ ID NO:14 and SEQ ID NO:15, respectively. This fragment needed to be circularized and could be propagated in E. coli as an autonomous plasmid, due to the presence of the ColE1 on and the ampicillin resistance gene.

A map of the elements and their arrangement in the gene-synthesized DNA fragment is provided in FIG. 10, including position of additionally added unique restriction enzyme sites that can be used to excise or to replace any of the functional elements of the expression vector.

The sequence of the 2774 bp long gene-synthesized fragment is provided as SEQ ID NO:21 below at the end of this Example:

These two gene fragments allowed the construction of both PiggyBac and Sleeping Beauty transposable vectors by ligating fragments from these vectors, upon digestion with different restriction enzymes, followed by ligation, as follows:

The PiggyBac transposable vector was cloned by ligating EcoRI-ClaI fragments from SEQ ID NO:20 and SEQ ID NO:21, such that the resulting construct contains the entire PiggyBac ITR-flanked expression cassette of SEQ ID NO:20, and the ColE1-amp containing backbone without the Sleeping Beauty ITRs of Sq-ID21. Conversely, the ligation of XbaI-MluI fragments from SEQ ID NO:20 and SEQ ID NO:21 resulted in the ligation of the expression cassette without the PiggyBac ITRs into the linearized plasmid backbone of SEQ ID NO:21 still containing the Sleeping Beauty ITRs. Miniprep plasmids resulting from the two ligations were analyzed by diagnostic restriction enzyme digestions using a mixture of XhoI-NheI-BamHI and in addition with PvuI restriction enzymes, in order to identify correctly ligated plasmids. One selected DNA clone of each ligation was retransformed into E. coli to generate a DNA maxiprep, which was verified by DNA sequencing using sequencing primers allowing sequencing of the entire plasmid sequence.

The entire sequences of PiggyBac and Sleeping beauty transposable vectors (containing the "empty" human gamma1-HC expression cassette) generated as described above and verified by DNA sequencing is provided as SEQ ID NO:22 (PiggyBac transposable vector) and SEQ ID NO:23 (Sleeping Beauty transposable vector) below, at the end of this Example.

$V_H$ and $V_L$ coding regions of chimeric anti-human CD30 antibody brentuximab (clone Ac10) could be retrieved from sequences 1 and 9 of patent application US2008213289A1, and are provided below as SEQ ID NO:24 and SEQ ID NO:25, respectively.

$V_H$ and $V_L$ coding regions of humanized anti-human CD19 antibody hBU12 were retrieved from patent document U.S. Pat. No. 8,242,252 B2 as sequence variants HF and LG, respectively, and are provided in SEQ ID NO:26 and SEQ ID NO:27 further below, at the end of the Example.

In order to allow construction of final PiggyBac and Sleeping Beauty transposable anti-CD30 and anti-CD19 IgHC expression vectors, the DNA fragments for the $V_H$ domains were designed to have flanking NheI and Nod restriction enzyme sites. The nucleotide sequence encoding the $V_H$ of anti-CD30 antibody brentuximab (clone Ac10) has additionally been modified to also contain a leader sequence for mammalian cell expression. The DNA sequences of the NotI-NheI fragments encoding the $V_H$ of anti-CD30 and anti-CD19 mAbs are provided in SEQ ID NO:28 and SEQ ID NO:29 at the end of this Example. The DNA fragments had been gene synthesized by GeneArt, Regensburg, Germany (NotI and NheI sites are underlined).

In order to generate anti-CD30 and anti-CD19 IgH chain expression vectors that are transposable with either PiggyBac or Sleeping Beauty transposase, the NotI-NheI digested fragments of SEQ ID NO:28 SEQ ID NO:29 were ligated into NotI-NheI linearized vectors disclosed in SEQ ID NO:22 or SeqID23, respectively. This resulted in the generation of four vectors containing a fully functional heavy chain (HC) of anti-CD30 mAb brentuximab (clone Ac10) and of anti-CD19 mAb hBU12 and the constructs were designated: pPB-EGFP-HC-Ac10, pPB-EGFP-HC-hBU12, pSB-EGFP-HC-Ac10, and pSB-EGFP-HC-hBU12 and their vector maps are provided in FIG. 11. These vectors have specifically been designed to allow surface expression of the heavy chains, and, upon co-expression of light chains, surface IgG expression. However, simple omission of the coding region of for the membrane spanning region of the Ig heavy chains would result in transposable expression vectors for secreted IgG.

In order to generate anti-CD30 and anti-CD19 IgL chain expression vectors that are transposable with either PiggyBac or Sleeping Beauty transposase, the IgH constant region genes from the vectors disclosed in SEQ ID NO:22 and SEQ ID NO:23 needed to be replaced with IgL chain coding regions of anti-CD30 and anti-CD19 antibodies. This was achieved by gene synthesizing gene fragments containing the $V_L$ coding regions as disclosed in SEQ ID NO:25 and SEQ ID NO:27 fused in-frame to a human constant kappa light chain coding region, with a leader sequence at the 5' end and flanked by NotI-BstBI cloning sites that allow the ligation of the NotI-BstBI digested fragment into NotI-BstBI linearized vectors disclosed in SEQ ID NO:22 and SEQ ID NO:23, thereby replacing the IgH constant coding region of SEQ ID NO:22 and SEQ ID NO:23 with the IgL coding regions of anti-CD30 mAb Ac10 and anti-CD19 mAb hBU12.

The gene-fragments containing the IgL coding regions of anti-CD30 mAb Ac10 and anti-CD19 mAb hBU12, with leader sequence and flanked by NotI-BstBI cloning sites is disclosed in SEQ ID NO:30 and SEQ ID NO:31 below, at the end of the Example. The gene synthesis of these DNA fragments was performed by Genscript (Piscataway, N.J., USA).

In order to generate anti-CD30 and anti-CD19 IgL chain expression vectors that are transposable with either PiggyBac or Sleeping Beauty transposase, NotI-BstBI digested fragments of SEQ ID NO:30 and SEQ ID NO:31 had been ligated into NotI-BstBI linearized vectors disclosed in SEQ ID NO:22 or SeqID23. The resulting four vectors were called: pPB-EGFP-LC-Ac10, pPB-EGFP-LC-hBU12, pSB-EGFP-LC-Ac10, and pSB-EGFP-LC-hBU12 and their vector maps are provided in FIG. 11.

Complete sequences of the PiggyBac and Sleeping beauty anti-CD30 and anti-CD19 IgH and IgL constructs (eight combinations) are provided in SEQ ID NO:32 (pPB-EGFP-HC-Ac10), SEQ ID NO:33 (pPB-EGFP-HC-hBU12), SEQ ID NO:34 (pSB-EGFP-HC-Ac10), SEQ ID NO:35 (pSB-EGFP-HC-hBU12), and in SEQ ID NO:36 (pPB-EGFP-LC-Ac10), SEQ ID NO:37 (pPB-EGFP-LC-hBU12), SEQ ID NO:38 pSB-EGFP-LC-Ac10), and SEQ ID NO:39 (pSB-EGFP-LC-hBU12) below, at the end of this Example Sequences Referred to in this Example:

SEQ ID NO:20 (4975 bp long DNA sequence containing a PiggyBac ITR-flanked expression cassette for membrane spanning human Ig-gamma1 heavy chains)

SEQ ID NO:21 (2774 bp long DNA sequence containing vector backbone components ColE1 and ampicillin resistance flanked by 5' and 3' ITRs of Sleeping Beauty)

SEQ ID NO:22 (7242 bp long sequence of PiggyBac transposable "empty" human gamma1-HC vector)

SEQ ID NO:23 (7146 bp long sequence of Sleeping Beauty transposable "empty" human gamma1-HC vector)

SeqID-24 (351 bp long $V_H$ coding region of anti-human CD30 antibody brentuximab)

SEQ ID NO:25 (333 bp long $V_L$ coding region of anti-human CD30 antibody brentuximab)

SEQ ID NO:26 (417 bp long $V_H$ coding region of anti-human CD19 mAb huB12, including leader)

SEQ ID NO:27 (375 bp long $V_L$ coding region of anti-human CD19 mAb huB12, including leader)

SEQ ID NO:28 (423 bp long DNA fragment, containing NotI-NheI-flanked $V_H$ coding region of the $V_H$ domain of anti-human CD30 mAb brentuximab)

SEQ ID NO:29 (432 bp long DNA fragment, containing NotI-NheI-flanked $V_H$ coding region of the $V_H$ domain of anti-human CD19 mAb hBU12)

SEQ ID NO:30 (733 bp long DNA fragment containing IgL coding region of anti-CD30 mAb Ac10 and flanked by NotI and BstBI restriction enzyme sites)

SEQ ID NO:31 (718 bp long DNA fragment containing IgL coding region of anti-CD19 mAb hBU12 and flanked by NotI and BstBI restriction enzyme sites)

SEQ ID NO:32 (7645 bp sequence of pPB-EGFP-HC-Ac10

SEQ ID NO:33 (7654 bp sequence of pPB-EGFP-HC-hBU12)

SEQ ID NO:34 (7549 bp sequence of pSB-EGFP-HC-Ac10)

SEQ ID NO:35 (7558 bp sequence of pSB-EGFP-HC-hBU12)

SEQ ID NO:36 (6742 bp long sequence of pPB-EGFP-LC-Ac10)

SEQ ID NO:37 (6727 bp long sequence of pPB-EGFP-LC-hBU12)

SEQ ID NO:38 (6646 bp long sequence of pSB-EGFP-LC-Ac10)

SEQ ID NO:39 (6631 bp long sequence of pSB-EGFP-LC-hBU12)

Example 5: Instructions for Cloning of a PiggyBac Transposase Expression Vector

The ORF of functional PiggyBac transposase enzyme can be retrieved from U.S. Pat. No. 7,105,343 B1 (incorporated herein by reference in its entirety) and is provided in SEQ ID NO:11 below, at the end of this Example. The DNA sequence of SEQ ID NO:11 translates into the amino acid SEQ ID NO:12 also provided at the end of this Example.

In order to generate a vertebrate cell expression vector for the PiggyBac transposase enzyme, this ORF can be gene synthesized and cloned as a blunt ended DNA into the unique, blunt-cutting restriction enzyme site EcoRV in the standard vertebrate cell expression vector pCDNA3.1-hygro (+) (catalogue # V870-20, Invitrogen, Carlsbad, Calif., USA), by methods know in the art. The correct ligation of the PiggyBac ORF, relative to the pCDNA3 promoter can be verified by diagnostic restriction enzyme digestion, and/or by DNA sequencing of the cloned PiggyBac expression construct pCDNA3.1-hygro(+)-PB (FIG. 7). The construction of a PiggyBac expression vector was performed as described herein and the vector design was verified by diagnostic restriction enzyme digestion, and DNA sequencing.

The sequence of the PiggyBac expression construct pCDNA3.1-hygro(+)-PB is provided as SEQ ID NO: 13, below at the end of this Example Sequences Referred to in this Example 5:
SEQ ID NO:11 (ORF of PiggyBac transposase)
SEQ ID NO:12 (amino acid sequence of PiggyBac transposase)
SEQ ID NO:13 (pCDNA3.1-hygro(+)-PiggyBac expression vector)

Example 6: Instructions for Cloning of a Sleeping Beauty Transposase Expression Vector The open reading frame (ORF) of the Sleeping Beauty transposase enzyme can be found in patent reference US7160682B1/US2003154500A1. The sequence is provided in SEQ ID NO:17, below at the end of this Example. This DNA sequence of SEQ ID NO:17 translates into the amino acid sequence of SEQ ID NO:18, also provided at the end of this Example, further below.

In order to generate a vertebrate cell expression vector for the Sleeping Beauty transposase enzyme, this ORF can be gene synthesized and cloned as a blunt ended DNA into the unique, blunt-cutting restriction enzyme site EcoRV in the standard vertebrate cell expression vector pCDNA3.1-hygro (+) (catalogue # V870-20, Invitrogen, Carlsbad, Calif., USA), by methods know in the art. The correct ligation of the Sleeping Beauty ORF, relative to the pCDNA3 promoter can be verified by diagnostic restriction enzyme digestion, and/or by DNA sequencing of the cloned Sleeping Beauty expression construct pCDNA3.1-hygro(+)-SB (FIG. 9).

The sequence of the Sleeping Beauty expression construct pCDNA3.1-hygro(+)-SB is provided in SEQ ID NO:19, below, at the end of this Example.

The construction of a Sleeping Beauty expression vector was performed as described herein and the vector design was verified by diagnostic restriction enzyme digestion, and DNA sequencing. The coding regions for PiggyBac and Sleeping Beauty transposase enzymes had been gene synthesized by Genscript, Piscataway, N.J. With the eight different transposable IgH and IgL expression vectors for PiggyBac and Sleeping Beauty transposases, and the pCDNA3.1-hygro(+) expression vectors for PiggyBac and Sleeping Beauty transposase enzymes, all vectors have been generated that allow the expression of anti-CD30 and anti-CD19 antibodies on the cell surface of mammalian cells.

Sequences Referred to in this Example 6:
SEQ ID NO:17 (ORF of Sleeping Beauty transposase enzyme)
SEQ ID NO:18 (amino acid sequence of Sleeping Beauty transposase)
SEQ ID NO:19 (DNA sequence of Sleeping Beauty expression vector pCDNA3.1-hygro(+)-SB)

Example 7: Generation of Murine preB Cells Stably Expressing Membrane Bound Human IgG from Stably Transposed Expression Vectors In order to demonstrate stable expression of human IgG antibodies in mammalian cells, transposable human IgH and IgL expression constructs have been transfected into Abelson murine leukemia virus (A-MuLV) transformed proB cell line 63-12, originally derived from RAG-2 deficient mice (Shinkai et al. (1992) *Cell* 68, 855-867) and therefore unable to initiate V(D)J recombination. This host cell line represents a B cell lineage lymphocyte cell type that expresses all cellular components for optimal membrane bound antibody expression, including the B cell receptor co-factors Ig-alpha (CD79a or mb-1) and Ig-beta (CD79b or B29) that interact with the transmembrane spanning amino acids of membrane bound immunoglobulin. Therefore, these cells optimally anchor IgG molecules with a trans-membrane spanning region in the cell surface membrane. 63-12 cells were grown in static culture in suspension using IMDM medium supplemented with 2% FCS, 0.03% Primatone™ RL-UF (Sheffield Bioscience), 2 mM L-glutamine, 50 μM 2-mercaptoethanol, at 37° C. in a humidified incubator and a 10% $CO_2$ atmosphere. For the co-transfection of the transposable IgH and IgL expression vectors (Example 4) with a transposon expression vector (Examples 5 or 6), the cells were passaged 24 hours prior to transfection and seeded at a density of $5 \times 10^5$ cells/ml, in order to allow the cells to enter into log-phase growth until the time-point of transfection.

At the day of transfection, 63-12 cells were harvested by centrifugation and resuspended in RPMI 1640 medium without any supplements or serum at a density of $5 \times 10^6$ cells/ml. 400 μl of this cell suspension (corresponding to $2 \times 10^6$ cells) were transferred into 0.4 cm electroporation cuvettes (BioRad order #165-2081) and mixed with 400 μl of RPMI 1640 medium containing the desired plasmid DNA (or a mixture of plasmids). Cells were then transfected using a BioRad Gene Pulser II at 950 μF/300V settings and incubated for 5 min at room temperature after a single electroporation pulse. After this, the cells were transferred into 5 ml IMDM-based growth medium and the cells were centrifuged once, in order to remove cell debris and DNA from the electroporation, before the cells were transferred into IMDM-based growth medium for recovery and expression of proteins from transfected plasmids.

The electroporation settings have been determined as the most optimal transfection conditions for A-MuLV transformed proB cell line 63-12 that routinely resulted in transient transfection efficiencies ranging between 30-40%. The result of such a transfection by electroporation is documented in the FACS analyses depicted in FIG. 12, where the transfection controls, two days post transfection, are depicted on the left column panels. The negative control (labeled NC), that was mock-electroporated without DNA, as expected, does not show any green fluorescent cells, whereas the transfection control that was transfected with 15 μg pEGFP-N3 plasmid (Clontech, order #6080-1), showed that 38.8% of the cells were transiently transfected, as detected by cells expressing enhanced green fluorescent protein (see cell in lower right quadrant). As expected, the transfection controls do not show any Ig-kappa signal, because none of the transfection controls was transfected with an Ig-expression construct.

For transposition of IgH and IgL expression vectors, 63-12 cells were also transfected by electroporation with a mix of 5 μg each of a transposable IgH expression vector, 5 μg of a transposable IgL expression vector, and 5 μg of an expression vector allowing expression of a transposase mediating the transposition of the IgH and IgL expression vector. The result of this transfection is also shown in FIG. 12.

Expression of human IgG on the surface of the cells was detected by a biotinylated anti-human kappa light chain specific antibody (Affymetrix, ebioscience, order #13-9970-82) detected with streptavidin-allophycocyanin (strep-APC) (Affymetrix, ebioscience, order #17-4317-82), and is shown on the Y-axis of the FACS dot-plots. As can be seen in FIG.

10, the measurements depicted in the second column from left show the analysis of cells transfected with IgH+IgL+ transposase expression vectors two days after electroporation (labeled "d2 post TF"). The FACS analysis after two days of transfection showed that between 1.8% and 2.8% of the cells express human IgH+IgL on the cell surface, because IgL expression on the cell surface can only be detected, if IgH chains are co-expressed in the cells, such that a complete IgG can be expressed on the surface of the cells.

From this data it can be inferred that if ca. 38% of the cells are transiently transfected, ca. 5-7.5% of these cells have been co-transfected with both IgH and IgL expression vectors. From this experiment it is concluded that the transposable IgH and IgL expression constructs allow high-level expression of human IgG on the surface of murine A-MuLV transformed proB cells, which is comparable to surface IgG signals obtained by staining of human peripheral B lymphocytes with the same antibody staining reagents (data not shown).

As expected the cells showing IgG expression also displayed EGFP expression, because the EGFP expression was transcriptionally coupled to IgH or IgL expression via IRES sequences. However, the EGFP expression was significantly lower, as compared to the EGFP expression from the pEGFP-N3 control plasmid, which is expected, as the EGFP expression in pEGFP-N3 is directly driven by a strong constitutive promoter, whereas EGFP expression in the transposable IgH and IgL expression vectors is effected by transcriptional coupling to the IgH and IgL coding region using an internal ribosomal entry site (IRES). Nevertheless, as expected, cells displaying higher IgG expression also displayed higher EGFP signals (leading to a slightly diagonal Ig-kappa$^+$/EGFP$^+$ population), which clearly demonstrates, that both expression levels are coupled.

When cells were analyzed without cell sorting after one week of transfection, the EGFP signal in pEGFP-N3 control transfections was no longer detectable (data not shown), showing that the cells do not stably integrate expression constructs at any significant frequency. In contrast, a low ca. 1-2% IgG-EGFP double-positive population of cells was maintained in cells that have been co-transfected with transposable IgH&IgL vectors together with a transposase expression vector, already indicating that ca. 3-6% of the cell transiently transfected cells stably integrate simultaneously the transposable IgH and IgL expression vectors into their genome (data not shown).

In order to enrich for these stably transposed cells, Ig-kappa light chain and EGFP double positive cells have been FACS sorted at day 2 post transfection, as indicated by the sorting gates (black rectangles in the second left column FACS dot plots). Each 5'000 cells falling into this gate have been sorted from the PiggyBac transpositions with IgH&IgL of anti-CD30 mAb Ac10 (top row), and of anti-CD19 mAb hBU12 (middle row), and 3'000 cells have been sorted from the Sleeping Beauty transposition with IgH&IgL of anti-CD30 mAb Ac10 (bottom row), as indicated in FIG. 12.

The FACS-sorted cells were expanded for one week (representing day 9 post transfection), and were re-analyzed again for surface IgG expression by detection of IgG with an anti-kappa light chain antibody, as described above. As can be seen in FIG. 10 (second column from the right), over 30%, 50% and 5% of the one-time sorted cells stably expressed IgG on the cell surface, while these cells, as expected, were also EGFP-positive. This demonstrates that a significant percentage of transiently IgH & IgL co-transfected cells stably maintain IgG expression. The PiggyBac mediated transpositions in this experimental set-up appear to have occurred with about 6-10-fold higher efficiency than the Sleeping Beauty mediated transpositions.

A couple of additional conclusions can be drawn from this transposition experiment: First, from the IgG/EGFP double positive cells sorted on day two post transfection, about 75% of cells remained stably EGFP+ in the PiggyBac transpositions, as ca. 40% and 30% of the PB-Ac10 and PB-hBU12 transposition generate EGFP+ cells lacking IgG surface expression. These cells most likely have stably transposed only one of the two transposable IgH and IgL expression vectors, which does not allow for surface IgG expression, but sufficient to render the cells EGFP-positive. This also means that from the ca. 38% originally transiently transfected cells, at least 5% are stably transposed with at least one transposable Ig expression vector.

The numbers of stably transposed cells for the Sleeping Beauty transposition were lower, than those of the PiggyBac transposition, and after a first round of FACS sorting of IgH+IgL+transposase co-transfected cells, only about 5% of stably IgG expressing cells was obtained. However, if also the stably EGFP positive cells are considered, about 9% of stably transposed cells were obtained after the first FACS sorting cycle using Sleeping Beauty transposase.

When these stably IgG-positive and IgH/IgL transposed cells were FACS sorted again, over 99% stably IgG expressing cells were obtained (FIG. 12, rightmost column), and the stable expression phenotype was maintained for over four weeks, without any change in the percentage of IgG+ cells (data not shown). Therefore, it is concluded that the transposable expression vectors for human IgH and IgL chains, as disclosed in this invention, are functional and can stably be integrated into a mammalian host cell genome with high efficiency.

Example 8: Enrichment of Stably IgG Transposed and IgG Expressing Cells Via Specific Antigen Binding In order to demonstrate that human IgG expressing proB cells, generated by transposition of IgH and IgL expression vectors, as disclosed in Example 7 above, can be used for the isolation of antigen-specific cells, decreasing numbers of the proB cell line 63-12, expressing anti-CD30 mAb (see d16, 2× sorted, 63-12+PB-Ac10, of FIG. 12) were mixed with proB cell line 63-12 expressing anti-CD19 mAb (see d16, 2× sorted, 63-12+PB-hBU12, of FIG. 12) at ratios $10^{-2}$, $10^{-3}$, $10^{-4}$, $10^{-5}$, $10^{-6}$ (see FIG. 13). A total of $10^7$ cells were stained in 1 ml PBS, supplemented with 2% FCS, for 30 min on ice, with the following reagents:

0.1 µg 6×His-tagged, recombinant human CD30 (Sino Biological Inc., Beijing, China, order #10777-H08H), and 10 µl mouse anti-human Ig-kappaLC-APC labeled antibody (Life Technologies, Invitrogen, order #MH10515).

After these primary reagents were removed from the cells, by centrifugation and washing in PBS, 2% FCS, a secondary staining was performed in 1 ml PBS, supplemented with 2% FCS, for 30 min on ice, with:

0.1 µg biotinylated anti-His-tag antibody (IBA Life Sciences, Göttingen, Germany, order #2-1590-001)

After this secondary reagent was removed from the cells, by centrifugation and washing in PBS, 2% FCS, the CD30-6×His/anti-His-tag-bio combination was detected by staining in 1 ml PBS, 2% FCS, for 30 min on ice, with:

1/500 diluted streptavidin-Phycoerythrin (strep-PE) (Affymetrix ebioscience, order #12-4317-87) reagent.

After the final FACS staining, the cells were again washed twice in ice-cold PBS, 2% FCS, and then resuspended in 1.0 ml PBS, 2% FCS, after which the cells were subjected to FACS analysis and cell sorting of Ig-kappaLC/CD30 positive cells (see FIG. 13).

As can be seen from the results disclosed in FIG. 13, a specific population of IgG positive and anti-CD30 reactive cells is detectable in the upper-right quadrant of the FACS-plots of the positive control, and as expected the intensity of the FACS signal for surface IgG (detected via anti-Ig-kappa-APC) correlates with the FACS signal for anti-CD30 resulting in a diagonal staining pattern for this population.

In the mixtures of anti-CD30 mAb expressing cells with anti-CD19 mAb expressing cells, the level of dilution of the specific anti-CD30 mAb expressing cells is very well reflected by the frequency of CD30 antigen specific cells in the upper right quadrant and the stringently defined FACS sorting gate (black square in the upper right quadrant). The very rare events corresponding to CD30-reactive/IgG positive cells upon increased dilution of the specific cells (1:10'000, 1:100'000, 1:1'000'000) are hardly visible on the printouts of the FACS-dot-plots, even, if increasing numbers of events were acquired, as indicated above the individual dot plots. However, the frequency of CD30 detectable cells correlated well with their frequency as expected from the dilution factor. From this result it is concluded that the display and antigen-specific detection of cells expressing an antigen-specific antibody by means of transposition mediated human IgG expression on the surface of mammalian and proB cells, as shown here, can reliably be performed.

The bottom row of FACS dot-plots in FIG. 13 shows the re-analysis of the FACS sorted cells from the different spike-in dilution experiments. As can be seen from the results, the re-analysis of the cells FACS sorted from the 1:100, 1:1'000 and 1:10'000 dilution resulted in almost the same cell population being enriched, which showing ca. 90-95% antigen reactive cells. The FACS sorted cells from the 1:100'000 dilution contained a small, additional population that did not fall into the gate of IgG-positive/CD30 reactive cells, but also in this experiment ca. 85% of the FACS sorted cells were antigen-specific IgG-expressing cells. Surprisingly, the highest purity of cells, with regard to CD30-reactivity and IgG expression, resulted from the 1:1'000'000 FACS sort, in which only 1 in 1'000'000 had been CD30 antigen specific, and where only ca. 14 cells had been sorted. This can only be explained that her almost clonal effects need to be considered such that the sort was not a mixture from IgG-positive-CD30 reactive cells, but rather a few clones that all represented IgG-positive-CD30 reactive cell clones.

Nevertheless, the results of the specific antigen-mediated staining and identification of antigen-specific antibody expressing cells and their successful enrichment by preparative FACS-mediated cell sorting clearly demonstrates the feasibility of the method disclosed herein for the isolation of cells expressing antibodies with a desired binding phenotype.

Example 9: Instruction for the Generation and Use of Transposable IgH Expression Vectors that can be Used to Switch from Membrane Bound to Secreted Antibody Expression The transposable Ig expression vectors disclosed in Examples 1 to 4 only allow expression of human IgG on the surface of mammalian cells, such that the binding phenotype of antibodies can readily be identified and enriched for by antigen-binding to the cells, by means of FACS, as exemplified in Example 8, or by cell-panning or batch enrichment methods (e.g. magnetic bead activated cell sorting, MACS). However, it is often desired to rapidly analyze the antigen-binding properties of a given antibody displayed by a cell also as a secreted antibody in solution. While it is possible to PCR-amplify the relevant $V_H$ and $V_L$ coding regions of an antigen-specific cell clone into expression vectors for secreted IgG expression, this approach is time consuming and labour intensive.

In the detailed description of the invention it is already disclosed that transposable IgH expression constructs can be employed that exploit the natural "switch" from membrane bound to secreted antibody expression, based on alternative splicing of genomic IgH chain constructs.

This switch from membrane bound to secreted antibody expression can be achieved as follows:

Instead of a cDNA-based expression cassette for human Ig-gamma1 heavy chains, the original genomic organization of human Ig-gamma1 gene locus needs to be cloned into the IgH expression vectors as disclosed before in Example 4. The sequence of the entire immunoglobulin gene locus in germline configuration can be retrieved from contig NT_010168 of the human genome project, which covers the human Ig heavy chain locus located on chromosome 14. The human Ig-gamma1 heavy chain gene locus starting from the first amino acid of the $C_H1$ domain at the 5' end to 500 bp downstream of the last stop codon of the second membrane-spanning exon gamma1-M2 at the 3' end has a length of 5807 base pairs and displays no internal NheI or BstBI sites. Therefore, this gene locus can be synthesized with flanking NheI and BstBI sites, that can be used for directional cloning. Such a gene synthesized fragment can then directly be used to replace the cDNA coding region of the membrane-bound gamma1-constant coding region in pPB-EGFP-HC-Ac10 (SEQ ID NO:32)

The DNA sequence of a genomic human Ig-gamma1 fragment to be synthesized is provided in SEQ ID NO:40 below, at the end of this Example (5'-NheI and 3'-BstBI sites are highlights in boldface print).

The organization of the exon and introns of the human Ig-gamma1-heavy chain germline locus, including their membrane spanning exons M1 and M2 is depicted in FIG. 14. The coding and non-coding regions in this genomic gene fragment left in its original genomic configuration are supposed to contain all required cis-regulatory elements to allow alternative splicing of an Ig-gamma1 mRNA depending on the differentiation stage of the B-lineage cells, in which the mRNA is processed (Peterson et al. (2002) Mol. Cell. Biol. 22, 5606-5615). The cloning of fragment SEQ ID NO:40 into a transposable Ig-gamma1 HC expression vector can be performed by replacing the C-gamma1 coding region in pPB-EGFP-HC-Ac10 bp digesting pPB-EGFP-HC-Ac10 with NheI and BstBI restriction enzymes and ligating the genomic fragment of SEQ ID NO:40 as a NheI-BstBI digested fragment into the NheI-BstBI linearized vector fragment of pPB-EGFP-HC-Ac10.

The result of this ligation is shown schematically in FIG. 14, and the sequence of the construct is provided in SEQ ID NO:41 below at the end of this Example.

A-MuLV transformed proB cells, like 63-12 cells, represent a suitable cell line to exploit the natural mechanism of alternative splicing of a genomic Ig-gamma1 HC construct, as it is possible to effect phenotypic differentiation of these cells to more mature B-lineage cells, if the transforming activity of the Abl-kinase is inhibited. This can specifically be achieved with the Abl-kinase inhibitor Gleevec (also known as Imatinib, or STI-571) (Muljo and Schlissel (2003) Nature Immunol. 4, 31-37). However, if A-MuLV transformed proB cells are treated with Gleevec, they not only initiate phenotypic differentiation to more mature B lineage stages, but this process is also associated with an induction of apoptosis (unpublished observation). This can be prevented by first establishing a 63-12 A-MuLV transformed cell line that is stably transfected with a bcl-2 expression vector.

The mouse bcl-2 mRNA sequence can be found in NCBI-Genbank entry NM_009741, and has the following sequence SEQ ID NO:42, shown below at the end of this Example. This open reading frame translates into the following amino acid sequence SEQ ID NO:43, also provided below, at the end of the Example.

In order to generate a mammalian bcl-2 expression vector, the murine bcl-2 coding region can be gene synthesized with flanking KpnI and XhoI restriction enzyme sites that are not present in the coding region of bcl-2 and a KpnI-XhoI double digested gene-synthesized DNA fragment can be ligated into pCDNA3.1-hygro(+) described further above in order to generate a mammalian expression vector for bcl-2 that can stably be transfected into 63-12 cells in order to select for stable bcl-2 transfectants.

The entire sequence of the pCDNA3.1-hygro(+) expression vector containing the murine bcl-2 gene inserted into the KpnI and XhoI restriction sites of the multiple cloning site is provided as SEQ ID NO:44 below, at the end of this Example.

In order to facilitate the generation of stable transfectants, this vector can e.g. be linearized outside of the expression cassettes for bcl-2 or hygromycinB using the enzyme FspI, that linearizes the vector in the bacterial ampicillin resistance gene. 20 µg of such a linearized vector can be transfected into $2 \times 10^6$ 63-12 cells by electroporation at 950 µF/300V exactly as disclosed further above for the transfection of transposable vectors. Following electroporation, the cells can then be diluted in 100 ml growth medium and plated into five 96-well plates with each 200 µl/well, which will result in the plating of ca. $4 \times 10^3$ cells/well.

Stable transfectants can then selected by adding 800 µg/ml hygromycinB 48 hours post transfection. Individual stably transfected cell clones, of which 20-100 can be expected from such an experiment, can then be obtained 2-3 weeks later. Stable bcl-2 transfected cell clones are best functionally tested for their ability to protect cells from apoptosis, by measuring the survival of individual clones upon exposure of 0.1 to 1 mM Gleevec (Imatinib, or STI-571). Once a 63-12 stable bcl-2 transfectant is identified that has high resistance to Gleevec (Imatinib, or STI-571), this clone can be utilized as a host cell for expression of human IgG from transposable genomic Ig-gamma1 HC and Ig-kappa LC expression vectors, e.g. utilizing vectors SEQ ID NO:41 and SEQ ID NO:36.

These vector can be co-transfected with PiggyBac expression vector (SEQ ID NO:13) into the stably Bcl-2 transfected 63-12 cells, and stably transposed and IgG expressing cells can be established as described further above (equivalent to Example 7). Because proB cells represent a differentiation stage, where endogenous immunoglobulin is expressed as membrane bound immunoglobulin, it can be expected that also the Ig-HC expressed from a transposable Ig-gamma1 HC expression vector in genomic configuration will be expressed as membrane bound version.

However, if the cells are treated with 0.1 to 1 mM Gleevec (Imatinib, or STI-571), the Abl-kinase encoded by the A-MuLV is specifically inhibited, the cells are no longer transformed and continue their intrinsic differentiation program to more mature B cell differentiation stages. In vitro, this differentiation is independent of functionally expressed Ig proteins (Grawunder et al. (1995) Int. Immunol. 7, 1915-1925). It has even been shown that in vitro differentiation of non-transformed proB cells renders them responsive to T cell derived anti-IL4 and CD40 stimulation, upon which the cells even differentiate into plasma cell stage cells undergoing class-switch recombination and where they can be fused with myeloma cells to generate hybridomas (Rolink et al. (1996) Immunity 5, 319-330).

This means that also A-MuLV transformed 63-12 cells, which are rendered resistant to apoptosis by stable expression of bcl-2 can be differentiated into cells of the plasma cell stage upon treatment with Gleevec and simultaneous incubation with 10 µg/ml agonistic anti-CD40 antibody, and 100 U/ml recombinant IL4, exactly as described in Rolink et al. (1996) Immunity 5, 319-330.

This treatment will induce a change in the cellular differentiation program, that will change the cellular alternative splicing program from membrane bound IgG expression to secreted IgG expression from an Ig HC expression construct in genomic organization. This will allow the production of secreted antibody from replica plated cell clones identified and isolated by surface display and antigen binding, without the need to re-clone $V_H$ and $V_L$ coding regions from selected cell clones and without the need to ligate them into expression vectors for secreted IgG antibodies. This is a functional feature of the vectors that cannot easily be incorporated in most mammalian cell expression system, particularly not into many virus-based expression systems, in which such extended genomic expression vectors cannot easily be inserted.

Sequences Referred to in this Example 9:
SEQ ID NO:40 (5812 bp long genomic human Ig-gamma1-heavy chain gene)
SEQ ID NO:41 (transposable Ig-gamma1-HC expression vector in genomic configuration)
SEQ ID NO:42 (murine bcl-2 coding region)
SEQ ID NO:43 (amino acid sequence of murine Bcl-2 protein
SEQ ID NO:44 (pCDNA3.1-hygro(+)-bcl2 mammalian expression vector)

Example 10: Instruction for the Generation of Vectors Encoding Basic Human Antibody Heavy and Light Chain Libraries as PiggyBac Transposable Vectors In order to generate simple transposable DNA libraries encoding human antibody heavy and light chain libraries, only the $V_L$ and $V_H$ regions from transposable vectors pIRES-EGFP-T1T2-IgL of Example 2 and pIRES-EGFP-T1T2-IgH of Example 3, respectively, need to be replaced. This can be done by gene synthesizing human $V_H$ and $V_L$ coding regions flanked by ClaI and Eco47III restriction enzyme sites, and by allowing nucleotide variations in certain HCDR and LCDR positions, as provided in SEQ ID NO:9, which encodes libraries for variable heavy chain domains, and SEQ ID NO:10, which encodes libraries for variable light chain domains, and which are provided at the end of this Example. Both of these sequences contain a stretch of N-sequences in the HCDR3 (boldface), and LCDR3 (boldface), respectively. Both SEQ ID NO:9 and SEQ ID NO:10 sequences are flanked by ClaI and Eco47III restriction enzymes (underlined), respectively, including four nucleotides flanking the restriction enzyme sites (highlighted in lowercase letters at the ends of the sequence), allowing proper restriction enzyme digestion of the gene-synthesized DNA fragments and directed ligation into ClaI-Eco47III linearized pIRES-EGFP-T1T2-IgH and pIRES-EGFP-T1T2-IgL backbones, respectively.

This way, diverse transposable DNA libraries, encoding antibody heavy and light chains on separate vectors, in which the expression of the antibody chains are transcriptionally and therefore operably linked to a green fluorescent marker protein can be generated.

SEQ ID NO:9 (VL domain coding region with variable N-sequence variation at positions encoding LCDR3)

SEQ ID NO:10 ($V_H$ domain coding region with variable N-sequence variation at positions encoding HCDR3)

Example 11: Instructions for the Generation of a Basic Sleeping Beauty Transposable Human Ig-Kappa Light Chain Expression Library In order to generate a diverse Sleeping Beauty transposable DNA library encoding human antibody light chain libraries, the $V_L$ region of Sleeping Beauty transposable vector pIRES-EGFP-sbT1T2-IgL of Example 5 needs to be replaced with a diverse $V_L$ gene repertoire. This can be done by gene synthesizing of human $V_L$ coding regions flanked by ClaI and Eco47III restriction enzyme sites, and by allowing nucleotide variations in certain HCDR and LCDR positions, as already provided in SEQ ID NO:10 above. The SEQ ID NO:10 sequence is flanked by ClaI and Eco47III restriction enzymes allowing directed ligation into ClaI-Eco47III linearized pIRES-EGFP-sbT1T2-IgL. This way a Sleeping Beauty transposable DNA library encoding diverse human antibody light chain can be generated.

This way, diverse transposable DNA libraries, encoding antibody heavy and light chains on separate vectors, in which the expression of the antibody chains are transcriptionally and therefore operably linked to a green fluorescent marker protein can be generated.

Example 12: Cloning of a Transposable IgL Chain Expression Library

A V-kappa light chain library with randomized LCDR3 region was constructed as described below. Six amino acid residues were randomized, i.e. encoded by the codon NNK (N=any nucleotide; K=T or G), which accommodates each of the 20 amino acids. The library was based on germline human Vkappa1-5 and Jkappa2 gene segments and was randomized between the conserved cysteine at the end of the framework 3 region and the Jkappa2-based framework 4 region as follows: Gln-Gln-(NNK)$_6$-Thr. The sequence and overall design of the kappa light chain library is shown in FIG. 15.

A linear DNA molecule encoding the kappa light chain library was generated by PCR. For this, two templates were generated by total gene synthesis (performed by GenScript, Piscataway, N.J., USA). On one hand, a synthetic construct was generated comprising the Vkappa1-5 gene segment cloned into the EcoRV site of pUC57 (Genscript order #SD1176), pUC57_Vkappa1-5 (SEQ ID NO:45); on the other hand, a synthetic construct was generated comprising the Jkappa2 gene segment fused to the Ckappa coding region cloned into the EcoRV site of pUC57, pUC57_Jkappa2-Ckappa (SEQ ID NO:46).

A first linear DNA comprising the Vkappa1-5 gene segment was PCR amplified from pUC57_Vkappa1-5 using the primers pUC57-1 (5'-CGT TGT AAA ACG ACG GCC AG-3') and LCDR3-B (5'-CTG TTG GCA GTA ATA AGT TGC-3'). A second linear DNA comprising the randomized CDR3 region (Gln-Gln-(NNK)$_6$-Thr), the Jkappa2 gene segment and the Ckappa constant region was amplified from pUC57_Jkappa2-Ckappa using the primers LCDR3-NNK6-F (5'-GCA ACT TAT TAC TGC CAA CAG NNK NNK NNK NNK NNK NNK ACT TTT GGC CAG GGG ACC AAG-3') and pUC57-2 (5'-TCA CAC AGG AAA CAG CTA TG-3'). To prevent introduction of a sequence bias due to priming of the randomized region of the primer LCDR3-NNK6-F on pUC57_Jkappa2-Ckappa, the plasmid was first linearized by digestion with the restriction enzyme ScaI (FIG. 17A).

The resulting DNA molecules (SEQ ID NO:47 and SEQ ID NO:48) displayed an overlap of 21 bp and were assembled by PCR overlap extension using the primers pUC57-1 and pUC57-2, generating a DNA molecule comprising the kappa light chain library flanked by NotI and AsuII (=BstBI) restriction sites as shown in FIG. 15. The PCR amplicon of the V-kappa light chain library was subjected to PCR-fragment sequencing, and the result shown in FIG. 18, demonstrate that indeed the expected diversity was introduced as designed in the positions of the LCDR3, as evidenced by overlapping electropherogram signals in the randomized positions. This PCR fragment was digested with the restriction endonucleases NotI and BstBI (an isoschizomer of AsuII) and cloned into the PiggyBac-transposable vector pPB-EGFP_HC-g1 (SEQ ID NO:049, resulting in a library consisting of $5.2 \times 10^7$ independent clones. The size of this library can easily be increased by a factor 10 by scaling up the ligation reaction.

Light chain libraries incorporating distinct randomization designs, or comprising Vkappa and Jkappa gene segments other than the ones used in this example, can be produced the same way. Likewise, the strategy described here can be employed for the production of Vlambda light chain libraries.

Sequences Referred to in this Example 12:
SEQ ID NO:45 (pUC57_Vkappa1-5)
SEQ ID NO:46 (pUC57_Jkappa2-C-kappa)
SEQ ID NO:47 (Vkappa1-5 PCR product)
SEQ ID NO:48 (NNK6-Jkappa2-C-kappa PCR product

Example 13: Cloning of Transposable IgH Chain Expression Libraries with Variable HCDR3 Length A human gamma1 heavy chain library with randomized HCDR3 region was constructed as described below. Several amino acid residues were randomized, i.e. encoded by the codon NNK (N=any nucleotide; K=T or G), which accommodates each of the 20 amino acids. The library was based on the $V_H$3-30 and $J_H$4 gene segments and was randomized between the conserved Cysteine residue at the end of the framework 3 region and the $J_H$4-based framework 4 region as follows: Ala-Lys/Arg-(NNK)$_n$-Asp-NNK. Various HCDR3 lengths were explored, with n=4, 6, 8, or 10 (NNK4, NNK6, NNK8, and NNK10 randomization). The sequence and overall design of the gamma heavy chain library is shown in FIG. 16.

A linear DNA molecule encoding the heavy chain variable region ($V_H$) library was generated by PCR. For this, two templates were generated by total gene synthesis (performed by GenScript, Piscataway, N.J., USA). On one hand, a synthetic construct was generated comprising the $V_H$3-30 gene segment cloned into the EcoRV site of pUC57, pUC57_V$_H$3-30 (SEQ ID NO:49); on the other hand, a synthetic construct was generated comprising the J$_H$4 gene segment cloned into the EcoRV site of pUC57, pUC57_J$_H$4 (SEQ ID NO:50).

A first linear DNA comprising the V$_H$3-30 gene segment was PCR amplified from pUC57_V$_H$3-30 using the primers V$_H$3-30-F (5'-GAT ATC CAA TGC GGC CGC ATG-3') and HCDR3-B (5'-CGC ACA GTA ATA CAC AGC CGT G-3'). Additional linear DNA molecules comprising the randomized HCDR3 regions Ala-Lys/Arg-(NNK)$_4$-Asp-NNK, Ala-Lys/Arg-(NNK)$_6$-Asp-NNK, Ala-Lys/Arg-(NNK)$_8$-Asp-NNK, or Ala-Lys/Arg-(NNK)$_{10}$-Asp-NNK fused to the J$_H$4 gene segment were amplified from pUC57_JH4 using, respectively, the primers HCDR3-NNK4-F (5'-CAC GGC TGT GTA TTA CTG TGC GAR GNN KNN KNN KNN KGA CNN KTG GGG CCA AGG AAC CCT GGT C-3'), HCDR3-NNK6-F (5'-CAC GGC TGT GTA TTA CTG TGC GAR GNN KNN KNN KNN KNN KNN KGA CNN KTG GGG CCA AGG AAC CCT GGT C-3'), HCDR3-NNK8-F (5'-CAC GGC TGT GTA TTA CTG TGC GAR GNN KNN KNN KNN KNN KNN KNN KNN KGA CNN KTG GGG CCA AGG AAC CCT GGT C-3'), or HDR3-NNK10-F (5'-CAC GGC TGT GTA TTA CTG TGC GAR GNN KNN KNN KNN KNN KNN KNN KNN KNN KNN KGA CNN KTG GGG CCA AGG AAC CCT GGT C-3') in combination with the primer pUC57-3 (5'-CAG GTT TCC CGA CTG GAA AG-3'). To prevent introduction of a sequence bias due to priming of the randomized region of the primers HCDR3-NNK4-F, HCDR3-NNK6-F, HCDR3-NNK8-F and HCDR3-NNK10-F on pUC57_J$_H$4, the plasmid was first linearized by digestion with the restriction enzyme DrdI (FIG. 17B).

The resulting V$_H$3-30 PCR product (SEQ ID NO:51) displayed an overlap of 22 bp with the NNK4-J$_H$4, NNK6-J$_H$4, NNK8-J$_H$4 and NNK10-J$_H$4 PCR products (SEQ ID NO:52 to 55), and was assembled with each by PCR overlap extension in 4 separate reactions, using the primers V$_H$3-30-F and pUC57-3. The resulting DNA molecules comprised the V$_H$ library flanked by NotI and NheI restriction sites as shown in FIG. 16. All PCR amplicons obtained from the PCRs employing the NNK4-J$_H$4, NNK6-J$_H$4, NNK8-J$_H$4 and NNK10-J$_H$4 degenerate oligos were subjected to direct DNA sequencing, and it was confirmed that the designed randomization of the HCDR3 positions was obtained, as expected. This is shown by way of example in FIG. 18 (B), where the electropherogram of the region spanning the HCDR3 is provided. The randomized positions show expected sequence peak overlays demonstrating the nucleotide diversity in these positions (FIG. 18). The 4 different V$_H$ library DNAs were mixed in equimolar ratio, digested with the restriction endonucleases Nod and NheI and cloned into the PiggyBac-transposable vector pPB-EGFP_HC-gamma1 (SEQ ID NO:22), upstream of the gamma1 heavy chain constant region, resulting in a library consisting of 3.7×10$^7$ independent clones. The size of this library can easily be increased by a factor 10 bp scaling up the ligation reaction.

Heavy chain libraries incorporating distinct randomization designs, or comprising V$_H$ and J$_H$ gene segments other than the ones used in this example, can be produced the same way.

DNA Sequences Referred to in this Example 13:
SEQ ID NO:49 (pUC57_VH3-30)
SEQ ID NO:50 (pUC57_J$_H$4)
SEQ ID NO:51 (V$_H$3-30 PCR product)
SEQ ID NO:52 (NNK4-J$_H$4 PCR product)
SEQ ID NO:53 (NNK6-J$_H$4 PCR product)
SEQ ID NO:54 (NNK8-J$_H$4 PCR product)
SEQ ID NO:55 (NNK10-J$_H$4 PCR product)

Example 14: Identification of Variable Light and Heavy Chain Coding Regions from Antigen-Reactive, Enriched and Stably Transposed Host Cells Due to the stable integration of the transposable expression vectors encoding antibody heavy and light chains in the host, the variable heavy and light chain coding regions can be re-isolated in a straightforward way by standard PCR amplification followed by direct sequencing of the PCR amplicons or, upon re-cloning, from re-cloned plasmid vectors. For this, isolated cells or cell clones, expressing antigen-specific antibodies are centrifuged for 5 minutes at 1200×g. Total RNA is isolated from these cells using TRIzol reagent (Sigma-Aldrich). First strand cDNA can be synthesized with PowerScript (Clontech-Life Technologies) using an oligo-dT primer. The light chain coding regions can then amplified by PCR using the primers SP-F (5'-GAG GAG GAG GCG GCC GCC ATG AAT TTT GGA C-3') and CK-rev (5'-GAG GAG GAG TTC GAA AGC GCT AAC ACT CTC-3'), which will result in a PCR amplicon of ca. 740 bp, depending on length of the V-kappa region contained in the PCR amplicon. If desired, this PCR amplicon can be digested with restriction endonucleases NotI and BstBI, and cloned into the vector pPB-EGFP_HC-g1 (SEQ ID NO:22), in order to subclone individual clones of the PCR amplicon for further sequence identification. Individual V-kappa region clones can then be subjected to sequencing using the primer pPB-seq13 (5'-GGC CAG CTT GGC ACT TGA TG-3'), binding in the EF1-alpha promoter, upstream of the cloned V-coding region.

The heavy chain variable regions can be PCR amplified on cDNA, generated as above, using the primers SP-F (5'-GAG GAG GAG GCG GCC GCC ATG AAT TTT GGA C-3') and CG-revseq-1 (5'-GTT CGG GGA AGT AGT CCT TG-3') that will result in a PCR amplicon of ca. 530 bp expected size, depending in the length of the V$_H$-region contained in the PCR amplicon. If desired, this PCR amplicon can be digested with restriction endonucleases NotI and NheI, and cloned into the vector pPB-EGFP_HC-g1 (SEQ ID NO:22). Individual clones are then subjected to sequencing of the V$_H$-region using the primer pPB-seq13 (5'-GGC CAG CTT GGC ACT TGA TG-3'), binding in the EF1-alpha promoter, upstream of the cloned V-coding region.

EXEMPLARY EMBODIMENTS OF THE INVENTION

Embodiment A1

A method for identifying a polypeptide having a desired binding specificity or functionality, comprising:
(i) generating a diverse collection of polynucleotides encoding polypeptides having different binding specificities or functionalities, wherein said polynucleotides comprise a sequence coding for a polypeptide disposed between first and second inverted terminal repeat sequences that are recognized by and functional with a least one transposase enzyme;
(ii) introducing the diverse collection of polynucleotides of (i) into host cells;
(iii) expressing at least one transposase enzyme functional with said inverted terminal repeat sequences in said host cells so that said diverse collection of polynucleotides is integrated into the host cell genome to provide a host cell population that expresses said diverse collection of polynucleotides encoding polypeptides having different binding specificities or functionalities;
(iv) screening said host cells to identify a host cell expressing a polypeptide having a desired binding specificity or functionality; and
(v) isolating the polynucleotide sequence encoding said polypeptide from said host cell.

Embodiment A2

A method according to Embodiment A1, wherein said polynucleotides are DNA molecules.

Embodiment A3

A method according to Embodiment A1, wherein said polynucleotides comprise a ligand-binding sequence of a receptor or a target-binding sequence of a binding molecule.

Embodiment A4

A method according to Embodiment A1, wherein said polynucleotides comprise an antigen-binding sequence of an antibody.

Embodiment A5

A method according to Embodiment A1, wherein said polynucleotides comprise a sequence encoding a VH or VL region of an antibody, or an antigen-binding fragment thereof.

Embodiment A6

A method according to Embodiment A1, wherein said polynucleotides comprise a sequence encoding an antibody VH region and an antibody VL region.

Embodiment A7

A method according to Embodiment A1, wherein said polynucleotides comprise a sequence encoding a full-length immunoglobulin heavy chain or light chain, or an antigen-binding fragment thereof.

Embodiment A8

A method according to Embodiment A1, wherein said polynucleotides comprise a sequence encoding a single-chain Fv or a Fab domain.

Embodiment A9

A method according to Embodiment A1, wherein generating said diverse collection of polynucleotides comprises subjecting V region gene sequences to PCR under mutagenizing conditions.

Embodiment A10

A method according to Embodiment A1, wherein generating said diverse collection of polynucleotides comprises gene synthesis.

Embodiment A11

A method according to Embodiment A1, wherein generating said diverse collection of polynucleotides comprises PCR amplification of V region repertoires from vertebrate B cells.

Embodiment A12

A method according to Embodiment A1, wherein said diverse collection of polynucleotides comprises plasmid vectors.

Embodiment A13

A method according to Embodiment A1, wherein said diverse collection of polynucleotides comprises double-stranded DNA PCR amplicons.

Embodiment A14

A method according to Embodiment A4, wherein said antigen-binding sequence is of a vertebrate.

Embodiment A15

A method according to Embodiment A4, wherein said antigen-binding sequence is mammalian.

Embodiment A16

A method according to Embodiment A4, wherein said antigen-binding sequence is human.

Embodiment A17

A method according to Embodiment A12, wherein said plasmid vectors further encode a marker gene.

Embodiment A18

A method according to Embodiment A17, wherein said marker is selected from the group consisting of: a fluorescent marker, a cell surface marker and a selectable marker.

Embodiment A19

A method according to Embodiment A17, wherein said marker gene sequence is upstream or downstream of the sequence encoding the polypeptide having a binding specificity or functionality, but between the inverted terminal repeat sequences.

Embodiment A20

A method according to Embodiment A17, wherein said marker gene sequence is downstream of said sequence encoding a polypeptide having binding specificity or functionality and separated by an internal ribosomal entry site.

Embodiment A21

A method according to Embodiment A1, wherein step (ii) comprises introducing into said host cells polynucleotides comprising sequences encoding immunoglobulin VH or VL regions, or antigen-binding fragments thereof, and wherein said VH and VL region sequences are encoded on separate vectors.

Embodiment A22

A method according to Embodiment A21, wherein step (ii) comprises introducing into said host cells polynucleotides comprising sequences encoding full-length immunoglobulin heavy or light chains, or antigen-binding fragments thereof, wherein said full-length heavy and light chain sequences are on separate vectors.

Embodiment A23

A method according to Embodiment A21, wherein said vectors comprising VH sequences and said vectors comprising VL sequences are introduced into said host cells simultaneously.

Embodiment A24

A method according to Embodiment A21, wherein said vectors comprising VH sequences and said vectors comprising VL sequences are introduced into said host cells sequentially.

Embodiment A25

A method according to Embodiment A1, wherein step (ii) comprises introducing into said host cells a vector comprising sequences encoding antibody VH and VL chains.

Embodiment A26

A method according to Embodiment A1, wherein step (ii) comprises introducing into said host cells a vector comprising sequences encoding a full-length immunoglobulin heavy chain and a full-length immunoglobulin light chain.

Embodiment A27

A method according to Embodiment A21, wherein said vector comprising the VH sequence comprises inverted terminal repeat sequences that are recognized by a different transposase enzyme than the inverted terminal repeat sequences in the vector comprising the VL sequence.

Embodiment A28

A method according to Embodiment A1, wherein the host cells of step (ii) are vertebrate cells.

Embodiment A29

A method according to Embodiment A28, wherein said host cells are mammalian.

Embodiment A30

A method according to Embodiment A29, wherein said host cells are human or rodent cells.

Embodiment A31

A method according to Embodiment A28, wherein said vertebrate host cells are lymphoid cells.

Embodiment A32

A method according to Embodiment A31, wherein said host cells are B cells.

Embodiment A33

A method according to Embodiment A32, wherein said host cells are progenitor B cells or precursor B cells.

Embodiment A34

A method according to Embodiment A33, wherein said host cells are selected from the group consisting of: Abelson-Murine Leukemia virus transformed progenitor B cells or precursor B cells and early, immunoglobulin-null EBV transformed human proB and preB cells.

Embodiment A35

A method according to Embodiment A32, wherein said host cells are selected from the group consisting of: Sp2/0 cells, NSO cells, X63 cells, and Ag8653 cells.

Embodiment A36

A method according to Embodiment A29, wherein said host cells are selected from the group consisting of: CHO cells, Per.C6 cells, BHK cells, and 293 cells.

Embodiment A37

A method according to Embodiment A1, wherein said expressing step (iii) comprises introducing into said host cells an expression vector encoding a transposase enzyme that recognizes and is functional with an least one inverted terminal repeat sequence.

Embodiment A38

A method according to Embodiment A37, wherein said vector encoding said transposase enzyme is introduced into said host cells concurrently with or prior or subsequent to the diverse collection of polynucleotides.

Embodiment A39

A method according to Embodiment A37, wherein said transposase enzyme is transiently expressed in said host cell.

Embodiment A40

A method according to Embodiment A1, wherein said expressing step (iii) comprises inducing an inducible expression system that is stably integrated into the host cell genome.

Embodiment A41

A method according to Embodiment A40, wherein said inducible expression system is tetracycline-inducible or tamoxifen-inducible.

Embodiment A42

A method according to Embodiment A1, wherein said screening step (iv) comprises magnetic activated cell sorting (MACS), fluorescence activated cell sorting (FACS), panning against molecules immobilized on a solid surface panning, selection for binding to cell-membrane associated molecules incorporated into a cellular, natural or artificially reconstituted lipid bilayer membrane, or high-throughput screening of individual cell clones in multi-well format for a desired functional or binding phenotype.

Embodiment A43

A method according to Embodiment A1, wherein said screening step (iv) comprises screening to identify polypeptides having a desired target-binding specificity or functionality.

Embodiment A44

A method according to Embodiment A1, wherein said screening step (iv) comprises screening to identify antigen-binding molecules having a desired antigen specificity.

Embodiment A45

A method according to Embodiment A44, wherein said screening step further comprises screening to identify antigen-binding molecules having one or more desired functional properties.

Embodiment A46

A method according to Embodiment A1, wherein said screening step (iv) comprises multiple cell enrichment cycles with host cell expansion between individual cell enrichment cycles.

Embodiment A47

A method according to Embodiment A1, wherein said step (v) of isolating the polynucleotide sequence encoding the polypeptide having a desired binding specificity or functionality comprises genomic or RT-PCR amplification or next-generation deep sequencing.

Embodiment A48

A method according to Embodiment A1, further comprising (vi) affinity optimizing the polynucleotide sequence obtained in (v).

Embodiment A49

A method according to Embodiment A48, wherein said affinity optimization comprises genomic PCR or RT-PCR under mutagenizing conditions.

Embodiment A50

A method according to Embodiment A49, further comprising subjecting the mutagenized sequences to steps (i)-(v) of Embodiment A1.

Embodiment A51

A method according to Embodiment A1, wherein said inverted terminal repeat sequences are from the PiggyBac transposon system.

Embodiment A52

A method according to Embodiment A51, wherein the sequence encoding the upstream PiggyBac inverted terminal repeat sequence comprises SEQ ID NO:1.

Embodiment A53

A method according to Embodiment A51, wherein the sequence encoding the downstream PiggyBac inverted terminal repeat sequence comprises SEQ ID NO:2.

Embodiment A54

A method according to Embodiment A5, wherein said VH or VL region sequences encode a sequence derived from a human anti-TNF alpha antibody.

Embodiment A55

A method according to Embodiment A54, wherein said human anti-TNF alpha antibody is D2E7.

Embodiment A56

A method according to Embodiment A55, wherein the VH and VL regions of D2E7 are encoded by separate transposable vectors.

Embodiment A57

A method according to Embodiment A56, wherein said vector comprising said VL region sequence comprises SEQ ID NO:5.

Embodiment A58

A method according to Embodiment A56, wherein said vector comprising said VH region sequence comprises SEQ ID NO:8.

Embodiment A59

A method according to Embodiment A56, wherein said vector comprising said VH region sequence comprises a randomized sequence as set forth in SEQ ID NO:9.

Embodiment A60

A method according to Embodiment A56, wherein said vector comprising said VL region sequence comprises a randomized sequence as set forth in SEQ ID NO:10.

Embodiment A61

A method according to Embodiment A1, wherein step (iii) comprises introducing into said host cell a vector comprising a sequence encoding a functional PiggyBac transposase.

Embodiment A62

A method according to Embodiment A61, wherein said vector comprises SEQ ID NO:11.

Embodiment A63

A method according to Embodiment A61, wherein said vector encodes SEQ ID NO:12, or a sequence with at least 95% amino acid sequence homology and having the same or similar inverted terminal repeat sequence specificity.

Embodiment A64

A method according to Embodiment A1, wherein said inverted terminal repeat sequences are recognized by and functional with at least one transposase selected from the group consisting of: PiggyBac, Sleeping Beauty, Frog Prince, Himar1, Passport, Minos, hAT, Tol1, Tol2, Ac/Ds, PIF, Harbinger, Harbinger3-DR, and Hsmar1.

Embodiment B65

A library of polynucleotide molecules encoding polypeptides having different binding specificities or functionalities, comprising a plurality of polynucleotide molecules, wherein said polynucleotide molecules comprise a sequence encoding a polypeptide having a binding specificity or functionality disposed between inverted terminal repeat sequences that are recognized by and functional with at least one transposase enzyme.

Embodiment B66

A library according to Embodiment B65, wherein said polynucleotides are DNA molecules.

Embodiment B67

A library according to Embodiment B65, wherein said polynucleotides comprise a ligand-binding sequence of a receptor or a target-binding sequence of a binding molecule.

Embodiment B68

A library according to Embodiment B65, wherein said polynucleotides comprise at least one sequence encoding an antigen-binding sequence of an antibody.

Embodiment B69

A library according to Embodiment B65, wherein said polynucleotides comprise a sequence encoding a VH or VL region of an antibody or an antigen-binding fragment thereof.

Embodiment B70

A library according to Embodiment B65, wherein said polynucleotides comprise a sequence encoding an antibody VH region and an antibody VL region.

Embodiment B71

A library according to Embodiment B65, wherein said polynucleotides comprise a sequence encoding a full-length immunoglobulin heavy chain or light chain, or an antigen-binding fragment thereof.

Embodiment B72

A library according to Embodiment B65, wherein said polynucleotides comprise a sequence encoding a single-chain Fv or a Fab domain.

Embodiment B73

A library according to Embodiment B65, wherein said polynucleotide molecules are plasmids.

Embodiment B74

A library according to Embodiment B65, wherein said polynucleotide molecules are double stranded DNA PCR amplicons.

Embodiment B75

A library according to Embodiment B73, wherein said plasmids further comprise a sequence encoding a marker gene.

Embodiment B76

A library according to Embodiment B73, wherein said plasmids further comprise a sequence encoding a transposase enzyme that recognizes and is functional with the inverted terminal repeat sequences.

Embodiment C77

A method for generating a library of transposable polynucleotides encoding polypeptides having different binding specificities or functionality, comprising:
(i) generating a diverse collection of polynucleotides comprising sequences encoding polypeptides having different binding specificities or functionalities, wherein said polynucleotides comprise a sequence encoding polypeptide having a binding specificity or functionality disposed between inverted terminal repeat sequences that are recognized by and functional with a least one transposase enzyme.

Embodiment D78

A vector comprising a sequence encoding a VH or VL region of an antibody, or antigen-binding portion thereof, disposed between inverted terminal repeat sequences that are recognized by and functional with at least one transposase enzyme.

Embodiment D79

A vector according to Embodiment D78, comprising a sequence encoding a full-length heavy or light chain of an immunoglobulin.

Embodiment D80

A vector according to Embodiment D78, wherein said VH or VL region sequence is randomized.

Embodiment D81

A vector according to Embodiment D78, wherein said inverted terminal repeat sequences are recognized by and functional with the PiggyBac transposase.

Embodiment D82

A vector according to Embodiment D78, wherein said VH or VL region sequence is derived from an anti-TNF alpha antibody.

Embodiment D83

A vector according to Embodiment D82, wherein said antibody is D2E7.

Embodiment D84

A vector according to Embodiment D78, comprising at least one sequence selected from the group consisting of: SEQ ID NO:5, SEQ ID NO:8, SEQ ID NO:9, SEQ ID NO:10, SEQ ID NO:11, SEQ ID NO:13, SEQ ID NO:16, SEQ ID NO:17, and SEQ ID NO:19.

Embodiment D85

A host cell comprising a vector according to any one of Embodiments D78-D84.

Embodiment D86

A host cell according to Embodiment D85 further comprising an expression vector comprising a sequence encoding a transposase that recognizes and is functional with at least one inverted terminal repeat sequence in the vector encoding said VH or VL region sequence.

Embodiment E87

An antibody produced by a method according to Embodiment A1.

Embodiment E88

A method according to Embodiment A1, wherein said inverted terminal repeat sequences are from the Sleeping Beauty transposon system.

Embodiment E89

A method according to Embodiment A88, wherein the sequence encoding the upstream Sleeping Beauty inverted terminal repeat sequence comprises SEQ ID NO:14.

Embodiment E90

A method according to Embodiment A88, wherein the sequence encoding the downstream Sleeping Beauty inverted terminal repeat sequence comprises SEQ ID NO:15.

Embodiment E91

A method according to Embodiment A88, wherein step (iii) comprises expressing in said host cell a vector comprising a functional Sleeping Beauty transposase.

Embodiment A92

A method according to Embodiment A48, wherein said polynucleotide sequence obtained in (v) comprises a sequence encoding a VH or VL region of an antibody, or an antigen-binding fragment thereof, and wherein said antibody optimization comprises introducing one or more mutations into a complementarity determining region or framework region of said VH or VL.

Embodiment B93

A library according to Embodiment B71, wherein said full-length immunoglobulin heavy chain comprises the natural intron/exon structure of an antibody heavy chain.

Embodiment B94

A library according to Embodiment B93, wherein said full-length immunoglobulin heavy chain comprises the endogenous membrane anchor domain.

Embodiment F95

A method for generating a population of host cells capable of expressing polypeptides having different binding specificities or functionalities, comprising:
(i) generating a diverse collection of polynucleotides comprising sequences encoding polypeptides having different binding specificities or functionalities, wherein said polynucleotides comprise a sequence encoding a polypeptide having a binding specificity or functionality disposed between inverted terminal repeat sequences that are recognized by and functional with a least one transposase enzyme; and
(ii) introducing said diverse collection of polynucleotides into host cells.

Embodiment D96

A vector according to Embodiment D78, wherein said inverted terminal repeat sequences are recognized by and functional with the Sleeping Beauty transposase

Embodiment A97

A method according to Embodiment A91, wherein step (iii) comprises expressing in said host cell a vector comprising SEQ ID NO:17.

Embodiment A98

A method according to Embodiment A91, wherein said vector encodes SEQ ID NO:18, or a sequence with at least 95% amino acid sequence homology and having the same or similar inverted terminal repeat sequence specificity.

---

What is claimed is:

1. A method of obtaining an antibody or Fab, $Fab_2$ or $F_V$ fragment thereof having a desired target or epitope binding specificity, comprising:

(i) generating a diverse collection of polynucleotides encoding at least $10^2$ unique antibodies or fragments thereof having different target or epitope binding specificities, each encoding polynucleotide disposed between first and second inverted terminal repeat sequences that are recognized by and functional with a least one transposase enzyme;

(ii) introducing the diverse collection of polynucleotides of (i) into vertebrate host cells;

(iii) expressing at least one transposase enzyme functional with said inverted terminal repeat sequences in said vertebrate host cells so that said diverse collection of polynucleotides is integrated into the vertebrate host cell genomes to provide a vertebrate host cell population that expresses said antibodies or fragments thereof having different target or epitope binding specificities;

(iv) screening said vertebrate host cells to identify a vertebrate host cell expressing an antibody or fragment thereof having a desired target or epitope binding specificity; and (v) isolating the polynucleotide sequence encoding said antibody or fragment thereof identified in step (iv) from said vertebrate host cell, wherein the polynucleotides of the diverse collection of polynucleotides of step (ii) encode (a) immunoglobulin $V_H$ and $V_L$ regions, or antigen-binding fragments thereof, wherein said $V_H$ and $V_L$ region sequences are encoded on separate vectors, or (b) full-length immunoglobulin heavy and light chains, or antigen-binding fragments thereof, wherein said full-length heavy and light chain sequences are encoded on separate vectors, and wherein (a) said inverted terminal repeat sequences are from the PiggyBac transposon system or the Sleeping Beauty transposon system, and/or (b) step (iii) comprises introducing into said host cells a vector comprising a sequence encoding a functional PiggyBac transposase or Sleeping Beauty transposase.

2. A method according to claim 1, wherein generating said diverse collection of polynucleotides comprises subjecting $V_H$ and/or $V_L$ region gene sequences to PCR under mutagenizing conditions.

3. A method according to claim 1, wherein said expressing step (iii) comprises introducing into said host cells an expression vector encoding a transposase enzyme that recognizes and is functional with at least one inverted terminal repeat sequence, wherein said transposase enzyme is transiently expressed in said host cells.

4. A method according to claim 1, wherein said screening step (iv) comprises: magnetic activated cell sorting (MACS), fluorescence activated cell sorting (FACS), panning against molecules immobilized on a solid surface, selection for binding to cell-membrane associated molecules incorporated into a cellular, natural or artificially reconstituted lipid bilayer membrane, or high-throughput screening of individual cell clones in a multi-well format for a desired target or epitope binding phenotype.

5. A method according to claim 1, wherein said step (v) of isolating the polynucleotide sequence encoding the antibody or fragment thereof having a desired target or epitope binding specificity or functionality comprises genomic or RT-PCR amplification or next-generation deep sequencing.

6. A method of making a library of polynucleotide molecules encoding at least $10^2$ unique antibodies or Fab, $Fab_2$, or Fv fragments thereof having different target or epitope binding specificities, comprising:

generating a diverse collection of polynucleotides comprising sequences encoding antibodies or Fab, $Fab_2$ or Fv fragments thereof having different target or epitope binding specificities each encoding polynucleotide disposed between inverted terminal repeat sequences that are recognized by and functional with a least one transposase enzyme wherein the polynucleotides of the diverse collection of polynucleotides encode (a) immunoglobulin $V_H$ and $V_L$ regions, or antigen-binding fragments thereof, wherein said $V_H$ and $V_L$ region sequences are encoded on separate vectors, or (b) full-length immunoglobulin heavy and light chains, or antigen-binding fragments thereof, wherein said full-length heavy and light chain sequences are encoded on separate vectors; and wherein said inverted terminal repeat sequences are from the PiggyBac transposon system or the Sleeping Beauty transposon system.

7. A method for generating a population of host cells capable of expressing antibodies or Fab, $Fab_2$, or Fv fragments thereof having different target or epitope binding specificities or functionalities, comprising:

(i) generating a diverse collection of polynucleotides comprising sequences encoding antibodies or fragments thereof having different target or epitope binding specificities, each encoding polynucleotide disposed between inverted terminal repeat sequences that are recognized by and functional with a least one transposase enzyme; and (ii) introducing said diverse collection of polynucleotides into the vertebrate host cells, wherein the polynucleotides of the diverse collection of polynucleotides encode (a) immunoglobulin $V_H$ and $V_L$ regions, or antigen-binding fragments thereof, wherein said $V_H$ and $V_L$ region sequences are encoded on separate vectors, or (b) full-length immunoglobulin heavy and light chains, or antigen-binding fragments thereof, wherein said full-length heavy and light chain sequences are encoded on separate vectors;

and wherein said inverted terminal repeat sequences are from the PiggyBac transposon system or the Sleeping Beauty transposon system.

\* \* \* \* \*

SEQUENCE LISTING

<160> NUMBER OF SEQ ID NOS: 55

<210> SEQ ID NO 1
<211> LENGTH: 327
<212> TYPE: DNA
<213> ORGANISM: Artificial sequence
<220> FEATURE:
<223> OTHER INFORMATION: PiggyBac ITR sequence

<400> SEQUENCE: 1

```
atatcaattg ttaaccctag aaagatagtc tgcgtaaaat tgacgcatgc attcttgaaa    60
tattgctctc tctttctaaa tagcgcgaat ccgtcgctgt gcatttagga catctcagtc   120
gccgcttgga gctcccgtga ggcgtgcttg tcaatgcggt aagtgtcact gattttgaac   180
tataacgacc gcgtgagtca aaatgacgca tgattatctt ttacgtgact tttaagattt   240
aactcatacg ataattatat tgttatttca tgttctactt acgtgataac ttattatata   300
tatattttct tgttatacaa ttgatat                                       327
```

<210> SEQ ID NO 2
<211> LENGTH: 264
<212> TYPE: DNA
<213> ORGANISM: Artificial Sequence
<220> FEATURE:
<223> OTHER INFORMATION: downstream PiggyBac ITR sequence

<400> SEQUENCE: 2

```
atatctcgag ttaaccctag aaagataatc atattgtgac gtacgttaaa gataatcatg    60
cgtaaaattg acgcatgtgt tttatcggtc tgtatatcga ggtttattta ttaatttgaa   120
tagatattaa gttttattat atttacactt acatactaat aataaattca acaaacaatt   180
tatttatgtt tatttattta ttaaaaaaaa acaaaaactc aaaatttctt ctataaagta   240
acaaaacttt tatcctcgag atat                                         264
```

<210> SEQ ID NO 3
<211> LENGTH: 711
<212> TYPE: DNA
<213> ORGANISM: Artificial Sequence
<220> FEATURE:
<223> OTHER INFORMATION: V region of D2E7

<400> SEQUENCE: 3

```
atggacatga gggtccctgc tcagctcctg ggactcctgc tgctctggct cccaggtgcc    60
agatgtgaca tccagatgac ccagtctcca tcctccctgt ctgcatctgt aggggacaga   120
gtcaccatca cttgtcgggc aagtcagggc atcagaaatt acttagcctg gtatcagcaa   180
aaaccaggga agcccctaag ctcctgatct atgctgcatc cactttgcaa tcaggggtc   240
ccatctcggt tcagtggcag tggatctggg acagatttca ctctcaccat cagcagccta   300
cagcctgaag atgttgcaac ttattactgt caaaggtata accgtgcacc gtatactttt   360
ggccagggga ccaaggtgga atcaagcgc tctgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta a            711
```

<210> SEQ ID NO 4
<211> LENGTH: 236
<212> TYPE: PRT
<213> ORGANISM: Artificial Sequence
<220> FEATURE:
<223> OTHER INFORMATION: Protein sequence of V region of D2E7

<400> SEQUENCE: 4

Met Asp Met Arg Val Pro Ala Gln Leu Leu Gly Leu Leu Leu Leu Trp
1               5                   10                  15

Leu Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Tyr Leu Ala Trp Tyr Gln Gln Lys Pro Gly Lys
    50                  55                  60

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Val Ala Thr Tyr Tyr Cys Gln Arg
            100                 105                 110

Tyr Asn Arg Ala Pro Tyr Thr Phe Gly Gln Gly Thr Lys Val Glu Ile
        115                 120                 125

Lys Arg Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 5
<211> LENGTH: 6436
<212> TYPE: DNA
<213> ORGANISM: Artificial Sequence
<220> FEATURE:
<223> OTHER INFORMATION: pIRES-EGFP-T1T2-IgL

<400> SEQUENCE: 5
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgttaa ccctagaaag     180
atagtctgcg taaaattgac gcatgcattc ttgaaatatt gctctctctt tctaaatagc     240
gcgaatccgt cgctgtgcat ttaggacatc tcagtcgccg cttggagctc ccgtgaggcg     300
tgcttgtcaa tgcggtaagt gtcactgatt ttgaactata acgaccgcgt gagtcaaaat     360
gacgcatgat tatcttttac gtgactttta agatttaact catacgataa ttatattgtt     420
atttcatgtt ctacttacgt gataacttat tatatatata ttttcttgtt atacaattgc     480
atgaagaatc tgcttagggt taggcgtttt gcgctgcttc gcgatgtacg ggccagatat     540
acgcgttgac attgattatt gactagttat taatagtaat caattacggg gtcattagtt     600
catagcccat atatggagtt ccgcgttaca taacttacgg taaatggccc gcctggctga     660
ccgcccaacg acccccgccc attgacgtca ataatgacgt atgttcccat agtaacgcca     720

```
ataggqactt  tccattgacg  tcaatgggtg  gactatttac  ggtaaactgc  ccacttggca   780
gtacatcaag  tgtatcatat  gccaagtacg  cccctattg   acgtcaatga  cggtaaatgg   840
cccgcctggc  attatgccca  gtacatgacc  ttatgggact  ttcctacttg  gcagtacatc   900
tacgtattag  tcatcgctat  taccatggtg  atgcggtttt  ggcagtacat  caatgggcgt   960
ggatagcggt  ttgactcacg  gggatttcca  agtctccacc  ccattgacgt  caatgggagt  1020
ttgttttggc  accaaaatca  acgggacttt  ccaaaatgtc  gtaacaactc  cgccccattg  1080
acgcaaatgg  gcggtaggcg  tgtacggtgg  gaggtctata  taagcagagc  tctctggcta  1140
actagagaac  ccactgctta  ctggcttatc  gaaattaata  cgactcacta  tagggagacc  1200
caagcttggt  accgagctcg  gatcgatatg  gacatgaggg  tccctgctca  gctcctggga  1260
ctcctgctgc  tctggctccc  aggtgccaga  tgtgacatcc  agatgaccca  gtctccatcc  1320
tccctgtctg  catctgtagg  ggacagagtc  accatcactt  gtcgggcaag  tcagggcatc  1380
agaaattact  tagcctggta  tcagcaaaaa  ccagggaaag  cccctaagct  cctgatctat  1440
gctgcatcca  ctttgcaatc  aggggtccca  tctcggttca  gtggcagtgg  atctgggaca  1500
gatttcactc  tcaccatcag  cagcctacag  cctgaagatg  ttgcaactta  ttactgtcaa  1560
aggtataacc  gtgcaccgta  acttttggc  caggggacca  aggtggaaat  caagcgctct  1620
gtggctgcac  catctgtctt  catcttcccg  ccatctgatg  agcagttgaa  atctggaact  1680
gcctctgttg  tgtgcctgct  gaataacttc  tatcccagag  aggccaaagt  acagtggaag  1740
gtggataacg  ccctccaatc  gggtaactcc  caggagagtg  tcacagagca  ggacagcaag  1800
gacagcacct  acagcctcag  cagcaccctg  acgctgagca  aagcagacta  cgagaaacac  1860
aaagtctacg  cctgcgaagt  cacccatcag  ggcctgagct  cgcccgtcac  aaagagcttc  1920
aacaggggag  agtgttaaat  ctgcggccgc  gtcgacggaa  ttcagtggat  ccactagtaa  1980
cggccgccag  tgtgctggaa  ttaattcgct  gtctgcgagg  ccagctgtt   ggggtgagta  2040
ctccctctca  aaagcgggca  tgacttctgc  gctaagattg  tcagtttcca  aaaacgagga  2100
ggatttgata  ttcacctggc  ccgcggtgat  gcctttgagg  gtggccgcgt  ccatctggtc  2160
agaaaagaca  atcttttgt   tgtcaagctt  gaggtgtggc  aggcttgaga  tctggccata  2220
cacttgagtg  acaatgacat  ccactttgcc  tttctctcca  caggtgtcca  ctcccaggtc  2280
caactgcagg  tcgagcatgc  atctagggcg  gccaattccg  cccctctccc  tcccccccc   2340
ctaacgttac  tggccgaagc  cgcttggaat  aaggccggtg  tgcgtttgtc  tatatgtgat  2400
tttccaccat  attgccgtct  tttggcaatg  tgagggcccg  gaaacctggc  cctgtcttct  2460
tgacgagcat  tcctaggggt  cttcccctc   tcgccaaagg  aatgcaaggt  ctgttgaatg  2520
tcgtgaagga  agcagttcct  ctggaagctt  cttgaagaca  acaacgtct   gtagcgaccc  2580
tttgcaggca  gcggaacccc  ccacctggcg  acaggtgcct  ctgcggccaa  aagccacgtg  2640
tataagatac  acctgcaaag  gcggcacaac  cccagtgcca  cgttgtgagt  tggatagttg  2700
tggaaagagt  caaatggctc  tcctcaagcg  tattcaacaa  ggggctgaag  gatgcccaga  2760
aggtacccca  ttgtatggga  tctgatctgg  ggcctcggtg  cacatgcttt  acatgtgttt  2820
agtcgaggtt  aaaaaacgt   ctaggccccc  gaaccacgg   ggacgtggtt  ttcctttgaa  2880
aaacacgatg  ataagcttgc  cacaacccgg  gatccaccgg  tcgccaccat  ggtgagcaag  2940
ggcgaggagc  tgttcaccgg  ggtggtgccc  atcctggtcg  agctggacgg  cgacgtaaac  3000
ggccacaagt  tcagcgtgtc  cggcgagggc  gagggcgatg  ccacctacgg  caagctgacc  3060
ctgaagttca  tctgcaccac  cggcaagctg  cccgtgccct  ggcccaccct  cgtgaccacc  3120
```

```
ctgacctacg gcgtgcagtg cttcagccgc tacccgacc acatgaagca gcacgacttc   3180
ttcaagtccg ccatgcccga aggctacgtc caggagcgca ccatcttctt caaggacgac   3240
ggcaactaca agacccgcgc cgaggtgaag ttcgagggcg acaccctggt gaaccgcatc   3300
gagctgaagg gcatcgactt caaggaggac ggcaacatcc tggggcacaa gctggagtac   3360
aactacaaca gccacaacgt ctatatcatg gccgacaagc agaagaacgg catcaaggtg   3420
aacttcaaga tccgccacaa catcgaggac ggcagcgtgc agctcgccga ccactaccag   3480
cagaacaccc ccatcggcga cggccccgtg ctgctgcccg acaaccacta cctgagcacc   3540
cagtccgccc tgagcaaaga ccccaacgag aagcgcgatc acatggtcct gctggagttc   3600
gtgaccgccg ccgggatcac tctcggcatg gacgagctgt acaagtaaag cggccctaga   3660
gctcgctgat cagcctcgac tgtgccttcta gttgccagcc atctgttgtt tgcccctccc   3720
ccgtgccttc cttgaccctg gaaggtgcca ctcccactgt cctttcctaa taaaatgagg   3780
aaattgcatc gcattgtctg agtaggtgtc attctattct ggggggtggg gtggggcagg   3840
acagcaaggg ggaggattgg gaagacaata gcaggcatgc tggggatgcg gtgggctcta   3900
tggcttctga gcggaaaga accagctggg gctcgaggat aaaagttttg ttactttata   3960
gaagaaattt tgagttttg tttttttta ataataaat aaacataaat aaattgttg   4020 ttgaatttat tattagtatg taagtgtaaa tataataaaa cttaatatct attcaaatta   4080
ataaataaac ctcgatatac agaccgataa acacatgcg tcaattttac gcatgattat   4140
ctttaacgta cgtcacaata tgattatctt tctagggtta actcgagtgc attctagttg   4200
tggtttgtcc aaactcatca atgtatctta tcatgtctgt ataccgtcga cctctagcta   4260
gagcttggcg taatcatggt catagctgtt cctgtgtga aattgttatc cgctcacaat   4320
tccacacaac atacgagccg gaagcataaa gtgtaaagcc tggggtgcct aatgagtgag   4380
ctaactcaca ttaattgcgt tgcgctcact gcccgctttc cagtcgggaa acctgtcgtg   4440
ccagctgcat taatgaatcg gccaacgcgc ggggagaggc ggtttgcgta ttgggcgctc   4500
ttccgcttcc tcgctcactg actcgctgcg ctcggtcgtt cggctgcggc gagcggtatc   4560
agctcactca aaggcggtaa tacggttatc cacagaatca ggggataacg caggaaagaa   4620
catgtgagca aaaggccagc aaaaggccag gaaccgtaaa aaggccgcgt tgctggcgtt   4680
tttccatagg ctccgccccc ctgacagca tcacaaaaat cgacgctcaa gtcagaggtg   4740
gcgaaacccg acaggactat aaagatacca ggcgtttccc cctggaagct ccctcgtgcg   4800
ctctcctgtt ccgaccctgc cgcttaccgg atacctgtcc gcctttctcc cttcgggaag   4860
cgtggcgctt tctcaatgct cacgctgtag gtatctcagt tcggtgtagg tcgttcgctc   4920
caagctgggc tgtgtgcacg aaccccccgt tcagcccgac cgctgcgcct tatccggtaa   4980
ctatcgtctt gagtccaacc cggtaagaca cgacttatcg ccactggcag cagccactgg   5040
taacaggatt agcagagcga ggtatgtagg cggtgctaca gagttcttga agtggtggcc   5100
taactacggc tacactagaa ggacagtatt tggtatctgc gctctgctga agccagttac   5160
cttcggaaaa agagttggta gctcttgatc cggcaaacaa accaccgctg gtagcggtgg   5220
tttttttgtt tgcaagcagc agattacgcg cagaaaaaaa ggatctcaag aagatccttt   5280
gatcttttct acggggtctg acgctcagtg aacgaaaac tcacgttaag ggattttggt   5340
catgagatta tcaaaaagga tcttcaccta gatccttta aattaaaaat gaagttttaa   5400
atcaatctaa agtatatatg agtaaacttg gtctgacagt taccaatgct taatcagtga   5460
```

| | |
|---|---|
| ggcacctatc tcagcgatct gtctatttcg ttcatccata gttgcctgac tccccgtcgt | 5520 |
| gtagataact acgatacggg agggcttacc atctggcccc agtgctgcaa tgataccgcg | 5580 |
| agacccacgc tcaccggctc cagatttatc agcaataaac cagccagccg aagggccga | 5640 |
| gcgcagaagt ggtcctgcaa ctttatccgc ctccatccag tctattaatt gttgccggga | 5700 |
| agctagagta agtagttcgc cagttaatag tttgcgcaac gttgttgcca ttgctacagg | 5760 |
| catcgtggtg tcacgctcgt cgtttggtat ggcttcattc agctccggtt cccaacgatc | 5820 |
| aaggcgagtt acatgatccc ccatgttgtg caaaaaagcg gttagctcct tcggtcctcc | 5880 |
| gatcgttgtc agaagtaagt tggccgcagt gttatcactc atggttatgg cagcactgca | 5940 |
| taattctctt actgtcatgc catccgtaag atgcttttct gtgactggtg agtactcaac | 6000 |
| caagtcattc tgagaatagt gtatgcggcg accgagttgc tcttgcccgg cgtcaatacg | 6060 |
| ggataatacc gcgccacata gcagaacttt aaaagtgctc atcattggaa aacgttcttc | 6120 |
| ggggcgaaaa ctctcaagga tcttaccgct gttgagatcc agttcgatgt aacccactcg | 6180 |
| tgcacccaac tgatcttcag catcttttac tttcaccagc gtttctgggt gagcaaaaac | 6240 |
| aggaaggcaa aatgccgcaa aaaagggaat aagggcgaca cggaaatgtt gaatactcat | 6300 |
| actcttcctt tttcaatatt attgaagcat ttatcagggt tattgtctca tgagcggata | 6360 |
| catatttgaa tgtatttaga aaaataaaca ataggggtt ccgcgcacat ttccccgaaa | 6420 |
| agtgccacct gacgtc | 6436 |

<210> SEQ ID NO 6
<211> LENGTH: 1642
<212> TYPE: DNA
<213> ORGANISM: Artificial Sequence
<220> FEATURE:
<223> OTHER INFORMATION: VH region of D2E7 with restriction sites

<400> SEQUENCE: 6

| | |
|---|---|
| aattatcgat atggagtttg ggctgagctg ggttttcctt gttgcgattt tagaaggtgt | 60 |
| ccagtgtgag gtgcagctgg tggagtctgg gggaggcttg gtacagcccg gcaggtccct | 120 |
| gagactctcc tgtgcggcct ctggattcac ctttgatgat tatgccatgc actgggtccg | 180 |
| gcaagctcca gggaagggcc tggaatgggt ctcagctatc acttggaata gtggtcacat | 240 |
| agactatgcg gactctgtgg agggccgatt caccatctcc agagacaacg ccaagaactc | 300 |
| cctgtatctg caaatgaaca gtctgagagc tgaggatacg gccgtatatt actgtgcgaa | 360 |
| agtctcgtac cttagcaccg cgtcctccct tgactattgg ggccaaggta ccctggtcac | 420 |
| cgtctcgagc gcttccacca agggcccatc ggtcttcccc ctggcaccct cctccaagag | 480 |
| cacctctggg ggcacagcag ccctgggctg cctggtcaag gactacttcc ccgaaccggt | 540 |
| gacggtgtcg tggaactcag gcgccctgac cagcggcgtg cacaccttcc cggctgtcct | 600 |
| acagtcctca ggactctact ccctcagcag cgtggtgacc gtgccctcca gcagcttggg | 660 |
| cacccagacc tacatctgca acgtgaatca caagcccagc aacaccaagg tggacaagaa | 720 |
| agttgagccc aaatcttgtg acaaaactca cacatgccca ccgtgcccag cacctgaact | 780 |
| cctgggggga ccgtcagtct tcctcttccc cccaaaaccc aaggacaccc tcatgatctc | 840 |
| ccggacccct gaggtcacat gcgtggtggt ggacgtgagc cacgaagacc ctgaggtcaa | 900 |
| gttcaactgg tacgtggacg gcgtggaggt gcataatgcc aagacaaagc cgcgggagga | 960 |
| gcagtacaac agcacgtacc gtgtggtcag cgtcctcacc gtcctgcacc aggactggct | 1020 |
| gaatggcaag gagtacaagt gcaaggtctc caacaaagcc ctcccagccc ccatcgagaa | 1080 |

```
aaccatctcc aaagccaaag ggcagccccg agaaccacag gtgtacaccc tgcccccatc    1140
ccgggatgag ctgaccaaga accaggtcag cctgacctgc ctggtcaaag gcttctatcc    1200
cagcgacatc gccgtggagt gggagagcaa tgggcagccg agaacaact  acaagaccac    1260 gcctcccgtg ctggactccg acggctcctt cttcctctac agcaagctca ccgtggacaa    1320
gagcaggtgg cagcagggga acgtcttctc atgctccgtg atgcatgagg ctctgcacaa    1380
ccactacaca cagaagagcc tctccctgtc tccggagctg caactggagg agagctgtgc    1440
ggaggcgcag gacggggagc tggacgggct gtggacgacc atcaccatct tcatcacact    1500
cttcctgtta agcgtgtgct acagtgccac cgtcaccttc ttcaaggtga agtggatctt    1560
ctcctcggtg gtggacctga agcagaccat catccccgac tacaggaaca tgatcggaca    1620
gggggcctag gcggccgcgt cg                                              1642
```

<210> SEQ ID NO 7
<211> LENGTH: 539
<212> TYPE: PRT
<213> ORGANISM: Artificial Sequence
<220> FEATURE:
<223> OTHER INFORMATION: Protein sequence translated from Seq ID No 6

<400> SEQUENCE: 7

```
Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255
```

```
Leu Leu Gly Gly Pro Ser Val Phe Leu Phe Pro Lys Pro Lys Asp
            260                 265                 270

Thr Leu Met Ile Ser Arg Thr Pro Glu Val Thr Cys Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
        405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Glu Leu Gln Leu Glu Glu Ser Cys Ala Glu Ala Gln
465                 470                 475                 480

Asp Gly Glu Leu Asp Gly Leu Trp Thr Thr Ile Thr Ile Phe Ile Thr
                485                 490                 495

Leu Phe Leu Leu Ser Val Cys Tyr Ser Ala Thr Val Thr Phe Phe Lys
            500                 505                 510

Val Lys Trp Ile Phe Ser Ser Val Val Asp Leu Lys Gln Thr Ile Ile
        515                 520                 525

Pro Asp Tyr Arg Asn Met Ile Gly Gln Gly Ala
530                 535

<210> SEQ ID NO 8
<211> LENGTH: 7341
<212> TYPE: DNA
<213> ORGANISM: Artificial Sequence
<220> FEATURE:
<223> OTHER INFORMATION: sequence for the transposable human antibody
      gamma-1 heavy chain vector pIRES-EGFP- T1T2-IgH

<400> SEQUENCE: 8
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgttaa ccctagaaag     180
atagtctgcg taaaattgac gcatgcattc ttgaaatatt gctctctctt tctaaatagc     240
gcgaatccgt cgctgtgcat ttaggacatc tcagtcgccg cttggagctc ccgtgaggcg     300
tgcttgtcaa tgcggtaagt gtcactgatt tgaactata acgaccgcgt gagtcaaaat     360
gacgcatgat tatcttttac gtgactttta agatttaact catacgataa ttatattgtt     420
```

```
atttcatgtt ctacttacgt gataacttat tatatatata ttttcttgtt atacaattgc    480
atgaagaatc tgcttagggt taggcgtttt gcgctgcttc gcgatgtacg ggccagatat    540
acgcgttgac attgattatt gactagttat taatagtaat caattacggg gtcattagtt    600
catagcccat atatggagtt ccgcgttaca taacttacgg taaatggccc gcctggctga    660
ccgcccaacg accccgccc attgacgtca ataatgacgt atgttcccat agtaacgcca    720
atagggactt tccattgacg tcaatgggtg gactatttac ggtaaactgc ccacttggca    780
gtacatcaag tgtatcatat gccaagtacg cccctattg acgtcaatga cggtaaatgg    840
cccgcctggc attatgccca gtacatgacc ttatgggact ttcctacttg gcagtacatc    900
tacgtattag tcatcgctat taccatggtg atgcggtttt ggcagtacat caatgggcgt    960
ggatagcggt ttgactcacg gggatttcca agtctccacc ccattgacgt caatgggagt    1020
ttgttttggc accaaaatca acgggacttt ccaaaatgtc gtaacaactc cgccccattg    1080
acgcaaatgg gcggtaggcg tgtacggtgg gaggtctata taagcagagc tctctggcta    1140
actagagaac ccactgctta ctggcttatc gaaattaata cgactcacta tagggagacc    1200
caagcttggt accgagctcg gatcgatatg gagtttgggc tgagctgggt tttccttgtt    1260
gcgattttag aaggtgtcca gtgtgaggtg cagctggtgg agtctggggg aggcttggta    1320
cagcccggca ggtccctgag actctcctgt gcggcctctg gattcacctt tgatgattat    1380
gccatgcact gggtccggca agctccaggg aagggcctgg aatgggtctc agctatcact    1440
tggaatagtg gtcacataga ctatgcggac tctgtggagg gccgattcac catctccaga    1500
gacaacgcca agaactccct gtatctgcaa atgaacagtc tgagagctga ggatacggcc    1560
gtatattact gtgcgaaagt ctcgtacctt agcaccgcgt cctcccttga ctattgggc    1620 caaggtaccc tggtcaccgt ctcgagcgct tccaccaagg gcccatcggt cttccccctg    1680
gcaccctcct ccaagagcac ctctgggggc acagcagccc tgggctgcct ggtcaaggac    1740
tacttccccg aaccggtgac ggtgtcgtgg aactcaggcg ccctgaccag cggcgtgcac    1800
accttcccgg ctgtcctaca gtcctcagga ctctactccc tcagcagcgt ggtgaccgtg    1860
ccctccagca gcttgggcac ccagacctac atctgcaacg tgaatcacaa gcccagcaac    1920
accaaggtgg acaagaaagt tgagcccaaa tcttgtgaca aaactcacac atgcccaccg    1980
tgcccagcac ctgaactcct ggggggaccg tcagtcttcc tcttccccc aaaacccaag    2040 gacaccctca tgatctcccg gacccctgag gtcacatgcg tggtggtgga cgtgagccac    2100
gaagaccctg aggtcaagtt caactggtac gtggacggcg tggaggtgca taatgccaag    2160
acaaagccgc gggaggagca gtacaacagc acgtaccgtg tggtcagcgt cctcaccgtc    2220
ctgcaccagg actggctgaa tggcaaggag tacaagtgca aggtctccaa caaagccctc    2280
ccagccccca tcgagaaaac catctccaaa gccaagggc agccccgaga accacaggtg    2340
tacaccctgc ccccatcccg ggatgagctg accaagaacc aggtcagcct gacctgcctg    2400
gtcaaaggct tctatcccag cgacatcgcc gtggagtggg agagcaatgg gcagccggag    2460
aacaactaca agaccacgcc tcccgtgctg gactccgacg gctccttctt cctctacagc    2520
aagctcaccg tggacaagag caggtggcag caggggaacg tcttctcatg ctccgtgatg    2580
catgaggctc tgcacaacca ctacacacag aagagcctct ccctgtctcc ggagctgcaa    2640
ctggaggaga gctgtgcgga ggcgcaggac ggggagctgg acgggctgtg gacgaccatc    2700
accatcttca tcacactctt cctgttaagc gtgtgctaca gtgccaccgt caccttcttc    2760
aaggtgaagt ggatcttctc ctcggtggtg gacctgaagc agaccatcat ccccgactac    2820
```

```
aggaacatga tcggacaggg ggcctaggcg gccgcgtcga cggaattcag tggatccact   2880
agtaacggcc gccagtgtgc tggaattaat tcgctgtctg cgagggccag ctgttggggt   2940
gagtactccc tctcaaaagc gggcatgact tctgcgctaa gattgtcagt ttccaaaaac   3000
gaggaggatt tgatattcac ctggcccgcg gtgatgcctt tgagggtggc cgcgtccatc   3060
tggtcagaaa agacaatctt tttgttgtca agcttgaggt gtggcaggct tgagatctgg   3120
ccatacactt gagtgacaat gacatccact ttgcctttct ctccacaggt gtccactccc   3180
aggtccaact gcaggtcgag catgcatcta gggcggccaa ttccgcccct ctccctcccc   3240
cccccctaac gttactggcc gaagccgctt ggaataaggc cggtgtgcgt ttgtctatat   3300
gtgattttcc accatattgc cgtcttttgg caatgtgagg gcccggaaac ctggccctgt   3360
cttcttgacg agcattccta ggggtctttc ccctctcgcc aaaggaatgc aaggtctgtt   3420
gaatgtcgtg aaggaagcag ttcctctgga agcttcttga agacaaacaa cgtctgtagc   3480
gaccctttgc aggcagcgga accccccacc tggcgacagg tgcctctgcg gccaaaagcc   3540
acgtgtataa gatacacctg caaaggcggc acaaccccag tgccacgttg tgagttggat   3600
agttgtggaa agagtcaaat ggctctcctc aagcgtattc aacaaggggc tgaaggatgc   3660
ccagaaggta ccccattgta tgggatctga tctggggcct cggtgcacat gctttacatg   3720
tgtttagtcg aggttaaaaa aacgtctagg cccccccgaac cacggggacg tggttttcct   3780
ttgaaaaaca cgatgataag cttgccacaa cccgggatcc accggtcgcc accatggtga   3840
gcaagggcga ggagctgttc accggggtgg tgcccatcct ggtcgagctg gacggcgacg   3900
taaacggcca caagttcagc gtgtccggcg agggcgaggg cgatgccacc tacggcaagc   3960
tgaccctgaa gttcatctgc accaccggca agctgcccgt gccctggccc accctcgtga   4020
ccaccctgac ctacggcgtg cagtgcttca gccgctaccc cgaccacatg aagcagcacg   4080
acttcttcaa gtccgccatg cccgaaggct acgtccagga gcgcaccatc ttcttcaagg   4140
acgacggcaa ctacaagacc cgcgccgagg tgaagttcga gggcgacacc ctggtgaacc   4200
gcatcgagct gaagggcatc gacttcaagg aggacggcaa catcctgggg cacaagctgg   4260
agtacaacta caacagccac aacgtctata tcatggccga caagcagaag aacggcatca   4320
aggtgaactt caagatccgc cacaacatcg aggacggcag cgtgcagctc gccgaccact   4380
accagcagaa cacccccatc ggcgacggcc ccgtgctgct gcccgacaac cactacctga   4440
gcacccagtc cgccctgagc aaagacccca acgagaagcg cgatcacatg gtcctgctgg   4500
agttcgtgac cgccgccggg atcactctcg gcatggacga gctgtacaag taaagcggcc   4560
ctagagctcg ctgatcagcc tcgactgtgc ctctagttgc cagccatctg ttgtttgccc   4620 ctccccgtg ccttccttga ccctggaagg tgccactccc actgtccttt cctaataaaa   4680
tgaggaaatt gcatcgcatt gtctgagtag gtgtcattct attctggggg gtggggtggg   4740
gcaggacagc aagggggagg attgggaaga caatagcagg catgctgggg atgcggtggg   4800
ctctatggct tctgaggcgg aaagaaccag ctggggctcg aggataaaag ttttgttact   4860
ttatagaaga aattttgagt ttttgttttt ttttaataaa taaataaaca taaataaatt   4920
gtttgttgaa tttattatta gtatgtaagt gtaaatataa taaacttaa tatctattca   4980 aattaataaa taaacctcga tatacagacc gataaaacac atgcgtcaat tttacgcatg   5040
attatcttta acgtacgtca caatatgatt atctttctag ggttaactcg agtgcattct   5100
agttgtggtt tgtccaaact catcaatgta tcttatcatg tctgtatacc gtcgacctct   5160
```

```
agctagagct tggcgtaatc atggtcatag ctgtttcctg tgtgaaattg ttatccgctc    5220
acaattccac acaacatacg agccggaagc ataaagtgta aagccggggg tgcctaatga    5280
gtgagctaac tcacattaat tgcgttgcgc tcactgcccg ctttccagtc gggaaacctg    5340
tcgtgccagc tgcattaatg aatcggccaa cgcgcgggga gaggcggttt gcgtattggg    5400
cgctcttccg cttcctcgct cactgactcg ctgcgctcgg tcgttcggct gcggcgagcg    5460
gtatcagctc actcaaaggc ggtaatacgg ttatccacag aatcagggga taacgcagga    5520
aagaacatgt gagcaaaagg ccagcaaaag gccaggaacc gtaaaaaggc cgcgttgctg    5580
gcgtttttcc ataggctccg ccccccctgac gagcatcaca aaaatcgacg ctcaagtcag    5640
aggtggcgaa acccgacagg actataaaga taccaggcgt ttccccctgg aagctccctc    5700
gtgcgctctc ctgttccgac cctgccgctt accggatacc tgtccgcctt ctcccttcg     5760
ggaagcgtgg cgctttctca atgctcacgc tgtaggtatc tcagttcggt gtaggtcgtt    5820
cgctccaagc tgggctgtgt gcacgaaccc ccgttcagc ccgaccgctg cgccttatcc     5880
ggtaactatc gtcttgagtc caacccggta agacacgact tatcgccact ggcagcagcc    5940
actggtaaca ggattagcag agcgaggtat gtaggcggtg ctacagagtt cttgaagtgg    6000
tggcctaact acggctacac tagaaggaca gtatttggta tctgcgctct gctgaagcca    6060
gttaccttcg gaaaaagagt tggtagctct tgatccggca acaaaccac cgctggtagc     6120
ggtggttttt tgtttgcaa gcagcagatt acgcgcagaa aaaaggatc tcaagaagat     6180
cctttgatct tttctacggg gtctgacgct cagtggaacg aaaactcacg ttaagggatt    6240
ttggtcatga gattatcaaa aaggatcttc acctagatcc ttttaaatta aaaatgaagt    6300
tttaaatcaa tctaaagtat atatgagtaa acttggtctg acagttacca atgcttaatc    6360
agtgaggcac ctatctcagc gatctgtcta tttcgttcat ccatagttgc ctgactcccc    6420
gtcgtgtaga taactacgat acgggagggc ttaccatctg gccccagtgc tgcaatgata    6480
ccgcgagacc cacgctcacc ggctccagat ttatcagcaa taaaccagcc agccggaagg    6540
gccgagcgca gaagtggtcc tgcaacttta tccgcctcca tccagtctat taattgttgc    6600
cgggaagcta gagtaagtag ttcgccagtt aatagtttgc gcaacgttgt tgccattgct    6660
acaggcatcg tggtgtcacg ctcgtcgttt ggtatggctt cattcagctc cggttcccaa    6720
cgatcaaggc gagttacatg atccccccatg ttgtgcaaaa aagcggttag ctccttcggt    6780
cctccgatcg ttgtcagaag taagttggcc gcagtgttat cactcatggt tatggcagca    6840
ctgcataatt ctcttactgt catgccatcc gtaagatgct tttctgtgac tggtgagtac    6900
tcaaccaagt cattctgaga atagtgtatg cggcgaccga gttgctcttg cccggcgtca    6960
atacgggata taccgcgcc acatagcaga actttaaaag tgctcatcat ggaaaacgt     7020
tcttcggggc gaaaactctc aaggatctta ccgctgttga tccagttc gatgtaaccc      7080
actcgtgcac ccaactgatc ttcagcatct tttactttca ccagcgtttc tgggtgagca    7140
aaaacaggaa ggcaaaatgc cgcaaaaaag ggaataaggg cgacacggaa atgttgaata    7200
ctcatactct tcctttttca atattattga agcatttatc agggttattg tctcatgagc    7260
ggatacatat ttgaatgtat ttagaaaaat aaacaaatag gggttccgcg cacatttccc    7320
cgaaaagtgc cacctgacgt c                                              7341

<210> SEQ ID NO 9
<211> LENGTH: 437
<212> TYPE: DNA
<213> ORGANISM: Artificial Sequence
```

```
<220> FEATURE:
<223> OTHER INFORMATION: libraries for variable heavy chain domains
      containing N-sequences in the HCDR3 and flanked by ClaI and
      Eco47III restriction sites
<220> FEATURE:
<221> NAME/KEY: misc_feature
<222> LOCATION: (362)..(385)
<223> OTHER INFORMATION: N = wildcard, nucleotide can be any of the
      four nucleotides occuring in DNA

<400> SEQUENCE: 9
aattatcgat atggagtttg ggctgagctg ggttttcctt gttgcgattt tagaaggtgt       60
ccagtgtgag gtgcagctgg tggagtctgg gggaggcttg gtacagcccg gcaggtccct      120
gagactctcc tgtgcggcct ctggattcac ctttgatgat tatgccatgc actgggtccg      180
gcaagctcca gggaagggcc tggaatgggt ctcagctatc acttggaata gtggtcacat      240
agactatgcg gactctgtgg agggccgatt caccatctcc agagacaacg ccaagaactc      300
cctgtatctg caaatgaaca gtctgagagc tgaggatacg gccgtatatt actgtgcgaa      360
annnnnnnnn nnnnnnnnnn nnnntccct tgactattgg ggccaaggta ccctggtcac      420
cgtctcgagc gctgcat                                                     437

<210> SEQ ID NO 10
<211> LENGTH: 395
<212> TYPE: DNA
<213> ORGANISM: Artificial Sequence
<220> FEATURE:
<223> OTHER INFORMATION: libraries for variable light chain domains
      containing N-sequences in the LCDR3 and flanked by ClaI and
      Eco47III restriction sites
<220> FEATURE:
<221> NAME/KEY: misc_feature
<222> LOCATION: (337)..(351)
<223> OTHER INFORMATION: N = wildcard, nucleotide can be any of the four
      nucleotides occuring in DNA

<400> SEQUENCE: 10
atggacatga gggtccctgc tcagctcctg ggactcctgc tgctctggct cccaggtgcc       60
agatgtgaca tccagatgac ccagtctcca tcctccctgt ctgcatctgt aggggacaga      120
gtcaccatca cttgtcgggc aagtcagggc atcagaaatt acttagcctg gtatcagcaa      180
aaaccaggga aagcccctaa gctcctgatc tatgctgcat ccactttgca atcaggggtc      240
ccatctcggt tcagtggcag tggatctggg acagatttca ctctcaccat cagcagccta      300
cagcctgaag atgttgcaac ttattactgt caaaggnnnn nnnnnnnnnn ntatactttt      360
ggccagggga ccaaggtgga atcaagcgc tgcat                                  395

<210> SEQ ID NO 11
<211> LENGTH: 1784
<212> TYPE: DNA
<213> ORGANISM: Artificial Sequence
<220> FEATURE:
<223> OTHER INFORMATION: ORF of functional PiggyBac transposase enzyme

<400> SEQUENCE: 11
atgggtagtt ctttagacga tgagcatatc ctctctgctc ttctgcaaag cgatgacgag       60
cttgttggtg aggattctga cagtgaaata tcagatcacg taagtgaaga tgacgtccag      120
agcgatacag aagaagcgtt tatagatgag gtacatgaag tgcagccaac gtcaagcggt      180
agtgaaatat tagacgaaca aaatgttatt gaacaaccag gttcttcatt ggcttctaac      240
agaatcttga ccttgccaca gaggactatt agaggtaaga ataaacattg ttggtcaact      300
```

```
tcaaagtcca cgaggcgtag ccgagtctct gcactgaaca ttgtcagatc tcaaagaggt    360
ccgacgcgta tgtgccgcaa tatatatgac ccacttttat gcttcaaact attttttact    420
gatgagataa tttcggaaat tgtaaaatgg acaaatgctg agatatcatt gaaacgtcgg    480
gaatctatga caggtgctac atttcgtgac acgaatgaag atgaaatcta tgctttcttt    540
ggtattctgg taatgacagc agtgagaaaa gataaccaca tgtccacaga tgacctcttt    600
gatcgatctt tgtcaatggt gtacgtctct gtaatgagtc gtgatcgttt tgattttttg    660
atacgatgtc ttagaatgga tgacaaaagt atacggccca cacttcgaga aaacgatgta    720
tttactcctg ttagaaaaat atgggatctc tttatccatc agtgcataca aaattacact    780 ccagggctc atttgaccat agatgaacag ttacttggtt ttagaggacg gtgtccgttt    840
aggatgtata tcccaaacaa gccaagtaag tatggaataa aaatcctcat gatgtgtgac    900
agtggtacga agtatatgat aaatggaatg ccttatttgg gaagaggaac acagaccaac    960
ggagtaccac tcggtgaata ctacgtgaag gagttatcaa agcctgtgca cggtagttgt   1020
cgtaatatta cgtgtgacaa ttggttcacc tcaatcccct tggcaaaaaa cttactacaa   1080
gaaccgtata agttaaccat tgtgggaacc gtgcgatcaa acaaacgcga gataccggaa   1140
gtactgaaaa acagtcgctc caggccagtg ggaacatcga tgttttgttt tgacggaccc   1200
cttactctcg tctcatataa accgaagcca gctaagatgg tatacttatt atcatcttgt   1260
gatgaggatg cttctatcaa cgaaagtacc ggtaaaccgc aaatggttat gtattataat   1320
caaactaaag gcggagtgga cacgctagac caaatgtgtt ctgtgatgac ctgcagtagg   1380
aagacgaata ggtggcctat ggcattattg tacggaatga taaacattgc ctgcataaat   1440
tcttttatta tatacagcca taatgtcagt agcaagggag aaaaggttca agtcgcaaa    1500 aaatttatga gaacccttta catgagcctg acgtcatcgt ttatgcgtaa gcgtttagaa   1560
gctcctactt tgaagagata tttgcgcgat aatatctcta atattttgcc aaatgaagtg   1620
cctggtacat cagatgacag tactgaagag ccagtaatga aaaacgtac ttactgtact    1680 tactgccct ctaaaataag gcgaaaggca atgcatcgt gcaaaaatg caaaaaagtt     1740 atttgtcgag agcataatat tgatatgtgc caaagttgtt ttag                   1784
```

<210> SEQ ID NO 12
<211> LENGTH: 593
<212> TYPE: PRT
<213> ORGANISM: Artificial Sequence
<220> FEATURE:
<223> OTHER INFORMATION: Protein sequence of functional PiggyBac
      transposase enzyme

<400> SEQUENCE: 12

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95
```

```
Cys Trp Ser Thr Ser Lys Ser Thr Arg Arg Ser Arg Val Ser Ala Leu
                100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
```

```
                515                 520                 525
Arg Asp Asn Ile Ser Asn Ile Leu Pro Asn Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys
```

<210> SEQ ID NO 13
<211> LENGTH: 7385
<212> TYPE: DNA
<213> ORGANISM: Artificial Sequence
<220> FEATURE:
<223> OTHER INFORMATION: sequence of the PiggyBac expression construct pCDNA3.1-hygro(+)-PB

<400> SEQUENCE: 13

```
gacggatcgg gagatctccc gatcccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgcc ccattgacgc aaatgggcg    780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgagctcgg atccactagt ccagtgtggt ggaattctgc   960
agatatgggt agttctttag acgatgagca tatcctctct gctcttctgc aaagcgatga  1020
cgagcttgtt ggtgaggatt ctgacagtga aatatcagat cacgtaagtg aagatgacgt  1080
ccagagcgat acagaagaag cgtttataga tgaggtacat gaagtgcagc aacgtcaag   1140
cggtagtgaa atattagacg aacaaaatgt tattgaacaa ccaggttctt cattggcttc  1200
taacagaatc ttgaccttgc cacagaggac tattagaggt aagaataaac attgttggtc  1260
aacttcaaag tccacgaggc gtagccgagt ctctgcactg aacattgtca gatctcaaag  1320
aggtccgacg cgtatgtgcc gcaatatata tgacccactt ttatgcttca actatttt   1380
tactgatgag ataatttcgg aaattgtaaa atggacaaat gctgagatat cattgaaacg  1440
tcgggaatct atgacaggtg ctacatttcg tgacacgaat gaagatgaaa tctatgcttt  1500
ctttggtatt ctggtaatga cagcagtgag aaaagataac cacatgtcca cagatgacct  1560
```

```
ctttgatcga tctttgtcaa tggtgtacgt ctctgtaatg agtcgtgatc gttttgattt      1620
tttgatacga tgtcttagaa tggatgacaa aagtatacgg cccacacttc gagaaaacga      1680
tgtatttact cctgttagaa aaatatggga tctctttatc catcagtgca tacaaaatta      1740
cactccaggg gctcatttga ccatagatga acagttactt ggttttagag gacggtgtcc      1800
gtttaggatg tatatcccaa acaagccaag taagtatgga ataaaaatcc tcatgatgtg      1860
tgacagtggt acgaagtata tgataaatgg aatgccttat ttgggaagag gaacacagac      1920
caacggagta ccactcggtg aatactacgt gaaggagtta tcaaagcctg tgcacggtag      1980
ttgtcgtaat attacgtgtg acaattggtt cacctcaatc cctttggcaa aaaacttact      2040
acaagaaccg tataagttaa ccattgtggg aaccgtgcga tcaaacaaac gcgagatacc      2100
ggaagtactg aaaaacagtc gctccaggcc agtgggaaca tcgatgtttt gttttgacgg      2160
accccttact ctcgtctcat ataaaccgaa gccagctaag atggtatact tattatcatc      2220
ttgtgatgag gatgcttcta tcaacgaaag taccggtaaa ccgcaaatgg ttatgtatta      2280
taatcaaact aaaggcggag tggacacgct agaccaaatg tgttctgtga tgacctgcag      2340
taggaagacg aataggtggc ctatggcatt attgtacgga atgataaaca ttgcctgcat      2400
aaattctttt attatataca gccataatgt cagtagcaag ggagaaaagg ttcaaagtcg      2460
caaaaaattt atgagaaacc tttacatgag cctgacgtca tcgtttatgc gtaagcgttt      2520
agaagctcct actttgaaga gatatttgcg cgataatatc tctaatattt tgccaaatga      2580
agtgcctggt acatcagatg acagtactga agagccagta atgaaaaaac gtacttactg      2640
tacttactgc ccctctaaaa taaggcgaaa ggcaaatgca tcgtgcaaaa aatgcaaaaa      2700
agttatttgt cgagagcata atattgatat gtgccaaagt tgttttagat ccagcacagt      2760
ggcggccgct cgagtctaga gggcccgttt aaacccgctg atcagcctcg actgtgcctt      2820
ctagttgcca gccatctgtt gtttgcccct cccccgtgcc ttccttgacc ctggaaggtg      2880
ccactcccac tgtccttttcc taataaaatg aggaaattgc atcgcattgt ctgagtaggt      2940
gtcattctat tctggggggt ggggtggggc aggacagcaa ggggggaggat tgggaagaca      3000 atagcaggca tgctggggat gcggtgggct ctatggcttc tgaggcggaa agaaccagct      3060
ggggctctag ggggtatccc cacgcgccct gtagcggcgc attaagcgcg gcgggtgtgg      3120
tggttacgcg cagcgtgacc gctacacttg ccagcgccct agcgcccgct cctttcgctt      3180
tcttcccttc ctttctcgcc acgttcgccg gctttccccg tcaagctcta aatcggggca      3240
tccctttagg gttccgattt agtgctttac ggcacctcga ccccaaaaaa cttgattagg      3300
gtgatggttc acgtagtggg ccatcgccct gatagacggt ttttcgccct ttgacgttgg      3360
agtccacgtt ctttaatagt ggactcttgt tccaaactgg aacaacactc aaccctatct      3420
cggtctattc ttttgattta agggattttt gggaatttt ggcctattgg ttaaaaaatg      3480
agctgattta acaaaaattt aacgcgaatt aattctgtgg aatgtgtgtc agttagggtg      3540
tggaaagtcc ccaggctccc caggcaggca gaagtatgca aagcatgcat ctcaattagt      3600
cagcaaccag gtgtggaaag tccccaggct ccccagcagg cagaagtatg caaagcatgc      3660
atctcaatta gtcagcaacc atagtcccgc ccctaactcc gcccatcccg ccctaactc      3720 cgcccagttc cgcccattct ccgccccatg gctgactaat ttttttttatt tatgcagagg      3780 ccgaggccgc ctctgcctct gagctattcc agaagtagtg aggaggcttt tttggaggcc      3840
taggcttttg caaaaagctc ccgggagctt gtatatccat tttcggatct gatcagcacg      3900
tgatgaaaaa gcctgaactc accgcgacgt ctgtcgagaa gtttctgatc gaaaagttcg      3960
```

```
acagcgtctc cgacctgatg cagctctcgg agggcgaaga atctcgtgct ttcagcttcg    4020
atgtaggagg gcgtggatat gtcctgcggg taaatagctg cgccgatggt ttctacaaag    4080
atcgttatgt ttatcggcac tttgcatcgg ccgcgctccc gattccggaa gtgcttgaca    4140
ttggggaatt cagcgagagc ctgacctatt gcatctcccg ccgtgcacag ggtgtcacgt    4200
tgcaagacct gcctgaaacc gaactgcccg ctgttctgca gccggtcgcg gaggccatgg    4260
atgcgatcgc tgcggccgat cttagccaga cgagcgggtt cggcccattc ggaccgcaag    4320
gaatcggtca atacactaca tggcgtgatt tcatatgcgc gattgctgat ccccatgtgt    4380
atcactggca aactgtgatg gacgacaccg tcagtgcgtc cgtcgcgcag gctctcgatg    4440
agctgatgct ttgggccgag gactgccccg aagtccggca cctcgtgcac gcggatttcg    4500
gctccaacaa tgtcctgacg gacaatggcc gcataacagc ggtcattgac tggagcgagg    4560
cgatgttcgg ggattcccaa tacgaggtcg ccaacatctt cttctggagg ccgtggttgg    4620
cttgtatgga gcagcagacg cgctacttcg agcggaggca tccggagctt gcaggatcgc    4680
cgcggctccg ggcgtatatg ctccgcattg gtcttgacca actctatcag agcttggttg    4740
acggcaattt cgatgatgca gcttgggcgc agggtcgatg cgacgcaatc gtccgatccg    4800
gagccgggac tgtcgggcgt acacaaatcg cccgcagaag cgcggccgtc tggaccgatg    4860
gctgtgtaga agtactcgcc gatagtggaa accgacgccc cagcactcgt ccgagggcaa    4920
aggaatagca cgtgctacga gatttcgatt ccaccgccgc cttctatgaa aggttgggct    4980
tcggaatcgt tttccgggac gccggctgga tgatcctcca gcgcggggat ctcatgctgg    5040
agttcttcgc ccacccaac ttgtttattg cagcttataa tggttacaaa taaagcaata    5100
gcatcacaaa tttcacaaat aaagcatttt tttcactgca ttctagttgt ggtttgtcca    5160
aactcatcaa tgtatcttat catgtctgta taccgtcgac ctctagctag agcttggcgt    5220
aatcatggtc atagctgttt cctgtgtgaa attgttatcc gctcacaatt ccacacaaca    5280
tacgagccgg aagcataaag tgtaaagcct ggggtgccta atgagtgagc taactcacat    5340
taattgcgtt gcgctcactg cccgctttcc agtcggaaaa cctgtcgtgc cagctgcatt    5400
aatgaatcgg ccaacgcgcg gggagaggcg gtttgcgtat tgggcgctct tccgcttcct    5460
cgctcactga ctcgctgcgc tcggtcgttc ggctgcggcg agcggtatca gctcactcaa    5520
aggcggtaat acggttatcc acagaatcag gggataacgc aggaaagaac atgtgagcaa    5580
aaggccagca aaaggccagg aaccgtaaaa aggccgcgtt gctggcgttt ttccataggc    5640
tccgcccccc tgacgagcat cacaaaaatc gacgctcaag tcagaggtgg cgaaacccga    5700
caggactata aagataccag gcgtttcccc ctggaagctc cctcgtgcgc tctcctgttc    5760
cgaccctgcc gcttaccgga tacctgtccg cctttctccc ttcgggaagc gtggcgcttt    5820
ctcaatgctc acgctgtagg tatctcagtt cggtgtaggt cgttcgctcc aagctgggct    5880
gtgtgcacga accccccgtt cagcccgacc gctgcgcctt atccggtaac tatcgtcttg    5940
agtccaaccc ggtaagacac gacttatcgc cactggcagc agccactggt aacaggatta    6000
gcagagcgag gtatgtaggc ggtgctacag agttcttgaa gtggtggcct aactacggct    6060
acactagaag gacagtattt ggtatctgcg ctctgctgaa gccagttacc ttcggaaaaa    6120
gagttggtag ctcttgatcc ggcaaacaaa ccaccgctgg tagcggtggt ttttttgttt    6180
gcaagcagca gattacgcgc agaaaaaaag gatctcaaga agatcctttg atcttttcta    6240
cggggtctga cgctcagtgg aacgaaaact cacgttaagg gattttggtc atgagattat    6300
```

```
caaaaaggat cttcacctag atcctttaa attaaaaatg aagttttaaa tcaatctaaa      6360
gtatatatga gtaaacttgg tctgacagtt accaatgctt aatcagtgag gcacctatct      6420
cagcgatctg tctatttcgt tcatccatag ttgcctgact ccccgtcgtg tagataacta      6480
cgatacggga gggcttacca tctggcccca gtgctgcaat gataccgcga gacccacgct      6540
caccggctcc agatttatca gcaataaacc agccagccgg aagggccgag cgcagaagtg      6600
gtcctgcaac tttatccgcc tccatccagt ctattaattg ttgccgggaa gctagagtaa      6660
gtagttcgcc agttaatagt ttgcgcaacg ttgttgccat tgctacaggc atcgtggtgt      6720
cacgctcgtc gtttggtatg gcttcattca gctccggttc caacgatca aggcgagtta       6780 catgatcccc catgttgtgc aaaaaagcgg ttagctcctt cggtcctccg atcgttgtca      6840
gaagtaagtt ggccgcagtg ttatcactca tggttatggc agcactgcat aattctctta      6900
ctgtcatgcc atccgtaaga tgcttttctg tgactggtga gtactcaacc aagtcattct      6960
gagaatagtg tatgcggcga ccgagttgct cttgcccggc gtcaatacgg ataataccg       7020 cgccacatag cagaacttta aaagtgctca tcattggaaa acgttcttcg ggcgaaaac       7080 tctcaaggat cttaccgctg ttgagatcca gttcgatgta acccactcgt gcacccaact     7140
gatcttcagc atcttttact ttcaccacgc tttctgggtg agcaaaaaca ggaaggcaaa     7200
atgccgcaaa aaagggaata agggcgacac ggaaatgttg aatactcata ctcttccttt     7260
ttcaatatta ttgaagcatt tatcagggtt attgtctcat gagcggatac atatttgaat     7320
gtatttagaa aaataaacaa ataggggttc cgcgcacatt tccccgaaaa gtgccacctg     7380
acgtc                                                                 7385

<210> SEQ ID NO 14
<211> LENGTH: 246
<212> TYPE: DNA
<213> ORGANISM: Artificial Sequence
<220> FEATURE:
<223> OTHER INFORMATION: upstream Sleeping beauty 5'ITR sequence

<400> SEQUENCE: 14
atatcaattg agttgaagtc ggaagtttac atacacttaa gttggagtca ttaaaactcg       60
tttttcaact acaccacaaa tttcttgtta acaaacaata gttttggcaa gtcagttagg      120
acatctactt tgtgcatgac acaagtcatt tttccaacaa ttgttacag acagattatt      180 tcacttataa ttcactgtat cacaattcca gtgggtcaga agtttacata cactaacaat      240
tgatat                                                                 246

<210> SEQ ID NO 15
<211> LENGTH: 248
<212> TYPE: DNA
<213> ORGANISM: Artificial Sequence
<220> FEATURE:
<223> OTHER INFORMATION: downstream Sleeping beauty 3'ITR sequence

<400> SEQUENCE: 15
atatctcgag ttgagtgtat gttaacttct gacccactgg gaatgtgatg aagaaataa       60 aagctgaaat gaatcattct ctctactatt attctgatat ttcacattct aaaataaag      120 tggtgatcct aactgacctt aagacaggga atctttactc ggattaaatg tcaggaattg     180
tgaaaaagtg agtttaaatg tatttggcta aggtgtatgt aaacttccga cttcaactct     240
cgagatat                                                               248
```

<210> SEQ ID NO 16
<211> LENGTH: 6339
<212> TYPE: DNA
<213> ORGANISM: Artificial Sequence
<220> FEATURE:
<223> OTHER INFORMATION: sequence of the human Ig-kappa LC expression
      vector pIRES-EGFP-sbT1T2-IgL

<400> SEQUENCE: 16

| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgagtt | gaagtcggaa | 180 |
| gtttacatac | acttaagttg | gagtcattaa | aactcgtttt | tcaactacac | cacaaatttc | 240 |
| ttgttaacaa | acaatagttt | tggcaagtca | gttaggacat | ctactttgtg | catgacacaa | 300 |
| gtcattttc | caacaattgt | ttacagacag | attatttcac | ttataattca | ctgtatcaca | 360 |
| attccagtgg | gtcagaagtt | tacatacact | aacaattgca | tgaagaatct | gcttagggtt | 420 |
| aggcgttttg | cgctgcttcg | cgatgtacgg | gccagatata | cgcgttgaca | ttgattattg | 480 |
| actagttatt | aatagtaatc | aattacgggg | tcattagttc | atagcccata | tatggagttc | 540 |
| cgcgttacat | aacttacggt | aaatggcccg | cctggctgac | cgcccaacga | cccccgccca | 600 |
| ttgacgtcaa | taatgacgta | tgttcccata | gtaacgccaa | tagggacttt | ccattgacgt | 660 |
| caatgggtgg | actatttacg | gtaaactgcc | cacttggcag | tacatcaagt | gtatcatatg | 720 |
| ccaagtacgc | cccctattga | cgtcaatgac | ggtaaatggc | ccgcctggca | ttatgcccag | 780 |
| tacatgacct | tatgggactt | tcctacttgg | cagtacatct | acgtattagt | catcgctatt | 840 |
| accatggtga | tgcggttttg | gcagtacatc | aatgggcgtg | gatagcggtt | tgactcacgg | 900 |
| ggatttccaa | gtctccaccc | cattgacgtc | aatgggagtt | tgttttggca | ccaaaatcaa | 960 |
| cgggactttc | caaaatgtcg | taacaactcc | gccccattga | cgcaaatggg | cggtaggcgt | 1020 |
| gtacggtggg | aggtctatat | aagcagagct | ctctggctaa | ctagagaacc | cactgcttac | 1080 |
| tggcttatcg | aaattaatac | gactcactat | agggagaccc | aagcttggta | ccgagctcgg | 1140 |
| atcgatatgg | acatgagggt | ccctgctcag | ctcctgggac | tcctgctgct | ctggctccca | 1200 |
| ggtgccagat | gtgacatcca | gatgacccag | tctccatcct | ccctgtctgc | atctgtaggg | 1260 |
| gacagagtca | ccatcacttg | tcgggcaagt | cagggcatca | gaaattactt | agcctggtat | 1320 |
| cagcaaaaac | cagggaaagc | ccctaagctc | ctgatctatg | ctgcatccac | tttgcaatca | 1380 |
| ggggtcccat | ctcggttcag | tggcagtgga | tctgggacag | atttcactct | caccatcagc | 1440 |
| agcctacagc | ctgaagatgt | tgcaacttat | tactgtcaaa | ggtataaccg | tgcaccgtat | 1500 |
| acttttggcc | aggggaccaa | ggtggaaatc | aagcgctctg | tggctgcacc | atctgtcttc | 1560 |
| atcttcccgc | catctgatga | gcagttgaaa | tctggaactg | cctctgttgt | gtgcctgctg | 1620 |
| aataacttct | atcccagaga | ggccaaagta | cagtggaagg | tggataacgc | cctccaatcg | 1680 |
| ggtaactccc | aggagagtgt | cacagagcag | gacagcaagg | acagcaccta | cagcctcagc | 1740 |
| agcaccctga | cgctgagcaa | agcagactac | gagaaacaca | aagtctacgc | ctgcgaagtc | 1800 |
| acccatcagg | gcctgagctc | gcccgtcaca | aagagcttca | acaggggaga | gtgttaaatc | 1860 |
| tgcggccgcg | tcgacggaat | tcagtggatc | cactagtaac | ggccgccagt | gtgctggaat | 1920 |
| taattcgctg | tctgcgaggg | ccagctgttg | gggtgagtac | tccctctcaa | aagcgggcat | 1980 |
| gacttctgcg | ctaagattgt | cagtttccaa | aaacgaggag | gatttgatat | tcacctggcc | 2040 |
| cgcggtgatg | cctttgaggg | tggccgcgtc | catctggtca | gaaaagacaa | tcttttttgtt | 2100 |

```
gtcaagcttg aggtgtggca ggcttgagat ctggccatac acttgagtga caatgacatc    2160
cactttgcct ttctctccac aggtgtccac tcccaggtcc aactgcaggt cgagcatgca    2220
tctagggcgg ccaattccgc ccctctccct cccccccccc taacgttact ggccgaagcc    2280
gcttggaata aggccggtgt gcgtttgtct atatgtgatt ttccaccata ttgccgtctt    2340
ttggcaatgt gagggcccgg aaacctggcc ctgtcttctt gacgagcatt cctaggggtc    2400
tttcccctct cgccaaagga atgcaaggtc tgttgaatgt cgtgaaggaa gcagttcctc    2460
tggaagcttc ttgaagacaa acaacgtctg tagcgaccct ttgcaggcag cggaaccccc    2520
cacctggcga caggtgcctc tgcggccaaa agccacgtgt ataagataca cctgcaaagg    2580
cggcacaacc ccagtgccac gttgtgagtt ggatagttgt ggaaagagtc aaatggctct    2640
cctcaagcgt attcaacaag gggctgaagg atgcccagaa ggtacccat tgtatgggat    2700 ctgatctggg gcctcggtgc acatgcttta catgtgttta gtcgaggtta aaaaaacgtc    2760 taggccccc gaaccacggg gacgtggttt tcctttgaaa aacacgatga taagcttgcc    2820
acaacccggg atccaccggt cgccaccatg gtgagcaagg gcgaggagct gttcaccggg    2880
gtggtgccca tcctggtcga gctggacggc gacgtaaacg gccacaagtt cagcgtgtcc    2940
ggcgagggcg agggcgatgc cacctacggc aagctgaccc tgaagttcat ctgcaccacc    3000
ggcaagctgc ccgtgccctg gcccaccctc gtgaccaccc tgacctacgg cgtgcagtgc    3060
ttcagccgct accccgacca catgaagcag cacgacttct tcaagtccgc catgcccgaa    3120
ggctacgtcc aggagcgcac catcttcttc aaggacgacg gcaactacaa gacccgcgcc    3180
gaggtgaagt tcgagggcga caccctggtg aaccgcatcg agctgaaggg catcgacttc    3240
aaggaggacg gcaacatcct ggggcacaag ctggagtaca actacaacag ccacaacgtc    3300
tatatcatgg ccgacaagca gaagaacggc atcaaggtga acttcaagat ccgccacaac    3360
atcgaggacg gcagcgtgca gctcgccgac cactaccagc agaacacccc catcggcgac    3420
ggccccgtgc tgctgcccga caaccactac ctgagcaccc agtccgccct gagcaaagac    3480
cccaacgaga agcgcgatca catggtcctg ctggagttcg tgaccgccgc cgggatcact    3540
ctcggcatgg acgagctgta caagtaaagc ggccctagag ctcgctgatc agcctcgact    3600
gtgcctctag ttgccagcca tctgttgttt gcccctcccc cgtgccttcc ttgaccctgg    3660
aaggtgccac tcccactgtc ctttcctaat aaaatgagga aattgcatcg cattgtctga    3720
gtaggtgtca ttctattctg ggggtgggg tggggcagga cagcaagggg gaggattggg    3780
aagacaatag caggcatgct ggggatgcgg tgggctctat ggcttctgag gcggaaagaa    3840
ccagctgggg ctcgagttga gtgtatgtta acttctgacc cactgggaat gtgatgaaag    3900
aaataaaagc tgaaatgaat cattctctct actattattc tgatatttca cattcttaaa    3960
ataaagtggt gatcctaact gaccttaaga cagggaatct ttactcggat taaatgtcag    4020
gaattgtgaa aaagtgagtt taaatgtatt tggctaaggt gtatgtaaac ttccgacttc    4080
aactctcgag tgcattctag ttgtggtttg tccaaactca tcaatgtatc ttatcatgtc    4140
tgtataccgt cgacctctag ctagagcttg gcgtaatcat ggtcatagct gtttcctgtg    4200
tgaaattgtt atccgctcac aattccacac aacatacgag ccgaagcat aaagtgtaaa    4260 gcctggggtg cctaatgagt gagctaactc acattaattg cgttgcgctc actgcccgct    4320
ttccagtcgg gaaacctgtc gtgccagctg cattaatgaa tcggccaacg cgcgggaga    4380 ggcggtttgc gtattgggcg ctcttccgct tcctcgctca ctgactcgct gcgctcggtc    4440
```

```
gttcggctgc ggcgagcggt atcagctcac tcaaaggcgg taatacggtt atccacagaa    4500 tcagggqata acgcaggaaa gaacatgtga gcaaaaggcc agcaaaaggc caggaaccgt    4560
aaaaaggccg cgttgctggc gttttccat aggctccgcc ccctgacga gcatcacaaa     4620 aatcgacgct caagtcagag gtggcgaaac ccgacaggac tataaagata ccaggcgttt    4680
ccccctggaa gctccctcgt gcgctctcct gttccgaccc tgccgcttac cggatacctg    4740
tccgcctttc tcccttcggg aagcgtggcg ctttctcaat gctcacgctg taggtatctc    4800
agttcggtgt aggtcgttcg ctccaagctg ggctgtgtgc acgaaccccc cgttcagccc    4860
gaccgctgcg ccttatccgg taactatcgt cttgagtcca acccgqtaag acacqactta    4920 tcgccactgg cagcagccac tggtaacagg attagcagag cgaggtatgt aggcggtgct    4980
acagagttct tgaagtggtg gcctaactac ggctacacta aaggacagt atttggtatc     5040 tgcgctctgc tgaagccagt taccttcgga aaaagagttg gtagctcttg atccggcaaa    5100
caaaccaccg ctggtagcgg tggtttttt gtttgcaagc agcagattac gcgcagaaaa     5160
aaaggatctc aagaagatcc tttgatcttt tctacggggt ctgacgctca gtggaacgaa    5220
aactcacgtt aagggatttt ggtcatgaga ttatcaaaaa ggatcttcac ctagatcctt    5280
ttaaattaaa aatgaagttt taaatcaatc taaagtatat atgagtaaac ttggtctgac    5340
agttaccaat gcttaatcag tgaggcacct atctcagcga tctgtctatt tcgttcatcc    5400
atagttgcct gactccccgt cgtgtagata actacgatac gggagggctt accatctggc    5460
cccagtgctg caatgatacc gcgagaccca cgctcaccgg ctccagattt atcagcaata    5520
aaccagccag ccggaagggc cgagcgcaga agtggtcctg caactttatc cgcctccatc    5580
cagtctatta attgttgccg ggaagctaga gtaagtagtt cgccagttaa tagtttgcgc    5640
aacgttgttg ccattgctac aggcatcgtg gtgtcacgct cgtcgtttgg tatggcttca    5700
ttcagctccg gttcccaacg atcaaggcga gttacatgat cccccatgtt gtgcaaaaaa    5760
gcggttagct ccttcggtcc tccgatcgtt gtcagaagta agttggccgc agtgttatca    5820
ctcatggtta tggcagcact gcataattct cttactgtca tgccatccgt aagatgcttt    5880
tctgtgactg gtgagtactc aaccaagtca ttctgagaat agtgtatgcg gcgaccgagt    5940
tgctcttgcc cggcgtcaat acgggataat accgcgccac atagcagaac tttaaaagtg    6000
ctcatcattg gaaaacgttc ttcggggcga aaactctcaa ggatcttacc gctgttgaga    6060
tccagttcga tgtaacccac tcgtgcaccc aactgatctt cagcatcttt tactttcacc    6120
agcgtttctg ggtgagcaaa aacaggaagg caaaatgccg caaaaaaggg aataagggcg    6180
acacggaaat gttgaatact catactcttc ctttttcaat attattgaag catttatcag    6240
ggttattgtc tcatgagcgg atacatattt gaatgtattt agaaaaataa acaaataggg    6300
gttccgcgca catttccccg aaaagtgcca cctgacgtc                           6339
```

<210> SEQ ID NO 17
<211> LENGTH: 1023
<212> TYPE: DNA
<213> ORGANISM: Artificial Sequence
<220> FEATURE:
<223> OTHER INFORMATION: open reading frame (ORF) of the Sleeping Beauty
      transposase enzyme

<400> SEQUENCE: 17

```
atgggaaaat caaagaaat cagccaagac ctcagaaaaa aaattgtaga cctccacaag     60
tctggttcat ccttgggagc aatttccaaa cgcctgaaag taccacgttc atctgtacaa    120
```

```
acaatagtac gcaagtataa acaccatggg accacgcagc cgtcataccg ctcaggaagg    180
agacgcgttc tgtctcctag agatgaacgt actttggtgc gaaaagtgca atcaatccc     240
agaacaacag caaaggacct tgtgaagatg ctggaggaaa caggtacaaa agtatctata    300
tccacagtaa aacgagtcct atatcgacat aacctgaaag ccgctcagc aaggaagaag     360
ccactgctcc aaaaccgaca taagaaagcc agactacggt ttgcaactgc acatggggac    420
aaagatcgta cttttggag aaatgtcctc tggtctgatg aaacaaaaat agaactgttt     480
ggccataatg accatcgtta tgtttggagg aagaagggg aggcttgcaa gccgaagaac     540
accatcccaa ccgtgaagca cgggggtggc agcatcatgt tgtgggggtg ctttgctgca    600
ggagggactg gtgcacttca caaatagat ggcatcatga ggaaggaaaa ttatgtggat     660
atattgaagc aacatctcaa gacatcagtc aggaagttaa agcttggtcg caaatgggtc    720
ttccaaatgg acaatgaccc caagcatact tccaaagttg tggcaaaatg gcttaaggac    780
aacaaagtca aggtattgga gtggccatca caaagccctg acctcaatcc tatagaaaat    840
ttgtgggcag aactgaaaaa gcgtgtgcga gcaaggaggc ctacaaacct gactcagtta    900
caccagctct gtcaggagga atgggccaaa attcacccaa cttattgtgg gaagcttgtg    960
gaaggctacc cgaaacgttt gacccaagtt aaacaattta aaggcaatgc taccaaatac   1020
tag                                                                1023
```

```
<210> SEQ ID NO 18
<211> LENGTH: 340
<212> TYPE: PRT
<213> ORGANISM: Artificial Sequence
<220> FEATURE:
<223> OTHER INFORMATION: Protein sequence of the Sleeping Beauty
      transposase enzyme

<400> SEQUENCE: 18
```

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

```
Met Leu Trp Gly Cys Phe Ala Ala Gly Gly Thr Gly Ala Leu His Lys
            195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 19
<211> LENGTH: 6624
<212> TYPE: DNA
<213> ORGANISM: Artificial Sequence
<220> FEATURE:
<223> OTHER INFORMATION: sequence of the Sleeping Beauty expression
      construct pCDNA3.1-hygro(+)-SB

<400> SEQUENCE: 19
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattctgc     960
agatatggga aaatcaaaag aaatcagcca agacctcaga aaaaaaattg tagacctcca    1020
caagtctggt tcatccttgg gagcaatttc caaacgcctg aaagtaccac gttcatctgt    1080
acaaacaata gtacgcaagt ataaacacca tgggaccacg cagccgtcat accgctcagg    1140
```

```
aaggagacgc gttctgtctc ctagagatga acgtactttg gtgcgaaaag tgcaaatcaa      1200
tcccagaaca acagcaaagg accttgtgaa gatgctggag gaaacaggta caaaagtatc      1260
tatatccaca gtaaaacgag tcctatatcg acataacctg aaaggccgct cagcaaggaa      1320
gaagccactg ctccaaaacc gacataagaa agccagacta cggtttgcaa ctgcacatgg      1380
ggacaaagat cgtactttt  ggagaaatgt cctctggtct gatgaaacaa aaatagaact      1440
gtttggccat aatgaccatc gttatgtttg gaggaagaag ggggaggctt gcaagccgaa      1500
gaacaccatc ccaaccgtga agcacgggggg tggcagcatc atgttgtggg ggtgctttgc     1560
tgcaggaggg actggtgcac ttcacaaaat agatggcatc atgaggaagg aaaattatgt      1620
ggatatattg aagcaacatc tcaagacatc agtcaggaag ttaaagcttg gtcgcaaatg      1680
ggtcttccaa atggacaatg accccaagca tacttccaaa gttgtggcaa aatggcttaa      1740
ggacaacaaa gtcaaggtat tggagtggcc atcacaaagc cctgacctca atcctataga      1800
aaatttgtgg gcagaactga aaaagcgtgt gcgagcaagg aggcctacaa acctgactca      1860
gttacaccag ctctgtcagg aggaatgggc caaaattcac ccaacttatt gtgggaagct      1920
tgtggaaggc tacccgaaac gtttgaccca agttaaacaa tttaaaggca atgctaccaa      1980
atactagatc cagcacagtg gcggccgctc gagtctagag ggcccgttta aacccgctga      2040
tcagcctcga ctgtgccttc tagttgccag ccatctgttg tttgcccctc ccccgtgcct      2100
tccttgaccc tggaaggtgc cactcccact gtcctttcct aataaaatga ggaaattgca      2160
tcgcattgtc tgagtaggtg tcattctatt ctggggggtg gggtggggca ggacagcaag      2220
ggggaggatt gggaagacaa tagcaggcat gctgggggatg cggtgggctc tatggcttct      2280
gaggcggaaa gaaccagctg gggctctagg gggtatcccc acgcgccctg tagcggcgca      2340
ttaagcgcgg cgggtgtggt ggttacgcgc agcgtgaccg ctacacttgc cagcgcccta      2400
gcgcccgctc cttttcgctt tcttcccttc cttctcgcca cgttcgccgg ctttccccgt      2460
caagctctaa atcggggcat ccctttaggg ttccgattta gtgctttacg gcacctcgac      2520
cccaaaaaac ttgattaggg tgatggttca cgtagtgggc catcgccctg atagacggtt      2580
tttcgccctt tgacgttgga gtccacgttc tttaatagtg gactcttgtt ccaaactgga      2640
acaacactca accctatctc ggtctattct tttgatttat aagggatttt ggggatttcg      2700
gcctattggt taaaaaatga gctgatttaa caaaaattta acgcgaatta attctgtgga      2760
atgtgtgtca gttagggtgt ggaaagtccc caggctcccc aggcaggcag aagtatgcaa      2820
agcatgcatc tcaattagtc agcaaccagg tgtggaaagt ccccaggctc ccagcaggc      2880 agaagtatgc aaagcatgca tctcaattag tcagcaacca tagtcccgcc cctaactccg      2940
cccatcccgc ccctaactcc gcccagttcc gcccattctc cgccccatgg ctgactaatt      3000
ttttttattt atgcagaggc cgaggccgcc tctgcctctg agctattcca gaagtagtga      3060
ggaggctttt ttggaggcct aggcttttgc aaaaagctcc cgggagcttg tatatccatt      3120
ttcggatctg atcagcacgt gatgaaaaag cctgaactca ccgcgacgtc tgtcgagaag      3180
tttctgatcg aaaagttcga cagcgtctcc gacctgatgc agctctcgga gggcgaagaa      3240
tctcgtgctt tcagcttcga tgtaggaggg cgtggatatg tcctgcgggt aaatagctgc      3300
gccgatggtt tctacaaaga tcgttatgtt tatcggcact ttgcatcggc cgcgctcccg      3360
attccggaag tgcttgacat tggggaattc agcgagagcc tgacctattg catctcccgc      3420
cgtgcacagg gtgtcacgtt gcaagacctg cctgaaaccg aactgcccgc tgttctgcag      3480
ccggtcgcgg aggccatgga tgcgatcgct gcggccgatc ttagccagac gagcgggttc      3540
```

```
ggcccattcg gaccgcaagg aatcggtcaa tacactacat ggcgtgattt catatgcgcg    3600
attgctgatc cccatgtgta tcactggcaa actgtgatgg acgacaccgt cagtgcgtcc    3660
gtcgcgcagg ctctcgatga gctgatgctt tgggccgagg actgccccga agtccggcac    3720
ctcgtgcacg cggatttcgg ctccaacaat gtcctgacgg acaatggccg cataacagcg    3780
gtcattgact ggagcgaggc gatgttcggg gattcccaat acgaggtcgc caacatcttc    3840
ttctggaggc cgtggttggc ttgtatggag cagcagacgc gctacttcga gcggaggcat    3900
ccggagcttg caggatcgcc gcggctccgg gcgtatatgc tccgcattgg tcttgaccaa    3960
ctctatcaga gcttggttga cggcaatttc gatgatgcag cttgggcgca gggtcgatgc    4020
gacgcaatcg tccgatccgg agccgggact gtcgggcgta cacaaatcgc ccgcagaagc    4080
gcggccgtct ggaccgatgg ctgtgtagaa gtactcgccg atagtggaaa ccgacgcccc    4140
agcactcgtc cgagggcaaa ggaatagcac gtgctacgag atttcgattc caccgccgcc    4200
ttctatgaaa ggttgggctt cggaatcgtt ttccggacg ccggctggat gatcctccag    4260
cgcggggatc tcatgctgga gttcttcgcc cacccccaact tgtttattgc agcttataat    4320
ggttacaaat aaagcaatag catcacaaat ttcacaaata aagcattttt ttcactgcat    4380
tctagttgtg gtttgtccaa actcatcaat gtatcttatc atgtctgtat accgtcgacc    4440
tctagctaga gcttggcgta atcatggtca tagctgtttc ctgtgtgaaa ttgttatccg    4500
ctcacaattc cacacaacat acgagccgga agcataaagt gtaaagcctg gggtgcctaa    4560
tgagtgagct aactcacatt aattgcgttg cgctcactgc ccgctttcca gtcgggaaac    4620
ctgtcgtgcc agctgcatta atgaatcggc caacgcgcgg ggagaggcgg tttgcgtatt    4680
gggcgctctt ccgcttcctc gctcactgac tcgctgcgct cggtcgttcg gctgcggcga    4740
gcggtatcag ctcactcaaa ggcggtaata cggttatcca cagaatcagg ggataacgca    4800
ggaaagaaca tgtgagcaaa aggccagcaa aaggccagga accgtaaaaa ggccgcgttg    4860
ctggcgtttt tccataggct ccgcccccct gacgagcatc acaaaaatcg acgctcaagt    4920
cagaggtggc gaaacccgac aggactataa agataccagg cgtttccccc tggaagctcc    4980
ctcgtgcgct ctcctgttcc gaccctgccg cttaccggat acctgtccgc ctttctccct    5040
tcgggaagcg tggcgctttc tcaatgctca cgctgtaggt atctcagttc ggtgtaggtc    5100
gttcgctcca agctgggctg tgtgcacgaa ccccccgttc agcccgaccg ctgcgcctta    5160
tccggtaact atcgtcttga gtccaacccg gtaagacacg acttatcgcc actggcagca    5220
gccactggta acaggattag cagagcgagg tatgtaggcg gtgctacaga gttcttgaag    5280
tggtggccta actacggcta cactagaagg acagtatttg gtatctgcgc tctgctgaag    5340
ccagttacct tcggaaaaag agttggtagc tcttgatccg gcaaacaaac caccgctggt    5400
agcggtggtt ttttgtttg caagcagcag attacgcgca gaaaaaaagg atctcaagaa    5460
gatcctttga tcttttctac ggggtctgac gctcagtgga acgaaaactc acgttaaggg    5520
attttggtca tgagattatc aaaaaggatc ttcacctaga tccttttaaa ttaaaaatga    5580
agttttaaat caatctaaag tatatatgag taaacttggt ctgacagtta ccaatgctta    5640
atcagtgagg cacctatctc agcgatctgt ctatttcgtt catccatagt tgcctgactc    5700
cccgtcgtgt agataactac gatacgggag ggcttaccat ctggccccag tgctgcaatg    5760
ataccgcgag acccacgctc accggctcca gatttatcag caataaacca gccagccgga    5820
agggccgagc gcagaagtgg tcctgcaact ttatccgcct ccatccagtc tattaattgt    5880
```

```
tgccgggaag ctagagtaag tagttcgcca gttaatagtt tgcgcaacgt tgttgccatt    5940
gctacaggca tcgtggtgtc acgctcgtcg tttggtatgg cttcattcag ctccggttcc    6000
caacgatcaa ggcgagttac atgatccccc atgttgtgca aaaaagcggt tagctccttc    6060
ggtcctccga tcgttgtcag aagtaagttg gccgcagtgt tatcactcat ggttatggca    6120
gcactgcata attctcttac tgtcatgcca tccgtaagat gcttttctgt gactggtgag    6180
tactcaacca agtcattctg agaatagtgt atgcggcgac cgagttgctc ttgcccggcg    6240
tcaatacggg ataataccgc gccacatagc agaactttaa aagtgctcat cattggaaaa    6300
cgttcttcgg ggcgaaaact ctcaaggatc ttaccgctgt tgagatccag ttcgatgtaa    6360
cccactcgtg cacccaactg atcttcagca tcttttactt tcaccagcgt ttctgggtga    6420
gcaaaaacag gaaggcaaaa tgccgcaaaa aagggaataa gggcgacacg gaaatgttga    6480
atactcatac tcttcctttt tcaatattat tgaagcattt atcagggtta ttgtctcatg    6540
agcggataca tatttgaatg tatttagaaa aataaacaaa tagggggttcc gcgcacattt    6600 ccccgaaaag tgccacctga cgtc                                          6624
```

<210> SEQ ID NO 20
<211> LENGTH: 4975
<212> TYPE: DNA
<213> ORGANISM: Artificial Sequence
<220> FEATURE:
<223> OTHER INFORMATION: DNA sequence containing a PiggyBac ITR-flanked
      expression cassette for membrane spanning human Ig-gamma1 heavy
      chains

<400> SEQUENCE: 20

```
gaattcttaa ccctagaaag atagtctgcg taaaattgac gcatgcattc ttgaaatatt    60
gctctctctt tctaaatagc gcgaatccgt cgctgtgcat ttaggacatc tcagtcgccg    120
cttggagctc ccgtgaggcg tgcttgtcaa tgcggtaagt gtcactgatt ttgaactata    180
acgaccgcgt gagtcaaaat gacgcatgat tatcttttac gtgacttta agatttaact    240 catacgataa ttatattgtt atttcatgtt ctacttacgt gataacttat tatatatata    300
ttttcttgtt atacctcgag gctagtctag agagtaattc atacaaaagg actcgcccct    360
gccttgggga atcccaggga ccgtcgttaa actcccacta acgtagaacc cagagatcgc    420
tgcgttcccg ccccctcacc cgccgcgctct cgtcatcact gaggtggaga agagcatgcg    480
tgaggctccg gtgcccgtca gtgggcagag cgcacatcgc ccacagtccc cgagaagttg    540
gggggagggg tcggcaattg aaccggtgcc tagagaaggt ggcgcgggt aaactgggaa    600 agtgatgtcg tgtactggct ccgccttttt cccgagggtg ggggagaacc gtatataagt    660
gcagtagtcg ccgtgaacgt tctttttcgc aacgggtttg ccgccagaac acaggtaagt    720
gccgtgtgtg gttcccgcgg gcctggcctc tttacgggtt atggcccttg cgtgccttga    780
attacttcca cgcccctggc tgcagtacgt gattcttgat cccgagcttc gggttggaag    840
tgggtgggag agttcgaggc cttgcgctta aggagcccct tcgcctcgtg cttgagttga    900
ggcctggctt gggcgctggg gccgccgcgt gcgaatctgg tggcaccttc gcgcctgtct    960
cgctgctttc gataagtctc tagccattta aaattttga tgacctgctg cgacgctttt    1020
tttctggcaa gatagtcttg taaatgcggg ccaagatctg cacactggta tttcggtttt    1080
tggggccgcg ggcggcgacg gggcccgtgc gtcccagcgc acatgttcgg cgaggcgggg    1140
cctgcgagcg cggccaccga gaatcggacg ggggtagtct caagctggcc ggcctgctct    1200
ggtgcctggc ctcgcgccgc cgtgtatcgc cccgccctgg gcggcaaggc tggcccggtc    1260
```

```
ggcaccagtt gcgtgagcgg aaagatggcc gcttcccggc cctgctgcag ggagctcaaa    1320
atggaggacg cggcgctcgg gagagcgggc gggtgagtca cccacacaaa ggaaaagggc    1380
ctttccgtcc tcagccgtcg cttcatgtga ctccacggag taccgggcgc cgtccaggca    1440
cctcgattag ttctcgagct tttggagtac gtcgtcttta ggttgggggg aggggttta    1500 tgcgatggag tttccccaca ctgagtgggt ggagactgaa gttaggccag cttggcactt    1560
gatgtaattc tccttggaat ttgcccttt tgagtttgga tcttggttca ttctcaagcc     1620
tcagacagtg gttcaaagtt tttttcttcc atttcaggtg tcgtgagcgg ccgctagatt    1680
gctagcacca agggcccatc ggtcttcccc ctggcaccct cctccaagag cacctctggg    1740
ggcacagcag ccctgggctg cctggtcaag gactacttcc ccgaaccggt gacggtgtcg    1800
tggaactcag gcgccctgac cagcggcgtg cacaccttcc cggctgtcct acagtcctca    1860
ggactctact ccctcagcag cgtggtgacc gtgccctcca gcagcttggg cacccagacc    1920
tacatctgca acgtgaatca caagcccagc aacaccaagg tggacaagaa agttgagccc    1980
aaatcttgtg acaaaactca cacatgccca ccgtgcccag cacctgaact cctgggggga    2040
ccgtcagtct tcctcttccc cccaaaaccc aaggacaccc tcatgatctc ccggaccct     2100 gaggtcacat gcgtggtggt ggacgtgagc cacgaagacc ctgaggtcaa gttcaactgg    2160
tacgtggacg gcgtggaggt gcataatgcc aagacaaagc cgcgggagga gcagtacaac    2220
agcacgtacc gtgtggtcag cgtcctcacc gtcctgcacc aggactggct gaatggcaag    2280
gagtacaagt gcaaggtctc caacaaagcc ctcccagccc ccatcgagaa aaccatctcc    2340
aaagccaaag ggcagccccg agaaccacag gtgtacaccc tgcccccatc ccgggatgag    2400
ctgaccaaga accaggtcag cctgacctgc ctggtcaaag gcttctatcc cagcgacatc    2460
gccgtggagt gggagagcaa tgggcagccg gagaacaact acaagaccac gcctcccgtg    2520
ctggactccg acggctcctt cttcctctac agcaagctca ccgtggacaa gagcaggtgg    2580
cagcagggga acgtcttctc atgctccgtg atgcatgagg ctctgcacaa ccactacaca    2640
cagaagagcc tctccctgtc tccggagctg caactggagg agagctgtgc ggaggcgcag    2700
gacggggagc tggacgggct gtggacgacc atcaccatct tcatcacact cttcctgtta    2760
agcgtgtgct acagtgccac cgtcaccttc ttcaaggtga agtggatctt ctcctcggtg    2820
gtggacctga agcagaccat catccccgac tacaggaaca tgatcggaca gggggcctag    2880
taagcttagc gctttcgaag ggcaggtaag tatcaaggtt acaagacagg tttaaggaga    2940
ccaatagaaa ctgggcttgt cgagacagag aagactcttg cgtttctgat aggcacctat    3000
tggtcttact gacatccact ttgcctttct ctccacaggt gcctacgta gcgatcgcca     3060 attccgcccc tctccctccc cccccctaa cgttactggc cgaagccgct tggaataagg    3120
ccggtgtgcg tttgtctata tgtgattttc caccatattg ccgtcttttg gcaatgtgag    3180
ggcccggaaa cctggccctg tcttcttgac gagcattcct aggggtcttt ccctctcgc     3240 caaaggaatg caaggtctgt tgaatgtcgt gaaggaagca gttcctctgg aagcttcttg    3300
aagacaaaca acgtctgtag cgacccttg caggcagcgg aacccccac ctggcgacag      3360 gtgcctctgc ggccaaaagc cacgtgtata agatacacct gcaaaggcgg cacaacccca    3420
gtgccacgtt gtgagttgga tagttgtgga aagagtcaaa tggctctcct caagcgtatt    3480
caacaagggg ctgaaggatg cccagaaggt accccattgt atgggatctg atctggggcc    3540
tcggtgcaca tgctttacat gtgtttagtc gaggttaaaa aaacgtctag gcccccgaa     3600
```

```
ccacgggac  gtggttttcc  tttgaaaaac  acgatgataa  gcttgccaca  acccggttta    3660
aacggatccc  gccaccatgg  tgagcaaggg  cgaggagctg  ttcaccgggg  tggtgcccat    3720
cctggtcgag  ctggacggcg  acgtaaacgg  ccacaagttc  agcgtgtccg  gcgagggcga    3780
gggcgatgcc  acctacggca  agctgaccct  gaagttcatc  tgcaccaccg  gcaagctgcc    3840
cgtgccctgg  cccaccctcg  tgaccaccct  gacctacggc  gtgcagtgct  tcagccgcta    3900
ccccgaccac  atgaagcagc  acgacttctt  caagtccgcc  atgcccgaag  gctacgtcca    3960
ggagcgcacc  atcttcttca  aggacgacgg  caactacaag  acccgcgccg  aggtgaagtt    4020
cgagggcgac  accctggtga  accgcatcga  gctgaagggc  atcgacttca  aggaggacgg    4080
caacatcctg  gggcacaagc  tggagtacaa  ctacaacagc  cacaacgtct  atatcatggc    4140
cgacaagcag  aagaacggca  tcaaggtgaa  cttcaagatc  cgccacaaca  tcgaggacgg    4200
cagcgtgcag  ctcgccgacc  actaccagca  gaacaccccc  atcggcgacg  gccccgtgct    4260
gctgcccgac  aaccactacc  tgagcaccca  gtccgccctg  agcaaagacc  ccaacgagaa    4320
gcgcgatcac  atggtcctgc  tggagttcgt  gaccgccgcc  gggatcactc  tcggcatgga    4380
cgagctgtac  aagtaaagcg  gcatatgcgc  cggcggatat  ccggcgcgcc  gagctcgctg    4440
atcagcctcg  actgtgcctc  tagttgccag  ccatctgttg  tttgccctc   cccgtgcctt    4500 tccttgaccc  tggaaggtgc  cactcccact  gtcctttcct  aataaaatga  ggaaattgca    4560
tcgcattgtc  tgagtaggtg  tcattctatt  ctggggggtg  gggtgggca   ggacagcaag    4620 ggggaggatt  gggaagacaa  tagcaggcat  gctgggatg   cggtgggctc  tatggcttct    4680
gaggcggaaa  gaaccagctg  gggttaatta  acgcgttta   accctagaaa  gataatcata    4740
ttgtgacgta  cgttaaagat  aatcatgcgt  aaaattgacg  catgtgtttt  atcggtctgt    4800
atatcgaggt  ttatttatta  atttgaatag  atattaagtt  ttattatatt  tacacttaca    4860
tactaataat  aaattcaaca  aacaatttat  ttatgtttat  ttatttatta  aaaaaaaaca    4920
aaaactcaaa  atttcttcta  taaagtaaca  aaactttat   atcgattcgc  gcgcg         4975
```

<210> SEQ ID NO 21
<211> LENGTH: 2774
<212> TYPE: DNA
<213> ORGANISM: Artificial Sequence
<220> FEATURE:
<223> OTHER INFORMATION: DNA sequence containing vector backbone
      components ColE1 and ampicillin resistance flanked by 5' and 3'
      ITRs of Sleeping Beauty

<400> SEQUENCE: 21

```
ttaattaaac  gcgtttgagt  gtatgttaac  ttctgaccca  ctgggaatgt  gatgaaagaa     60
ataaaagctg  aaatgaatca  ttctctctac  tattattctg  atatttcaca  ttcttaaaat    120
aaagtggtga  tcctaactga  ccttaagaca  gggaatcttt  actcggatta  aatgtcagga    180
attgtgaaaa  agtgagttta  atgtatttg   gctaaggtgt  atgtaaactt  ccgacttcaa    240
ctatcgattc  gcgcgcgtgc  attctagttg  tggtttgtcc  aaaactcatca  atgtatctta    300 tcatgtctgt  ataccgtcga  cctctagcta  gagcttggcg  taatcatggt  catagctgtt    360
tcctgtgtga  aattgttatc  cgctcacaat  tccacacaac  atacgagccg  gaagcataaa    420
gtgtaaagcc  tggggtgcct  aatgagtgag  ctaactcaca  ttaattgcgt  tgcgctcact    480
gcccgctttc  cagtcgggaa  acctgtcgtg  ccagctgcat  taatgaatcg  gccaacgcgc    540
ggggagaggc  ggtttgcgta  ttgggcgctc  ttccgcttcc  tcgctcactg  actcgctgcg    600
ctcggtcgtt  cggctgcggc  gagcggtatc  agctcactca  aaggcggtaa  tacggttatc    660
```

```
cacagaatca ggggataacg caggaaagaa catgtgagca aaaggccagc aaaaggccag      720
gaaccgtaaa aaggccgcgt tgctggcgtt tttccatagg ctccgcccc ctgacgagca      780 tcacaaaaat cgacgctcaa gtcagaggtg gcgaaaccg acaggactat aaagatacca      840
ggcgtttccc cctggaagct ccctcgtgcg ctctcctgtt ccgaccctgc cgcttaccgg      900
atacctgtcc gcctttctcc cttcgggaag cgtggcgctt tctcaatgct cacgctgtag      960
gtatctcagt tcggtgtagg tcgttcgctc caagctgggc tgtgtgcacg aaccccccgt     1020
tcagcccgac cgctgcgcct tatccggtaa ctatcgtctt gagtccaacc cggtaagaca     1080
cgacttatcg ccactggcag cagccactgg taacaggatt agcagagcga ggtatgtagg     1140
cggtgctaca gagttcttga agtggtggcc taactacggc tacactagaa ggacagtatt     1200
tggtatctgc gctctgctga agccagttac cttcggaaaa agagttggta gctcttgatc     1260
cggcaaacaa accaccgctg gtagcggtgg ttttttgtt tgcaagcagc agattacgcg     1320
cagaaaaaaa ggatctcaag aagatccttt gatcttttct acggggtctg acgctcagtg     1380
gaacgaaaac tcacgttaag ggattttggt catgagatta tcaaaaagga tcttcaccta     1440
gatcctttta aattaaaaat gaagttttaa atcaatctaa agtatatatg agtaaacttg     1500
gtctgacagt taccaatgct taatcagtga ggcacctatc tcagcgatct gtctatttcg     1560
ttcatccata gttgcctgac tccccgtcgt gtagataact acgatacggg agggcttacc     1620
atctggcccc agtgctgcaa tgataccgcg agacccacgc tcaccggctc cagatttatc     1680
agcaataaac cagccagccg gaagggccga gcgcagaagt ggtcctgcaa ctttatccgc     1740
ctccatccag tctattaatt gttgccggga agctagagta agtagttcgc cagttaatag     1800
tttgcgcaac gttgttgcca ttgctacagg catcgtggtg tcacgctcgt cgtttggtat     1860
ggcttcattc agctccggtt cccaacgatc aaggcgagtt acatgatccc ccatgttgtg     1920
caaaaaagcg gttagctcct tcggtcctcc gatcgttgtc agaagtaagt tggccgcagt     1980
gttatcactc atggttatgg cagcactgca taattctctt actgtcatgc catccgtaag     2040
atgcttttct gtgactggtg agtactcaac caagtcattc tgagaatagt gtatgcggcg     2100
accgagttgc tcttgcccgg cgtcaatacg ggataatacc gcgccacata gcagaacttt     2160
aaaagtgctc atcattggaa aacgttcttc ggggcgaaaa ctctcaagga tcttaccgct     2220
gttgagatcc agttcgatgt aacccactcg tgcacccaac tgatcttcag catcttttac     2280
tttcaccagc gtttctgggt gagcaaaaac aggaaggcaa aatgccgcaa aaaagggaat     2340
aagggcgaca cggaaatgtt gaatactcat actcttcctt tttcaatatt attgaagcat     2400
ttatcagggt tattgtctca tgagcggata catatttgaa tgtatttaga aaaataaaca     2460
aataggggtt ccgcgcacat ttccccgaaa agtgccacct gacgtcgacg gatcgggcct     2520
gcaggaattc agttgaagtc ggaagtttac atacacttaa gttggagtca ttaaaactcg     2580
tttttcaact acaccacaaa tttcttgtta acaaacaata gttttggcaa gtcagttagg     2640
acatctactt tgtgcatgac acaagtcatt tttccaacaa ttgtttacag acagattatt     2700
tcacttataa ttcactgtat cacaattcca gtgggtcaga agtttacata cactaacctc     2760
gaggctagtc taga                                                      2774
```

<210> SEQ ID NO 22
<211> LENGTH: 7242
<212> TYPE: DNA
<213> ORGANISM: Artificial Sequence
<220> FEATURE:

<223> OTHER INFORMATION: sequence of PiggyBac transposable "empty" human gamma1-HC vector

<400> SEQUENCE: 22

```
gaattcttaa ccctagaaag atagtctgcg taaaattgac gcatgcattc ttgaaatatt      60
gctctctctt tctaaatagc gcgaatccgt cgctgtgcat ttaggacatc tcagtcgccg     120
cttggagctc ccgtgaggcg tgcttgtcaa tgcggtaagt gtcactgatt ttgaactata     180
acgaccgcgt gagtcaaaat gacgcatgat tatcttttac gtgacttttta agatttaact   240
catacgataa ttatattgtt atttcatgtt ctacttacgt gataacttat tatatatata    300
ttttcttgtt atacctcgag gctagtctag agagtaattc atacaaaagg actcgcccct    360
gccttgggga atcccaggga ccgtcgttaa actcccacta acgtagaacc cagagatcgc    420
tgcgttcccg cccctcacc cgcccgctct cgtcatcact gaggtggaga agagcatgcg    480
tgaggctccg gtgcccgtca gtgggcagag cgcacatcgc ccacagtccc cgagaagttg    540
ggggagggg tcggcaattg aaccggtgcc tagagaaggt ggcgcggggt aaactgggaa     600
agtgatgtcg tgtactggct ccgccttttt cccgagggtg ggggagaacc gtatataagt    660
gcagtagtcg ccgtgaacgt tcttttttcgc aacgggtttg ccgccagaac acaggtaagt   720
gccgtgtgtg gttcccgcgg gcctggcctc tttacgggtt atggcccttg cgtgccttga    780
attacttcca cgcccctggc tgcagtacgt gattcttgat cccgagcttc gggttggaag    840
tgggtgggag agttcgaggc cttgcgctta aggagcccct tcgcctcgtg cttgagttga    900
ggcctggctt gggcgctggg gccgccgcgt gcgaatctgg tggcaccttc gcgcctgtct    960
cgctgctttc gataagtctc tagccattta aaattttttga tgacctgctg cgacgctttt  1020
tttctggcaa gatagtcttg taaatgcggg ccaagatctg cacactggta tttcggtttt   1080
tgggggccgcg ggcggcgacg gggcccgtgc gtcccagcgc acatgttcgg cgaggcgggg  1140
cctgcgagcg cggccaccga gaatcggacg ggggtagtct caagctggcc ggcctgctct   1200
ggtgcctggc ctcgcgccgc cgtgtatcgc cccgccctgg gcggcaaggc tggcccggtc   1260
ggcaccagtt gcgtgagcgg aaagatggc gcttcccggc cctgctgcag ggagctcaaa   1320
atggaggacg cggcgctcgg gagagcgggc gggtgagtca cccacacaaa ggaaaagggc   1380
ctttccgtcc tcagccgtcg cttcatgtga ctccacggag taccgggcgc cgtccaggca   1440
cctcgattag ttctcgagct tttggagtac gtcgtctttta ggttgggggg aggggttttta  1500
tgcgatggag tttccccaca ctgagtgggt ggagactgaa gttaggccag cttggcactt    1560
gatgtaattc tccttggaat ttgcccttttt tgagtttgga tcttggttca ttctcaagcc    1620
tcagacagtg gttcaaagtt ttttttcttcc atttcaggtg tcgtgagcgg ccgctagatt    1680
gctagcacca agggcccatc ggtcttcccc ctggcaccct cctccaagag cacctctggg    1740
ggcacagcag ccctgggctg cctggtcaag gactacttcc ccgaaccggt gacggtgtcg    1800
tggaactcag cgccctgac cagcggcgtg cacaccttcc cggctgtcct acagtcctca    1860
ggactctact ccctcagcag cgtggtgacc gtgccctcca gcagcttggg cacccagacc    1920
tacatctgca acgtgaatca caagcccagc aacaccaagg tggacaagaa agttgagccc    1980
aaatcttgtg acaaaactca cacatgccca ccgtgcccag cacctgaact cctggggggga  2040
ccgtcagtct cctcttccc cccaaaaccc aaggacaccc tcatgatctc ccggacccct    2100
gaggtcacat gcgtggtggt ggacgtgagc cacgaagacc ctgaggtcaa gttcaactgg   2160
tacgtggacg gcgtggaggt gcataatgcc aagacaaagc cgcgggagga gcagtacaac    2220
```

```
agcacgtacc gtgtggtcag cgtcctcacc gtcctgcacc aggactggct gaatggcaag    2280
gagtacaagt gcaaggtctc caacaaagcc ctcccagccc ccatcgagaa aaccatctcc    2340
aaagccaaag gcagccccg agaaccacag gtgtacaccc tgcccccatc ccgggatgag    2400
ctgaccaaga accaggtcag cctgacctgc ctggtcaaag gcttctatcc cagcgacatc    2460
gccgtggagt gggagagcaa tgggcagccg gagaacaact acaagaccac gcctcccgtg    2520
ctggactccg acggctcctt cttcctctac agcaagctca ccgtggacaa gagcaggtgg    2580
cagcagggga acgtcttctc atgctccgtg atgcatgagg ctctgcacaa ccactacaca    2640
cagaagagcc tctccctgtc tccggagctg caactggagg agagctgtgc ggaggcgcag    2700
gacggggagc tggacgggct gtggacgacc atcaccatct tcatcacact cttcctgtta    2760
agcgtgtgct acagtgccac cgtcaccttc ttcaaggtga agtggatctt ctcctcggtg    2820
gtggacctga agcagaccat catccccgac tacaggaaca tgatcggaca gggggcctag    2880
taagcttagc gctttcgaag ggcaggtaag tatcaaggtt acaagacagg tttaaggaga    2940
ccaatagaaa ctgggcttgt cgagacagag aagactcttg cgtttctgat aggcacctat    3000
tggtcttact gacatccact ttgccttct ctccacaggt gtcctacgta gcgatcgcca    3060
attccgcccc tctccctccc ccccccctaa cgttactggc cgaagccgct tggaataagg    3120
ccggtgtgcg tttgtctata tgtgattttc caccatattg ccgtcttttg gcaatgtgag    3180
ggcccggaaa cctggccctg tcttcttgac gagcattcct aggggtcttt ccctctcgc    3240 caaaggaatg caaggtctgt tgaatgtcgt gaaggaagca gttcctctgg aagcttcttg    3300
aagacaaaca acgtctgtag cgaccctttg caggcagcgg aacccccac ctggcgacag    3360 gtgcctctgc ggccaaaagc cacgtgtata agatacacct gcaaaggcgg cacaaccccca    3420 gtgccacgtt gtgagttgga tagttgtgga aagagtcaaa tggctctcct caagcgtatt    3480
caacaagggg ctgaaggatg cccagaaggt accccattgt atgggatctg atctggggcc    3540
tcggtgcaca tgctttacat gtgtttagtc gaggttaaaa aaacgtctag gccccccgaa    3600
ccacggggac gtggttttcc tttgaaaaac acgatgataa gcttgccaca acccggttta    3660
aacggatccc gccaccatgg tgagcaaggg cgaggagctg ttcaccgggg tggtgcccat    3720
cctggtcgag ctggacggcg acgtaaacgg ccacaagttc agcgtgtccg gcgagggcga    3780
gggcgatgcc acctacggca agctgaccct gaagttcatc tgcaccaccg gcaagctgcc    3840
cgtgccctgg cccaccctcg tgaccaccct gacctacggc gtgcagtgct tcagccgcta    3900
ccccgaccac atgaagcagc acgacttctt caagtccgcc atgcccgaag gctacgtcca    3960
ggagcgcacc atcttcttca aggacgacgg caactacaag acccgcgccg aggtgaagtt    4020
cgagggcgac accctggtga accgcatcga gctgaagggc atcgacttca aggaggacgg    4080
caacatcctg gggcacaagc tggagtacaa ctacaacagc cacaacgtct atatcatggc    4140
cgacaagcag aagaacggca tcaaggtgaa cttcaagatc cgccacaaca tcgaggacgg    4200
cagcgtgcag ctcgccgacc actaccagca gaacaccccc atcggcgacg gccccgtgct    4260
gctgcccgac aaccactacc tgagcaccca gtccgccctg agcaaagacc ccaacgagaa    4320
gcgcgatcac atggtcctgc tggagttcgt gaccgccgcc gggatcactc tcggcatgga    4380
cgagctgtac aagtaaagcg gcatatgcgc cggcggatat ccggcgcgcc gagctcgctg    4440
atcagcctcg actgtgcctc tagttgccag ccatctgttg tttgcccctc ccccgtgcct    4500
tccttgaccc tggaaggtgc cactcccact gtccttcct aataaaatga ggaaattgca    4560
tcgcattgtc tgagtaggtg tcattctatt ctggggggtg gggtggggca ggacagcaag    4620
```

```
ggggaggatt gggaagacaa tagcaggcat gctggggatg cggtgggctc tatggcttct   4680
gaggcggaaa gaaccagctg gggttaatta aacgcgttta accctagaaa gataatcata   4740
ttgtgacgta cgttaaagat aatcatgcgt aaaattgacg catgtgtttt atcggtctgt   4800
atatcgaggt ttatttatta atttgaatag atattaagtt ttattatatt tacacttaca   4860
tactaataat aaattcaaca aacaatttat ttatgtttat ttatttatta aaaaaaaaca   4920
aaaactcaaa atttcttcta taaagtaaca aaacttttat atcgattcgc gcgcgtgcat   4980
tctagttgtg gtttgtccaa actcatcaat gtatcttatc atgtctgtat accgtcgacc   5040
tctagctaga gcttggcgta atcatggtca tagctgtttc ctgtgtgaaa ttgttatccg   5100
ctcacaattc cacacaacat acgagccgga agcataaagt gtaaagcctg gggtgcctaa   5160
tgagtgagct aactcacatt aattgcgttg cgctcactgc ccgctttcca gtcgggaaac   5220
ctgtcgtgcc agctgcatta atgaatcggc caacgcgcgg ggagaggcgg tttgcgtatt   5280
gggcgctctt ccgcttcctc gctcactgac tcgctgcgct cggtcgttcg gctgcggcga   5340
gcggtatcag ctcactcaaa ggcggtaata cggttatcca cagaatcagg ggataacgca   5400
ggaaagaaca tgtgagcaaa aggccagcaa aaggccagga accgtaaaaa ggccgcgttg   5460
ctggcgtttt tccataggct ccgcccccct gacgagcatc acaaaaatcg acgctcaagt   5520
cagaggtggc gaaacccgac aggactataa agataccagg cgtttccccc tggaagctcc   5580
ctcgtgcgct ctcctgttcc gaccctgccg cttaccggat acctgtccgc ctttctccct   5640 tcggaagcg tggcgctttc tcaatgctca cgctgtaggt atctcagttc ggtgtaggtc   5700
gttcgctcca agctgggctg tgtgcacgaa ccccccgttc agcccgaccg ctgcgcctta   5760
tccggtaact atcgtcttga gtccaacccg gtaagacacg acttatcgcc actggcagca   5820
gccactggta acaggattag cagagcgagg tatgtaggcg gtgctacaga gttcttgaag   5880
tggtggccta actacggcta cactagaagg acagtatttg gtatctgcgc tctgctgaag   5940
ccagttacct tcggaaaaag agttggtagc tcttgatccg gcaaacaaac caccgctggt   6000
agcggtggtt tttttgtttg caagcagcag attacgcgca gaaaaaaagg atctcaagaa   6060
gatcctttga tcttttctac ggggtctgac gctcagtgga acgaaaactc acgttaaggg   6120
attttggtca tgagattatc aaaaaggatc ttcacctaga tccttttaaa ttaaaaatga   6180
agttttaaat caatctaaag tatatatgag taaacttggt ctgacagtta ccaatgctta   6240
atcagtgagg cacctatctc agcgatctgt ctatttcgtt catccatagt tgcctgactc   6300
cccgtcgtgt agataactac gatacgggag ggcttaccat ctggccccag tgctgcaatg   6360
ataccgcgag acccacgctc accggctcca gatttatcag caataaacca gccagccgga   6420
agggccgagc gcagaagtgg tcctgcaact ttatccgcct ccatccagtc tattaattgt   6480
tgccgggaag ctagagtaag tagttcgcca gttaatagtt tgcgcaacgt tgttgccatt   6540
gctacaggca tcgtggtgtc acgctcgtcg tttggtatgg cttcattcag ctccggttcc   6600
caacgatcaa ggcgagttac atgatccccc atgttgtgca aaaaagcggt tagctccttc   6660
ggtcctccga tcgttgtcag aagtaagttg gccgcagtgt tatcactcat ggttatggca   6720
gcactgcata attctcttac tgtcatgcca tccgtaagat gcttttctgt gactggtgag   6780
tactcaacca agtcattctg agaatagtgt atgcggcgac cgagttgctc ttgcccggcg   6840
tcaatacggg ataataccgc gccacatagc agaactttaa aagtgctcat cattggaaaa   6900
cgttcttcgg ggcgaaaact ctcaaggatc ttaccgctgt tgagatccag ttcgatgtaa   6960
```

| cccactcgtg cacccaactg atcttcagca tcttttactt tcaccagcgt ttctgggtga | 7020 |
| gcaaaaacag gaaggcaaaa tgccgcaaaa aagggaataa gggcgacacg gaaatgttga | 7080 |
| atactcatac tcttcctttt tcaatattat tgaagcattt atcagggtta ttgtctcatg | 7140 |
| agcggataca tatttgaatg tatttagaaa aataaacaaa tagggggttcc gcgcacattt | 7200 |
| ccccgaaaag tgccacctga cgtcgacgga tcgggcctgc ag | 7242 |

<210> SEQ ID NO 23
<211> LENGTH: 7146
<212> TYPE: DNA
<213> ORGANISM: Artificial Sequence
<220> FEATURE:
<223> OTHER INFORMATION: sequence of Sleeping Beauty transposable
      "empty" human gamma1-HC vector

<400> SEQUENCE: 23

| gaattcagtt gaagtcggaa gtttacatac acttaagttg gagtcattaa aactcgtttt | 60 |
| tcaactacac cacaaatttc ttgttaacaa acaatagttg tggcaagtca gttaggacat | 120 |
| ctactttgtg catgacacaa gtcatttttc caacaattgt ttacagacag attatttcac | 180 |
| ttataattca ctgtatcaca attccagtgg gtcagaagtt tacatacact aacctcgagg | 240 |
| ctagtctaga gagtaattca tacaaaagga ctcgcccctg ccttgggaa tcccagggac | 300 |
| cgtcgttaaa ctcccactaa cgtagaaccc agagatcgct cgcgttcccgc ccctcaccc | 360 |
| gcccgctctc gtcatcactg aggtggagaa gagcatgcgt gaggctccgg tgcccgtcag | 420 |
| tgggcagagc gcacatcgcc cacagtcccc gagaagttgg ggggaggggt cggcaattga | 480 |
| accggtgcct agagaaggtg gcgcggggta aactgggaaa gtgatgtcgt gtactggctc | 540 |
| cgccttttc ccgagggtgg gggagaaccg tatataagtg cagtagtcgc cgtgaacgtt | 600 |
| ctttttcgca acgggtttgc cgccagaaca caggtaagtg ccgtgtgtgg ttcccgcggg | 660 |
| cctggcctct ttacgggtta tggcccttgc gtgccttgaa ttacttccac gcccctggct | 720 |
| gcagtacgtg attcttgatc ccgagcttcg ggttggaagt gggtgggaga gttcgaggcc | 780 |
| ttgcgcttaa ggagcccctt cgcctcgtgc ttgagttgag gcctggcttg ggcgctgggg | 840 |
| ccgccgcgtg cgaatctggt ggcaccttcg cgcctgtctc gctgctttcg ataagtctct | 900 |
| agccattaa aattttgat gacctgctgc gacgcttttt ttctggcaag atagtcttgt | 960 |
| aaatgcgggc caagatctgc acactggtat ttcggttttt ggggccgcgg gcggcgacgg | 1020 |
| ggcccgtgcg tcccagcgca catgttcggc gaggcgggc ctgcgagcgc ggccaccgag | 1080 |
| aatcggacgg gggtagtctc aagctggccg gcctgctctg gtgcctggcc tcgcgccgcc | 1140 |
| gtgtatcgcc ccgccctggg cggcaaggct ggcccggtcg gcaccagttg cgtgagcgga | 1200 |
| aagatggccg cttcccggcc ctgctgcagg gagctcaaaa tggaggacgc ggcgctcggg | 1260 |
| agagcgggcg ggtgagtcac ccacacaaag gaaaagggcc tttccgtcct cagccgtcgc | 1320 |
| ttcatgtgac tccacggagt accggcgcc gtccaggcac ctcgattagt tctcgagctt | 1380 |
| ttggagtacg tcgtctttag gttgggggga ggggttttat gcgatggagt ttccccacac | 1440 |
| tgagtgggtg gagactgaag ttaggccagc ttggcacttg atgtaattct ccttggaatt | 1500 |
| tgccctttt gagtttggat cttggttcat tctcaagcct cagacagtgg ttcaaagttt | 1560 |
| ttttcttcca tttcaggtgt cgtgagcggc cgctagattg ctagcaccaa gggcccatcg | 1620 |
| gtcttccccc tggcaccctc ctccaagagc acctctgggg gcacagcagc cctgggctgc | 1680 |
| ctggtcaagg actacttccc cgaaccggtg acggtgtcgt ggaactcagg cgccctgacc | 1740 |

-continued

```
agcggcgtgc acaccttccc ggctgtccta cagtcctcag gactctactc cctcagcagc    1800
gtggtgaccg tgccctccag cagcttgggc acccagacct acatctgcaa cgtgaatcac    1860
aagcccagca acaccaaggt ggacaagaaa gttgagccca atcttgtga caaaactcac    1920 acatgcccac cgtgcccagc acctgaactc ctggggggac cgtcagtctt cctcttcccc    1980
ccaaaaccca aggacaccct catgatctcc cggacccctg aggtcacatg cgtggtggtg    2040
gacgtgagcc acgaagaccc tgaggtcaag ttcaactggt acgtggacgg cgtggaggtg    2100
cataatgcca agacaaagcc gcgggaggag cagtacaaca gcacgtaccg tgtggtcagc    2160
gtcctcaccg tcctgcacca ggactggctg aatggcaagg agtacaagtg caaggtctcc    2220
aacaaagccc tcccagcccc catcgagaaa accatctcca aagccaaagg gcagcccga    2280 gaaccacagg tgtacaccct gcccccatcc cgggatgagc tgaccaagaa ccaggtcagc    2340
ctgacctgcc tggtcaaagg cttctatccc agcgacatcg ccgtggagtg ggagagcaat    2400
gggcagccgg agaacaacta caagaccacg cctcccgtgc tggactccga cggctccttc    2460
ttcctctaca gcaagctcac cgtggacaag agcaggtggc agcagggaa cgtcttctca    2520 tgctccgtga tgcatgaggc tctgcacaac cactacacac agaagagcct ctccctgtct    2580
ccggagctga actggagga gagctgtgcg gaggcgcagg acggggagct ggacgggctg    2640
tggacgacca tcaccatctt catcacactc ttcctgttaa gcgtgtgcta cagtgccacc    2700
gtcaccttct tcaaggtgaa gtggatcttc tcctcggtgg tggacctgaa gcagaccatc    2760
atccccgact acaggaacat gatcggacag ggggcctagt aagcttagcg ctttcgaagg    2820
gcaggtaagt atcaaggtta caagacaggt ttaaggagac caatagaaac tgggcttgtc    2880
gagacagaga agactcttgc gtttctgata ggcacctatt ggtcttactg acatccactt    2940
tgcctttctc tccacaggtg tcctacgtag cgatcgccaa ttccgcccct ctccctcccc    3000
cccccctaac gttactggcc gaagccgctt ggaataaggc cggtgtgcgt ttgtctatat    3060 gtgatttttcc accatattgc cgtcttttgg caatgtgagg gcccggaaac ctggccctgt    3120
cttcttgacg agcattccta ggggtctttc cctctcgcc aaaggaatgc aaggtctgtt    3180
gaatgtcgtg aaggaagcag ttcctctgga agcttcttga agacaaacaa cgtctgtagc    3240 gacccctttgc aggcagcgga accccccacc tggcgacagg tgcctctgcg gccaaaagcc    3300
acgtgtataa gatacacctg caaaggcggc acaaccccag tgccacgttg tgagttggat    3360
agttgtggaa agagtcaaat ggctctcctc aagcgtattc aacaaggggc tgaaggatgc    3420
ccagaaggta ccccattgta tgggatctga tctgggggcct cggtgcacat gctttacatg    3480
tgtttagtcg aggttaaaaa aacgtctagg cccccgaac cacggggacg tggttttcct    3540
ttgaaaaaca cgatgataag cttgccacaa cccggttta acggatcccg ccaccatggt    3600
gagcaagggc gaggagctgt tcaccggggt ggtgcccatc ctggtcgagc tggacggcga    3660
cgtaaacggc cacaagttca gcgtgtccgg cgagggcgag ggcgatgcca cctacggcaa    3720
gctgaccctg aagttcatct gcaccaccgg caagctgccc gtgccctggc ccaccctcgt    3780
gaccaccctg acctacggcg tgcagtgctt cagccgctac cccgaccaca tgaagcagca    3840
cgacttcttc aagtccgcca tgcccgaagg ctacgtccag gagcgcacca tcttcttcaa    3900
ggacgacggc aactacaaga cccgcgccga ggtgaagttc gagggcgaca ccctggtgaa    3960
ccgcatcgag ctgaagggca tcgacttcaa ggaggacggc aacatcctgg ggcacaagct    4020
ggagtacaac tacaacagcc acaacgtcta tatcatggcc gacaagcaga agaacggcat    4080
caaggtgaac ttcaagatcc gccacaacat cgaggacggc agcgtgcagc tcgccgacca    4140
```

```
ctaccagcag aacaccccca tcggcgacgg ccccgtgctg ctgcccgaca accactacct   4200
gagcacccag tccgccctga gcaaagaccc aacgagaag cgcgatcaca tggtcctgct    4260
ggagttcgtg accgccgccg ggatcactct cggcatggac gagctgtaca agtaaagcgg   4320
catatgcgcc ggcggatatc cggcgcgccg agctcgctga tcagcctcga ctgtgcctct   4380
agttgccagc catctgttgt ttgcccctcc cccgtgcctt ccttgaccct ggaaggtgcc   4440
actcccactg tcctttccta ataaaatgag gaaattgcat cgcattgtct gagtaggtgt   4500
cattctattc tggggggtgg ggtggggcag gacagcaagg gggaggattg ggaagacaat   4560
agcaggcatg ctgggatgc ggtgggctct atggcttctg aggcggaaag aaccagctgg    4620
ggttaattaa acgcgtttga gtgtatgtta acttctgacc cactgggaat gtgatgaaag   4680
aaataaaagc tgaaatgaat cattctctct actattattc tgatatttca cattcttaaa   4740
ataaagtggt gatcctaact gaccttaaga cagggaatct ttactcggat taaatgtcag   4800
gaattgtgaa aaagtgagtt taaatgtatt tggctaaggt gtatgtaaac ttccgacttc   4860
aactatcgat tcgcgcgcgt gcattctagt tgtggtttgt ccaaactcat caatgtatct   4920
tatcatgtct gtataccgtc gacctctagc tagagcttgg cgtaatcatg gtcatagctg   4980
tttcctgtgt gaaattgtta tccgctcaca attccacaca acatacgagc cggaagcata   5040
aagtgtaaag cctggggtgc ctaatgagtg agctaactca cattaattgc gttgcgctca   5100
ctgcccgctt ccagtcggg aaacctgtcg tgccagctgc attaatgaat cggccaacgc    5160
gcggggagag gcggtttgcg tattgggcgc tcttccgctt cctcgctcac tgactcgctg   5220
cgctcggtcg ttcggctgcg gcgagcggta tcagctcact caaaggcggt aatacggtta   5280
tccacagaat caggggataa cgcaggaaag aacatgtgag caaaaggcca gcaaaaggcc   5340
aggaaccgta aaaaggccgc gttgctggcg ttttccata ggctccgccc ccctgacgag    5400
catcacaaaa atcgacgctc aagtcagagg tggcgaaacc cgacaggact ataaagatac   5460
caggcgtttc ccctggaag ctccctcgtg cgctctcctg ttccgaccct gccgcttacc    5520
ggatacctgt ccgcctttct cccttcggga agcgtggcgc tttctcaatg ctcacgctgt   5580
aggtatctca gttcggtgta ggtcgttcgc tccaagctgg gctgtgtgca cgaaccccc    5640 gttcagcccg accgctgcgc cttatccggt aactatcgtc ttgagtccaa cccggtaaga   5700
cacgacttat cgccactggc agcagccact ggtaacagga ttagcagagc gaggtatgta   5760
ggcggtgcta cagagttctt gaagtggtgg cctaactacg ctacactag aaggacagta    5820 tttggtatct gcgctctgct gaagccagtt accttcggaa aaagagttgg tagctcttga   5880
tccggcaaac aaaccaccgc tggtagcggt ggtttttttg tttgcaagca gcagattacg   5940
cgcagaaaaa aaggatctca agaagatcct ttgatctttt ctacgggtc tgacgctcag    6000 tggaacgaaa actcacgtta agggattttg gtcatgagat tatcaaaaag gatcttcacc   6060
tagatccttt taaattaaaa atgaagtttt aaatcaatct aaagtatata tgagtaaact   6120
tggtctgaca gttaccaatg cttaatcagt gaggcaccta tctcagcgat ctgtctattt   6180
cgttcatcca tagttgcctg actccccgtc gtgtagataa ctacgatacg ggagggctta   6240
ccatctggcc ccagtgctgc aatgataccg cgagacccac gctcaccggc tccagattta   6300
tcagcaataa accagccagc cggaagggcc gagcgcagaa gtggtcctgc aactttatcc   6360
gcctccatcc agtctattaa ttgttgccgg gaagctagag taagtagttc gccagttaat   6420
agtttgcgca acgttgttgc cattgctaca ggcatcgtgg tgtcacgctc gtcgtttggt   6480
```

```
atggcttcat tcagctccgg ttcccaacga tcaaggcgag ttacatgatc ccccatgttg   6540
tgcaaaaaag cggttagctc cttcggtcct ccgatcgttg tcagaagtaa gttggccgca   6600
gtgttatcac tcatggttat ggcagcactg cataattctc ttactgtcat gccatccgta   6660
agatgctttt ctgtgactgg tgagtactca accaagtcat tctgagaata gtgtatgcgg   6720
cgaccgagtt gctcttgccc ggcgtcaata cgggataata ccgcgccaca tagcagaact   6780
ttaaaagtgc tcatcattgg aaaacgttct cggggcgaaa actctcaag gatcttaccg    6840 ctgttgagat ccagttcgat gtaacccact cgtgcaccca actgatcttc agcatctttt   6900
actttcacca gcgtttctgg gtgagcaaaa acaggaaggc aaaatgccgc aaaaaaggga   6960
ataagggcga cacggaaatg ttgaatactc atactcttcc ttttcaata ttattgaagc    7020 atttatcagg gttattgtct catgagcgga tacatatttg aatgtattta gaaaaataaa   7080
caaatagggg ttccgcgcac atttccccga aaagtgccac ctgacgtcga cggatcgggc   7140
ctgcag                                                              7146

<210> SEQ ID NO 24
<211> LENGTH: 351
<212> TYPE: DNA
<213> ORGANISM: Artificial Sequence
<220> FEATURE:
<223> OTHER INFORMATION: VH coding region of anti-human CD30 antibody
      brentuximab

<400> SEQUENCE: 24
cagatccagc tgcagcagtc tggacctgag gtggtgaagc tgggggcttc agtgaagata   60
tcctgcaagg cttctggcta caccttcact gactactata taacctgggt gaagcagaag  120
cctggacagg gacttgagtg gattggatgg atttatcctg gaagcggtaa tactaagtac  180
aatgagaagt tcaagggcaa ggccacattg actgtagaca tcctccag cacagccttc    240 atgcagctca gcagcctgac atctgaggac actgctgtct atttctgtgc gaactatggt  300
aactactggt ttgcttactg gggccaaggg actcaggtca ctgtctctgc a            351

<210> SEQ ID NO 25
<211> LENGTH: 333
<212> TYPE: DNA
<213> ORGANISM: Artificial Sequence
<220> FEATURE:
<223> OTHER INFORMATION: VL coding region of anti-human CD30 antibody
      brentuximab

<400> SEQUENCE: 25
gacattgtgc tgacccaatc tccagcttct ttggctgtgt ctctagggca gagggccacc   60
atctcctgca aggccagcca aagtgttgat tttgatggtg atagttatat gaactggtac  120
caacagaaac caggacagcc acccaaagtc ctcatctatg ctgcatccaa tctagaatct  180
gggatcccag ccaggtttag tggcagtggg tctgggacag acttcaccct caacatccat  240
cctgtggagg aggaggatgc tgcaacctat tactgtcagc aaagtaatga ggatccgtgg  300
acgttcggtg gaggcaccaa gctggaaatc aaa                                333

<210> SEQ ID NO 26
<211> LENGTH: 417
<212> TYPE: DNA
<213> ORGANISM: Artificial Sequence
<220> FEATURE:
<223> OTHER INFORMATION: VH coding region of anti-human CD19 mAb huB12,
      including leader sequence
```

```
<400> SEQUENCE: 26
atgggatgga gctggatctt tcttttcctc ctgtcaggaa ctgcaggtgt ccattgtcag        60
gttcagctgc aagagtctgg ccctgggttg gttaagccct cccagaccct cagtctgact       120
tgtactgtgt ctgggggttc aatcagcact tctggtatgg gtgtaggctg gattaggcag       180
cacccaggga agggtctgga gtggattgga cacatttggt gggatgatga caagagatat       240
aacccagccc tgaagagcag agtgacaatc tctgtggata cctccaagaa ccagtttagc       300
ctcaagctgt ccagtgtgac agctgcagat actgctgtct actactgtgc tagaatggaa       360
ctttggtcct actatttga ctactggggc caaggcaccc ttgtcacagt ctcctca          417

<210> SEQ ID NO 27
<211> LENGTH: 375
<212> TYPE: DNA
<213> ORGANISM: Artificial Sequence
<220> FEATURE:
<223> OTHER INFORMATION: VL coding region of anti-human CD19 mAb huB12,
      including leader sequence

<400> SEQUENCE: 27
atgaagttgc ctgttaggct gttggtgctg atgttctgga ttcctgcttc cagcagtgaa        60
attgttctca cccagtctcc agcaaccctg tctctctctc caggggaaag ggctaccctg       120
agctgcagtg ccagctcaag tgtaagttac atgcactggt accagcagaa gccagggcag       180
gctcccagac tcctgattta tgacacatcc aaactggctt ctggtattcc agcaaggttc       240
agtggcagtg gtctgggaac agattttaca ctcacaatca gcagcctgga gccagaggat       300
gttgctgtct attactgttt tcagggagt gtatacccat tcacttttgg ccaagggaca       360
aagttggaaa tcaaa                                                         375

<210> SEQ ID NO 28
<211> LENGTH: 423
<212> TYPE: DNA
<213> ORGANISM: Artificial Sequence
<220> FEATURE:
<223> OTHER INFORMATION: DNA fragment, containing NotI-NheI-flanked VH
      coding region of the VH domain of anti-human CD30 mAb brentuximab

<400> SEQUENCE: 28
gcggccgcca tgaattttgg actgaggctg attttcctgg tgctgaccct gaaaggcgtc        60
cagtgtcaga tccagctgca gcagtctgga cctgaggtgg tgaagcctgg ggcttcagtg       120
aagatatcct gcaaggcttc tggctacacc ttcactgact actatataac ctgggtgaag       180
cagaagcctg gacagggact tgagtggatt ggatggattt atcctggaag cggtaatact       240
aagtacaatg agaagttcaa gggcaaggcc acattgactg tagacacatc ctccagcaca       300
gccttcatgc agctcagcag cctgacatct gaggacactg ctgtctattt ctgtgcgaac       360
tatggtaact actggtttgc ttactggggc caagggactc aggtcactgt ctctgcagct       420
agc                                                                      423

<210> SEQ ID NO 29
<211> LENGTH: 432
<212> TYPE: DNA
<213> ORGANISM: Artificial Sequence
<220> FEATURE:
<223> OTHER INFORMATION: DNA fragment, containing NotI-NheI-flanked VH
      coding region of the VH domain of anti-human CD19 mAb hBU12

<400> SEQUENCE: 29
```

```
gcggccgcca tgaattttgg actgaggctg attttcctgg tgctgaccct gaaaggcgtc    60
cagtgtcagg tgcagctgca ggaatctggc cctggcctcg tgaagccttc ccagaccctg   120
tctctgacct gcaccgtgtc cggcggctcc atctctacct ctggcatggg cgtgggctgg   180
atcagacagc atcctggcaa gggcctggaa tggatcggcc acatttggtg ggacgacgac   240
aagcggtaca ccccgccct gaagtccaga gtgaccatct ccgtggacac ctccaagaac   300
cagttctccc tgaagctgtc ctccgtgacc gccgctgata ccgccgtgta ctactgcgcc   360
cggatggaac tgtggtccta ctacttcgac tactggggcc agggcaccct cgtgaccgtg   420
tcatctgcta gc                                                      432
```

<210> SEQ ID NO 30
<211> LENGTH: 733
<212> TYPE: DNA
<213> ORGANISM: Artificial Sequence
<220> FEATURE:
<223> OTHER INFORMATION: DNA fragment containing IgL coding region of
     anti-CD30 mAb Ac10 and flanked by NotI and BstBI restriction
     enzyme sites

<400> SEQUENCE: 30

```
gcggccgcca tgaattttgg actgaggctg attttcctgg tgctgaccct gaaaggcgtc    60
cagtgtgaca ttgtgctgac ccaatctcca gcttctttgg ctgtgtctct agggcagagg   120
gccaccatct cctgcaaggc cagccaaagt gttgattttg atggtgatag ttatatgaac   180
tggtaccaac agaaaccagg acagccaccc aaagtcctca tctatgctgc atccaatcta   240
gaatctggga tcccagccag gtttagtggc agtgggtctg gacagactt cacccctcaac   300 atccatcctg tggaggagga ggatgctgca acctattact gtcagcaaag taatgaggat   360
ccgtggacgt tcggtggagg caccaagctg gaaatcaaac gtacggtggc tgcaccatct   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga aacacaaagt ctacgcctgc   660
gaagtcaccc atcagggcct gagctcgccc gtcacaaaga gcttcaacag gggagagtgt   720
tagcgctttc gaa                                                     733
```

<210> SEQ ID NO 31
<211> LENGTH: 718
<212> TYPE: DNA
<213> ORGANISM: Artificial Sequence
<220> FEATURE:
<223> OTHER INFORMATION: DNA fragment containing IgL coding region of
     anti-CD19 mAb hBU12 and flanked by NotI and BstBI restriction
     enzyme sites

<400> SEQUENCE: 31

```
gcggccgcca tgaattttgg actgaggctg attttcctgg tgctgaccct gaaaggcgtc    60
cagtgtgaaa ttgttctcac ccagtctcca gcaaccctgt ctctctctcc aggggaaagg   120
gctaccctga ctgcagtgc cagctcaagt gtaagttaca tgcactggta ccagcagaag   180
ccagggcagg ctcccagact cctgatttat gacacatcca actggcttc tggtattcca   240 gcaaggttca gtgcagtgg gtctggaaca gatttacac tcacaatcag cagcctggag   300
ccagaggatt ttgctgtcta ttactgtttt caggggagtg tatacccatt cacttttggc   360
caagggacaa agttggaaat caaacgtacg gtggctgcac catctgtctt catcttcccg   420
```

```
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgttagcg ctttcgaa     718

<210> SEQ ID NO 32
<211> LENGTH: 7645
<212> TYPE: DNA
<213> ORGANISM: Artificial Sequence
<220> FEATURE:
<223> OTHER INFORMATION: sequence of pPB-EGFP-HC-Ac10

<400> SEQUENCE: 32
gaattcttaa ccctagaaag atagtctgcg taaaattgac gcatgcattc ttgaaatatt     60
gctctctctt tctaaatagc gcgaatccgt cgctgtgcat ttaggacatc tcagtcgccg    120
cttggagctc ccgtgaggcg tgcttgtcaa tgcggtaagt gtcactgatt ttgaactata    180
acgaccgcgt gagtcaaaat gacgcatgat tatcttttac gtgactttta agatttaact    240
catacgataa ttatattgtt atttcatgtt ctacttacgt gataacttat tatatatata    300
ttttcttgtt atacctcgag gctagtctag agagtaattc atacaaaagg actcgcccct    360
gccttgggga atcccaggga ccgtcgttaa actcccacta acgtagaacc cagagatcgc    420
tgcgttcccg cccccctcacc cgcccgctct cgtcatcact gaggtggaga agagcatgcg    480
tgaggctccg gtgcccgtca gtgggcagag cgcacatcgc ccacagtccc cgagaagttg    540
gggggagggg tcggcaattg aaccggtgcc tagagaaggt ggcgcggggt aaactgggaa    600
agtgatgtcg tgtactggct ccgcctttttt cccgagggtg ggggagaacc gtatataagt    660
gcagtagtcg ccgtgaacgt tcttttttcgc aacgggtttg ccgccagaac acaggtaagt    720
gccgtgtgtg gttcccgcgg gcctggcctc tttacgggtt atggcccttg cgtgccttga    780
attacttcca cgcccctggc tgcagtacgt gattcttgat cccgagcttc gggttggaag    840
tgggtgggag agttcgaggc cttgcgctta aggagcccct tcgcctcgtg cttgagttga    900
ggcctggctt gggcgctggg gccgccgcgt gcgaatctgg tggcaccttc gcgcctgtct    960
cgctgctttc gataagtctc tagccatttta aaattttttga tgacctgctg cgacgctttt   1020
tttctggcaa gatagtcttg taaatgcggg ccaagatctg cacactggta tttcggtttt    1080
tggggccgcg gcggcgacg gggcccgtgc gtcccagcgc acatgttcgg cgaggcgggg    1140
cctgcgagcg cggccaccga gaatcggacg ggggtagtct caagctggcc ggcctgctct    1200
ggtgcctggc ctcgcgccgc cgtgtatcgc cccgccctgg gcggcaaggc tggcccggtc    1260
ggcaccagtt gcgtgagcgg aaagatggcc gcttcccggc cctgctgcag ggagctcaaa    1320
atggaggacg cggcgctcgg gagagcgggc gggtgagtca cccacacaaa ggaaaagggc    1380
ctttccgtcc tcagccgtcg cttcatgtga ctccacggag taccgggcgc cgtccaggca    1440
cctcgattag ttctcgagct tttggagtac gtcgtcttta ggttgggggg aggggtttta    1500
tgcgatggag tttccccaca ctgagtgggt ggagactgaa gttaggccag cttggcactt    1560
gatgtaattc tccttggaat ttgccctttt tgagtttgga tcttggttca ttctcaagcc    1620
tcagacagtg gttcaaagtt tttttcttcc atttcaggtg tcgtgagcgg ccgccatgaa    1680
ttttggactg aggctgattt tcctggtgct gaccctgaaa ggcgtccagt gtcagatcca    1740
```

```
gctgcagcag tctggccccg aggtcgtgaa acctggcgcc tccgtgaaga tctcctgcaa   1800
ggcctccggc tacaccttca ccgactacta catcacctgg gtcaagcaga agcccggcca   1860
gggcctggaa tggatcggct ggatctatcc cggctccggc aacaccaagt acaacgagaa   1920
gttcaagggc aaggccaccc tgaccgtgga cacctcctct tccaccgcct tcatgcagct   1980
gtcctccctg acctccgagg ataccgccgt gtacttctgc gccaactacg caactattg    2040
gttcgcctac tggggccagg gcacacaagt gaccgtgtct gctgctagca ccaagggccc   2100
atcggtcttc cccctggcac cctcctccaa gagcacctct gggggcacag cagccctggg   2160
ctgcctggtc aaggactact ccccgaaccc ggtgacggtg tcgtggaact caggcgccct   2220
gaccagcggc gtgcacacct tcccggctgt cctacagtcc tcaggactct actccctcag   2280
cagcgtggtg accgtgccct ccagcagctt gggcacccag acctacatct gcaacgtgaa   2340
tcacaagccc agcaacacca aggtggacaa gaaagttgag cccaaatctt gtgacaaaac   2400
tcacacatgc ccaccgtgcc cagcacctga actcctgggg ggaccgtcag tcttcctctt   2460
ccccccaaaa cccaaggaca ccctcatgat ctcccggacc cctgaggtca catgcgtggt   2520
ggtggacgtg agccacgaag accctgaggt caagttcaac tggtacgtgg acggcgtgga   2580
ggtgcataat gccaagacaa agccgcggga ggagcagtac aacagcacgt accgtgtggt   2640
cagcgtcctc accgtcctgc accaggactg gctgaatggc aaggagtaca agtgcaaggt   2700
ctccaacaaa gccctcccag cccccatcga gaaaaccatc tccaaagcca agggcagcc   2760
ccgagaacca caggtgtaca ccctgccccc atcccgggat gagctgacca agaaccaggt   2820
cagcctgacc tgcctggtca aaggcttcta tcccagcgac atcgccgtgg agtgggagag   2880
caatgggcag ccggagaaca actacaagac cacgcctccc gtgctggact ccgacggctc   2940
cttcttcctc tacagcaagc tcaccgtgga caagagcagg tggcagcagg gaacgtctt    3000
ctcatgctcc gtgatgcatg aggctctgca caaccactac acacagaaga gcctctccct   3060
gtctccggag ctgcaactgg aggagagctg tgcggaggcg caggacgggg agctggacgg   3120
gctgtggacg accatcacca tcttcatcac actcttcctg ttaagcgtgt gctacagtgc   3180
caccgtcacc ttcttcaagg tgaagtggat cttctcctcg gtggtggacc tgaagcagac   3240
catcatcccc gactacagga acatgatcgg acagggggcc tagtaagctt agcgctttcg   3300
aagggcaggt aagtatcaag gttacaagac aggtttaagg agaccaatag aaactgggct   3360
tgtcgagaca gagaagactc ttgcgtttct dataggcacc tattggtctt actgacatcc   3420
actttgcctt tctctccaca ggtgtcctac gtagcgatcg ccaattccgc ccctctccct   3480
cccccccccc taacgttact ggccgaagcc gcttggaata aggccggtgt gcgtttgtct   3540
atatgtgatt ttccaccata ttgccgtctt ttggcaatgt gagggcccgg aaacctggcc   3600
ctgtcttctt gacgagcatt cctaggggtc tttcccctct cgccaaagga atgcaaggtc   3660
tgttgaatgt cgtgaaggaa gcagttcctc tggaagcttc ttgaagacaa acaacgtctg   3720
tagcgaccct ttgcaggcag cggaaccccc cacctggcga caggtgcctc tgcggccaaa   3780
agccacgtgt ataagataca cctgcaaagg cggcacaacc ccagtgccac gttgtgagtt   3840
ggatagttgt ggaaagagtc aaatggctct cctcaagcgt attcaacaag ggctgaagg    3900
atgcccagaa ggtaccccat tgtatgggat ctgatctggg gcctcggtgc acatgcttta   3960
catgtgttta gtcgaggtta aaaaaacgtc taggccccccc gaaccacggg gacgtggttt   4020
tcctttgaaa aacacgatga taagcttgcc acaacccggt ttaaacggat cccgccacca   4080
tggtgagcaa gggcgaggag ctgttcaccg gggtggtgcc catcctggtc gagctggacg   4140
```

```
gcgacgtaaa cggccacaag ttcagcgtgt ccggcgaggg cgagggcgat gccacctacg    4200
gcaagctgac cctgaagttc atctgcacca ccggcaagct gcccgtgccc tggcccaccc    4260
tcgtgaccac cctgacctac ggcgtgcagt gcttcagccg ctaccccgac cacatgaagc    4320
agcacgactt cttcaagtcc gccatgcccg aaggctacgt ccaggagcgc accatcttct    4380
tcaaggacga cggcaactac aagacccgcg ccgaggtgaa gttcgagggc gacaccctgg    4440
tgaaccgcat cgagctgaag ggcatcgact caaggagga cggcaacatc ctggggcaca    4500
agctggagta caactacaac agccacaacg tctatatcat ggccgacaag cagaagaacg    4560
gcatcaaggt gaacttcaag atccgccaca acatcgagga cggcagcgtg cagctcgccg    4620
accactacca gcagaacacc cccatcggcg acggccccgt gctgctgccc gacaaccact    4680
acctgagcac ccagtccgcc ctgagcaaag accccaacga gaagcgcgat cacatggtcc    4740
tgctggagtt cgtgaccgcc gccgggatca ctctcggcat ggacgagctg tacaagtaaa    4800
gcggcatatg cgccggcgga tatccggcgc gccgagctcg ctgatcagcc tcgactgtgc    4860
ctctagttgc cagccatctg ttgtttgccc ctcccccgtg ccttccttga ccctggaagg    4920
tgccactccc actgtccttt cctaataaaa tgaggaaatt gcatcgcatt gtctgagtag    4980
gtgtcattct attctggggg gtggggtggg gcaggacagc aaggggagg attgggaaga    5040 caatagcagg catgctgggg atgcggtggg ctctatggct tctgaggcgg aaagaaccag    5100
ctggggttaa ttaaacgcgt ttaaccctag aaagataatc atattgtgac gtacgttaaa    5160
gataatcatg cgtaaaattg acgcatgtgt tttatcggtc tgtatatcga ggtttattta    5220
ttaatttgaa tagatattaa gttttattat atttacactt acatactaat aataaattca    5280
acaaacaatt tatttatgtt tatttatttta ttaaaaaaaa acaaaaactc aaaatttctt    5340
ctataaagta acaaaacttt tatatcgatt cgcgcgcgtg cattctagtt gtggtttgtc    5400
caaactcatc aatgtatctt atcatgtctg tataccgtcg acctctagct agagcttggc    5460
gtaatcatgg tcatagctgt ttcctgtgtg aaattgttat ccgctcacaa ttccacacaa    5520
catacgagcc ggaagcataa agtgtaaagc ctggggtgcc taatgagtga gctaactcac    5580
attaattgcg ttgcgctcac tgcccgcttt ccagtcggga aacctgtcgt gccagctgca    5640
ttaatgaatc ggccaacgcg cggggagagg cggtttgcgt attgggcgct cttccgcttc    5700
ctcgctcact gactcgctgc gctcggtcgt tcggctgcgg cgagcggtat cagctcactc    5760
aaaggcggta atacggttat ccacagaatc aggggataac gcaggaaaga acatgtgagc    5820
aaaaggccag caaaaggcca ggaaccgtaa aaaggccgcg ttgctggcgt ttttccatag    5880
gctccgcccc cctgacgagc atcacaaaaa tcgacgctca gtcagaggt ggcgaaaccc    5940 gacaggacta taaagatacc aggcgtttcc ccctggaagc tccctcgtgc gctctcctgt    6000
tccgaccctg ccgcttaccg gatacctgtc cgcctttctc ccttcgggaa gcgtggcgct    6060
ttctcaatgc tcacgctgta ggtatctcag ttcggtgtag tcgttcgct ccaagctggg    6120 ctgtgtgcac gaaccccccg ttcagcccga ccgctgcgcc ttatccggta actatcgtct    6180
tgagtccaac ccggtaagac acgacttatc gccactggca gcagccactg gtaacaggat    6240
tagcagagcg aggtatgtag gcggtgctac agagttcttg aagtggtggc ctaactacgg    6300
ctacactaga aggacagtat ttggtatctg cgctctgctg aagccagtta ccttcggaaa    6360
aagagttggt agctcttgat ccggcaaaca aaccaccgct ggtagcggtg gtttttttgt    6420
ttgcaagcag cagattacgc gcagaaaaaa aggatctcaa gaagatcctt tgatcttttc    6480
```

```
tacggggtct gacgctcagt ggaacgaaaa ctcacgttaa gggatttttgg tcatgagatt    6540
atcaaaaagg atcttcacct agatcctttt aaattaaaaa tgaagtttta aatcaatcta    6600
aagtatatat gagtaaactt ggtctgacag ttaccaatgc ttaatcagtg aggcacctat    6660
ctcagcgatc tgtctatttc gttcatccat agttgcctga ctccccgtcg tgtagataac    6720
tacgatacgg agggcttac catctggccc cagtgctgca atgataccgc gagacccacg    6780
ctcaccggct ccagatttat cagcaataaa ccagccagcc ggaagggccg agcgcagaag    6840
tggtcctgca actttatccg cctccatcca gtctattaat tgttgccggg aagctagagt    6900
aagtagttcg ccagttaata gtttgcgcaa cgttgttgcc attgctacag gcatcgtggt    6960
gtcacgctcg tcgtttggta tggcttcatt cagctccggt tcccaacgat caaggcgagt    7020
tacatgatcc cccatgttgt gcaaaaaagc ggttagctcc ttcggtcctc cgatcgttgt    7080
cagaagtaag ttggccgcag tgttatcact catggttatg gcagcactgc ataattctct    7140
tactgtcatg ccatccgtaa gatgcttttc tgtgactggt gagtactcaa ccaagtcatt    7200
ctgagaatag tgtatgcggc gaccgagttg ctcttgcccg gcgtcaatac gggataatac    7260
cgcgccacat agcagaactt taaaagtgct catcattgga aaacgttctt cggggcgaaa    7320
actctcaagg atcttaccgc tgttgagatc cagttcgatg taacccactc gtgcacccaa    7380
ctgatcttca gcatctttta ctttcaccag cgtttctggg tgagcaaaaa caggaaggca    7440
aaatgccgca aaaagggaa taagggcgac acggaaatgt tgaatactca tactcttcct    7500
ttttcaatat tattgaagca tttatcaggg ttattgtctc atgagcggat acatatttga    7560
atgtatttag aaaaataaac aaatagggg tccgcgcaca tttccccgaa aagtgccacc    7620
tgacgtcgac ggatcgggcc tgcag                                         7645

<210> SEQ ID NO 33
<211> LENGTH: 7654
<212> TYPE: DNA
<213> ORGANISM: Artificial Sequence
<220> FEATURE:
<223> OTHER INFORMATION: sequence of pPB-EGFP-HC-hBU12

<400> SEQUENCE: 33
gaattcttaa ccctagaaag atagtctgcg taaaattgac gcatgcattc ttgaaatatt     60
gctctctctt tctaaatagc gcgaatccgt cgctgtgcat ttaggacatc tcagtcgccg    120
cttggagctc ccgtgaggcg tgcttgtcaa tgcggtaagt gtcactgatt ttgaactata    180
acgaccgcgt gagtcaaaat gacgcatgat tatcttttac gtgactttta agatttaact    240
catacgataa ttatattgtt atttcatgtt ctacttacgt gataacttat tatatatata    300
ttttcttgtt atacctcgag gctagtctag agagtaattc atacaaaagg actcgcccct    360
gccttgggga atcccaggga ccgtcgttaa actcccacta acgtagaacc cagagatcgc    420
tgcgttcccg cccctcacc cgcccgctct cgtcatcact gaggtggaga agagcatgcg    480
tgaggctccg gtgcccgtca gtgggcagag cgcacatcgc ccacagtccc cgagaagttg    540
gggggagggg tcggcaattg aaccggtgcc tagagaaggt ggcgcggggt aaactgggaa    600
agtgatgtcg tgtactggct ccgccttttt cccgagggtg ggggagaacc gtatataagt    660
gcagtagtcg ccgtgaacgt tctttttcgc aacgggtttg ccgccagaac acaggtaagt    720
gccgtgtgtg gttcccgcgg gcctggcctc tttacgggtt atggcccttg cgtgccttga    780
attacttcca cgcccctggc tgcagtacgt gattcttgat cccgagcttc gggttggaag    840
tgggtgggag agttcgaggc cttgcgctta aggagcccct tcgcctcgtg cttgagttga    900
```

```
ggcctggctt gggcgctggg gccgccgcgt gcgaatctgg tggcaccttc gcgcctgtct    960
cgctgctttc gataagtctc tagccattta aaattttga tgacctgctg cgacgctttt   1020
tttctggcaa gatagtcttg taaatgcggg ccaagatctg cacactggta tttcggtttt   1080
tggggccgcg ggcggcgacg gggcccgtgc gtcccagcgc acatgttcgg cgaggcgggg   1140
cctgcgagcg cggccaccga gaatcggacg ggggtagtct caagctggcc ggcctgctct   1200
ggtgcctggc ctcgcgccgc cgtgtatcgc cccgccctgg gcggcaaggc tggcccggtc   1260
ggcaccagtt gcgtgagcgg aaagatggcc gcttccggc cctgctgcag ggagctcaaa    1320
atggaggacg cggcgctcgg gagagcgggc gggtgagtca cccacacaaa ggaaaagggc   1380
ctttccgtcc tcagccgtcg cttcatgtga ctccacggag taccgggcgc cgtccaggca   1440
cctcgattag ttctcgagct tttggagtac gtcgtcttta ggttgggggg aggggtttta   1500
tgcgatggag tttccccaca ctgagtgggt ggagactgaa gttaggccag cttggcactt   1560
gatgtaattc tccttggaat ttgccctttt tgagtttgga tcttggttca ttctcaagcc   1620
tcagacagtg gttcaaagtt ttttcttcc atttcaggtg tcgtgagcgg ccgccatgaa    1680
ttttggactg aggctgatt tcctggtgct gacccctgaaa ggcgtccagt gtcaggtgca    1740
gctgcaggaa tctggccctg gcctcgtgaa gccttcccag accctgtctc tgacctgcac   1800
cgtgtccggc ggctccatct ctacctctgg catgggcgtg ggctggatca gacagcatcc   1860
tggcaagggc ctgaatgga tcggccacat ttggtgggac gacgacaagc ggtacaaccc    1920
cgccctgaag tccagagtga ccatctccgt ggacacctcc aagaaccagt tctccctgaa   1980
gctgtcctcc gtgaccgccg ctgataccgc cgtgtactac tgcgcccgga tggaactgtg   2040
gtcctactac ttcgactact ggggccaggg caccctcgtg accgtgtcat ctgctagcac   2100
caagggccca tcggtcttcc ccctggcacc ctcctccaag agcacctctg ggggcacagc   2160
agccctgggc tgcctggtca aggactactt ccccgaaccg gtgacggtgt cgtggaactc   2220
aggcgccctg accagcggcg tgcacacctt cccggctgtc ctacagtcct caggactcta   2280
ctccctcagc agcgtggtga ccgtgccctc cagcagcttg ggcacccaga cctacatctg   2340
caacgtgaat cacaagccca gcaacaccaa ggtggacaag aaagttgagc ccaaatcttg   2400
tgacaaaact cacacatgcc caccgtgccc agcacctgaa ctcctggggg gaccgtcagt   2460
cttcctcttc cccccaaaac ccaaggacac cctcatgatc tcccggaccc ctgaggtcac   2520
atgcgtggtg gtggacgtga gccacgaaga ccctgaggtc aagttcaact ggtacgtgga   2580
cggcgtggag gtgcataatg ccaagacaaa gccgcgggag gagcagtaca acagcacgta   2640
ccgtgtggtc agcgtcctca ccgtcctgca ccaggactgg ctgaatggca aggagtacaa   2700
gtgcaaggtc tccaacaaag ccctcccagc ccccatcgag aaaaccatct ccaaagccaa   2760
agggcagccc cgagaaccac aggtgtacac cctgccccca tcccgggatg agctgaccaa   2820
gaaccaggtc agcctgacct gcctggtcaa aggcttctat cccagcgaca tcgccgtgga   2880
gtgggagagc aatgggcagc cggagaacaa ctacaagacc acgcctcccg tgctggactc   2940
cgacggctcc ttcttcctct acagcaagct caccgtggac aagagcaggt ggcagcaggg   3000
gaacgtcttc tcatgctccg tgatgcatga ggctctgcac aaccactaca cacagaagag   3060
cctctccctg tctccgggtaaa
```

```
gaagcagacc atcatccccg actacaggaa catgatcgga caggggcct agtaagctta    3300
gcgctttcga agggcaggta agtatcaagg ttacaagaca ggtttaagga gaccaataga    3360
aactgggctt gtcgagacag agaagactct tgcgtttctg ataggcacct attggtctta    3420
ctgacatcca ctttgccttt ctctccacag gtgtcctacg tagcgatcgc caattccgcc    3480
cctctccctc ccccccccct aacgttactg gccgaagccg cttggaataa ggccggtgtg    3540
cgtttgtcta tatgtgattt tccaccatat tgccgtcttt tggcaatgtg agggcccgga    3600
aacctggccc tgtcttcttg acgagcattc ctaggggtct ttcccctctc gccaaaggaa    3660
tgcaaggtct gttgaatgtc gtgaaggaag cagttcctct ggaagcttct tgaagacaaa    3720
caacgtctgt agcgaccctt tgcaggcagc ggaaccccc acctggcgac aggtgcctct    3780
gcggccaaaa gccacgtgta taagatacac ctgcaaaggc ggcacaaccc cagtgccacg    3840
ttgtgagttg atagttgtg gaaagagtca aatggctctc ctcaagcgta ttcaacaagg    3900
ggctgaagga tgcccagaag gtaccccatt gtatgggatc tgatctgggg cctcggtgca    3960
catgctttac atgtgtttag tcgaggttaa aaaaacgtct aggccccccg aaccacgggg    4020
acgtggtttt cctttgaaaa acacgatgat aagcttgcca caacccggtt taaacggatc    4080
ccgccaccat ggtgagcaag ggcgaggagc tgttcaccgg ggtggtgccc atcctggtcg    4140
agctggacgg cgacgtaaac ggccacaagt tcagcgtgtc cggcgagggc gagggcgatg    4200
ccacctacgg caagctgacc ctgaagttca tctgcaccac cggcaagctg cccgtgccct    4260
ggcccaccct cgtgaccacc ctgacctacg gcgtgcagtg cttcagccgc taccccgacc    4320
acatgaagca gcacgacttc ttcaagtccg ccatgcccga aggctacgtc caggagcgca    4380
ccatcttctt caaggacgac ggcaactaca agacccgcgc cgaggtgaag ttcgagggcg    4440
acaccctggt gaaccgcatc gagctgaagg gcatcgactt caaggaggac ggcaacatcc    4500
tggggcacaa gctggagtac aactacaaca gccacaacgt ctatatcatg gccgacaagc    4560
agaagaacgg catcaaggtg aacttcaaga tccgccacaa catcgaggac ggcagcgtgc    4620
agctcgccga ccactaccag cagaacaccc ccatcggcga cggccccgtg ctgctgcccg    4680
acaaccacta cctgagcacc cagtccgccc tgagcaaaga ccccaacgag aagcgcgatc    4740
acatggtcct gctggagttc gtgaccgccg ccgggatcac tctcggcatg gacgagctgt    4800
acaagtaaag cggcatatgc gccggcggat atccggcgcg ccgagctcgc tgatcagcct    4860
cgactgtgcc tctagttgcc agccatctgt tgtttgcccc tcccccgtgc cttccttgac    4920
cctggaaggt gccactccca ctgtcctttc ctaataaaat gaggaaattg catcgcattg    4980
tctgagtagg tgtcattcta ttctgggggg tggggtgggg caggacagca agggggagga    5040
ttgggaagac aatagcaggc atgctgggga tgcggtgggc tctatggctt ctgaggcgga    5100
aagaaccagc tggggttaat taaacgcgtt taaccctaga aagataatca tattgtgacg    5160
tacgttaaag ataatcatgc gtaaaattga cgcatgtgtt ttatcggtct gtatatcgag    5220
gtttatttat taatttgaat agatattaag ttttattata tttacactta catactaata    5280
ataaattcaa caaacaattt atttatgttt atttatttat taaaaaaaaa caaaaactca    5340
aaatttcttc tataaagtaa caaaacttttt atatcgattc gcgcgcgtgc attctagttg    5400
tggtttgtcc aaaactcatca atgtatctta tcatgtctgt ataccgtcga cctctagcta    5460
gagcttggcg taatcatggt catagctgtt tcctgtgtga aattgttatc cgctcacaat    5520
tccacacaac atacgagccg gaagcataaa gtgtaaagcc tggggtgcct aatgagtgag    5580
ctaactcaca ttaattgcgt tgcgctcact gcccgctttc cagtcgggaa acctgtcgtg    5640
```

```
ccagctgcat taatgaatcg gccaacgcgc ggggagaggc ggtttgcgta ttgggcgctc    5700
ttccgcttcc tcgctcactg actcgctgcg ctcggtcgtt cggctgcggc gagcggtatc    5760
agctcactca aaggcggtaa tacggttatc cacagaatca ggggataacg caggaaagaa    5820
catgtgagca aaaggccagc aaaaggccag gaaccgtaaa aaggccgcgt tgctggcgtt    5880
tttccatagg ctccgccccc ctgacgagca tcacaaaaat cgacgctcaa gtcagaggtg    5940
gcgaaacccg acaggactat aaagatacca ggcgtttccc cctggaagct ccctcgtgcg    6000
ctctcctgtt ccgaccctgc cgcttaccgg atacctgtcc gcctttctcc cttcgggaag    6060
cgtggcgctt tctcaatgct cacgctgtag gtatctcagt tcggtgtagg tcgttcgctc    6120
caagctgggc tgtgtgcacg aaccccccgt tcagcccgac cgctgcgcct tatccggtaa    6180
ctatcgtctt gagtccaacc cggtaagaca cgacttatcg ccactggcag cagccactgg    6240
taacaggatt agcagagcga ggtatgtagg cggtgctaca gagttcttga agtggtggcc    6300
taactacggc tacactagaa ggacagtatt tggtatctgc gctctgctga gccagttac    6360 cttcggaaaa agagttggta gctcttgatc cggcaaacaa accaccgctg gtagcggtgg    6420
tttttttgtt tgcaagcagc agattacgcg cagaaaaaaa ggatctcaag aagatccttt    6480
gatcttttct acggggtctg acgctcagtg aacgaaaac tcacgttaag ggattttggt    6540
catgagatta tcaaaaagga tcttcaccta gatccttta aattaaaaat gaagttttaa    6600
atcaatctaa agtatatatg agtaaacttg gtctgacagt taccaatgct taatcagtga    6660
ggcacctatc tcagcgatct gtctatttcg ttcatccata gttgcctgac tccccgtcgt    6720
gtagataact acgatacggg agggcttacc atctggcccc agtgctgcaa tgataccgcg    6780
agacccacgc tcaccggctc cagatttatc agcaataaac cagccagccg aagggccga    6840 gcgcagaagt ggtcctgcaa ctttatccgc ctccatccag tctattaatt gttgccggga    6900
agctagagta gtagttcgc cagttaatag tttgcgcaac gttgttgcca ttgctacagg    6960
catcgtggtg tcacgctcgt cgtttggtat ggcttcattc agctccggtt cccaacgatc    7020
aaggcgagtt acatgatccc ccatgttgtg caaaaaagcg gttagctcct tcggtcctcc    7080
gatcgttgtc agaagtaagt tggccgcagt gttatcactc atggttatgg cagcactgca    7140
taattctctt actgtcatgc catccgtaag atgcttttct gtgactggtg agtactcaac    7200
caagtcattc tgagaatagt gtatgcggcg accgagttgc tcttgcccgg cgtcaatacg    7260
ggataatacc gcgccacata gcagaacttt aaaagtgctc atcattggaa aacgttcttc    7320
ggggcgaaaa ctctcaagga tcttaccgct gttgagatcc agttcgatgt aacccactcg    7380
tgcacccaac tgatcttcag catcttttac tttcaccagc gtttctgggt gagcaaaaac    7440
aggaaggcaa aatgccgcaa aaagggaat aaggggcgaca cggaaatgtt gaatactcat    7500
actcttcctt tttcaatatt attgaagcat ttatcagggt tattgtctca tgagcggata    7560
catatttgaa tgtatttaga aaataaaca aatagggtt ccgcgcacat ttccccgaaa    7620
agtgccacct gacgtcgacg gatcgggcct gcag                                7654
```

<210> SEQ ID NO 34
<211> LENGTH: 7549
<212> TYPE: DNA
<213> ORGANISM: Artificial Sequence
<220> FEATURE:
<223> OTHER INFORMATION: sequence of pSB-EGFP-HC-Ac10

<400> SEQUENCE: 34

```
gaattcagtt gaagtcggaa gtttacatac acttaagttg gagtcattaa aactcgtttt      60
tcaactacac cacaaatttc ttgttaacaa acaatagttt tggcaagtca gttaggacat     120
ctactttgtg catgacacaa gtcatttttc caacaattgt ttacagacag attatttcac     180
ttataattca ctgtatcaca attccagtgg gtcagaagtt tacatacact aacctcgagg     240
ctagtctaga gagtaattca tacaaaagga ctcgcccctg ccttgggaa tcccagggac      300
cgtcgttaaa ctcccactaa cgtagaaccc agagatcgct gcgttccgc ccctcaccc      360
gcccgctctc gtcatcactg aggtggagaa gagcatgcgt gaggctccgg tgcccgtcag     420
tgggcagagc gcacatcgcc cacagtcccc gagaagttgg ggggagggt cggcaattga     480
accggtgcct agagaaggtg gcgcggggta aactgggaaa gtgatgtcgt gtactggctc     540
cgccttttc ccgagggtgg gggagaaccg tatataagtg cagtagtcgc cgtgaacgtt     600
cttttcgca acgggtttgc cgccagaaca caggtaagtg ccgtgtgtgg ttcccgcggg     660
cctggcctct ttacgggtta tggcccttgc gtgccttgaa ttacttccac gcccctggct    720
gcagtacgtg attcttgatc ccgagcttcg ggttggaagt gggtgggaga gttcgaggcc    780
ttgcgcttaa ggagcccctt cgcctcgtgc ttgagttgag gcctggcttg ggcgctgggg    840
ccgccgcgtg cgaatctggt ggcaccttcg cgcctgtctc gctgctttcg ataagtctct    900
agccatttaa aattttgat gacctgctgc gacgcttttt ttctggcaag atagtcttgt     960
aaatgcgggc caagatctgc acactggtat ttcggttttt ggggccgcgg gcggcgacgg   1020
ggcccgtgcg tcccagcgca catgttcggc gaggcgggc ctgcgagcgc ggccaccgag    1080
aatcggacgg gggtagtctc aagctggccg gcctgctctg gtgcctggcc tcgcgccgcc   1140
gtgtatcgcc ccgccctggg cggcaaggct ggcccggtcg gcaccagttg cgtgagcgga   1200
aagatggccg cttcccggcc ctgctgcagg gagctcaaaa tggaggacgc ggcgctcggg   1260
agagcgggcg ggtgagtcac ccacacaaag gaaaagggcc tttccgtcct cagccgtcgc   1320
ttcatgtgac tccacggagt accgggcgcc gtccaggcac ctcgattagt tctcgagctt   1380
ttggagtacg tcgtctttag gttgggggga ggggttttat gcgatggagt ttccccacac   1440
tgagtgggtg gagactgaag ttaggccagc ttggcacttg atgtaattct ccttggaatt   1500
tgcccttttt gagtttggat cttggttcat tctcaagcct cagacagtgg ttcaaagttt   1560
ttttcttcca tttcaggtgt cgtgagcggc cgccatgaat tttggactga ggctgatttt   1620
cctggtgctg acccctgaaag gcgtccagtg tcagatccag ctgcagcagt ctggccccga   1680
ggtcgtgaaa cctggcgcct ccgtgaagat ctcctgcaag gcctccggct acaccttcac   1740
cgactactac atcacctggg tcaagcagaa gcccggccag ggcctggaat ggatcggctg   1800
gatctatccc ggctccggca acaccaagta caacgagaag ttcaagggca aggccaccct   1860
gaccgtggac acctcctctt ccaccgcctt catgcagctg tcctccctga cctccgagga   1920
taccgccgtg tacttctgcg ccaactacgg caactattgg ttcgcctact ggggccaggg   1980
cacacaagtg accgtgtctg ctgctagcac caagggccca tcggtcttcc ccctggcacc   2040
ctcctccaag agcacctctg ggggcacagc agccctgggc tgcctggtca aggactactt   2100
ccccgaaccg gtgacggtgt cgtggaactc aggcgccctg accagcggcg tgcacacctt   2160
cccggctgtc ctacagtcct caggactcta ctccctcagc agcgtggtga ccgtgccctc   2220
cagcagcttg ggcacccaga cctacatctg caacgtgaat cacaagccca gcaacaccaa   2280
ggtggacaag aaagttgagc ccaaatcttg tgacaaaact cacacatgcc caccgtgccc   2340
agcacctgaa ctcctggggg gaccgtcagt cttcctcttc cccccaaaac ccaaggacac   2400
```

| | |
|---|---|
| cctcatgatc tcccggaccc ctgaggtcac atgcgtggtg gtggacgtga gccacgaaga | 2460 |
| ccctgaggtc aagttcaact ggtacgtgga cggcgtggag gtgcataatg ccaagacaaa | 2520 |
| gccgcgggag gagcagtaca acagcacgta ccgtgtggtc agcgtcctca ccgtcctgca | 2580 |
| ccaggactgg ctgaatggca aggagtacaa gtgcaaggtc tccaacaaag ccctcccagc | 2640 |
| ccccatcgag aaaaccatct ccaaagccaa agggcagccc cgagaaccac aggtgtacac | 2700 |
| cctgcccca tcccgggatg agctgaccaa gaaccaggtc agcctgacct gcctggtcaa | 2760 |
| aggcttctat cccagcgaca tcgccgtgga gtgggagagc aatgggcagc cggagaacaa | 2820 |
| ctacaagacc acgcctcccg tgctggactc cgacggctcc ttcttcctct acagcaagct | 2880 |
| caccgtggac aagagcaggt ggcagcaggg gaacgtcttc tcatgctccg tgatgcatga | 2940 |
| ggctctgcac aaccactaca cacagaagag cctctccctg tctccggagc tgcaactgga | 3000 |
| ggagagctgt gcggaggcgc aggacgggga gctggacggg ctgtggacga ccatcaccat | 3060 |
| cttcatcaca ctcttcctgt taagcgtgtg ctacagtgcc accgtcacct tcttcaaggt | 3120 |
| gaagtggatc ttctcctcgg tggtggacct gaagcagacc atcatccccg actacaggaa | 3180 |
| catgatcgga caggggcct agtaagctta gcgctttcga agggcaggta agtatcaagg | 3240 |
| ttacaagaca ggtttaagga gaccaataga aactgggctt gtcgagacag agaagactct | 3300 |
| tgcgtttctg ataggcacct attggtctta ctgacatcca cttttgccttt ctctccacag | 3360 |
| gtgtcctacg tagcgatcgc caattccgcc cctctccctc ccccccccct aacgttactg | 3420 |
| gccgaagccg cttggaataa ggccggtgtg cgtttgtcta tatgtgattt tccaccatat | 3480 |
| tgccgtcttt tggcaatgtg agggcccgga aacctggccc tgtcttcttg acgagcattc | 3540 |
| ctaggggtct ttcccctctc gccaaaggaa tgcaaggtct gttgaatgtc gtgaaggaag | 3600 |
| cagttcctct ggaagcttct tgaagacaaa caacgtctgt agcgaccctt gcaggcagc | 3660 |
| ggaaccccc acctggcgac aggtgcctct gcggccaaaa gccacgtgta agatacac | 3720 |
| ctgcaaaggc ggcacaaccc cagtgccacg ttgtgagttg atagttgtg gaaagagtca | 3780 |
| aatggctctc ctcaagcgta ttcaacaagg ggctgaagga tgcccagaag gtaccccatt | 3840 |
| gtatgggatc tgatctgggg cctcggtgca catgctttac atgtgtttag tcgaggttaa | 3900 |
| aaaaacgtct aggccccccg aaccacgggg acgtggtttt cctttgaaaa acacgatgat | 3960 |
| aagcttgcca caacccggtt taaacggatc ccgccaccat ggtgagcaag ggcgaggagc | 4020 |
| tgttcaccgg ggtggtgccc atcctggtcg agctggacgg cgacgtaaac ggccacaagt | 4080 |
| tcagcgtgtc cggcgagggc gagggcgatg ccacctacgg caagctgacc ctgaagttca | 4140 |
| tctgcaccac cggcaagctg cccgtgccct ggcccaccct cgtgaccacc ctgacctacg | 4200 |
| gcgtgcagtg cttcagccgc taccccgacc acatgaagca gcacgacttc ttcaagtccg | 4260 |
| ccatgcccga aggctacgtc caggagcgca ccatcttctt caaggacgac ggcaactaca | 4320 |
| agacccgcgc cgaggtgaag ttcgagggcg acaccctggt gaaccgcatc gagctgaagg | 4380 |
| gcatcgactt caaggaggac ggcaacatcc tggggcacaa gctggagtac aactacaaca | 4440 |
| gccacaacgt ctatatcatg gccgacaagc agaagaacgg catcaaggtg aacttcaaga | 4500 |
| tccgccacaa catcgaggac ggcagcgtgc agctcgccga ccactaccag cagaacaccc | 4560 |
| ccatcggcga cggccccgtg ctgctgcccg acaaccacta cctgagcacc cagtccgccc | 4620 |
| tgagcaaaga cccaacgag aagcgcgatc acatggtcct gctggagttc gtgaccgccg | 4680 |
| ccgggatcac tctcggcatg gacgagctgt acaagtaaag cggcatatgc gccggcggat | 4740 |

```
atccggcgcg ccgagctcgc tgatcagcct cgactgtgcc tctagttgcc agccatctgt    4800
tgtttgcccc tccccgtgc cttccttgac cctggaaggt gccactccca ctgtcctttc     4860
ctaataaaat gaggaaattg catcgcattg tctgagtagg tgtcattcta ttctgggggg    4920
tggggtgggg caggacagca aggggagga ttgggaagac aatagcaggc atgctgggga     4980
tgcggtgggc tctatggctt ctgaggcgga agaaccagc tggggttaat taaacgcgtt     5040
tgagtgtatg ttaacttctg acccactggg aatgtgatga agaaataaa agctgaaatg    5100 aatcattctc tctactatta ttctgatatt tcacattctt aaaataaagt ggtgatccta    5160
actgacctta agacagggaa tctttactcg gattaaatgt caggaattgt gaaaaagtga    5220
gtttaaatgt atttggctaa ggtgtatgta aacttccgac ttcaactatc gattcgcgcg    5280
cgtgcattct agttgtggtt tgtccaaact catcaatgta tcttatcatg tctgtatacc    5340
gtcgacctct agctagagct tggcgtaatc atggtcatag ctgtttcctg tgtgaaattg    5400
ttatccgctc acaattccac acaacatacg agccggaagc ataaagtgta aagcctgggg    5460
tgcctaatga gtgagctaac tcacattaat tgcgttgcgc tcactgcccg ctttccagtc    5520
gggaaacctg tcgtgccagc tgcattaatg aatcggccaa cgcgcgggga gaggcggttt    5580
gcgtattggg cgctcttccg cttcctcgct cactgactcg ctgcgctcgg tcgttcggct    5640
gcggcgagcg gtatcagctc actcaaaggc ggtaatacgg ttatccacag aatcaggga    5700 taacgcagga aagaacatgt gagcaaaagg ccagcaaaag gccaggaacc gtaaaaaggc    5760
cgcgttgctg gcgttttcc ataggctccg cccccctgac gagcatcaca aaaatcgacg    5820
ctcaagtcag aggtggcgaa acccgacagg actataaaga taccaggcgt ttccccctgg    5880
aagctccctc gtgcgctctc ctgttccgac cctgccgctt accggatacc tgtccgcctt    5940
tctcccttcg ggaagcgtgg cgctttctca atgctcacgc tgtaggtatc tcagttcggt    6000
gtaggtcgtt cgctccaagc tgggctgtgt gcacgaaccc cccgttcagc ccgaccgctg    6060
cgccttatcc ggtaactatc gtcttgagtc aacccggta agacacgact tatcgccact    6120
ggcagcagcc actggtaaca ggattagcag agcgaggtat gtaggcggtg ctacagagtt    6180
cttgaagtgg tggcctaact acggctacac tagaaggaca gtatttggta tctgcgctct    6240
gctgaagcca gttaccttcg gaaaaagagt tggtagctct tgatccggca acaaaccac    6300 cgctggtagc ggtggttttt tgttttgcaa gcagcagatt acgcgcagaa aaaaaggatc    6360
tcaagaagat cctttgatct tttctacggg gtctgacgct cagtggaacg aaaactcacg    6420
ttaagggatt ttggtcatga gattatcaaa aaggatcttc acctagatcc ttttaaatta    6480
aaaatgaagt tttaaatcaa tctaaagtat atatgagtaa acttggtctg acagttacca    6540
atgcttaatc agtgaggcac ctatctcagc gatctgtcta tttcgttcat ccatagttgc    6600
ctgactcccc gtcgtgtaga taactacgat acgggagggc ttaccatctg gccccagtgc    6660
tgcaatgata ccgcgagacc cacgctcacc ggctccagat ttatcagcaa taaaccagcc    6720
agccggaagg gccgagcgca gaagtggtcc tgcaacttta tccgcctcca tccagtctat    6780
taattgttgc cgggaagcta gagtaagtag ttcgccagtt aatagtttgc gcaacgttgt    6840
tgccattgct acaggcatcg tggtgtcacg ctcgtcgttt ggtatggctt cattcagctc    6900
cggttcccaa cgatcaaggc gagttacatg atccccatg ttgtgcaaaa aagcggttag    6960
ctccttcggt cctccgatcg ttgtcagaag taagttggcc gcagtgttat cactcatggt    7020
tatggcagca ctgcataatt ctcttactgt catgccatcc gtaagatgct tttctgtgac    7080
tggtgagtac tcaaccaagt cattctgaga atagtgtatg cggcgaccga gttgctcttg    7140
```

```
cccggcgtca atacgggata ataccgcgcc acatagcaga actttaaaag tgctcatcat    7200
tggaaaacgt tcttcggggc gaaaactctc aaggatctta ccgctgttga gatccagttc    7260
gatgtaaccc actcgtgcac ccaactgatc ttcagcatct tttactttca ccagcgtttc    7320
tgggtgagca aaaacaggaa ggcaaaatgc cgcaaaaaag gaataagggg cgacacggaa    7380
atgttgaata ctcatactct ccttttttca atattattga agcatttatc agggttattg    7440
tctcatgagc ggatacatat ttgaatgtat ttagaaaaat aaacaaatag gggttccgcg    7500
cacatttccc cgaaaagtgc cacctgacgt cgacggatcg ggcctgcag              7549
```

<210> SEQ ID NO 35
<211> LENGTH: 7558
<212> TYPE: DNA
<213> ORGANISM: Artificial Sequence
<220> FEATURE:
<223> OTHER INFORMATION: sequence of pSB-EGFP-HC-hBU12

<400> SEQUENCE: 35

```
gaattcagtt gaagtcggaa gtttacatac acttaagttg gagtcattaa aactcgtttt      60
tcaactacac cacaaatttc ttgttaacaa acaatagttt tggcaagtca gttaggacat     120
ctactttgtg catgacacaa gtcattttc caacaattgt ttacagacag attatttcac      180
ttataattca ctgtatcaca attccagtgg gtcagaagtt tacatacact aacctcgagg     240
ctagtctaga gagtaattca tacaaaagga ctcgcccctg ccttgggaa tcccagggac      300 cgtcgttaaa ctcccactaa cgtagaaccc agagatcgct cgcgttccgc cccctcaccc    360
gcccgctctc gtcatcactg aggtggagaa gagcatgcgt gaggctccgg tgcccgtcag    420
tgggcagagc gcacatcgcc cacagtcccc gagaagttgg ggggaggggt cggcaattga    480
accggtgcct agagaaggtg gcgcggggta aactgggaaa gtgatgtcgt gtactggctc    540 cgccttttc ccgagggtgg gggagaaccg tatataagtg cagtagtcgc cgtgaacgtt     600 cttttcgca acgggtttgc cgccagaaca caggtaagtg ccgtgtgtgg ttcccgcggg    660
cctggcctct ttacgggtta tggcccttgc gtgccttgaa ttacttccac gcccctggct    720
gcagtacgtg attcttgatc ccgagcttcg ggttggaagt gggtgggaga gttcgaggcc    780
ttgcgcttaa ggagccccctt cgcctcgtgc ttgagttgag gcctggcttg ggcgctgggg    840
ccgccgcgtg cgaatctggt ggcaccttcg cgcctgtctc gctgctttcg ataagtctct    900
agccatttaa aattttttgat gacctgctgc gacgcttttt ttctggcaag atagtcttgt    960
aaatgcgggc caagatctgc acactggtat ttcggttttt ggggccgcgg gcggcgacgg   1020
ggcccgtgcg tcccagcgca catgttcggc gaggcgggc ctgcgagcgc ggccaccgag    1080
aatcggacgg gggtagtctc aagctggccg gcctgctctg gtgcctggcc tcgcgccgcc    1140
gtgtatcgcc ccgccctggg cggcaaggct ggcccggtcg gcaccagttg cgtgagcgga    1200
aagatgcccg cttccggcc ctgctgcagg gagctcaaaa tggaggacgc ggcgctcggg     1260
agagcgggcg ggtgagtcac ccacacaaag gaaaagggcc tttccgtcct cagccgtcgc    1320
ttcatgtgac tccacggagt accgggcgcc gtccaggcac ctcgattagt tctcgagctt    1380
ttggagtacg tcgtctttag gttgggggga ggggttttat gcgatggagt ttccccacac    1440
tgagtgggtg gagactgaag ttaggccagc ttggcacttg atgtaattct ccttggaatt    1500
tgcccttttt gagtttggat cttggttcat tctcaagcct cagacagtgg ttcaaagttt    1560
ttttcttcca tttcaggtgt cgtgagcggc cgccatgaat tttggactga ggctgatttt    1620
```

```
cctggtgctg accctgaaag gcgtccagtg tcaggtgcag ctgcaggaat ctggccctgg    1680
cctcgtgaag ccttcccaga ccctgtctct gacctgcacc gtgtccggcg gctccatctc    1740
tacctctggc atgggcgtgg gctggatcag acagcatcct ggcaagggcc tggaatggat    1800
cggccacatt tggtgggacg acgacaagcg gtacaacccc gccctgaagt ccagagtgac    1860
catctccgtg gacacctcca agaaccagtt ctccctgaag ctgtcctccg tgaccgccgc    1920
tgataccgcc gtgtactact gcgcccggat ggaactgtgg tcctactact cgactactg     1980
gggccagggc accctcgtga ccgtgtcatc tgctagcacc aagggcccat cggtcttccc    2040
cctggcaccc tcctccaaga gcacctctgg gggcacagca gccctgggct gcctggtcaa    2100
ggactacttc cccgaaccgg tgacggtgtc gtggaactca ggcgccctga ccagcggcgt    2160
gcacaccttc ccggctgtcc tacagtcctc aggactctac tccctcagca gcgtggtgac    2220
cgtgccctcc agcagcttgg gcacccagac ctacatctgc aacgtgaatc acaagcccag    2280
caacaccaag gtggacaaga agttgagccc aaatcttgt gacaaaactc acacatgccc    2340
accgtgccca gcacctgaac tcctgggggg accgtcagtc ttcctcttcc ccccaaaacc    2400
caaggacacc ctcatgatct cccggacccc tgaggtcaca tgcgtggtgg tggacgtgag    2460
ccacgaagac cctgaggtca agttcaactg gtacgtggac ggcgtggagg tgcataatgc    2520
caagacaaag ccgcgggagg agcagtacaa cagcacgtac cgtgtggtca gcgtcctcac    2580
cgtcctgcac caggactggc tgaatggcaa ggagtacaag tgcaaggtct ccaacaaagc    2640
cctcccagcc cccatcgaga aaaccatctc caaagccaaa gggcagcccc gagaaccaca    2700
ggtgtacacc ctgcccccat cccgggatga gctgaccaag aaccaggtca gcctgacctg    2760
cctggtcaaa ggcttctatc ccagcgacat cgccgtggag tgggagagca atgggcagcc    2820
ggagaacaac tacaagacca cgcctcccgt gctggactcc gacggctcct tcttcctcta    2880
cagcaagctc accgtggaca agagcaggtg gcagcagggg aacgtcttct catgctccgt    2940
gatgcatgag gctctgcaca accactacac acagaagagc ctctccctgt ctccgggagct   3000
gcaactggag gagagctgtg cggaggcgca ggacggggag ctggacgggc tgtggacgac    3060
catcaccatc ttcatcacac tcttcctgtt aagcgtgtgc tacagtgcca ccgtcacctt    3120
cttcaaggtg aagtggatct tctcctcggt ggtggacctg aagcagacca tcatccccga    3180
ctacaggaac atgatcggac aggggggccta gtaagcttag cgctttcgaa gggcaggtaa    3240
gtatcaaggt tacaagacag gtttaaggag accaatagaa actgggcttg tcgagacaga    3300
gaagactctt gcgtttctga taggcaccta ttggtcttac tgacatccac tttgcctttc    3360
tctccacagg tgtcctacgt agcgatcgcc aattccgccc ctctccctcc ccccccccta    3420
acgttactgg ccgaagccgc ttggaataag gccggtgtgc gtttgtctat atgtgatttt    3480
ccaccatatt gccgtctttt ggcaatgtga gggcccggaa acctggccct gtcttcttga    3540
cgagcattcc tagggtcttt cccctctcg ccaaaggaat gcaaggtctg ttgaatgtcg    3600
tgaaggaagc agttcctctg gaagcttctt gaagacaaac aacgtctgta gcgacccttt    3660
gcaggcagcg gaaccccca cctggcgaca ggtgcctctg cggccaaaag ccacgtgtat    3720
aagatacacc tgcaaaggcg gcacaacccc agtgccacgt tgtgagttgg atagttgtgg    3780
aaagagtcaa atggctctcc tcaagcgtat tcaacaaggg gctgaaggat gcccagaagg    3840
taccccattg tatgggatct gatctggggc ctcggtgcac atgctttaca tgtgtttagt    3900
cgaggttaaa aaaacgtcta ggccccccga accacgggga cgtggttttc ctttgaaaaa    3960
cacgatgata agcttgccac aacccggttt aaacggatcc cgccaccatg gtgagcaagg    4020
```

```
gcgaggagct gttcaccggg gtggtgccca tcctggtcga gctggacggc gacgtaaacg    4080
gccacaagtt cagcgtgtcc ggcgagggcg agggcgatgc cacctacggc aagctgaccc    4140
tgaagttcat ctgcaccacc ggcaagctgc ccgtgccctg cccaccctc gtgaccaccc     4200 tgacctacgg cgtgcagtgc ttcagccgct accccgacca catgaagcag cacgacttct    4260
tcaagtccgc catgcccgaa ggctacgtcc aggagcgcac catcttcttc aaggacgacg    4320
gcaactacaa gacccgcgcc gaggtgaagt tcgagggcga caccctggtg aaccgcatcg    4380
agctgaaggg catcgacttc aaggaggacg gcaacatcct ggggcacaag ctggagtaca    4440
actacaacag ccacaacgtc tatatcatgg ccgacaagca gaagaacggc atcaaggtga    4500
acttcaagat ccgccacaac atcgaggacg gcagcgtgca gctcgccgac cactaccagc    4560
agaacacccc catcggcgac ggccccgtgc tgctgcccga caaccactac ctgagcaccc    4620
agtccgccct gagcaaagac cccaacgaga gcgcgatca catggtcctg ctggagttcg    4680
tgaccgccgc cgggatcact ctcggcatgg acgagctgta caagtaaagc ggcatatgcg    4740
ccggcggata tccggcgcgc cgagctcgct gatcagcctc gactgtgcct ctagttgcca    4800
gccatctgtt gtttgcccct cccccgtgcc ttccttgacc ctggaaggtg ccactcccac    4860
tgtcctttcc taataaaatg aggaaattgc atcgcattgt ctgagtaggt gtcattctat    4920
tctggggggt ggggtggggc aggacagcaa ggggggagga tgggaagaca atagcaggca    4980
tgctggggat gcggtgggct ctatggcttc tgaggcggaa agaaccagct ggggttaatt    5040
aaacgcgttt gagtgtatgt taacttctga cccactggga atgtgatgaa agaaataaaa    5100
gctgaaatga atcattctct ctactattat tctgatattt cacattctta aaataaagtg    5160
gtgatcctaa ctgaccttaa gacagggaat ctttactcgg attaaatgtc aggaattgtg    5220
aaaaagtgag tttaaatgta tttggctaag gtgtatgtaa acttccgact caactatcg     5280 attcgcgcgc gtgcattcta gttgtggttt gtccaaactc atcaatgtat cttatcatgt    5340
ctgtataccg tcgacctcta gctagagctt ggcgtaatca tggtcatagc tgtttcctgt    5400
gtgaaattgt tatccgctca caattccaca acatacga gccggaagca taaagtgtaa    5460
agcctggggt gcctaatgag tgagctaact cacattaatt gcgttgcgct cactgcccgc    5520
tttccagtcg ggaaacctgt cgtgccagct gcattaatga atcggccaac gcgcgggag     5580 aggcggtttg cgtattgggc gctcttccgc ttcctcgctc actgactcgc tgcgctcggt    5640
cgttcggctg cggcgagcgg tatcagctca ctcaaaggcg gtaatacggt tatccacaga    5700
atcaggggat aacgcaggaa agaacatgtg agcaaaaggc cagcaaaagg ccaggaaccg    5760
taaaaaggcc gcgttgctgg cgttttccca taggctccgc cccctgacg agcatcacaa    5820 aaatcgacgc tcaagtcaga ggtggcgaaa cccgacagga ctataaagat accaggcgtt    5880
tccccctgga agctccctcg tgcgctctcc tgttccgacc ctgccgctta ccggatacct    5940
gtccgccttt ctcccttcgg gaagcgtggc gctttctcaa tgctcacgct gtaggtatct    6000
cagttcggtg taggtcgttc gctccaagct gggctgtgtg cacgaacccc cgttcagcc    6060 cgaccgctgc gccttatccg gtaactatcg tcttgagtcc aacccggtaa gacacgactt    6120
atcgccactg gcagcagcca ctggtaacag gattagcaga gcgaggtatg taggcggtgc    6180
tacagagttc ttgaagtggt ggcctaacta cggctacact agaaggacag tatttggtat    6240
ctgcgctctg ctgaagccag ttaccttcgg aaaaagagtt ggtagctctt gatccggcaa    6300
acaaaccacc gctggtagcg gtggtttttt tgtttgcaag cagcagatta cgcgcagaaa    6360
```

```
aaaaggatct caagaagatc ctttgatctt ttctacgggg tctgacgctc agtggaacga    6420
aaactcacgt taagggattt tggtcatgag attatcaaaa aggatcttca cctagatcct    6480
tttaaattaa aaatgaagtt ttaaatcaat ctaaagtata tatgagtaaa cttggtctga    6540
cagttaccaa tgcttaatca gtgaggcacc tatctcagcg atctgtctat ttcgttcatc    6600
catagttgcc tgactccccg tcgtgtagat aactacgata cgggagggct taccatctgg    6660
ccccagtgct gcaatgatac cgcgagaccc acgctcaccg gctccagatt tatcagcaat    6720
aaaccagcca gccggaaggg ccgagcgcag aagtggtcct gcaactttat ccgcctccat    6780
ccagtctatt aattgttgcc gggaagctag agtaagtagt tcgccagtta atagtttgcg    6840
caacgttgtt gccattgcta caggcatcgt ggtgtcacgc tcgtcgtttg gtatggcttc    6900
attcagctcc ggttcccaac gatcaaggcg agttacatga tcccccatgt tgtgcaaaaa    6960
agcggttagc tccttcggtc ctccgatcgt tgtcagaagt aagttggccg cagtgttatc    7020
actcatggtt atggcagcac tgcataattc tcttactgtc atgccatccg taagatgctt    7080
ttctgtgact ggtgagtact caaccaagtc attctgagaa tagtgtatgc ggcgaccgag    7140
ttgctcttgc ccggcgtcaa tacgggataa taccgcgcca catagcagaa ctttaaaagt    7200
gctcatcatt ggaaaacgtt cttcggggcg aaaactctca aggatcttac cgctgttgag    7260
atccagttcg atgtaaccca ctcgtgcacc caactgatct tcagcatctt ttactttcac    7320
cagcgtttct gggtgagcaa aaacaggaag gcaaaatgcc gcaaaaaagg gaataagggc    7380
gacacggaaa tgttgaatac tcatactctt ccttttcaa tattattgaa gcatttatca    7440
gggttattgt ctcatgagcg gatacatatt tgaatgtatt tagaaaaata aacaaatagg    7500
ggttccgcgc acatttcccc gaaaagtgcc acctgacgtc gacggatcgg gcctgcag     7558
```

<210> SEQ ID NO 36
<211> LENGTH: 6742
<212> TYPE: DNA
<213> ORGANISM: Artificial Sequence
<220> FEATURE:
<223> OTHER INFORMATION: sequence of pPB-EGFP-LC-Ac10

<400> SEQUENCE: 36

```
gaattcttaa ccctagaaag atagtctgcg taaaattgac gcatgcattc ttgaaatatt      60
gctctctctt tctaaatagc gcgaatccgt cgctgtgcat ttaggacatc tcagtcgccg     120
cttggagctc ccgtgaggcg tgcttgtcaa tgcggtaagt gtcactgatt ttgaactata     180
acgaccgcgt gagtcaaaat gacgcatgat tatctttac gtgactttta agatttaact     240
catacgataa ttatattgtt atttcatgtt ctacttacgt gataacttat tatatatata     300
ttttcttgtt atacctcgag gctagtctag agagtaattc atacaaaagg actcgcccct     360
gccttgggga atcccaggga ccgtcgttaa actcccacta acgtagaacc cagagatcgc     420
tgcgttcccg ccccctcacc cgcccgctct cgtcatcact gaggtggaga agagcatgcg     480
tgaggctccg gtgcccgtca gtgggcagag cgcacatcgc ccacagtccc cgagaagttg     540
gggggagggg tcggcaattg aaccggtgcc tagagaaggt ggcgcggggt aaactgggaa     600
agtgatgtcg tgtactggct ccgcctttt cccgagggtg ggggagaacc gtatataagt     660
gcagtagtcg ccgtgaacgt tcttttttcgc aacgggtttg ccgccagaac acaggtaagt     720
gccgtgtgtg gttcccgcgg gcctggcctc tttacgggtt atggcccttg cgtgccttga     780
attacttcca cgcccctggc tgcagtacgt gattcttgat cccagccttc ggggtggaag     840
tgggtgggag agttcgaggc cttgcgctta aggagcccct tcgcctcgtg cttgagttga     900
```

```
ggcctggctt gggcgctggg gccgccgcgt gcgaatctgg tggcaccttc gcgcctgtct      960
cgctgctttc gataagtctc tagccattta aaattttga tgacctgctg cgacgctttt     1020
tttctggcaa gatagtcttg taaatgcggg ccaagatctg cacactggta tttcggtttt     1080
tggggccgcg ggcggcgacg gggcccgtgc gtcccagcgc acatgttcgg cgaggcgggg     1140
cctgcgagcg cggccaccga gaatcggacg ggggtagtct caagctggcc ggcctgctct     1200
ggtgcctggc ctcgcgccgc cgtgtatcgc cccgccctgg gcggcaaggc tggcccggtc     1260
ggcaccagtt gcgtgagcgg aaagatggcc gcttcccggc cctgctgcag ggagctcaaa     1320
atggaggacg cggcgctcgg gagagcgggc gggtgagtca cccacacaaa ggaaaagggc     1380
cttccgtcc tcagccgtcg cttcatgtga ctccacggag taccgggcgc cgtccaggca     1440
cctcgattag ttctcgagct tttgagtac gtcgtcttta ggttgggggg aggggtttta     1500
tgcgatggag tttccccaca ctgagtgggt ggagactgaa gttaggccag cttggcactt     1560
gatgtaattc tccttggaat ttgcccttt tgagtttgga tcttggttca ttctcaagcc     1620
tcagacagtg gttcaaagtt ttttcttcc atttcaggtg tcgtgagcgg ccgccatgaa     1680
ttttggactg aggctgattt tcctggtgct gaccctgaaa ggcgtccagt gtgacattgt     1740
gctgacccaa tctccagctt ctttggctgt gtctctaggg cagagggcca ccatctcctg     1800
caaggccagc caaagtgttg attttgatgg tgatagttat atgaactggt accaacagaa     1860
accaggacag ccacccaaag tcctcatcta tgctgcatcc aatctagaat ctgggatccc     1920
agccaggttt agtggcagtg gtctgggac agacttcacc ctcaacatcc atcctgtgga     1980
ggaggaggat gctgcaacct attactgtca gcaaagtaat gaggatccgt ggacgttcgg     2040
tggaggcacc aagctggaaa tcaaacgtac ggtggctgca ccatctgtct tcatcttccc     2100
gccatctgat gagcagttga atctggaac tgcctctgtt gtgtgcctgc tgaataactt     2160
ctatcccaga gaggccaaag tacagtggaa ggtggataac gccctccaat cgggtaactc     2220
ccaggagagt gtcacagagc aggacagcaa ggacagcacc tacagcctca gcagcaccct     2280
gacgctgagc aaagcagact acgagaaaca caaagtctac gcctgcgaag tcacccatca     2340
gggcctgagc tcgcccgtca caaagagctt caacagggga gagtgttagc gctttcgaag     2400
ggcaggtaag tatcaaggtt acaagacagg tttaaggaga ccaatagaaa ctgggcttgt     2460
cgagacagag aagactcttg cgtttctgat aggcacctat tggtcttact gacatccact     2520
ttgccttct ctccacaggt gtcctacgta gcgatcgcca attccgcccc tctccctccc     2580
ccccccctaa cgttactggc cgaagccgct tggaataagg ccggtgtgcg tttgtctata     2640
tgtgattttc caccatattg ccgtcttttg gcaatgtgag ggcccggaaa cctggccctg     2700
tcttcttgac gagcattcct aggggtcttt cccctctcgc caaggaatg caaggtctgt     2760
tgaatgtcgt gaaggaagca gttcctctgg aagcttcttg aagacaaaca acgtctgtag     2820
cgacccttg caggcagcgg aaccccccac ctggcgacag gtgcctctgc ggccaaaagc     2880
cacgtgtata agatacacct gcaaaggcgg cacaacccca gtgccacgtt gtgagttgga     2940
tagttgtgga aagagtcaaa tggctctcct caagcgtatt caacaagggg ctgaaggatg     3000
cccagaaggt accccattgt atgggatctg atctggggcc tcggtgcaca tgctttacat     3060
gtgtttagtc gaggttaaaa aaacgtctag gccccccgaa ccacggggac gtggttttcc     3120
tttgaaaaac acgatgataa gcttgccaca acccggttta acggatcccg ccaccatgg     3180
tgagcaaggg cgaggagctg ttcaccgggg tggtgcccat cctggtcgag ctggacggcg     3240
```

```
acgtaaacgg ccacaagttc agcgtgtccg gcgagggcga gggcgatgcc acctacggca   3300
agctgaccct gaagttcatc tgcaccaccg gcaagctgcc cgtgccctgg cccaccctcg   3360
tgaccaccct gacctacggc gtgcagtgct tcagccgcta ccccgaccac atgaagcagc   3420
acgacttctt caagtccgcc atgcccgaag gctacgtcca ggagcgcacc atcttcttca   3480
aggacgacgg caactacaag acccgcgccg aggtgaagtt cgagggcgac accctggtga   3540
accgcatcga gctgaagggc atcgacttca aggaggacgg caacatcctg ggcacaagc    3600
tggagtacaa ctacaacagc cacaacgtct atatcatggc cgacaagcag aagaacggca   3660
tcaaggtgaa cttcaagatc cgccacaaca tcgaggacgg cagcgtgcag ctcgccgacc   3720
actaccagca gaacaccccc atcggcgacg gccccgtgct gctgcccgac aaccactacc   3780
tgagcaccca gtccgccctg agcaaagacc ccaacgagaa gcgcgatcac atggtcctgc   3840
tggagttcgt gaccgccgcc gggatcactc tcggcatgga cgagctgtac aagtaaagcg   3900
gcatatgcgc cggcggatat ccggcgcgcc gagctcgctg atcagcctcg actgtgcctc   3960
tagttgccag ccatctgttg tttgcccctc ccccgtgcct tccttgaccc tggaaggtgc   4020
cactcccact gtccttttcct aataaaatga ggaaattgca tcgcattgtc tgagtaggtg   4080
tcattctatt ctggggggtg gggtggggca ggacagcaag ggggaggatt gggaagacaa   4140
tagcaggcat gctggggatg cggtgggctc tatggcttct gaggcggaaa gaaccagctg   4200
gggttaatta aacgcgttta accctagaaa gataatcata ttgtgacgta cgttaaagat   4260
aatcatgcgt aaaattgacg catgtgtttt atcggtctgt atatcgaggt ttatttatta   4320
atttgaatag atattaagtt ttattatatt tacacttaca tactaataat aaattcaaca   4380
aacaatttat ttatgtttat ttatttatta aaaaaaaaca aaaactcaaa atttcttcta   4440
taaagtaaca aaacttttat atcgattcgc gcgcgtgcat tctagttgtg gtttgtccaa   4500
actcatcaat gtatcttatc atgtctgtat accgtcgacc tctagctaga gcttggcgta   4560
atcatggtca tagctgtttc ctgtgtgaaa ttgttatccg ctcacaattc cacacaacat   4620
acgagccgga agcataaagt gtaaagcctg gggtgcctaa tgagtgagct aactcacatt   4680
aattgcgttg cgctcactgc ccgctttcca gtcgggaaac ctgtcgtgcc agctgcatta   4740
atgaatcggc caacgcgcgg ggagaggcgg tttgcgtatt gggcgctctt ccgcttcctc   4800
gctcactgac tcgctgcgct cggtcgttcg gctgcggcga gcggtatcag ctcactcaaa   4860
ggcggtaata cggttatcca cagaatcagg ggataacgca ggaaagaaca tgtgagcaaa   4920
aggccagcaa aaggccagga accgtaaaaa ggccgcgttg ctggcgtttt tccataggct   4980
ccgcccccct gacgagcatc acaaaaatcg acgctcaagt cagaggtggc gaaacccgac   5040
aggactataa agataccagg cgtttccccc tggaagctcc ctcgtgcgct ctcctgttcc   5100
gaccctgccg cttaccggat acctgtccgc ctttctccct tcgggaagcg tggcgctttc   5160
tcaatgctca cgctgtaggt atctcagttc ggtgtaggtc gttcgctcca agctgggctg   5220
tgtgcacgaa ccccccgttc agcccgaccg ctgcgcctta tccggtaact atcgtcttga   5280
gtccaacccg gtaagacacg acttatcgcc actggcagca gccactggta acaggattag   5340
cagagcgagg tatgtaggcg gtgctacaga gttcttgaag tggtggccta actacggcta   5400
cactagaagg acagtatttg gtatctgcgc tctgctgaag ccagttacct tcggaaaaag   5460
agttggtagc tcttgatccg gcaaacaaac caccgctggt agcggtggtt ttttgtttg    5520
caagcagcag attacgcgca gaaaaaagg atctcaagaa gatcctttga tcttttctac    5580
ggggtctgac gctcagtgga acgaaaactc acgttaaggg attttggtca tgagattatc   5640
```

```
aaaaaggatc ttcacctaga tccttttaaa ttaaaaatga agttttaaat caatctaaag    5700
tatatatgag taaacttggt ctgacagtta ccaatgctta atcagtgagg cacctatctc    5760
agcgatctgt ctatttcgtt catccatagt tgcctgactc cccgtcgtgt agataactac    5820
gatacgggag ggcttaccat ctggccccag tgctgcaatg ataccgcgag acccacgctc    5880
accggctcca gatttatcag caataaacca gccagccgga agggccgagc gcagaagtgg    5940
tcctgcaact ttatccgcct ccatccagtc tattaattgt tgccgggaag ctagagtaag    6000
tagttcgcca gttaatagtt tgcgcaacgt tgttgccatt gctacaggca tcgtggtgtc    6060
acgctcgtcg tttggtatgg cttcattcag ctccggttcc caacgatcaa ggcgagttac    6120
atgatccccc atgttgtgca aaaaagcggt tagctccttc ggtcctccga tcgttgtcag    6180
aagtaagttg gccgcagtgt tatcactcat ggttatggca gcactgcata attctcttac    6240
tgtcatgcca tccgtaagat gcttttctgt gactggtgag tactcaacca agtcattctg    6300
agaatagtgt atgcggcgac cgagttgctc ttgcccggcg tcaatacggg ataataccgc    6360
gccacatagc agaactttaa aagtgctcat cattggaaaa cgttcttcgg gcgaaaact    6420 ctcaaggatc ttaccgctgt tgagatccag ttcgatgtaa cccactcgtg cacccaactg    6480
atcttcagca tcttttactt tcaccagcgt ttctgggtga gcaaaaacag gaaggcaaaa    6540
tgccgcaaaa aagggaataa gggcgacacg gaaatgttga atactcatac tcttcctttt    6600
tcaatattat tgaagcattt atcagggtta ttgtctcatg agcggataca tatttgaatg    6660
tatttagaaa aataaacaaa tagggggttcc gcgcacattt ccccgaaaag tgccacctga    6720
cgtcgacgga tcgggcctgc ag                                             6742
```

<210> SEQ ID NO 37
<211> LENGTH: 6727
<212> TYPE: DNA
<213> ORGANISM: Artificial Sequence
<220> FEATURE:
<223> OTHER INFORMATION: sequence of pPB-EGFP-LC-hBU12

<400> SEQUENCE: 37

```
gaattcttaa ccctagaaag atagtctgcg taaaattgac gcatgcattc ttgaaatatt      60
gctctctctt tctaaatagc gcgaatccgt cgctgtgcat ttaggacatc tcagtcgccg     120
cttggagctc ccgtgaggcg tgcttgtcaa tgcggtaagt gtcactgatt ttgaactata     180
acgaccgcgt gagtcaaaat gacgcatgat tatcttttac gtgactttta agatttaact     240
catacgataa ttatattgtt atttcatgtt ctacttacgt gataacttat tatatatata     300
ttttcttgtt atacctcgag gctagtctag agagtaattc atacaaaagg actcgcccct     360
gccttgggga atcccaggga ccgtcgttaa actcccacta acgtagaacc cagagatcgc     420
tgcgttcccg cccctcacc cgcccgctct cgtcatcact gaggtggaga agagcatgcg     480
tgaggctccg gtgcccgtca gtgggcagag cgcacatcgc ccacagtccc cgagaagttg     540
gggggagggg tcggcaattg aaccggtgcc tagagaaggt ggcgcggggt aaactgggaa     600
agtgatgtcg tgtactggct ccgccttttt cccgagggtg ggggagaacc gtatataagt     660
gcagtagtcg ccgtgaacgt tctttttcgc aacgggtttg ccgccagaac acaggtaagt     720
gccgtgtgtg gttccgcgcg gcctggcctc tttacgggtt atgcccttg cgtgccttga     780 attacttcca cgcccctggc tgcagtacgt gattcttgat cccgagcttc gggttggaag     840
tgggtgggag agttcgaggc cttgcgctta aggagcccct tcgcctcgtg cttgagttga     900
```

```
ggcctggctt gggcgctggg gccgccgcgt gcgaatctgg tggcaccttc gcgcctgtct      960
cgctgctttc gataagtctc tagccattta aaattttttga tgacctgctg cgacgctttt   1020
tttctggcaa gatagtcttg taaatgcggg ccaagatctg cacactggta tttcggtttt   1080
tggggccgcg ggcggcgacg gggcccgtgc gtcccagcgc acatgttcgg cgaggcgggg   1140
cctgcgagcg cggccaccga gaatcggacg ggggtagtct caagctggcc ggcctgctct   1200
ggtgcctggc ctcgcgccgc cgtgtatcgc cccgccctgg gcggcaaggc tggcccggtc   1260
ggcaccagtt gcgtgagcgg aaagatggcc gcttcccggc cctgctgcag ggagctcaaa   1320
atggaggacg cggcgctcgg gagagcgggc gggtgagtca cccacacaaa ggaaaagggc   1380
cttttccgtcc tcagccgtcg cttcatgtga ctccacggag taccgggcgc cgtccaggca   1440
cctcgattag ttctcgagct tttgagtac gtcgtcttta ggttgggggg aggggtttta   1500
tgcgatggag tttccccaca ctgagtgggt ggagactgaa gttaggccag cttggcactt   1560
gatgtaattc tccttggaat ttgccctttt tgagtttgga tcttggttca ttctcaagcc   1620
tcagacagtg gttcaaagtt tttttcttcc atttcaggtg tcgtgagcgg ccgccatgaa   1680
ttttggactg aggctgattt tcctggtgct gaccctgaaa ggcgtccagt gtgaaattgt   1740
tctcacccag tctccagcaa ccctgtctct ctctccaggg gaaagggcta ccctgagctg   1800
cagtgccagc tcaagtgtaa gttacatgca ctggtaccag cagaagccag gcaggctcc   1860
cagactcctg atttatgaca catccaaact ggcttctggt attccagcaa ggttcagtgg   1920
cagtgggtct ggaacagatt ttacactcac aatcagcagc ctggagccag aggatgttgc   1980
tgtctattac tgttttcagg ggagtgtata cccattcact tttggccaag gacaaagtt   2040
ggaaatcaaa cgtacggtgg ctgcaccatc tgtcttcatc ttcccgccat ctgatgagca   2100
gttgaaatct ggaactgcct ctgttgtgtg cctgctgaat aacttctatc ccagagaggc   2160
caaagtacag tggaaggtgg ataacgccct ccaatcgggt aactcccagg agagtgtcac   2220
agagcaggac agcaaggaca gcacctacag cctcagcagc accctgacgc tgagcaaagc   2280
agactacgag aaacacaaag tctacgcctg cgaagtcacc catcagggcc tgagctcgcc   2340
cgtcacaaag agcttcaaca ggggagagtg ttagcgcttt cgaagggcag gtaagtatca   2400
aggttacaag acaggtttaa ggagaccaat agaaactggg cttgtcgaga cagagaagac   2460
tcttgcgttt ctgataggca cctattggtc ttactgacat ccactttgcc tttctctcca   2520
caggtgtcct acgtagcgat cgccaattcc gcccctctcc ctccccccccc cctaacgtta   2580
ctggccgaag ccgcttggaa taaggccggt gtgcgtttgt ctatatgtga ttttccacca   2640
tattgccgtc ttttggcaat gtgagggccc ggaaacctgg ccctgtcttc ttgacgagca   2700
ttcctagggg tctttcccct ctcgccaaag gaatgcaagg tctgttgaat gtcgtgaagg   2760
aagcagttcc tctggaagct tcttgaagac aaacaacgtc tgtagcgacc ctttgcaggc   2820
agcggaaccc cccaccctggc gacaggtgcc tctgcggcca aaagccacgt gtataagata   2880
cacctgcaaa ggcggcacaa ccccagtgcc acgttgtgag ttggatagtt gtggaaagag   2940
tcaaatggct ctcctcaagc gtattcaaca aggggctgaa ggatgcccag aaggtacccc   3000
attgtatggg atctgatctg gggcctcggt gcacatgctt tacatgtgtt tagtcgaggt   3060
taaaaaaacg tctaggcccc ccgaaccacg gggacgtggt tttcctttga aaaacacgat   3120
gataagcttg ccacaacccg gtttaaacgg atcccgccac catggtgagc aagggcgagg   3180
agctgttcac cggggtggtg cccatcctgg tcgagctgga cggcgacgta aacggccaca   3240
agttcagcgt gtccggcgag ggcgagggcg atgccaccta cggcaagctg accctgaagt   3300
```

```
tcatctgcac caccggcaag ctgcccgtgc cctggcccac cctcgtgacc accctgacct    3360
acggcgtgca gtgcttcagc cgctacccg accacatgaa gcagcacgac ttcttcaagt    3420
ccgccatgcc cgaaggctac gtccaggagc gcaccatctt cttcaaggac gacggcaact    3480
acaagacccg cgccgaggtg aagttcgagg gcgacaccct ggtgaaccgc atcgagctga    3540
agggcatcga cttcaaggag gacggcaaca tcctggggca caagctggag tacaactaca    3600
acagccacaa cgtctatatc atggccgaca agcagaagaa cggcatcaag gtgaacttca    3660
agatccgcca caacatcgag gacggcagcg tgcagctcgc cgaccactac cagcagaaca    3720
cccccatcgg cgacggcccc gtgctgctgc ccgacaacca ctacctgagc cccagtccg    3780
ccctgagcaa agaccccaac gagaagcgcg atcacatggt cctgctggag ttcgtgaccg    3840
ccgccgggat cactctcggc atggacgagc tgtacaagta aagcggcata tgcgccggcg    3900
gatatccggc gcgccgagct cgctgatcag cctcgactgt gcctctagtt gccagccatc    3960
tgttgtttgc cctcccccg tgccttcctt gaccctggaa ggtgccactc ccactgtcct    4020
ttcctaataa aatgaggaaa ttgcatcgca ttgtctgagt aggtgtcatt ctattctggg    4080
gggtggggtg gggcaggaca gcaagggga ggattgggaa gacaatagca ggcatgctgg    4140
ggatgcggtg ggctctatgg cttctgaggc ggaaagaacc agctggggtt aattaaacgc    4200
gtttaaccct agaagataa tcatattgtg acgtacgtta aagataatca tgcgtaaaat    4260
tgacgcatgt gttttatcgg tctgtatatc gaggtttatt tattaatttg aatagatatt    4320
aagttttatt atatttacac ttacatacta ataataaatt caacaaacaa tttatttatg    4380
tttatttatt tattaaaaaa aaacaaaaac tcaaaatttc ttctataaag taacaaaact    4440
tttatatcga ttcgcgcgcg tgcattctag ttgtggtttg tccaaactca tcaatgtatc    4500
ttatcatgtc tgtataccgt cgacctctag ctagagcttg gcgtaatcat ggtcatagct    4560
gtttcctgtg tgaaattgtt atccgctcac aattccacac aacatacgag ccggaagcat    4620
aaagtgtaaa gcctggggtg cctaatgagt gagctaactc acattaattg cgttgcgctc    4680
actgcccgct ttccagtcgg gaaacctgtc gtgccagctg cattaatgaa tcggccaacg    4740
cgcggggaga ggcggtttgc gtattgggcg ctcttccgct tcctcgctca ctgactcgct    4800
gcgctcggtc gttcggctgc ggcgagcggt atcagctcac tcaaaggcgg taatacggtt    4860
atccacagaa tcaggggata acgcaggaaa gaacatgtga gcaaaaggcc agcaaaaggc    4920
caggaaccgt aaaaaggccg cgttgctggc gttttccat aggctccgcc cccctgacga    4980
gcatcacaaa aatcgacgct caagtcagag gtggcgaaac ccgacaggac tataaagata    5040
ccaggcgttt ccccctggaa gctccctcgt gcgctctcct gttccgaccc tgccgcttac    5100
cggatacctg tccgcctttc tcccttcggg aagcgtggcg ctttctcaat gctcacgctg    5160
taggtatctc agttcggtgt aggtcgttcg ctccaagctg ggctgtgtgc acgaaccccc    5220
cgttcagccc gaccgctgcg ccttatccgg taactatcgt cttgagtcca acccggtaag    5280
acacgactta tcgccactgg cagcagccac tggtaacagg attagcagag cgaggtatgt    5340
aggcggtgct acagagttct tgaagtggtg gcctaactac ggctacacta aggacagt    5400
atttggtatc tgcgctctgc tgaagccagt taccttcgga aaaagagttg gtagctcttg    5460
atccggcaaa caaaccaccg ctggtagcgg tggtttttt gtttgcaagc agcagattac    5520
gcgcagaaaa aaggatctc aagaagatcc tttgatcttt tctacggggt ctgacgctca    5580
gtggaacgaa aactcacgtt aagggatttt ggtcatgaga ttatcaaaaa ggatcttcac    5640
```

| | |
|---|---:|
| ctagatcctt ttaaattaaa aatgaagttt taaatcaatc taaagtatat atgagtaaac | 5700 |
| ttggtctgac agttaccaat gcttaatcag tgaggcacct atctcagcga tctgtctatt | 5760 |
| tcgttcatcc atagttgcct gactccccgt cgtgtagata actacgatac gggagggctt | 5820 |
| accatctggc cccagtgctg caatgatacc gcgagaccca cgctcaccgg ctccagattt | 5880 |
| atcagcaata accagccagc cggaagggc cgagcgcaga agtggtcctg caactttatc | 5940 |
| cgcctccatc cagtctatta attgttgccg ggaagctaga gtaagtagtt cgccagttaa | 6000 |
| tagtttgcgc aacgttgttg ccattgctac aggcatcgtg gtgtcacgct cgtcgtttgg | 6060 |
| tatggcttca ttcagctccg gttcccaacg atcaaggcga gttacatgat cccccatgtt | 6120 |
| gtgcaaaaaa gcggttagct ccttcggtcc tccgatcgtt gtcagaagta agttggccgc | 6180 |
| agtgttatca ctcatggtta tggcagcact gcataattct cttactgtca tgccatccgt | 6240 |
| aagatgcttt tctgtgactg gtgagtactc aaccaagtca ttctgagaat agtgtatgcg | 6300 |
| gcgaccgagt tgctcttgcc cggcgtcaat acgggataat accgcgccac atagcagaac | 6360 |
| tttaaaagtg ctcatcattg gaaaacgttc ttcggggcga aaactctcaa ggatcttacc | 6420 |
| gctgttgaga tccagttcga tgtaaccac tcgtgcaccc aactgatctt cagcatcttt | 6480 |
| tactttcacc agcgtttctg ggtgagcaaa aacaggaagg caaaatgccg caaaaaaggg | 6540 |
| aataagggcg acacggaaat gttgaatact catactcttc cttttcaat attattgaag | 6600 |
| catttatcag ggttattgtc tcatgagcgg atacatattt gaatgtattt agaaaaataa | 6660 |
| acaaataggg gttccgcgca catttccccg aaaagtgcca cctgacgtcg acggatcggg | 6720 |
| cctgcag | 6727 |

<210> SEQ ID NO 38
<211> LENGTH: 6646
<212> TYPE: DNA
<213> ORGANISM: Artificial Sequence
<220> FEATURE:
<223> OTHER INFORMATION: sequence of pSB-EGFP-LC-Ac10

<400> SEQUENCE: 38

| | |
|---|---:|
| gaattcagtt gaagtcggaa gtttacatac acttaagttg gagtcattaa aactcgtttt | 60 |
| tcaactacac cacaaatttc ttgttaacaa acaatagttt tggcaagtca gttaggacat | 120 |
| ctactttgtg catgacacaa gtcattttc caacaattgt ttacagacag attatttcac | 180 |
| ttataattca ctgtatcaca attccagtgg gtcagaagtt tacatacact aacctcgagg | 240 |
| ctagtctaga gagtaattca tacaaaagga ctcgccctg ccttgggaa tcccagggac | 300 |
| cgtcgttaaa ctcccactaa cgtagaaccc agagatcgct gcgttccgc cccctcaccc | 360 |
| gcccgctctc gtcatcactg aggtggaaa gagcatgcgt gaggctccgg tgcccgtcag | 420 |
| tgggcagagc gcacatcgcc cacagtcccc gagaagttgg ggggaggggt cggcaattga | 480 |
| accggtgcct agagaaggtg gcgcgggta aactgggaaa gtgatgtcgt gtactggctc | 540 |
| cgcctttttc ccgagggtgg gggagaaccg tatataagtg cagtagtcgc cgtgaacgtt | 600 |
| cttttttcgca acgggtttgc cgccagaaca caggtaagtg ccgtgtgtgg ttcccgcggg | 660 |
| cctggcctct ttacgggtta tggcccttgc gtgccttgaa ttacttccac gcccctggct | 720 |
| gcagtacgtg attcttgatc ccgagcttcg ggttggaagt gggtgggaga gttcgaggcc | 780 |
| ttgcgcttaa ggagcccctt cgcctcgtgc ttgagttgag gcctggcttg ggcgctgggg | 840 |
| ccgccgcgtg cgaatctggt ggcaccttcg cgcctgtctc gctgctttcg ataagtctct | 900 |
| agccatttaa aattttgat gacctgctgc gacgcttttt ttctggcaag atagtcttgt | 960 |

-continued

```
aaatgcgggc caagatctgc acactggtat ttcggttttt ggggccgcgg gcggcgacgg    1020
ggcccgtgcg tcccagcgca catgttcggc gaggcggggc ctgcgagcgc ggccaccgag    1080
aatcggacgg gggtagtctc aagctggccg gcctgctctg gtgcctggcc tcgcgccgcc    1140
gtgtatcgcc ccgccctggg cggcaaggct ggcccggtcg gcaccagttg cgtgagcgga    1200
aagatggccg cttcccggcc ctgctgcagg gagctcaaaa tggaggacgc ggcgctcggg    1260
agagcgggcg ggtgagtcac ccacacaaag gaaaagggcc tttccgtcct cagccgtcgc    1320
ttcatgtgac tccacggagt accgggcgcc gtccaggcac ctcgattagt tctcgagctt    1380
ttggagtacg tcgtctttag gttgggggga ggggttttat gcgatggagt ttccccacac    1440
tgagtgggtg gagactgaag ttaggccagc ttggcacttg atgtaattct ccttggaatt    1500
tgcccttttt gagtttggat cttggttcat tctcaagcct cagacagtgg ttcaaagttt    1560
ttttcttcca tttcaggtgt cgtgagcggc cgccatgaat tttggactga ggctgatttt    1620
cctggtgctg accctgaaag gcgtccagtg tgacattgtg ctgacccaat ctccagcttc    1680
tttggctgtg tctctagggc agagggccac catctcctgc aaggccagcc aaagtgttga    1740
ttttgatggt gatagttata tgaactggta ccaacagaaa ccaggacagc acccaaagt    1800 cctcatctat gctgcatcca atctagaatc tgggatccca gccaggttta gtggcagtgg    1860
gtctgggaca gacttcaccc tcaacatcca tcctgtggag gaggaggatg ctgcaaccta    1920
ttactgtcag caaagtaatg aggatccgtg gacgttcggt ggaggcacca agctggaaat    1980
caaacgtacg gtggctgcac catctgtctt catcttcccg ccatctgatg agcagttgaa    2040
atctggaact gcctctgttg tgtgcctgct gaataacttc tatcccagag aggccaaagt    2100
acagtggaag gtggataacg ccctccaatc gggtaactcc caggagagtg tcacagagca    2160
ggacagcaag gacagcacct acagcctcag cagcaccctg acgctgagca agcagacta    2220 cgagaaacac aaagtctacg cctgcgaagt cacccatcag ggcctgagct cgcccgtcac    2280
aaagagcttc aacaggggag agtgttagcg cttccgaagg gcaggtaagt atcaaggtta    2340
caagacaggt ttaaggagac caatagaaac tgggcttgtc gagacagaga agactcttgc    2400
gtttctgata ggcacctatt ggtcttactg acatccactt tgcctttctc tccacaggtg    2460
tcctacgtag cgatcgccaa ttccgcccct ctccctcccc cccccctaac gttactggcc    2520
gaagccgctt ggaataaggc cggtgtgcgt ttgtctatat gtgattttcc accatattgc    2580
cgtcttttgg caatgtgagg gcccggaaac ctggccctgt cttcttgacg agcattccta    2640
ggggtctttc cctctcgcc aaaggaatgc aaggtctgtt gaatgtcgtg aaggaagcag    2700
ttcctctgga agcttcttga agacaaacaa cgtctgtagc gacccttgc aggcagcgga    2760 accccccacc tggcgacagg tgcctctgcg gccaaaagcc acgtgtataa gatacacctg    2820
caaaggcggc acaaccccag tgccacgttg tgagttggat agttgtggaa agagtcaaat    2880
ggctctcctc aagcgtattc aacaaggggc tgaaggatgc ccagaaggta ccccattgta    2940
tgggatctga tctggggcct cggtgcacat gctttacatg tgtttagtcg aggttaaaaa    3000
aacgtctagg ccccccgaac cacggggacg tggttttcct ttgaaaaaca cgatgataag    3060
cttgccacaa cccggtttaa acggatcccg ccaccatggt gagcaaggc gaggagctgt    3120 tcaccggggt ggtgcccatc ctggtcgagc tggacggcga cgtaaacggc cacaagttca    3180
gcgtgtccgg cgagggcgag ggcgatgcca cctacggcaa gctgaccctg aagttcatct    3240
gcaccaccgg caagctgccc gtgccctggc ccaccctcgt gaccaccctg acctacggcg    3300
```

```
tgcagtgctt cagccgctac cccgaccaca tgaagcagca cgacttcttc aagtccgcca    3360
tgcccgaagg ctacgtccag gagcgcacca tcttcttcaa ggacgacggc aactacaaga    3420
cccgcgccga ggtgaagttc gagggcgaca ccctggtgaa ccgcatcgag ctgaagggca    3480
tcgacttcaa ggaggacggc aacatcctgg ggcacaagct ggagtacaac tacaacagcc    3540
acaacgtcta tatcatggcc gacaagcaga agaacggcat caaggtgaac ttcaagatcc    3600
gccacaacat cgaggacggc agcgtgcagc tcgccgacca ctaccagcag aacacccccca    3660
tcggcgacgg ccccgtgctg ctgcccgaca accactacct gagcacccag tccgccctga    3720
gcaaagaccc caacgagaag cgcgatcaca tggtcctgct ggagttcgtg accgccgccg    3780
ggatcactct cggcatggac gagctgtaca agtaaagcgg catatgcgcc ggcggatatc    3840
cggcgcgccg agctcgctga tcagcctcga ctgtgcctct agttgccagc catctgttgt    3900
ttgcccctcc cccgtgcctt ccttgaccct ggaaggtgcc actcccactg tcctttccta    3960
ataaaatgag gaaattgcat cgcattgtct gagtaggtgt cattctattc tggggggtgg    4020
ggtggggcag gacagcaagg gggaggattg ggaagacaat agcaggcatg ctggggatgc    4080
ggtgggctct atggcttctg aggcggaaag aaccagctgg ggttaattaa acgcgtttga    4140
gtgtatgtta acttctgacc cactgggaat gtgatgaaaa aataaaagc tgaaatgaat    4200
cattctctct actattattc tgatatttca cattcttaaa ataaagtggt gatcctaact    4260
gaccttaaga cagggaatct ttactcggat taaatgtcag gaattgtgaa aaagtgagtt    4320
taaatgtatt tggctaaggt gtatgtaaac ttccgacttc aactatcgat tcgcgcgcgt    4380
gcattctagt tgtggtttgt ccaaactcat caatgtatct tatcatgtct gtataccgtc    4440
gacctctagc tagagcttgg cgtaatcatg gtcatagctg tttcctgtgt gaaattgtta    4500
tccgctcaca attccacaca acatacgagc cggaagcata aagtgtaaag cctggggtgc    4560
ctaatgagtg agctaactca cattaattgc gttgcgctca ctgcccgctt tccagtcggg    4620
aaacctgtcg tgccagctgc attaatgaat cggccaacgc gcggggagag gcggtttgcg    4680
tattgggcgc tcttccgctt cctcgctcac tgactcgctg cgctcggtcg ttcggctgcg    4740
gcgagcggta tcagctcact caaaggcggt aatacggtta tccacagaat cagggggataa    4800
cgcaggaaag aacatgtgag caaaaggcca gcaaaaggcc aggaaccgta aaaaggccgc    4860
gttgctggcg tttttccata ggctccgccc ccctgacgag catcacaaaa atcgacgctc    4920
aagtcagagg tggcgaaacc cgacaggact ataaagatac caggcgtttc ccctggaag    4980
ctccctcgtg cgctctcctg ttccgaccct gccgcttacc ggatacctgt ccgcctttct    5040
cccttcggga agcgtggcgc tttctcaatg ctcacgctgt aggtatctca gttcggtgta    5100
ggtcgttcgc tccaagctgg gctgtgtgca cgaaccccccc gttcagcccg accgctgcgc    5160
cttatccggt aactatcgtc ttgagtccaa cccggtaaga cacgacttat cgccactggc    5220
agcagccact ggtaacagga ttagcagagc gaggtatgta ggcggtgcta cagagttctt    5280
gaagtggtgg cctaactacg gctacactag aaggacagta tttggtatct gcgctctgct    5340
gaagccagtt accttcggaa aaagagttgg tagctcttga tccggcaaac aaaccaccgc    5400
tggtagcggt ggtttttttg tttgcaagca gcagattacg cgcagaaaaa aaggatctca    5460
agaagatcct ttgatctttt ctacggggtc tgacgctcag tggaacgaaa actcacgtta    5520
agggattttg gtcatgagat tatcaaaaag gatcttcacc tagatccttt taaattaaaa    5580
atgaagtttt aaatcaatct aaagtatata tgagtaaact tggtctgaca gttaccaatg    5640
cttaatcagt gaggcaccta tctcagcgat ctgtctattt cgttcatcca gttgcctg    5700
```

-continued

```
actccccgtc gtgtagataa ctacgatacg ggagggctta ccatctggcc ccagtgctgc      5760
aatgataccg cgagacccac gctcaccggc tccagattta tcagcaataa accagccagc      5820
cggaagggcc gagcgcagaa gtggtcctgc aactttatcc gcctccatcc agtctattaa      5880
ttgttgccgg gaagctagag taagtagttc gccagttaat agtttgcgca acgttgttgc      5940
cattgctaca ggcatcgtgg tgtcacgctc gtcgtttggt atggcttcat tcagctccgg      6000
ttcccaacga tcaaggcgag ttacatgatc ccccatgttg tgcaaaaaag cggttagctc      6060
cttcggtcct ccgatcgttg tcagaagtaa gttggccgca gtgttatcac tcatggttat      6120
ggcagcactg cataattctc ttactgtcat gccatccgta agatgctttt ctgtgactgg      6180
tgagtactca accaagtcat tctgagaata gtgtatgcgg cgaccgagtt gctcttgccc      6240
ggcgtcaata cgggataata ccgcgccaca tagcagaact ttaaaagtgc tcatcattgg      6300
aaaacgttct cgggcgaa aactctcaag gatcttaccg ctgttgagat ccagttcgat      6360
gtaacccact cgtgcaccca actgatcttc agcatctttt actttcacca gcgtttctgg      6420
gtgagcaaaa acaggaaggc aaaatgccgc aaaaaaggga ataagggcga cacggaaatg      6480
ttgaatactc atactcttcc tttttcaata ttattgaagc atttatcagg gttattgtct      6540
catgagcgga tacatatttg aatgtattta gaaaaataaa caaatagggg ttccgcgcac      6600
atttccccga aaagtgccac ctgacgtcga cggatcgggc ctgcag                    6646
```

<210> SEQ ID NO 39
<211> LENGTH: 6631
<212> TYPE: DNA
<213> ORGANISM: Artificial Sequence
<220> FEATURE:
<223> OTHER INFORMATION: sequence of pSB-EGFP-LC-hBU12

<400> SEQUENCE: 39

```
gaattcagtt gaagtcggaa gtttacatac acttaagttg gagtcattaa aactcgtttt        60
tcaactacac cacaaatttc ttgttaacaa acaatagttt tggcaagtca gttaggacat       120
ctactttgtg catgacacaa gtcattttc caacaattgt ttacagacag attatttcac       180
ttataattca ctgtatcaca attccagtgg gtcagaagtt tacatacact aacctcgagg       240
ctagtctaga gagtaattca tacaaaagga ctcgcccctg ccttgggaa tcccagggac       300 cgtcgttaaa ctcccactaa cgtagaaccc agagatcgct cgttccgc cccctcaccc       360 gcccgctctc gtcatcactg aggtggagaa gagcatgcgt gaggctccgg tgcccgtcag      420
tgggcagagc gcacatcgcc cacagtcccc gagaagttgg gggagggt cggcaattga       480 accggtgcct agagaaggtg gcgcgggta aactgggaaa gtgatgtcgt gtactggctc       540 cgccttttc ccgagggtgg gggagaaccg tatataagtg cagtagtcgc cgtgaacgtt       600
ctttttcgca acgggtttgc cgccagaaca caggtaagtg ccgtgtgtgg ttcccgcggg      660
cctggcctct ttacgggtta tggcccttgc gtgccttgaa ttacttccac gcccctggct      720
gcagtacgtg attcttgatc ccgagcttcg ggttggaagt gggtgggaga gttcgaggcc      780
ttgcgcttaa ggagccccctt cgcctcgtgc ttgagttgag gcctggcttg ggcgctgggg      840
ccgccgcgtg cgaatctggt ggcaccttcg cgcctgtctc gctgctttcg ataagtctct      900
agccatttaa aattttgat gacctgctgc gacgcttttt ttctggcaag atagtcttgt      960
aaatgcgggc caagatctgc acactggtat ttcggttttt ggggccgcgg gcggcgacgg     1020
ggcccgtgcg tcccagcgca catgttcggc gaggcggggc ctgcgagcgc ggccaccgag     1080
```

```
aatcggacgg gggtagtctc aagctggccg gcctgctctg gtgcctggcc tcgcgccgcc    1140
gtgtatcgcc ccgccctggg cggcaaggct ggcccggtcg gcaccagttg cgtgagcgga    1200
aagatggccg cttcccggcc ctgctgcagg gagctcaaaa tggaggacgc ggcgctcggg    1260
agagcgggcg ggtgagtcac ccacacaaag gaaaagggcc tttccgtcct cagccgtcgc    1320
ttcatgtgac tccacggagt accgggcgcc gtccaggcac ctcgattagt tctcgagctt    1380
ttggagtacg tcgtctttag gttgggggga ggggttttat gcgatggagt ttccccacac    1440
tgagtgggtg gagactgaag ttaggccagc ttggcacttg atgtaattct ccttggaatt    1500
tgccctttt gagtttggat cttggttcat tctcaagcct cagacagtgg ttcaaagttt    1560
ttttcttcca tttcaggtgt cgtgagcggc cgccatgaat tttggactga ggctgatttt    1620
cctggtgctg accctgaaag gcgtccagtg tgaaattgtt ctcacccagt ctccagcaac    1680
cctgtctctc tctccagggg aaagggctac cctgagctgc agtgccagct caagtgtaag    1740
ttacatgcac tggtaccagc agaagccagg gcaggctccc agactcctga tttatgacac    1800
atccaaactg gcttctggta ttccagcaag gttcagtggc agtgggtctg gaacagattt    1860
tacactcaca atcagcagcc tggagccaga ggatgttgct gtctattact gttttcaggg    1920
gagtgtatac ccattcactt ttggccaagg gacaaagttg gaaatcaaac gtacggtggc    1980
tgcaccatct gtcttcatct tcccgccatc tgatgagcag ttgaaatctg gaactgcctc    2040
tgttgtgtgc ctgctgaata acttctatcc cagagaggcc aaagtacagt ggaaggtgga    2100
taacgccctc caatcgggta actcccagga gagtgtcaca gagcaggaca gcaaggacag    2160
cacctacagc ctcagcagca ccctgacgct gagcaaagca gactacgaga aacacaaagt    2220
ctacgcctgc gaagtcaccc atcagggcct gagctcgccc gtcacaaaga gcttcaacag    2280
gggagagtgt tagcgctttc gaagggcagg taagtatcaa ggttacaaga caggtttaag    2340
gagaccaata gaaactgggc ttgtcgagac agagaagact cttgcgtttc tgataggcac    2400
ctattggtct tactgacatc cactttgcct ttctctccac aggtgtccta cgtagcgatc    2460
gccaattccg cccctctccc tccccccccc ctaacgttac tggccgaagc cgcttggaat    2520
aaggccggtg tgcgtttgtc tatatgtgat tttccaccat attgccgtct tttggcaatg    2580
tgagggcccg gaaacctggc cctgtcttct tgacgagcat cctagggggt cttcccctc    2640
tcgccaaagg aatgcaaggt ctgttgaatg tcgtgaagga agcagttcct ctggaagctt    2700
cttgaagaca acaacgtct gtagcgaccc tttgcaggca gcggaacccc ccacctggcg    2760
acaggtgcct ctgcggccaa aagccacgtg tataagatac acctgcaaag gcggcacaac    2820
cccagtgcca cgttgtgagt tggatagttg tggaaagagt caaatggctc tcctcaagcg    2880
tattcaacaa ggggctgaag gatgcccaga aggtaccccca ttgtatggga tctgatctgg    2940
ggcctcggtg cacatgcttt acatgtgttt agtcgaggtt aaaaaaacgt ctaggccccc    3000
cgaaccacgg ggacgtggtt ttcctttgaa aaacacgatg ataagcttgc cacaacccgg    3060
tttaaacgga tcccgccacc atggtgagca agggcgagga gctgttcacc ggggtggtgc    3120
ccatcctggt cgagctggac ggcgacgtaa acggccacaa gttcagcgtg tccggcgagg    3180
gcgagggcga tgccacctac ggcaagctga ccctgaagtt catctgcacc accggcaagc    3240
tgcccgtgcc ctggcccacc ctcgtgacca ccctgaccta cggcgtgcag tgcttcagcc    3300
gctaccccga ccacatgaag cagcacgact tcttcaagtc cgccatgccc gaaggctacg    3360
tccaggagcg caccatcttc ttcaaggacg acggcaacta caagacccgc gccgaggtga    3420
agttcgaggg cgacaccctg gtgaaccgca tcgagctgaa gggcatcgac ttcaaggagg    3480
```

```
acggcaacat cctggggcac aagctggagt acaactacaa cagccacaac gtctatatca    3540
tggccgacaa gcagaagaac ggcatcaagg tgaacttcaa gatccgccac aacatcgagg    3600
acggcagcgt gcagctcgcc gaccactacc agcagaacac ccccatcggc gacggccccg    3660
tgctgctgcc cgacaaccac tacctgagca cccagtccgc cctgagcaaa gaccccaacg    3720
agaagcgcga tcacatggtc ctgctggagt tcgtgaccgc cgccgggatc actctcggca    3780
tggacgagct gtacaagtaa agcggcatat gcgccggcgg atatccggcg cgccgagctc    3840
gctgatcagc ctcgactgtg cctctagttg ccagccatct gttgtttgcc cctcccccgt    3900
gccttccttg accctggaag gtgccactcc cactgtcctt tcctaataaa atgaggaaat    3960
tgcatcgcat tgtctgagta ggtgtcattc tattctgggg ggtggggtgg ggcaggacag    4020 caaggggag gattgggaag acaatagcag gcatgctggg gatgcggtgg gctctatggc    4080
ttctgaggcg gaaagaacca gctggggtta attaaacgcg tttgagtgta tgttaacttc    4140
tgacccactg ggaatgtgat gaaagaaata aagctgaaa tgaatcattc tctctactat    4200
tattctgata tttcacattc ttaaaataaa gtggtgatcc taactgacct aagacaggg    4260 aatctttact cggattaaat gtcaggaatt gtgaaaaagt gagtttaaat gtatttggct    4320
aaggtgtatg taaacttccg acttcaacta tcgattcgcg cgcgtgcatt ctagttgtgg    4380
tttgtccaaa ctcatcaatg tatcttatca tgtctgtata ccgtcgacct ctagctagag    4440
cttggcgtaa tcatggtcat agctgtttcc tgtgtgaaat tgttatccgc tcacaattcc    4500
acacaacata cgagccggaa gcataaagtg taaagcctgg ggtgcctaat gagtgagcta    4560
actcacatta attgcgttgc gctcactgcc cgctttccag tcgggaaacc tgtcgtgcca    4620
gctgcattaa tgaatcggcc aacgcgcggg gagaggcggt ttgcgtattg ggcgctcttc    4680
cgcttcctcg ctcactgact cgctgcgctc ggtcgttcgg ctgcggcgag cggtatcagc    4740
tcactcaaag gcggtaatac ggttatccac agaatcaggg gataacgcag gaaagaacat    4800
gtgagcaaaa ggccagcaaa aggccaggaa ccgtaaaaag gccgcgttgc tggcgttttt    4860
ccataggctc cgcccccctg acgagcatca caaaaatcga cgctcaagtc agaggtggcg    4920
aaacccgaca ggactataaa gataccaggc gtttccccct ggaagctccc tcgtgcgctc    4980
tcctgttccg accctgccgc ttaccggata cctgtccgcc tttctccctt cgggaagcgt    5040
ggcgctttct caatgctcac gctgtaggta tctcagttcg gtgtaggtcg ttcgctccaa    5100
gctgggctgt gtgcacgaac cccccgttca gcccgaccgc tgcgccttat ccggtaacta    5160
tcgtcttgag tccaacccgg taagacacga cttatcgcca ctggcagcag ccactggtaa    5220
caggattagc agagcgaggt atgtaggcgg tgctacagag ttcttgaagt ggtggcctaa    5280
ctacggctac actagaagga cagtatttgg tatctgcgct ctgctgaagc cagttacctt    5340
cggaaaaaga gttggtagct cttgatccgg caaacaaacc accgctggta gcggtggttt    5400
ttttgtttgc aagcagcaga ttacgcgcag aaaaaaagga tctcaagaag atcctttgat    5460
cttttctacg gggtctgacg ctcagtggaa cgaaaactca cgttaaggga ttttggtcat    5520
gagattatca aaaaggatct tcacctagat ccttttaaat taaaaatgaa gttttaaatc    5580
aatctaaagt atatatgagt aaacttggtc tgacagttac caatgcttaa tcagtgaggc    5640
acctatctca gcgatctgtc tatttcgttc atccatagtt gcctgactcc ccgtcgtgta    5700
gataactacg atacgggagg gcttaccatc tggccccagt gctgcaatga taccgcgaga    5760
cccacgctca ccggctccag atttatcagc aataaaccag ccagccggaa gggccgagcg    5820
```

```
cagaagtggt cctgcaactt tatccgcctc catccagtct attaattgtt gccgggaagc    5880
tagagtaagt agttcgccag ttaatagttt gcgcaacgtt gttgccattg ctacaggcat    5940
cgtggtgtca cgctcgtcgt ttggtatggc ttcattcagc tccggttccc aacgatcaag    6000
gcgagttaca tgatccccca tgttgtgcaa aaaagcggtt agctccttcg gtcctccgat    6060
cgttgtcaga agtaagttgg ccgcagtgtt atcactcatg gttatggcag cactgcataa    6120
ttctcttact gtcatgccat ccgtaagatg ctttttctgtg actggtgagt actcaaccaa    6180
gtcattctga gaatagtgta tgcggcgacc gagttgctct tgcccggcgt caatacggga    6240
taataccgcg ccacatagca gaactttaaa agtgctcatc attggaaaac gttcttcggg    6300
gcgaaaactc tcaaggatct taccgctgtt gagatccagt tcgatgtaac ccactcgtgc    6360
acccaactga tcttcagcat cttttacttt caccagcgtt tctgggtgag caaaaacagg    6420
aaggcaaaat gccgcaaaaa agggaataag ggcgacacgg aaatgttgaa tactcatact    6480 cttcctttt caatattatt gaagcattta tcagggttat tgtctcatga gcggatacat    6540
atttgaatgt atttagaaaa ataaacaaat aggggttccg cgcacatttc cccgaaaagt    6600
gccacctgac gtcgacggat cgggcctgca g                                   6631
```

<210> SEQ ID NO 40
<211> LENGTH: 5812
<212> TYPE: DNA
<213> ORGANISM: Homo sapiens

<400> SEQUENCE: 40

```
gctagcacca agggcccatc ggtcttcccc ctggcaccct cctccaagag cacctctggg      60
ggcacagcag ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttggtgag     300
aggccagcac agggagggag ggtgtctgct ggaagccagg ctcagcgctc ctgcctggac     360
gcatcccgga tatgcagccc cagtccaggg cagcaaggca ggccccgtct gcctcttcac     420
ccggaggcct ctgcccgccc cactcatgct cagggagagg gtcttctggc tttttcccca     480
ggctctgggc aggcacaggc taggtgcccc taacccaggc cctgcacaca aaggggcagg     540
tgctgggctc agacctgcca agagccatat ccgggaggac cctgcccctg acctaagccc     600
accccaaagg ccaaactctc cactccctca gctcggacac cttctctcct cccagattcc     660
agtaactccc aatcttctct ctgcagagcc caaatcttgt gacaaaactc acacatgccc     720
accgtgccca ggtaagccag cccaggcctc gccctccagc tcaaggcggg acaggtgccc     780
tagagtagcc tgcatccagg acaggcccc agccggggtgc tgacacgtcc acctccatct     840
cttcctcagc acctgaactc ctgggggac cgtcagtctt cctcttcccc ccaaaaccca     900
aggacaccct catgatctcc cggacccctg aggtcacatg cgtggtggtg gacgtgagcc     960
acgaagaccc tgaggtcaag ttcaactggt acgtggacgg cgtggaggtg cataatgcca    1020
agacaaagcc gcgggaggag cagtacaaca gcacgtaccg tgtggtcagc gtcctcaccg    1080
tcctgcacca ggactggctg aatggcaagg agtacaagtg caaggtctcc aacaaagccc    1140
tcccagcccc catcgagaaa accatctcca aagccaaagg tgggacccgt ggggtgcgag    1200
ggccacatgg acagaggccg gctcggccca ccctctgccc tgagagtgac cgctgtacca    1260
acctctgtcc ctacagggca gccccgagaa ccacaggtgt acaccctgcc cccatcccgg    1320
```

```
gatgagctga ccaagaacca ggtcagcctg acctgcctgg tcaaaggctt ctatcccagc   1380
gacatcgccg tggagtggga gagcaatggg cagccggaga caactacaa gaccacgcct    1440 cccgtgctgg actccgacgg ctccttcttc ctctacagca agctcaccgt ggacaagagc   1500
aggtggcagc aggggaacgt cttctcatgc tccgtgatgc atgaggctct gcacaaccac   1560
tacacacaga gagcctctc cctgtctccg ggtaaatgag tgccacggcc ggcaagcccc    1620
cgctccccag gctctcgggg tcgcgcgagg atgcttggca cgtacccgt gtacatactt    1680 cccaggcacc cagcatggaa ataaagcacc cagcgcttcc ctgggcccct gcgagactgt   1740
gatggttctt tccacgggtc aggccgagtc tgaggcctga gtggcatgag ggaggcagag   1800
tgggtcccac tgtccccaca ctggcccagg ctgtgcaggt gtgcctgggc cgcctagggt   1860
ggggctcagc caggggctgc cctcggcagg gtgggggatt tgccagcgtg gccctccctc   1920
cagcagcagc tgccctgggc tgggccacga aagccctag gagccctgg ggacagacac     1980 acagcccctg cctctgtagg agactgtcct gttctgtgag cgcccgtcc tccgacccgc    2040 atgcccactc gggggcatgc ctagtccatg tgcgtaggga caggccctcc ctcacccatc   2100
tacccccacg gcactaaccc ctggcagccc tgcccagcct cgcacccgca tggggacaca   2160
accgactccg gggacatgca ctctcgggcc ctgtggagag actggtccag atgcccacac   2220
acacactcag cccagacccg ttcaacaaac cccgcactga ggttggccgg ccacacggcc   2280
accacacaca cacgtgcacg cctcacacac ggagcctcac ccgggcgaac cgcacagcac   2340
ccagaccaga gcaaggtcct cgcacacgtg aacactcctc ggacacaggc ccccacgagc   2400
cccacgcggc acctcaaggc ccacgagccg ctcggcagct tctccacatg ctgacctgct   2460
cagacaaacc cagccctcct ctcacaaggt gccctgcag ccgccacaca cacacagggg    2520
atcacacacc acgtcacgtc cctggccctg gcccacttcc cagtgccgcc cttccctgca   2580 gctgggtca catgaggtgt gggcttcacc atcctcctgc cctctgggcc tcagggaggg    2640
acacgggaga cggggagcgg gtcctgctga gggccaggtc gctatctagg gccgggtgtc   2700
tggctgagcc ccggggccaa agctggtgcc caggcgggc agctgtgggg agctgacctc    2760
aggacattgt tggcccatcc cggccgggcc ctacatcctg ggtcctgcca cagagggaat   2820 caccccccaga ggcccaagcc caggggggaca cagcactgac caccccccttc ctgtccagag 2880 ctgcaactgg aggagagctg tgcggaggcg caggacgggg agctggacgg gctgtggacg   2940
accatcacca tcttcatcac actcttcctg ttaagcgtgt gctacagtgc caccgtcacc   3000
ttcttcaagg tcggccgcac gttgtccca gctgtccttg acattgtccc ccatgctgtc    3060
acaaactgtc tctgacactg tcccacaggc tgtccccacc tgtccctgac gctgtccccc   3120
atgctctcac aaactgtccc tgacattgtc cccaatgctg cccccacctg tccaacagtg   3180
tcccccaggc tctccccaca tgtccccgac actgtccccc atgctgtccc catctgtccc   3240
caacactgtc cccaccctg tccccctttg tccccaacac tgtccccac agtttccacc    3300 tgtccctgac actgtccccc atgctttccc cacctgtccc tgacaccatc cccactctg   3360 tcccctatag ttcctggccc tgtccccac gctgtccct acagtacctg gcactgtccc    3420
ccatgctgtc cctcctgta tgaaaccctg tcccacatgc tgtccccacc tgtccgtgac   3480
aatatccccc acactgtccc cacctgtccc cgacactctc ctccacgttg ttcttaccta   3540
aacccgacac tttcctccat gctgtcccca cccatctccg acactgtacc ccacgttgtc   3600
cccacctgtc ctcaacactg tcccccatgc tgtccccacc tgtccccaac actctcctcc   3660
```

```
atgctgtccc cacctgtccc tgatattgtc ccccatgcag tctccacctg tccccaatgc    3720
tgtcccccag gctgtaccta ccagtacaac actgtccccc atgctgtccc cacctgtccc    3780
tgacactgtc ccccacgctg tccctcctg tccccgacac tgtccccac actgtcccca     3840
cctgtcccca acactatcct ccatgctgtc cctcctgtc cccacctgtc cctacactg     3900
tcccccatgc tgtccccacc agtccccaaa actttcctcc acactgtccc cacctgtccc    3960
caacactgtc ccccacgcta tccccctgt cccgacaat gtccccactg tttcctcctg     4020
ttccctccta tccctgacac tgtccgccat gctgtcccca cctgtccctg acactgtctc    4080
ccactctgtc ccctataatc cctgacactg tccccacgc cgtccctcc cgtatgcacc     4140
actgtccccc aagctgtccc cacctgtcct caacacagtc cccatgctg tccccacctg     4200
tccccaacac tctcctccat gtccccacct gtccctgata ttgtccccca tgcagtcccc    4260
acctgtcccc gatgctgtcc cccgggctgt acctaccagt ccaacactgt cccccacact    4320
ctccccacct gtccctgata ctgtccccca tgctgtcccc acctgtcccg gacactgttc    4380
tccacgctct cccctcctgt ccctgacact gtccccaca ctgtcccac ctgtcccaa      4440
cactatcctc catcctgtcc caacctgtct cctacactgt ccccatgct gtccccacca    4500
gtccccaaca ctgtcctcca tgctgtcccc catgtcccca acactgtccc ccatgctatc    4560
tcccctgtcc ctgacaatgt ccccactgtt tcctgtcccc tcctatccct gacactgtcc    4620
cccatgctgt ccccacctgt ccccacatg gtctccaccg gtccctgaca ctgtctccca    4680
ctctgtcccc tataatccct gacactgtcc cccacaccgt ccctcctgt atgcaccact    4740
gtcccccatg ctgtccccac ctgtccctga tgctgtcctc cacacagtcc ccacctctcc    4800
ctgacactgt ccccatctct ccccaacact ctcctccatg ctgtccttaa ctgtccccaa    4860
cactcttcca cactctgtct ccacctgtcc ctgacactgt ccccccacact gtcctcacct    4920
gtgtctgaca ctgtcccca cgctgtcccc acctgtccct gacgctgtct ctgtgctgt     4980
ccacatgctg ttggtgccct ggctctgctc tctatcacca agcctcagag caggcagtgg    5040
tgaggccatg gcacctgggt ggcatgaggg gccggatggg cctcaggggc agggctgtgg    5100
cctgcgtgga ctgacgggtg ggtgggcctt gggggcagag aggtggcctc agtgccctga    5160
ggggtgggtg gggctcgggg gcagggctgt ggcctcgctc accctgtgc tgtgccttgc    5220
ctacaggtga agtggatctt ctcctcggtg gtggacctga agcagaccat catccccgac    5280
tacaggaaca tgatcggaca ggggcctag ggccacccctc tgcgggtgt ccagggccgc    5340
ccagaccca cacaccagcc atgggccatg ctcagccacc cccaggcca cctgccccc     5400
cgacctcacc gccctcaacc ccatgactct ctggcctcgc agttgccctc tgaccctgac    5460
acacctgaca cgcccccctt ccagaccctg tgcatagcag gtctacccca gacctccgct    5520
gcttggtgca tgcagggcac tgggggccag gtgtcccctc agcaggacgt ccttgccctc    5580
cggaccacaa ggtgctcaca caaaaggagg cagtgaccgg tatcccaggc ccccacccag    5640
gcaggacctc gccctggagc caaccccgtc cacgccagcc tcctgaacac aggcgtggtt    5700
tccagatggt gagtgggagc gtcagccgcc aaggtaggga agccacagca ccatcaggcc    5760
ctgttgggga ggcttccgag agctgcgaag gctcactcag acggccttcg aa           5812
```

```
<210> SEQ ID NO 41
<211> LENGTH: 12238
<212> TYPE: DNA
<213> ORGANISM: Artificial Sequence
<220> FEATURE:
<223> OTHER INFORMATION: transposable Ig-gamma1-HC expression vector in
``` genomic configuration

<400> SEQUENCE: 41

```
gaattcttaa ccctagaaag atagtctgcg taaaattgac gcatgcattc ttgaaatatt    60
gctctctctt tctaaatagc gcgaatccgt cgctgtgcat ttaggacatc tcagtcgccg   120
cttggagctc ccgtgaggcg tgcttgtcaa tgcggtaagt gtcactgatt ttgaactata   180
acgaccgcgt gagtcaaaat gacgcatgat tatcttttac gtgactttta agatttaact   240
catacgataa ttatattgtt atttcatgtt ctacttacgt gataacttat tatatatata   300
ttttcttgtt atacctcgag gctagtctag agagtaattc atacaaaagg actcgcccct   360
gccttgggga atcccaggga ccgtcgttaa actcccacta acgtagaacc cagagatcgc   420
tgcgttcccg cccctcacc cgcccgctct cgtcatcact gaggtggaga agagcatgcg   480
tgaggctccg gtgcccgtca gtgggcagag cgcacatcgc ccacagtccc cgagaagttg   540
gggggagggg tcggcaattg aaccggtgcc tagagaaggt ggcgcgggt aaactgggaa   600
agtgatgtcg tgtactggct ccgccttttt cccgagggtg gggagaacc gtatataagt   660
gcagtagtcg ccgtgaacgt tcttttttcgc aacgggtttg ccgccagaac acaggtaagt   720
gccgtgtgtg gttcccgcgg gcctggcctc tttacgggtt atggcccttg cgtgccttga   780
attacttcca cgcccctggc tgcagtacgt gattcttgat cccgagcttc gggttggaag   840
tgggtgggag agttcgaggc cttgcgctta aggagcccct tcgcctcgtg cttgagttga   900
ggcctggctt gggcgctggg gccgccgcgt gcgaatctgg tggcaccttc gcgcctgtct   960
cgctgctttc gataagtctc tagccattta aaattttttga tgacctgctg cgacgctttt  1020
tttctggcaa gatagtcttg taaatgcggg ccaagatctg cacactggta tttcggtttt  1080
tggggccgcg ggcggcgacg gggcccgtgc gtcccagcgc acatgttcgg cgaggcgggg  1140
cctgcgagcg cggccaccga gaatcggacg ggggtagtct caagctggcc ggcctgctct  1200
ggtgcctggc ctcgcgccgc cgtgtatcgc cccgccctgg gcggcaaggc tggcccggtc  1260
ggcaccagtt gcgtgagcgg aaagatggcc gcttcccggc cctgctgcag ggagctcaaa  1320
atggaggacg cggcgctcgg gagagcgggc gggtgagtca cccacacaaa ggaaaagggc  1380
ctttccgtcc tcagccgtcg cttcatgtga ctccacggag taccgggcgc cgtccaggca  1440
cctcgattag ttctcgagct tttggagtac gtcgtcttta ggttgggggg aggggttttta  1500
tgcgatggag tttccccaca ctgagtgggt ggagactgaa gttaggccag cttggcactt  1560
gatgtaattc tccttggaat ttgcccttt tgagtttgga tcttggttca ttctcaagcc  1620
tcagacagtg gttcaaagtt tttttcttcc atttcaggtg tcgtgagcgg ccgccatgaa  1680
ttttggactg aggctgattt tcctggtgct gaccctgaaa ggcgtccagt gtcagatcca  1740
gctgcagcag tctggccccg aggtcgtgaa acctggcgcc tccgtgaaga tctcctgcaa  1800
ggcctccggc tacaccttca ccgactacta catcacctgg gtcaagcaga agcccggcca  1860
gggcctggaa tggatcggct ggatctatcc cggctccggc aacaccaagt acaacgagaa  1920
gttcaagggc aaggccaccc tgaccgtgga cacctcctct tccaccgcct tcatgcagct  1980
gtcctccctg acctccgagg ataccgccgt gtacttctgc gccaactacg gcaactattg  2040
gttcgcctac tggggccagg gcacacaagt gaccgtgtct gctgctagca ccaagggccc  2100
atcggtcttc cccctggcac cctcctccaa gagcacctct gggggcacag cagccctggg  2160
ctgcctggtc aaggactact tccccgaacc ggtgacggtg tcgtgaact caggcgcccc  2220
gaccagcggc gtgcacacct tcccggctgt cctacagtcc tcaggactct actccctcag  2280
```

```
cagcgtggtg accgtgccct ccagcagctt gggcacccag acctacatct gcaacgtgaa    2340
tcacaagccc agcaacacca aggtggacaa gaaagttggt gagaggccag cacagggagg    2400
gagggtgtct gctggaagcc aggctcagcg ctcctgcctg gacgcatccc ggctatgcag    2460
ccccagtcca gggcagcaag gcaggccccg tctgcctctt cacccggagg cctctgcccg    2520
ccccactcat gctcagggag agggtcttct ggcttttttcc ccaggctctg ggcaggcaca    2580
ggctaggtgc ccctaaccca ggccctgcac acaaaggggc aggtgctggg ctcagacctg    2640
ccaagagcca tatccgggag gaccctgccc ctgacctaag cccaccccaa aggccaaact    2700
ctccactccc tcagctcgga caccttctct cctcccagat tccagtaact cccaatcttc    2760
tctctgcaga gcccaaatct tgtgacaaaa ctcacacatg cccaccgtgc ccaggtaagc    2820
cagcccaggc ctcgccctcc agctcaaggc gggacaggtg ccctagagta gcctgcatcc    2880
agggacaggc cccagccggg tgctgacacg tccacctcca tctcttcctc agcacctgaa    2940
ctcctggggg gaccgtcagt cttcctcttc cccccaaaac ccaaggacac cctcatgatc    3000
tcccggaccc ctgaggtcac atgcgtggtg gtggacgtga gccacgaaga ccctgaggtc    3060
aagttcaact ggtacgtgga cggcgtggag gtgcataatg ccaagacaaa gccgcgggag    3120
gagcagtaca acagcacgta ccgtgtggtc agcgtcctca ccgtcctgca ccaggactgg    3180
ctgaatggca aggagtacaa gtgcaaggtc tccaacaaag cccctcccagc ccccatcgag    3240 aaaaccatct ccaaagccaa aggtgggacc cgtggggtgc gagggccaca tggacagagg    3300
ccggctcggc ccaccctctg ccctgagagt gaccgctgta ccaacctctg tccctacagg    3360
gcagccccga gaaccacagg tgtacaccct gcccccatcc cgggatgagc tgaccaagaa    3420
ccaggtcagc ctgacctgcc tggtcaaagg cttctatccc agcgacatcg ccgtggagtg    3480
ggagagcaat gggcagccgg agaacaacta caagaccacg cctcccgtgc tggactccga    3540
cggctccttc ttcctctaca gcaagctcac cgtggacaag agcaggtggc agcaggggaa    3600
cgtcttctca tgctccgtga tgcatgaggc tctgcacaac cactacacac agaagagcct    3660
ctccctgtct ccgggtaaat gagtgccacg gccggcaagc cccgctcccc aggctctcg    3720 gggtcgcgcg aggatgcttg gcacgtaccc cgtgtacata cttcccaggc acccagcatg    3780
gaaataaagc acccagcgct tccctgggcc cctgcgagac tgtgatggtt ctttccacgg    3840
gtcaggccga gtctgaggcc tgagtggcat gagggaggca gagtgggtcc cactgtcccc    3900
acactggccc aggctgtgca ggtgtgcctg ggccgcctag ggtggggctc agccaggggc    3960
tgccctcggc agggtgggggg atttgccagc gtggccctcc ctccagcagc agctgccctg    4020
ggctgggcca cgagaagccc taggagcccc tggggacaga cacacagccc ctgcctctgt    4080
aggagactgt cctgttctgt gagcgccctg tcctccgacc cgcatgccca ctcggggca    4140 tgcctagtcc atgtgcgtag ggacaggccc tccctcaccc atctaccccc acggcactaa    4200
cccctggcag ccctgcccag cctcgcaccc gcatggggac acaaccgact ccggggacat    4260
gcactctcgg gccctgtgga gagactggtc cagatgccca cacacacact cagcccagac    4320
ccgttcaaca aaccccgcac tgaggttggc cggccacacg ccaccacac acacacgtgc    4380 acgcctcaca cacggagcct cacccggggcg aaccgcacag cacccagacc agagcaaggt    4440
cctcgcacac gtgaacactc ctcggacaca ggccccacg agcccacgc ggcacctcaa    4500 ggcccacgag ccgctcggca gcttctccac atgctgacct gctcagacaa acccagccct    4560
cctctcacaa ggtgcccctg cagccgccac acacacacag gggatcacac accacgtcac    4620
```

```
gtccctggcc ctggcccact tcccagtgcc gcccttccct gcagctgggg tcacatgagg    4680
tgtgggcttc accatcctcc tgccctctgg gcctcaggga gggacacggg agacggggag    4740
cgggtcctgc tgagggccag gtcgctatct agggccgggt gtctggctga gccccggggc    4800
caaagctggt gcccagggcg ggcagctgtg gggagctgac ctcaggacat tgttggccca    4860
tcccggccgg gccctacatc ctgggtcctg ccacagaggg aatcacccccc agaggcccaa    4920
gcccaggggg acacagcact gaccacccccc ttcctgtcca gagctgcaac tggaggagag    4980
ctgtgcggag gcgcaggacg gggagctgga cgggctgtgg acgaccatca ccatcttcat    5040
cacactcttc ctgttaagcg tgtgctacag tgccaccgtc accttcttca aggtcggccg    5100
cacgttgtcc ccagctgtcc ttgacattgt cccccatgct gtcacaaact gtctctgaca    5160
ctgtcccaca ggctgtcccc acctgtccct gacgctgtcc cccatgctct cacaaactgt    5220
ccctgacatt gtccccaatg ctgcccccac ctgtccaaca gtgtccccca ggctctcccc    5280
acatgtcccc gacactgtcc cccatgctgt ccccatctgt ccccaacact gtcccccacc    5340
ctgtccccct ttgtccccaa cactgtcccc cacagtttcc acctgtccct gacactgtcc    5400
cccatgcttt ccccacctgt ccctgacacc atccccccact ctgtccccta tagttcctgg    5460
ccctgtcccc cacgctgtcc cctacagtac ctggcactgt cccccatgct gtcccctcct    5520
gtatgaaacc ctgtcccaca tgctgtcccc acctgtccgt gacaatatcc cccacactgt    5580
ccccacctgt ccccgacact ctcctccacg ttgttcttac ctaaacccga cactttcctc    5640
catgctgtcc ccacccatct ccgacactgt accccacgtt gtccccacct gtcctcaaca    5700
ctgtccccca tgctgtcccc acctgtcccc aacactctcc tccatgctgt ccccacctgt    5760
ccctgatatt gtccccccatg cagtctccac ctgtccccaa tgctgtcccc caggctgtac    5820
ctaccagtac aacactgtcc cccatgctgt ccccacctgt ccctgacact gtcccccacg    5880
ctgtcccctc ctgtccccga cactgtcccc cacactgtcc ccacctgtcc caacactat    5940
cctccatgct gtccccctcct gtccccacct gtccccctaca ctgtcccccca tgctgtcccc    6000
accagtcccc aaaactttcc tccacactgt ccccacctgt cccaacact gtcccccacg    6060
ctatcccccc tgtccccgac aatgtcccca ctgtttcctc ctgttccctc ctatccctga    6120
cactgtccgc catgctgtcc ccacctgtcc ctgacactgt ctcccactct gtccctata    6180
atccctgaca ctgtccccca cgccgtcccc tcccgtatgc accactgtcc cccaagctgt    6240
ccccacctgt cctcaacaca gtcccccatg ctgtccccac ctgtccccaa cactctcctc    6300
catgtcccca cctgtccctg atattgtccc ccatgcagtc cccacctgtc ccgatgctg    6360
tcccccgggc tgtacctacc agtccaacac tgtcccccac actctcccca cctgtccctg    6420
atactgtccc ccatgctgtc cccacctgtc ccggacactg ttctccacgc tctccccctcc    6480
tgtccctgac actgtccccc acactgtccc cacctgtccc caacactatc ctccatcctg    6540
tcccaacctg tctcctacac tgtccccat gctgtcccca ccagtcccca acactgtcct    6600
ccatgctgtc cccatgtcc ccaacactgt ccccatgct atctcccctg tccctgacaa    6660
tgtccccact gtttcctgtc ccctcctatc cctgacactg tccccccatgc tgtccccacc    6720
tgtccccac atggtctcca ccggtccctg acactgtctc ccactctgtc cctataatc    6780
cctgacactg tccccccacac cgtccccctcc tgtatgcacc actgtccccc atgctgtccc    6840
cacctgtccc tgatgctgtc ctccacacag tccccacctc tccctgacac tgtccccatc    6900
tctccccaac actctcctcc atgctgtcct taactgtccc caacactctt ccacactctg    6960
tctccaccttg tccctgacac tgtcccccac actgtcctca cctgtgtctg acactgtccc    7020
```

-continued

```
ccacgctgtc cccacctgtc cctgacgctg tcttctgtgc tgtccacatg ctgttggtgc    7080
cctggctctg ctctctatca ccaagcctca gagcaggcag tggtgaggcc atggcacctg    7140
ggtggcatga ggggccggat gggcctcagg ggcagggctg tggcctgcgt ggactgacgg    7200
gtgggtgggc cttgggggca gagaggtggc ctcagtgccc tgaggggtgg gtggggctcg    7260
ggggcagggc tgtggcctcg ctcacccctg tgctgtgcct tgcctacagg tgaagtggat    7320
cttctcctcg gtggtggacc tgaagcagac catcatcccc gactacagga acatgatcgg    7380
acaggggggcc tagggccacc ctctgcgggg tgtccagggc cgcccagacc ccacacacca    7440
gccatgggcc atgctcagcc accacccagg ccacacctgc ccccgacctc accgccctca    7500
accccatgac tctctggcct cgcagttgcc ctctgaccct gacacacctg acacgccccc    7560
cttccagacc ctgtgcatag caggtctacc ccagacctcc gctgcttggt gcatgcaggg    7620
cactgggggc caggtgtccc ctcagcagga cgtccttgcc ctccggacca caaggtgctc    7680
acacaaaagg aggcagtgac cggtatccca ggcccccacc caggcaggac ctcgccctgg    7740
agccaacccc gtccacgcca gcctcctgaa cacaggcgtg gtttccagat ggtgagtggg    7800
agcgtcagcc gccaaggtag ggaagccaca gcaccatcag gccctgttgg ggaggcttcc    7860
gagagctgcg aaggctcact cagacggcct tcgaagggca ggtaagtatc aaggttacaa    7920
gacaggttta aggagaccaa tagaaactgg gcttgtcgag acagagaaga ctcttgcgtt    7980
tctgataggc acctattggt cttactgaca tccactttgc ctttctctcc acaggtgtcc    8040
tacgtagcga tcgccaattc cgcccctctc cctccccccc ccctaacgtt actggccgaa    8100
gccgcttgga ataaggccgg tgtgcgtttg tctatatgtg attttccacc atattgccgt    8160
cttttggcaa tgtgagggcc cggaaacctg gccctgtctt cttgacgagc attcctaggg    8220
gtctttcccc tctcgccaaa ggaatgcaag gtctgttgaa tgtcgtgaag aagcagttc    8280
ctctggaagc ttcttgaaga caaacaacgt ctgtagcgac cctttgcagg cagcggaacc    8340
ccccacctgg cgacaggtgc ctctgcggcc aaaagccacg tgtataagat acacctgcaa    8400
aggcggcaca accccagtgc cacgttgtga gttggatagt tgtggaaaga gtcaaatggc    8460
tctcctcaag cgtattcaac aagggctga aggatgccca aaggtaccc cattgtatgg     8520
gatctgatct ggggcctcgg tgcacatgct ttacatgtgt ttagtcgagg ttaaaaaaac    8580
gtctaggccc cccgaaccac ggggacgtgg ttttcctttg aaaaacacga tgataagctt    8640
gccacaaccc ggtttaaacg gatcccgcca ccatggtgag caagggcgag gagctgttca    8700
ccggggtggt gcccatcctg gtcgagctgg acggcgacgt aaacggccac aagttcagcg    8760
tgtccggcga gggcgagggc gatgccacct acggcaagct gaccctgaag ttcatctgca    8820
ccaccggcaa gctgcccgtg ccctggccca ccctcgtgac caccctgacc tacggcgtgc    8880
agtgcttcag ccgctacccc gaccacatga agcagcacga cttcttcaag tccgccatgc    8940
ccgaaggcta cgtccaggag cgcaccatct tcttcaagga cgacggcaac tacaagaccc    9000
gcgccgaggt gaagttcgag ggcgacaccc tggtgaaccg catcgagctg aagggcatcg    9060
acttcaagga ggacggcaac atcctggggc acaagctgga gtacaactac aacagccaca    9120
acgtctatat catggccgac aagcagaaga acggcatcaa ggtgaacttc aagatccgcc    9180
acaacatcga ggacggcagc gtgcagctcg ccgaccacta ccagcagaac cccccatcg     9240
gcgacggccc cgtgctgctg cccgacaacc actacctgag cacccagtcc gccctgagca    9300
aagaccccaa cgagaagcgc gatcacatgg tcctgctgga gttcgtgacc gccgccggga    9360
```

```
tcactctcgg catggacgag ctgtacaagt aaagcggcat atgcgccggc ggatatccgg   9420
cgcgccgagc tcgctgatca gcctcgactg tgcctctagt tgccagccat ctgttgtttg   9480
cccctccccc gtgccttcct tgaccctgga aggtgccact cccactgtcc tttcctaata   9540
aaatgaggaa attgcatcgc attgtctgag taggtgtcat tctattctgg ggggtggggt   9600
ggggcaggac agcaaggggg aggattggga agacaatagc aggcatgctg gggatgcggt   9660
gggctctatg gcttctgagg cggaaagaac cagctgggt taattaaacg cgtttaaccc    9720
tagaaagata atcatattgt gacgtacgtt aaagataatc atgcgtaaaa ttgacgcatg   9780
tgttttatcg gtctgtatat cgaggtttat ttattaattt gaatagatat taagtttat    9840 tatatttaca cttacatact aataataaat tcaacaaaca atttatttat gtttatttat   9900
ttattaaaaa aaaacaaaaa ctcaaaattt cttctataaa gtaacaaaac ttttatatcg   9960
attcgcgcgc gtgcattcta gttgtggttt gtccaaactc atcaatgtat cttatcatgt  10020
ctgtataccg tcgacctcta gctagagctt ggcgtaatca tggtcatagc tgtttcctgt  10080
gtgaaattgt tatccgctca caattccaca caacatacga gccggaagca taaagtgtaa  10140 agcctgggt gcctaatgag tgagctaact cacattaatt gcgttgcgct cactgcccgc   10200
tttccagtcg ggaaacctgt cgtgccagct gcattaatga atcggccaac gcgcggggag  10260
aggcggtttg cgtattgggc gctcttccgc ttcctcgctc actgactcgc tgcgctcggt  10320
cgttcggctg cggcgagcgg tatcagctca ctcaaaggcg gtaatacggt tatccacaga  10380
atcaggggat aacgcaggaa agaacatgtg agcaaaaggc cagcaaaagg ccaggaaccg  10440
taaaaaggcc gcgttgctgg cgtttttcca taggctccgc ccccctgacg agcatcacaa  10500
aaatcgacgc tcaagtcaga ggtggcgaaa cccgacagga ctataaagat accaggcgtt  10560
tccccctgga agctccctcg tgcgctctcc tgttccgacc ctgccgctta ccggatacct  10620
gtccgccttt ctcccttcgg gaagcgtggc gctttctcaa tgctcacgct gtaggtatct  10680
cagttcggtg taggtcgttc gctccaagct gggctgtgtg cacgaacccc ccgttcagcc  10740
cgaccgctgc gccttatccg gtaactatcg tcttgagtcc aacccggtaa gacacgactt  10800
atcgccactg gcagcagcca ctggtaacag gattagcaga gcgaggtatg taggcggtgc  10860
tacagagttc ttgaagtggt ggcctaacta cggctacact agaaggacag tatttggtat  10920
ctgcgctctg ctgaagccag ttaccttcgg aaaaagagtt ggtagctctt gatccggcaa  10980
acaaaccacc gctggtagcg gtggtttttt tgtttgcaag cagcagatta cgcgcagaaa  11040
aaaaggatct caagaagatc ctttgatctt ttctacgggg tctgacgctc agtggaacga  11100
aaactcacgt taagggattt tggtcatgag attatcaaaa aggatcttca cctagatcct  11160
tttaaattaa aaatgaagtt ttaaatcaat ctaaagtata tatgagtaaa cttggtctga  11220
cagttaccaa tgcttaatca gtgaggcacc tatctcagcg atctgtctat ttcgttcatc  11280
catagttgcc tgactccccg tcgtgtagat aactacgata cgggagggct taccatctgg  11340
ccccagtgct gcaatgatac cgcgagaccc acgctcaccg gctccagatt tatcagcaat  11400
aaaccagcca gccggaaggg ccgagcgcag aagtggtcct gcaactttat ccgcctccat  11460
ccagtctatt aattgttgcc gggaagctag agtaagtagt tcgccagtta atagtttgcg  11520
caacgttgtt gccattgcta caggcatcgt ggtgtcacgc tcgtcgtttg gtatggcttc  11580
attcagctcc ggttcccaac gatcaaggcg agttacatga tcccccatgt tgtgcaaaaa  11640
agcggttagc tccttcggtc ctccgatcgt tgtcagaagt aagttggccg cagtgttatc  11700
actcatggtt atggcagcac tgcataattc tcttactgtc atgccatccg taagatgctt  11760
```

```
ttctgtgact ggtgagtact caaccaagtc attctgagaa tagtgtatgc ggcgaccgag    11820
ttgctcttgc ccggcgtcaa tacgggataa taccgcgcca catagcagaa ctttaaaagt    11880
gctcatcatt ggaaaacgtt cttcggggcg aaaactctca aggatcttac cgctgttgag    11940
atccagttcg atgtaaccca ctcgtgcacc caactgatct tcagcatctt ttactttcac    12000
cagcgtttct gggtgagcaa aacaggaag gcaaaatgcc gcaaaaagg gaataagggc    12060 gacacggaaa tgttgaatac tcatactctt ccttttcaa tattattgaa gcatttatca    12120
gggttattgt ctcatgagcg gatacatatt tgaatgtatt tagaaaaata aacaaatagg    12180
ggttccgcgc acatttcccc gaaaagtgcc acctgacgtc gacggatcgg gcctgcag     12238

<210> SEQ ID NO 42
<211> LENGTH: 711
<212> TYPE: DNA
<213> ORGANISM: Artificial Sequence
<220> FEATURE:
<223> OTHER INFORMATION: murine bcl-2 coding region

<400> SEQUENCE: 42
atggcgcaag ccgggagaac agggtatgat aaccgggaga tcgtgatgaa gtacatacat      60
tataagctgt cacagagggg ctacgagtgg gatgctggag atgcggacgc ggcgcccctg     120
ggggctgccc ccaccctgg catcttctcc ttccagcctg agagcaaccc aatgcccgct     180
gtgcaccggg acatggctgc caggacgtct cctctcaggc ccctcgttgc caccgctggg     240
cctgcgctca gccctgtgcc acctgtggtc catctgaccc tccgccgggc tggggatgac     300
ttctctcgtc gctaccgtcg tgacttcgca gagatgtcca gtcagctgca cctgacgccc     360
ttcaccgcga ggggacgctt tgccacggtg gtggaggaac tcttcaggga tggggtgaac     420 tggggggagga ttgtggcctt ctttgagttc ggtggggtca tgtgtgtgga gagcgtcaac     480
agggagatgt caccccctggt ggacaacatc gccctgtgga tgactgagta cctgaaccgg     540
catctgcaca cctggatcca ggataacgga ggctgggatg cctttgtgga actatatggc     600
cccagcatgc gacctctgtt tgatttctcc tggctgtctc tgaagaccct gctcagcctg     660
gccctggtcg gggcctgcat cactctgggt gcatacctgg gccacaagtg a              711

<210> SEQ ID NO 43
<211> LENGTH: 236
<212> TYPE: PRT
<213> ORGANISM: Artificial Sequence
<220> FEATURE:
<223> OTHER INFORMATION: amino acid sequence of murine Bcl-2 protein

<400> SEQUENCE: 43

Met Ala Gln Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Ala Asp Ala Ala Pro Leu Gly Ala Ala Pro Thr Pro Gly Ile
        35                  40                  45

Phe Ser Phe Gln Pro Glu Ser Asn Pro Met Pro Ala Val His Arg Asp
    50                  55                  60

Met Ala Ala Arg Thr Ser Pro Leu Arg Pro Leu Val Ala Thr Ala Gly
65                  70                  75                  80

Pro Ala Leu Ser Pro Val Pro Pro Val Val His Leu Thr Leu Arg Arg
                85                  90                  95
```

```
Ala Gly Asp Asp Phe Ser Arg Arg Tyr Arg Arg Asp Phe Ala Glu Met
            100                 105                 110

Ser Ser Gln Leu His Leu Thr Pro Phe Thr Ala Arg Gly Arg Phe Ala
        115                 120                 125

Thr Val Val Glu Glu Leu Phe Arg Asp Gly Val Asn Trp Gly Arg Ile
    130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
                165                 170                 175

Tyr Leu Asn Arg His Leu His Thr Trp Ile Gln Asp Asn Gly Gly Trp
            180                 185                 190

Asp Ala Phe Val Glu Leu Tyr Gly Pro Ser Met Arg Pro Leu Phe Asp
        195                 200                 205

Phe Ser Trp Leu Ser Leu Lys Thr Leu Leu Ser Leu Ala Leu Val Gly
    210                 215                 220

Ala Cys Ile Thr Leu Gly Ala Tyr Leu Gly His Lys
225                 230                 235

<210> SEQ ID NO 44
<211> LENGTH: 6250
<212> TYPE: DNA
<213> ORGANISM: Artificial Sequence
<220> FEATURE:
<223> OTHER INFORMATION: pCDNA3.1-hygro(+)-bcl2 mammalian expression
      vector

<400> SEQUENCE: 44
gacggatcgg gagatctccc gatcccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccatggcgca gccgggaga acagggtatg ataaccggga   960
gatcgtgatg aagtacatac attataagct gtcacagagg ggctacgagt gggatgctgg  1020
agatgcggac gcggcgcccc tgggggctgc ccccacccct ggcatcttct ccttccagcc  1080
tgagagcaac ccaatgcccg ctgtgcaccg gacatggct gccaggacgt ctcctctcag  1140
gcccctcgtt gccaccgctg ggcctgcgct cagcccgtg ccacctgtgg tccatctgac  1200
cctccgccgg gctggggatg acttctctcg tcgctaccgt cgtgacttcg cagagatgtc  1260
```

```
cagtcagctg cacctgacgc ccttcaccgc gagggacgc tttgccacgg tggtggagga    1320
actcttcagg gatgggtga actggggag gattgtggcc ttctttgagt tcggtggggt    1380
catgtgtgtg gagagcgtca acagggagat gtcacccctg gtggacaaca tcgccctgtg    1440
gatgactgag tacctgaacc ggcatctgca cacctggatc caggataacg gaggctggga    1500
tgcctttgtg gaactatatg gccccagcat gcgacctctg tttgatttct cctggctgtc    1560
tctgaagacc ctgctcagcc tggccctggt cggggcctgc atcactctgg gtgcatacct    1620
gggccacaag tgactcgagt ctagagggcc cgtttaaacc cgctgatcag cctcgactgt    1680
gccttctagt tgccagccat ctgttgtttg cccctccccc gtgccttcct tgaccctgga    1740
aggtgccact cccactgtcc tttcctaata aaatgaggaa attgcatcgc attgtctgag    1800
taggtgtcat tctattctgg ggggtggggt ggggcaggac agcaaggggg aggattggga    1860
agacaatagc aggcatgctg gggatgcggt gggctctatg gcttctgagg cggaaagaac    1920
cagctgggc tctagggggt atccccacgc gccctgtagc ggcgcattaa gcgcggcggg    1980
tgtggtggtt acgcgcagcg tgaccgctac acttgccagc gccctagcgc ccgctccttt    2040
cgctttcttc ccttcctttc tcgccacgtt cgccggcttt ccccgtcaag ctctaaatcg    2100
gggcatccct ttagggttcc gatttagtgc tttacggcac ctcgacccca aaaaacttga    2160
ttagggtgat ggttcacgta gtgggccatc gccctgatag acggttttc gcccttgac    2220
gttggagtcc acgttcttta atagtggact cttgttccaa actggaacaa cactcaaccc    2280
tatctcggtc tattcttttg atttataagg gattttgggg atttcggcct attggttaaa    2340
aaatgagctg atttaacaaa aatttaacgc gaattaattc tgtggaatgt gtgtcagtta    2400
gggtgtggaa agtccccagg ctccccaggc aggcagaagt atgcaaagca tgcatctcaa    2460
ttagtcagca accaggtgtg gaaagtcccc aggctcccca gcaggcagaa gtatgcaaag    2520
catgcatctc aattagtcag caaccatagt cccgccccta actccgccca tcccgcccct    2580
aactccgccc agttccgccc attctccgcc ccatggctga ctaattttt ttatttatgc    2640
agaggccgag gccgcctctg cctctgagct attccagaag tagtgaggag gctttttgg    2700
aggcctaggc ttttgcaaaa agctcccggg agcttgtata tccattttcg gatctgatca    2760
gcacgtgatg aaaaagcctg aactcaccgc gacgtctgtc gagaagtttc tgatcgaaaa    2820
gttcgacagc gtctccgacc tgatgcagct ctcggagggc gaagaatctc gtgctttcag    2880
cttcgatgta ggagggcgtg gatatgtcct gcgggtaaat agctgcgccg atggtttcta    2940
caaagatcgt tatgtttatc ggcactttgc atcggccgcg ctcccgattc cggaagtgct    3000
tgacattggg gaattcagcg agagcctgac ctattgcatc tcccgccgtg cacagggtgt    3060
cacgttgcaa gacctgcctg aaaccgaact gcccgctgtt ctgcagccgg tcgcggaggc    3120
catggatgcg atcgctgcgg ccgatcttag ccagacgagc gggttcggcc cattcggacc    3180
gcaaggaatc ggtcaataca ctacatgcg tgatttcata tgcgcgattg ctgatcccca    3240
tgtgtatcac tggcaaactg tgatggacga caccgtcagt gcgtccgtcg cgcaggctct    3300
cgatgagctg atgctttggg ccgaggactg ccccgaagtc cggcacctcg tgcacgcgga    3360
tttcggctcc aacaatgtcc tgacggacaa tggccgcata acagcggtca ttgactggag    3420
cgaggcgatg ttcggggatt cccaatacga ggtcgccaac atcttcttct ggaggccgtg    3480
gttggcttgt atggagcagc agacgcgcta cttcgagcgg aggcatccgg agcttgcagg    3540
atcgccgcgg ctccgggcgt atatgctccg cattggtctt gaccaactct atcagagctt    3600
```

```
ggttgacggc aatttcgatg atgcagcttg ggcgcagggt cgatgcgacg caatcgtccg   3660
atccggagcc gggactgtcg ggcgtacaca aatcgcccgc agaagcgcgg ccgtctggac   3720
cgatggctgt gtagaagtac tcgccgatag tggaaaccga cgccccagca ctcgtccgag   3780
ggcaaaggaa tagcacgtgc tacgagattt cgattccacc gccgccttct atgaaaggtt   3840
gggcttcgga atcgttttcc gggacgccgg ctggatgatc ctccagcgcg gggatctcat   3900
gctggagttc ttcgcccacc ccaacttgtt tattgcagct tataatggtt acaaataaag   3960
caatagcatc acaaatttca caaataaagc attttttca ctgcattcta gttgtggttt    4020
gtccaaactc atcaatgtat cttatcatgt ctgtataccg tcgacctcta gctagagctt   4080
ggcgtaatca tggtcatagc tgtttcctgt gtgaaattgt tatccgctca caattccaca   4140
caacatacga gccggaagca taaagtgtaa agcctggggt gcctaatgag tgagctaact   4200
cacattaatt gcgttgcgct cactgcccgc tttccagtcg ggaaacctgt cgtgccagct   4260
gcattaatga atcggccaac gcgcggggag aggcggtttg cgtattgggc gctcttccgc   4320
ttcctcgctc actgactcgc tgcgctcggt cgttcggctg cggcgagcgg tatcagctca   4380
ctcaaaggcg gtaatacggt tatccacaga atcaggggat aacgcaggaa agaacatgtg   4440
agcaaaaggc cagcaaaagg ccaggaaccg taaaaaggcc gcgttgctgg cgttttccca   4500
taggctccgc cccctgacg agcatcacaa aaatcgacgc tcaagtcaga ggtggcgaaa    4560
cccgacagga ctataaagat accaggcgtt tccccctgga agctccctcg tgcgctctcc   4620
tgttccgacc ctgccgctta ccggatacct gtccgccttt ctcccttcgg aagcgtggc    4680
gctttctcaa tgctcacgct gtaggtatct cagttcggtg taggtcgttc gctccaagct   4740
gggctgtgtg cacgaacccc ccgttcagcc cgaccgctgc gccttatccg gtaactatcg   4800
tcttgagtcc aacccggtaa gacacgactt atcgccactg gcagcagcca ctggtaacag   4860
gattagcaga gcgaggtatg taggcggtgc tacagagttc ttgaagtggt ggcctaacta   4920
cggctacact agaaggacag tatttggtat ctgcgctctg ctgaagccag ttaccttcgg   4980
aaaaagagtt ggtagctctt gatccggcaa acaaaccacc gctggtagcg gtggtttttt   5040
tgtttgcaag cagcagatta cgcgcagaaa aaaaggatct caagaagatc ctttgatctt   5100
ttctacgggg tctgacgctc agtggaacga aaactcacgt taagggattt tggtcatgag   5160
attatcaaaa aggatcttca cctagatcct tttaaattaa aaatgaagtt ttaaatcaat   5220
ctaaagtata tatgagtaaa cttggtctga cagttaccaa tgcttaatca gtgaggcacc   5280
tatctcagcg atctgtctat ttcgttcatc catagttgcc tgactccccg tcgtgtagat   5340
aactacgata cgggagggct taccatctgg ccccagtgct gcaatgatac cgcgagaccc   5400
acgctcaccg gctccagatt tatcagcaat aaaccagcca gccggaaggg ccgagcgcag   5460
aagtggtcct gcaactttat ccgcctccat ccagtctatt aattgttgcc gggaagctag   5520
agtaagtagt tcgccagtta atagtttgcg caacgttgtt gccattgcta caggcatcgt   5580
ggtgtcacgc tcgtcgtttg gtatggcttc attcagctcc ggttcccaac gatcaaggcg   5640
agttacatga tccccatgt tgtgcaaaaa agcggttagc tccttcggtc ctccgatcgt    5700
tgtcagaagt aagttggccg cagtgttatc actcatggtt atggcagcac tgcataattc   5760
tcttactgtc atgccatccg taagatgctt ttctgtgact ggtgagtact caaccaagtc   5820
attctgagaa tagtgtatgc ggcgaccgag ttgctcttgc ccggcgtcaa tacgggataa   5880
taccgcgcca catagcagaa ctttaaaagt gctcatcatt ggaaaacgtt cttcggggcg   5940
aaaactctca aggatcttac cgctgttgag atccagttcg atgtaaccca ctcgtgcacc   6000
```

| | | |
|---|---|---|
| caactgatct tcagcatctt ttactttcac cagcgtttct gggtgagcaa aaacaggaag | 6060 | |
| gcaaaatgcc gcaaaaaagg gaataagggc gacacgaaaa tgttgaatac tcatactctt | 6120 | |
| ccttttcaa tattattgaa gcatttatca gggttattgt ctcatgagcg gatacatatt | 6180 | |
| tgaatgtatt tagaaaaata aacaataggg gttccgcgc acatttcccc gaaaagtgcc | 6240 | |
| acctgacgtc | 6250 | |

<210> SEQ ID NO 45
<211> LENGTH: 3064
<212> TYPE: DNA
<213> ORGANISM: Artificial Sequence
<220> FEATURE:
<223> OTHER INFORMATION: pUC57_VkappaK1-5

<400> SEQUENCE: 45

| | | |
|---|---|---|
| tcgcgcgttt cggtgatgac ggtgaaaacc tctgacacat gcagctcccg gagacggtca | 60 | |
| cagcttgtct gtaagcggat gccgggagca gacaagcccg tcagggcgcg tcagcgggtg | 120 | |
| ttggcgggtg tcgggctgg cttaactatg cggcatcaga gcagattgta ctgagagtgc | 180 | |
| accatatgcg gtgtgaaata ccgcacagat gcgtaaggag aaaataccgc atcaggcgcc | 240 | |
| attcgccatt caggctgcgc aactgttggg aagggcgatc ggtgcgggcc tcttcgctat | 300 | |
| tacgccagct ggcgaaaggg ggatgtgctg caaggcgatt aagttgggta acgccagggt | 360 | |
| tttcccagtc acgacgttgt aaaacgacgg ccagtgaatt cgagctcggt acctcgcgaa | 420 | |
| tgcatctaga tccaatccaa tgcggccgca tggacatgag ggtccccgct cagctcctgg | 480 | |
| ggctcctgct gctctggctc ccaggtgcca atgtgacat ccagatgacc cagtctcctt | 540 | |
| ccaccctgtc tgcatctgta ggagacagag tcaccatcac ttgccgggcc agtcagagta | 600 | |
| ttagtagctg gttggcctgg tatcagcaga accagggaa agcccctaag ctcctgatct | 660 | |
| atgatgcctc cagtttggaa agtggggtcc catcaaggtt cagcggcagt ggatctggga | 720 | |
| cagaattcac tctcaccatc agcagcctgc agcctgatga ttttgcaact tattactgcc | 780 | |
| aacagatcgg atcccgggcc cgtcgactgc agaggcctgc atgcaagctt ggcgtaatca | 840 | |
| tggtcatagc tgtttcctgt gtgaaattgt tatccgctca caattccaca acatacga | 900 | |
| gccggaagca taaagtgtaa agcctggggt gcctaatgag tgagctaact cacattaatt | 960 | |
| gcgttgcgct cactgcccgc tttccagtcg ggaaacctgt cgtgccagct gcattaatga | 1020 | |
| atcggccaac gcgcggggag aggcggtttg cgtattgggc gctcttccgc ttcctcgctc | 1080 | |
| actgactcgc tgcgctcggt cgttcggctg cggcgagcgg tatcagctca ctcaaaggcg | 1140 | |
| gtaatacggt tatccacaga atcaggggat aacgcaggaa agaacatgtg agcaaaaggc | 1200 | |
| cagcaaaagg ccaggaaccg taaaaaggcc gcgttgctgg cgtttttcca taggctccgc | 1260 | |
| cccctgacg agcatcacaa aaatcgacgc tcaagtcaga ggtggcgaaa cccgacagga | 1320 | |
| ctataaagat accaggcgtt tccccctgga agctccctcg tgcgctctcc tgttccgacc | 1380 | |
| ctgccgctta ccggatacct gtccgccttt ctcccttcgg gaagcgtggc gctttctcat | 1440 | |
| agctcacgct gtaggtatct cagttcggtg taggtcgttc gctccaagct gggctgtgtg | 1500 | |
| cacgaacccc ccgttcagcc cgaccgctgc gccttatccg gtaactatcg tcttgagtcc | 1560 | |
| aacccggtaa gacacgactt atcgccactg gcagcagcca ctggtaacag gattagcaga | 1620 | |
| gcgaggtatg taggcggtgc tacagagttc ttgaagtggt ggcctaacta cggctacact | 1680 | |
| agaagaacag tatttggtat ctgcgctctg ctgaagccag ttaccttcgg aaaaagagtt | 1740 | |

| | |
|---|---|
| ggtagctctt gatccggcaa acaaaccacc gctggtagcg gtggttttttt tgtttgcaag | 1800 |
| cagcagatta cgcgcagaaa aaaggatct caagaagatc ctttgatctt ttctacgggg | 1860 |
| tctgacgctc agtggaacga aaactcacgt taagggattt tggtcatgag attatcaaaa | 1920 |
| aggatcttca cctagatcct tttaaattaa aatgaagtt ttaaatcaat ctaaagtata | 1980 |
| tatgagtaaa cttggtctga cagttaccaa tgcttaatca gtgaggcacc tatctcagcg | 2040 |
| atctgtctat ttcgttcatc catagttgcc tgactcccccg tcgtgtagat aactacgata | 2100 |
| cgggagggct taccatctgg ccccagtgct gcaatgatac cgcgagaccc acgctcaccg | 2160 |
| gctccagatt tatcagcaat aaaccagcca gccggaaggg ccgagcgcag aagtggtcct | 2220 |
| gcaactttat ccgcctccat ccagtctatt aattgttgcc gggaagctag agtaagtagt | 2280 |
| tcgccagtta atagtttgcg caacgttgtt gccattgcta caggcatcgt ggtgtcacgc | 2340 |
| tcgtcgtttg gtatggcttc attcagctcc ggttcccaac gatcaaggcg agttacatga | 2400 |
| tcccccatgt tgtgcaaaaa agcggttagc tccttcggtc ctccgatcgt tgtcagaagt | 2460 |
| aagttggccg cagtgttatc actcatggtt atggcagcac tgcataattc tcttactgtc | 2520 |
| atgccatccg taagatgctt ttctgtgact ggtgagtact caaccaagtc attctgagaa | 2580 |
| tagtgtatgc ggcgaccgag ttgctcttgc ccggcgtcaa tacgggataa taccgcgcca | 2640 |
| catagcagaa ctttaaaagt gctcatcatt ggaaaacgtt cttcggggcg aaaactctca | 2700 |
| aggatcttac cgctgttgag atccagttcg atgtaaccca ctcgtgcacc caactgatct | 2760 |
| tcagcatctt ttactttcac cagcgtttct gggtgagcaa aaacaggaag gcaaaatgcc | 2820 |
| gcaaaaaagg aataagggc gacacggaaa tgttgaatac tcatactctt ccttttcaa | 2880 |
| tattattgaa gcatttatca gggttattgt ctcatgagcg gatacatatt tgaatgtatt | 2940 |
| tagaaaaata aacaaatagg ggttccgcgc acatttcccc gaaaagtgcc acctgacgtc | 3000 |
| taagaaacca ttattatcat gacattaacc tataaaaata ggcgtatcac gaggcccttt | 3060 |
| cgtc | 3064 |

<210> SEQ ID NO 46
<211> LENGTH: 3100
<212> TYPE: DNA
<213> ORGANISM: Artificial Sequence
<220> FEATURE:
<223> OTHER INFORMATION: pUC57_JkappaK2-C-kappaK

<400> SEQUENCE: 46

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tccaatccaa tagtactttt ggccagggga ccaagctgga gatcaaacgt | 480 |
| acggtggctg caccatctgt cttcatcttc ccgccatctg atgagcagtt gaaatctgga | 540 |
| actgcctctg ttgtgtgcct gctgaataac ttctatccca gagaggccaa agtacagtgg | 600 |
| aaggtggata acgccctcca atcgggtaac tcccaggaga gtgtcacaga gcaggacagc | 660 |
| aaggacagca cctacagcct cagcagcacc ctgacgctga gcaaagcaga ctacgagaaa | 720 |

```
cacaaagtct acgcctgcga agtcacccat cagggcctga gctcgcccgt cacaaagagc    780
ttcaacaggg gagagtgtta gcgctttcga aattggattg gatcggatcc cgggcccgtc    840
gactgcagag gcctgcatgc aagcttggcg taatcatggt catagctgtt cctgtgtga    900 aattgttatc cgctcacaat tccacacaac atacgagccg gaagcataaa gtgtaaagcc    960
tggggtgcct aatgagtgag ctaactcaca ttaattgcgt tgcgctcact gcccgctttc   1020
cagtcgggaa acctgtcgtg ccagctgcat taatgaatcg gccaacgcgc ggggagaggc   1080
ggtttgcgta ttgggcgctc ttccgcttcc tcgctcactg actcgctgcg ctcggtcgtt   1140
cggctgcggc gagcggtatc agctcactca aaggcggtaa tacggttatc cacagaatca   1200
ggggataacg caggaaagaa catgtgagca aaaggccagc aaaaggccag gaaccgtaaa   1260
aaggccgcgt tgctggcgtt tttccatagg ctccgccccc ctgacgagca tcacaaaaat   1320
cgacgctcaa gtcagaggtg gcgaaacccg acaggactat aaagatacca ggcgtttccc   1380
cctggaagct ccctcgtgcg ctctcctgtt ccgaccctgc cgcttaccgg atacctgtcc   1440
gcctttctcc cttcgggaag cgtggcgctt tctcatagct cacgctgtag gtatctcagt   1500
tcggtgtagg tcgttcgctc caagctgggc tgtgtgcacg aaccccccgt tcagcccgac   1560
cgctgcgcct tatccggtaa ctatcgtctt gagtccaacc cggtaagaca cgacttatcg   1620
ccactggcag cagccactgg taacaggatt agcagagcga ggtatgtagg cggtgctaca   1680
gagttcttga agtggtggcc taactacggc tacactagaa gaacagtatt tggtatctgc   1740
gctctgctga agccagttac cttcggaaaa agagttggta gctcttgatc cggcaaacaa   1800
accaccgctg gtagcggtgg tttttttgtt tgcaagcagc agattacgcg cagaaaaaaa   1860
ggatctcaag aagatccttt gatcttttct acggggtctg acgctcagtg gaacgaaaac   1920
tcacgttaag ggattttggt catgagatta tcaaaaagga tcttcaccta gatccttta   1980 aattaaaaat gaagttttaa atcaatctaa agtatatatg agtaaacttg gtctgacagt   2040
taccaatgct taatcagtga ggcacctatc tcagcgatct gtctatttcg ttcatccata   2100
gttgcctgac tccccgtcgt gtagataact acgatacggg agggcttacc atctggcccc   2160
agtgctgcaa tgataccgcg agacccacgc tcaccggctc cagatttatc agcaataaac   2220
cagccagccg gaagggccga gcgcagaagt ggtcctgcaa ctttatccgc ctccatccag   2280
tctattaatt gttgccggga agctagagta agtagttcgc cagttaatag tttgcgcaac   2340
gttgttgcca ttgctacagg catcgtggtg tcacgctcgt cgtttggtat ggcttcattc   2400
agctccggtt cccaacgatc aaggcgagtt acatgatccc ccatgttgtg caaaaaagcg   2460
gttagctcct tcggtcctcc gatcgttgtc agaagtaagt tggccgcagt gttatcactc   2520
atggttatgg cagcactgca taattctctt actgtcatgc catccgtaag atgcttttct   2580
gtgactggtg agtactcaac caagtcattc tgagaatagt gtatgcggcg accgagttgc   2640
tcttgcccgg cgtcaatacg ggataatacc gcgccacata gcagaacttt aaaagtgctc   2700
atcattggaa aacgttcttc ggggcgaaaa ctctcaagga tcttaccgct gttgagatcc   2760
agttcgatgt aacccactcg tgcacccaac tgatcttcag catcttttac tttcaccagc   2820
gtttctgggt gagcaaaaac aggaaggcaa atgccgcaa aaagggaat aagggcgaca   2880 cggaaatgtt gaatactcat actcttcctt tttcaatatt attgaagcat ttatcagggt   2940
tattgtctca tgagcggata catatttgaa tgtatttaga aaataaaca aatagggtt   3000 ccgcgcacat ttccccgaaa agtgccacct gacgtctaag aaaccattat tatcatgaca   3060
```

```
ttaacctata aaaataggcg tatcacgagg ccctttcgtc                          3100
```

<210> SEQ ID NO 47
<211> LENGTH: 411
<212> TYPE: DNA
<213> ORGANISM: Artificial Sequence
<220> FEATURE:
<223> OTHER INFORMATION: VkappaK1-5 PCR product

<400> SEQUENCE: 47

```
cgttgtaaaa cgacggccag tgaattcgag ctcggtacct cgcgaatgca tctagatcca    60
atccaatgcg gccgcatgga catgagggtc cccgctcagc tcctggggct cctgctgctc   120
tggctcccag gtgccaaatg tgacatccag atgacccagt ctccttccac cctgtctgca   180
tctgtaggag acagagtcac catcacttgc cgggccagtc agagtattag tagctggttg   240
gcctggtatc agcagaaacc agggaaagcc cctaagctcc tgatctatga tgcctccagt   300
ttggaaagtg gggtcccatc aaggttcagc ggcagtggat ctgggacaga attcactctc   360
accatcagca gcctgcagcc tgatgatttt gcaacttatt actgccaaca g            411
```

<210> SEQ ID NO 48
<211> LENGTH: 495
<212> TYPE: DNA
<213> ORGANISM: Artificial Sequence
<220> FEATURE:
<223> OTHER INFORMATION: NNK6-JkappaK2-CK-kappa PCR product
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 48

```
gcaacttatt actgccaaca gnnknnknnk nnknnknnka cttttggcca ggggaccaag    60
ctggagatca aacgtacggt ggctgcacca tctgtcttca tcttcccgcc atctgatgag   120
cagttgaaat ctggaactgc ctctgttgtg tgcctgctga ataacttcta tcccagagag   180
gccaaagtac agtggaaggt ggataacgcc ctccaatcgg gtaactccca ggagagtgtc   240
acagagcagg acagcaagga cagcacctac agcctcagca gcaccctgac gctgagcaaa   300
gcagactacg agaaacacaa agtctacgcc tgcgaagtca cccatcaggg cctgagctcg   360
cccgtcacaa agagcttcaa caggggagag tgttagcgct tcgaaattg gattggatcg   420
gatcccgggc cgtcgactg cagaggcctg catgcaagct ggcgtaatc atggtcatag    480
ctgtttcctg tgtga                                                    495
```

```
<210> SEQ ID NO 49
<211> LENGTH: 3083
<212> TYPE: DNA
<213> ORGANISM: Artificial Sequence
<220> FEATURE:
<223> OTHER INFORMATION: pUC57_VH3-30

<400> SEQUENCE: 49
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctcgcgaa     420
tgcatctaga tccaatccaa tcgcacagta atacacagcc gtgtcctcag ctctcaggct     480
gttcatttgc agatacagcg tgttcttgga attgtctctg gagatggtga atcggccctt     540
cacggagtct gcgtagtatt tattacttcc atcatatgat ataactgcca cccactctag     600 cccccttgcct ggagcctggc ggacccagtg catagcatag ctactgaagg tgaatccaga     660
ggctgcacag gagagtctca gggacctccc aggctggacc acgcctcccc cagactccac     720
cagctgcacc tgacactgga cacctcttaa aagagcaacg aggaaaaccc agctcagccc     780
aaactccatg cggccgcatt ggatatcgga tcccgggccc gtcgactgca gaggcctgca     840
tgcaagcttg gcgtaatcat ggtcatagct gtttcctgtg tgaaattgtt atccgctcac     900
aattccacac aacatacgag ccggaagcat aaagtgtaaa gcctggggtg cctaatgagt     960
gagctaactc acattaattg cgttgcgctc actgcccgct ttccagtcgg gaaacctgtc    1020
gtgccagctg cattaatgaa tcggccaacg cgcggggaga gcggtttgc gtattgggcg    1080 ctcttccgct tcctcgctca ctgactcgct gcgctcggtc gttcggctgc ggcgagcggt    1140
atcagctcac tcaaaggcgg taatacggtt atccacagaa tcaggggata acgcaggaaa    1200
gaacatgtga gcaaaaggcc agcaaaaggc caggaaccgt aaaaaggccg cgttgctggc    1260
gtttttccat aggctccgcc cccctgacga gcatcacaaa aatcgacgct caagtcagag    1320
gtggcgaaac ccgacaggac tataaagata ccaggcgttt ccccctggaa gctccctcgt    1380
gcgctctcct gttccgaccc tgccgcttac cggatacctg tccgcctttc tcccttcggg    1440
aagcgtggcg ctttctcata gctcacgctg taggtatctc agttcggtgt aggtcgttcg    1500
ctccaagctg ggctgtgtgc acgaaccccc cgttcagccc gaccgctgcg ccttatccgg    1560
taactatcgt cttgagtcca acccggtaag acacgactta tcgccactgg cagcagccac    1620
tggtaacagg attagcagag cgaggtatgt aggcggtgct acagagttct tgaagtggtg    1680
gcctaactac ggctacacta gaagaacagt atttggtatc tgcgctctgc tgaagccagt    1740
taccttcgga aaaagagttg gtagctcttg atccggcaaa caaaccaccg ctggtagcgg    1800 tggtttttt gtttgcaagc agcagattac gcgcagaaaa aaggatctca agaagatcc    1860 tttgatcttt tctacgggt ctgacgctca gtggaacgaa aactcacgtt aagggatttt    1920
ggtcatgaga ttatcaaaaa ggatcttcac ctagatcctt ttaaattaaa aatgaagttt    1980
taaatcaatc taaagtatat atgagtaaac ttggtctgac agttaccaat gcttaatcag    2040
tgaggcacct atctcagcga tctgtctatt tcgttcatcc atagttgcct gactccccgt    2100
```

| | |
|---|---|
| cgtgtagata actacgatac gggagggctt accatctggc cccagtgctg caatgatacc | 2160 |
| gcgagaccca cgctcaccgg ctccagattt atcagcaata aaccagccag ccggaagggc | 2220 |
| cgagcgcaga agtggtcctg caactttatc cgcctccatc cagtctatta attgttgccg | 2280 |
| ggaagctaga gtaagtagtt cgccagttaa tagtttgcgc aacgttgttg ccattgctac | 2340 |
| aggcatcgtg gtgtcacgct cgtcgtttgg tatggcttca ttcagctccg gttcccaacg | 2400 |
| atcaaggcga gttacatgat cccccatgtt gtgcaaaaaa gcggttagct ccttcggtcc | 2460 |
| tccgatcgtt gtcagaagta agttggccgc agtgttatca ctcatggtta tggcagcact | 2520 |
| gcataattct cttactgtca tgccatccgt aagatgcttt tctgtgactg gtgagtactc | 2580 |
| aaccaagtca ttctgagaat agtgtatgcg gcgaccgagt tgctcttgcc cggcgtcaat | 2640 |
| acgggataat accgcgccac atagcagaac tttaaaagtg ctcatcattg gaaaacgttc | 2700 |
| ttcggggcga aaactctcaa ggatcttacc gctgttgaga tccagttcga tgtaacccac | 2760 |
| tcgtgcaccc aactgatctt cagcatcttt tactttcacc agcgtttctg ggtgagcaaa | 2820 |
| aacaggaagg caaaatgccg caaaaaaggg aataagggcg acacggaaat gttgaatact | 2880 |
| catactcttc ctttttcaat attattgaag catttatcag ggttattgtc tcatgagcgg | 2940 |
| atacatattt gaatgtattt agaaaaataa acaaataggg gttccgcgca catttccccg | 3000 |
| aaaagtgcca cctgacgtct aagaaaccat tattatcatg acattaacct ataaaaatag | 3060 |
| gcgtatcacg aggccctttc gtc | 3083 |

<210> SEQ ID NO 50
<211> LENGTH: 2760
<212> TYPE: DNA
<213> ORGANISM: Artificial Sequence
<220> FEATURE:
<223> OTHER INFORMATION: pUC57_JH4

<400> SEQUENCE: 50

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tgacgacatt ggggtcaggg aaccctggtc accgtctcct cagctagcga | 480 |
| catcggatcc cggccccgtc gactgcagag gcctgcatgc aagcttggcg taatcatggt | 540 |
| catagctgtt tcctgtgtga aattgttatc cgctcacaat tccacacaac atacgagccg | 600 |
| gaagcataaa gtgtaaagcc tggggtgcct aatgagtgag ctaactcaca ttaattgcgt | 660 |
| tgcgctcact gcccgctttc cagtcgggaa acctgtcgtg ccagctgcat taatgaatcg | 720 |
| gccaacgcgc ggggagaggc ggtttgcgta ttgggcgctc ttccgcttcc tcgctcactg | 780 |
| actcgctgcg ctcggtcgtt cggctgcggc gagcggtatc agctcactca aaggcggtaa | 840 |
| tacggttatc cacagaatca ggggataacg caggaaagaa catgtgagca aaaggccagc | 900 |
| aaaaggccag gaaccgtaaa aaggccgcgt tgctggcgtt tttccatagg ctccgccccc | 960 |
| ctgacgagca tcacaaaaat cgacgctcaa gtcagaggtg cgaaacccg acaggactat | 1020 |
| aaagatacca ggcgtttccc cctggaagct ccctcgtgcg ctctcctgtt ccgaccctgc | 1080 |

```
cgcttaccgg ataccTgtcc gccttTctcc cttcgggaag cgtggcgctt tctcatagct   1140
cacgctgtag gtatctcagt tcggtgtagg tcgttcgctc caagctgggc tgtgtgcacg   1200
aaccccccgt tcagcccgac cgctgcgcct tatccggtaa ctatcgtctt gagtccaacc   1260
cggtaagaca cgacttatcg ccactggcag cagccactgg taacaggatt agcagagcga   1320
ggtatgtagg cggtgctaca gagttcttga agtggtggcc taactacggc tacactagaa   1380
gaacagtatt tggtatctgc gctctgctga agccagttac cttcggaaaa agagttggta   1440
gctcttgatc cggcaaacaa accaccgctg gtagcggtgg ttttttTgtt tgcaagcagc   1500
agattacgcg cagaaaaaaa ggatctcaag aagatccttT gatcttttct acggggTctg   1560
acgctcagtg gaacgaaaac tcacgttaag ggattttggt catgagatta tcaaaagga   1620 tcttcaccta gatcctttTa aattaaaaat gaagttttaa atcaatctaa agtatatatg   1680
agtaaacttg gtctgacagt taccaatgct taatcagtga ggcacctatc tcagcgatct   1740
gtctatttcg ttcatccata gttgcctgac tccccgtcgt gtagataact acgatacggg   1800
agggcttacc atctggcccc agtgctgcaa tgataccgcg agacccacgc tcaccggctc   1860
cagatttatc agcaataaac cagccagccg aagggccga gcgcagaagt ggtcctgcaa   1920
ctttatccgc ctccatccag tctattaatt gttgccggga agctagagta agtagttcgc   1980
cagttaatag tttgcgcaac gttgttgcca ttgctacagg catcgtggtg tcacgctcgt   2040
cgtttggtat ggcttcattc agctccggtt cccaacgatc aaggcgagtt acatgatccc   2100
ccatgttgtg caaaaaagcg gttagctcct tcggtcctcc gatcgttgtc agaagtaagt   2160
tggccgcagt gttatcactc atggttatgg cagcactgca taattctctt actgtcatgc   2220
catccgtaag atgcttttct gtgactggtg agtactcaac caagtcattc tgagaatagt   2280
gtatgcggcg accgagttgc tcttgcccgg cgtcaatacg ggataatacc gcgccacata   2340
gcagaacttt aaaagtgctc atcattggaa aacgttcttc ggggcgaaaa ctctcaagga   2400
tcttaccgct gttgagatcc agttcgatgt aacccactcg tgcacccaac tgatcttcag   2460
catcttttac tttcaccagc gtttctgggt gagcaaaaac aggaaggcaa aatgccgcaa   2520
aaaagggaat aagggcgaca cggaaatgtt gaatactcat actcttcctt tttcaatatt   2580
attgaagcat ttatcagggt tattgtctca tgagcggata catatttgaa tgtatttaga   2640
aaaataaaca aataggggtt ccgcgcacat ttccccgaaa agtgccacct gacgtctaag   2700
aaaccattat tatcatgaca ttaacctata aaaataggcg tatcacgagg ccctttcgtc   2760
```

<210> SEQ ID NO 51
<211> LENGTH: 366
<212> TYPE: DNA
<213> ORGANISM: Artificial Sequence
<220> FEATURE:
<223> OTHER INFORMATION: VH3-30 PCR product

<400> SEQUENCE: 51

```
gatatccaat gcggccgcat ggagtttggg ctgagctggg ttttcctcgt tgctctttta    60
agaggtgtcc agtgtcaggt gcagctggtg gagtctgggg gaggcgtggt ccagcctggg   120
aggtccctga gactctcctg tgcagcctct ggattcacct tcagtagcta tgctatgcac   180
tgggtccgcc aggctccagg caaggggcta gagtgggtgg cagttatatc atatgatgga   240
agtaataaat actacgcaga ctccgtgaag ggccgattca ccatctccag agacaattcc   300
aagaacacgc tgtatctgca aatgaacagc ctgagagctg aggacacggc tgtgtattac   360
``` tgtgcg                                                          366

<210> SEQ ID NO 52
<211> LENGTH: 299
<212> TYPE: DNA
<213> ORGANISM: Artificial Sequence
<220> FEATURE:
<223> OTHER INFORMATION: NNK4-JH4 PCR product
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t

<400> SEQUENCE: 52
cacggctgtg tattactgtg cgargnnknn knnknnkgac nnktggggcc aaggaaccct      60
ggtcaccgtc tcctcagcta gcgacatcgg atcccgggcc cgtcgactgc agaggcctgc     120
atgcaagctt ggcgtaatca tggtcatagc tgtttcctgt gtgaaattgt tatccgctca     180
caattccaca caacatacga gccggaagca taaagtgtaa agcctggggt gcctaatgag     240
tgagctaact cacattaatt gcgttgcgct cactgcccgc tttccagtcg ggaaacctg      299

<210> SEQ ID NO 53
<211> LENGTH: 305
<212> TYPE: DNA
<213> ORGANISM: Artificial Sequence
<220> FEATURE:
<223> OTHER INFORMATION: NNK6-JH4 PCR product
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 53

```
cacggctgtg tattactgtg cgargnnknn knnknnknnk nnkgacnnkt ggggccaagg    60
aaccctggtc accgtctcct cagctagcga catcggatcc cgggcccgtc gactgcagag   120
gcctgcatgc aagcttggcg taatcatggt catagctgtt tcctgtgtga aattgttatc   180
cgctcacaat tccacacaac atacgagccg gaagcataaa gtgtaaagcc tggggtgcct   240
aatgagtgag ctaactcaca ttaattgcgt tgcgctcact gcccgctttc cagtcgggaa   300
acctg                                                               305
```

```
<210> SEQ ID NO 54
<211> LENGTH: 311
<212> TYPE: DNA
<213> ORGANISM: Artificial Sequence
<220> FEATURE:
<223> OTHER INFORMATION: NNK8-JH4 PCR product
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 54
```

```
cacggctgtg tattactgtg cgargnnknn knnknnknnk nnknnknnkg acnnktgggg    60
ccaaggaacc ctggtcaccg tctcctcagc tagcgacatc ggatcccggg cccgtcgact   120
gcagaggcct gcatgcaagc ttggcgtaat catggtcata gctgtttcct gtgtgaaatt   180
gttatccgct cacaattcca cacaacatac gagccggaag cataaagtgt aaagcctggg   240
gtgcctaatg agtgagctaa ctcacattaa ttgcgttgcg ctcactgccc gctttccagt   300
cgggaaacct g                                                        311
```

```
<210> SEQ ID NO 55
<211> LENGTH: 317
<212> TYPE: DNA
<213> ORGANISM: Artificial Sequence
<220> FEATURE:
<223> OTHER INFORMATION: NNK10-JH4 PCR product
<220> FEATURE:
```

```
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 55
cacggctgtg tattactgtg cgargnnknn knnknnknnk nnknnknnkn nknnkgacnn      60
ktggggccaa ggaaccctgg tcaccgtctc ctcagctagc gacatcggat cccgggcccg     120
tcgactgcag aggcctgcat gcaagcttgg cgtaatcatg gtcatagctg tttcctgtgt    180
gaaattgtta tccgctcaca attccacaca acatacgagc cggaagcata aagtgtaaag    240
cctggggtgc ctaatgagtg agctaactca cattaattgc gttgcgctca ctgcccgctt    300
tccagtcggg aaacctg                                                   317
```